US009809590B2

(12) United States Patent
Boys et al.

(10) Patent No.: US 9,809,590 B2
(45) Date of Patent: *Nov. 7, 2017

(54) SUBSTITUTED N-(1H-INDAZOL-4-YL)IMIDAZO[1,2-A]PYRIDINE-3-CARBOXAMIDE COMPOUNDS AS TYPE III RECEPTOR TYROSINE KINASE INHIBITORS

(71) Applicant: Array BioPharma Inc., Boulder, CO (US)

(72) Inventors: Mark Laurence Boys, Boulder, CO (US); Robert Kirk DeLisle, Lyons, CO (US); Erik James Hicken, Boulder, CO (US); April L. Kennedy, Denver, CO (US); David A. Mareska, McMurray, PA (US); Fredrik P. Marmsater, Boulder, CO (US); Mark C. Munson, Acton, MA (US); Brad Newhouse, Boulder, CO (US); Bryson Rast, Westminster, CO (US); James P. Rizzi, Addison, TX (US); Martha E. Rodriguez, Lafayette, CO (US); George T. Topalov, Pittsburgh, PA (US); Qian Zhao, El Cerrito, CA (US)

(73) Assignee: Array BioPharma Inc., Boulder, CO (US)

( * ) Notice: Subject to any disclaimer, the term of this patent is extended or adjusted under 35 U.S.C. 154(b) by 7 days.

This patent is subject to a terminal disclaimer.

(21) Appl. No.: 14/858,029

(22) Filed: Sep. 18, 2015

(65) Prior Publication Data

US 2016/0002232 A1    Jan. 7, 2016

Related U.S. Application Data

(63) Continuation of application No. 13/994,048, filed as application No. PCT/US2011/064549 on Dec. 13, 2011.

(60) Provisional application No. 61/422,547, filed on Dec. 13, 2010.

(51) Int. Cl.
*C07D 471/04* (2006.01)
*A61K 45/06* (2006.01)
*A61K 31/496* (2006.01)

(52) U.S. Cl.
CPC .......... *C07D 471/04* (2013.01); *A61K 31/496* (2013.01); *A61K 45/06* (2013.01)

(58) Field of Classification Search
None
See application file for complete search history.

(56) References Cited

U.S. PATENT DOCUMENTS 9,174,981 B2   11/2015   Boys et al.

FOREIGN PATENT DOCUMENTS

| WO | 2008078100 A2 | 7/2008 | |
| WO | 2008124323 A1 | 10/2008 | |
| WO | WO 2008124323 A1 * | 10/2008 | ........... C07D 471/04 |
| WO | 2009147189 | 12/2009 | |
| WO | 2011079076 A1 | 6/2011 | |
| WO | 2012080176 A2 | 6/2012 | |

OTHER PUBLICATIONS

Simone, Oncology: Introduction, Cecil Textbook of Medicine, 20th Edition, 1996 vol. 1, pp. 1004-1010.*
Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
Abbadie, Trends in Immunology, vol. 26 (10), 529-534 (2005).
Akhmetshina, et al., Arthritis & Rheumatism, vol. 60 (1), 219-224 (2009).
Aono, et al., Am. J. Resp. Crit. Care Med. vol. 171, 1279-1285 (2005).
Bonner, et al., Am. J. Physiol. 274 (Lung Cell. Mol. Physiol. 18): L72-L80 (1998).
Chitu, et al., Curr Opin Immunol 18, 39-48 (2006).
Danziger, "Automated Site-Directed Drug Design: A General Algorithm for Knowledge Acquisition about Hydrogen-Bonding Regions at Protein Surfaces", Proceedings of the Royal Society of London, Series B, Biological Sciences, 236 1283), 101-113 (1989).
Distler, et al., Arthritis & Rheumatism, vol. 58 (8), 2538-2542 (2008).
Fuehrer, et al., Arch Pathol Lab Med vol. 133, 1420-1425 (2009).
Hirose, et al., Int J Hematology 76, 349-353 (2002).
Huang, et al., "Pyrido[2,3-d]pyrimidin-5-ones: A Novel Class of Antiinflammatory Macrophage Colony-Stimulating Factor-1 Receptor Inhibitors", J. Med. Chem, 52, 1081-1099 (2009).
Kay, et al., Arthritis & Rheumatism, vol. 58 (8), 2543-2548 (2008).
Lewis, et al., J Cancer Res 66, 605-612 (2006).
Liu, et al., Pain 86, 25-32 (2000).
Novak, et al., J. Mini-Reviews in Med. Chem. 10, 624-634 (2010).
Ozel, et al., J. Pediatric Urology 6, 125-129 (2010).
Patent Cooperation Treaty, International Searching Authority for PCT/US2011/064549, 10 pages, Mar. 20, 2012.
Paulus, et al., Cancer Res 66, 4349-4356 (2006).
Pollard, Nature Reviews Cancer, vol. 4, 71-78 (2004).
Scott, et al., "Identification of 3-amido-4-anilinoquinolines as potent and selective inhibitors of CSF-1R kinase", Bioorg. & Med. Chem. Lett., 19, 697-700 (2009).
Simone, Introduction, Cecil Textbook of Medicine, 20th Edition, vol. 1, 1004-1010 (1996).

(Continued)

*Primary Examiner* — Kathrien Cruz
*Assistant Examiner* — Andrew Lee
(74) *Attorney, Agent, or Firm* — Viksnins Harris Padys Malen LLP; Sarah S. Mastous

(57) ABSTRACT

Compounds useful in the treatment of fibrosis, bone-related diseases, cancer, autoimmune disorders, inflammatory diseases, cardiovascular diseases, pain and burns in a mammal.

29 Claims, No Drawings

(56) References Cited

OTHER PUBLICATIONS

Tal, Current Review of Pain, 3, 440-446 (1999).
Toshner, et al., Am J Resp Crit Care Med., vol. 180, 780-787 (2009).
Vuorinen, Experimental Lung Res 333, 357-373 (2007).
Wong, et al., Histophathology 51, 758-762 (2007).
Yoshiji, et al., Int J Mol Med 17, 899-904 (2006).

* cited by examiner

SUBSTITUTED N-(1H-INDAZOL-4-YL)IMIDAZO[1,2-A]PYRIDINE-3-CARBOXAMIDE COMPOUNDS AS TYPE III RECEPTOR TYROSINE KINASE INHIBITORS

This application is a continuation of U.S. application Ser. No. 13/994,048, filed on Jun. 13, 2013, which is a U.S. National Stage filing from PCT/US11/64549, filed on Dec. 13, 2011, which claims the benefit of U.S. Provisional No. 61/422,547, filed on Dec. 13, 2010, each of which is incorporated by reference herein in its entirety.

The present invention relates to novel compounds, to pharmaceutical compositions comprising the compounds, to processes for making the compounds, and to the use of the compounds in therapy. More particularly, it relates to certain substituted N-(1H-indazol-4-yl)imidazo[1,2-a]pyridine-3-carboxamide compounds which are inhibitors of type III receptor tyrosine kinases such as PDGFR and/or cFMS and/or cKIT, which are useful in the treatment of fibrosis, bone-related diseases, cancer, autoimmune disorders, inflammatory diseases, cardiovascular diseases, pain and burns.

PDGFR is expressed on early stem cells, mast cells, myeloid cells, mesenchymal cells, and smooth muscles cells. PDGFR-β has been implicated in myeloid leukemias. Recently, it was shown that activating mutations in PDGFR-α kinase domain are present in gastrointestinal stromal tumors (GIST) (Wong et al., 2007, Histopathology 51(6): 758-762).

PDGFR has been shown to be a potent mitogen for myofibroblast formation, a signature of fibrotic conditions and implicated in the progression of fibrosis (Bonner, J. et al., 1998, American Journal Physiology 274 (1Pt1): L72-L80).

In addition, blockade of PDGF signaling has been demonstrated to reduce the development of fibrosis in various experimental models (Yoshiji, et al., 2006, Int. J. Mol. Med. 17:899-904). Imatinib, for example, a known inhibitor of PDGF signaling, has demonstrated anti-fibrotic activity in several animal models of fibrosis (Akhmetshina, A., et al., 2009, Arthritis Rheumatism 60(1): 219-224; Vuorinen, K., et al., 2007, Experimental Lung Research 33(7): 357-373; Aono, Y., et al., 2005, American Journal Respiratory Critical Care Medicine 171(11): 1279-1285). There are multiple case reports of patients with fibrotic conditions benefiting from treatment with Imatinib (Kay, J., et al., 2008, Arthritis Rheumatism 58(8): 2543-2548; Distler J., et al., 2008, Arthritis Rheumatism 58(8): 2538-2542; Hirose, Y., et al., 2002 International Journal Hematology 76(4): 349-353). Imatinib recently completed a randomized, placebo-controlled phase II study in patients with idiopathic pulmonary fibrosis (IPF).

Macrophage colony-stimulating factor-1 receptor (CSF-1R), a tyrosine receptor kinase also known as cFMS, is the receptor for colony stimulating factor-1 (CSF-1), also known as M-CSF. CSF-1 is an important growth factor for bone progenitor cells, monocytes, macrophages, and cells of macrophage lineage such as osteoclasts and dendritic cells. Binding of CSF-1 to the cFMS extracellular domain induces cFMS dimerization and trans-autophosphorylation of the intracellular cFMS kinase domain. Once phosphorylated, cFMS serves as a docking site for several cytoplasmic signaling molecules, the activation of which leads to de novo gene expression and proliferation. Robust expression of cFMS is restricted to monocytes, tissue macrophages, and osteoclasts, and therefore cFMS inhibitors may be useful in treating diseases where osteoclasts, dendritic cells and macrophages are pathogenic, such as autoimmune/inflammatory diseases, cancer and bone-related diseases.

Bone is a dynamic tissue, subject to a constant remodeling process that operates to maintain skeletal strength and health. This remodeling process entails two phases: an osteolysis phase and an osteogenesis phase. In osteolysis, osteoclast cells invade bone and erode it by releasing acids and enzymes that dissolve collagen and minerals. This creates a small cavity in the bone. In osteogenesis, osteoblast cells deposit new collagen and minerals into the cavity. When osteolysis and osteogenesis are in balance, no net change in bone mass results. However, in certain disease states, osteolysis is more active than osteogenesis, resulting in a net loss of bone.

One particularly serious cause of localized excessive osteolysis is cancer metastasis to bone. Cancer cells often secrete factors, such as M-CSF, that promote osteoclast development and activity. When such cancers establish themselves in bone, they promote extensive osteolytic damage and can result in, for example, bone fracture and spinal compression. Such tumor-associated osteolysis coincides with many types of malignancies, including hematological malignancies (e.g., myeloma and lymphoma) and solid tumors (e.g., breast, prostate, lung, renal and thyroid). Accordingly, there remains a need for therapies that reduce or delay complications which arise from the spread of cancer to the bone.

When excessive osteolysis occurs throughout broad areas of the skeleton, it falls under the generic description osteoporosis. Common types of osteoporosis include age-related, post-menopausal, treatment-induced bone loss (e.g., as a result of treatment with glucocorticoids, aromatase inhibitors, or anti-androgen therapy), diabetes-associated and disuse osteoporosis. In the United States alone, millions of individuals suffer from the disease and its attendant pain, deformities and debilitating fractures.

Osteoclasts are multinucleated cells that are derived from monocytic precursors and operate under the control of numerous cytokines and growth factors. Differentiation of the monocytic precursors into osteoclasts is a complex process that requires both M-CSF and RANKL (receptor activator of the NF-kappa B ligand). Inhibiting osteoclast development and function is a desirable approach to treating excessive osteolysis. However, the currently available substances that do so have limited utility, and often cause significant side effects. Thus, a continuing need exists for effective and practical treatments for excessive osteolytic conditions.

Macrophages, which are related to osteoclasts, play an important role in inflammatory disease, cancer and bone disorders. For example, macrophages, which are related to osteoclasts, are a major component of the host cellular response to cancers, and can contribute to tumor growth. In particular, macrophages, as well as tumor cells, secrete M-CSF, a key cytokine for development of osteoclasts from monocyte precursors. Macrophages, as well as monocytes and some tumor cells, also express M-CSF receptors.

Solid tumors comprise a number of cell types, including macrophages. These tumor-associated macrophages (TAMs) are believed to play a number of roles to promote tumor progression and metastasis (Pollard, J. W., Nat. Rev. Cancer, 2004, 4:71; Lewis, C. E. and Pollard, J. W., Cancer Res., 2006, 66:605). Upon recruitment to the tumor environment, macrophages release factors involved in the growth and motility of tumor cells. Monocyte/macrophage development and proliferation depends upon the signaling pathway of CSF-1R and its ligand CSF-1. Recent depletion studies in cancer models showed a role for M-CSF in promoting tumor growth and progression to metastasis (Chitu, V. and Stanley, E. R., Curr. Opin. Immunol., 2006, 18:39-48; Pollard, J. W., Nature Rev. Cancer, 2004, 80:59-65; Paulus, P., et al., Cancer Res. 2006, 66:4349-4356) Inhibition of this pathway therefore could reduce TAM levels, leading to multiple effects on tumor types in which macrophages have a significant presence.

Macrophages are also a predominant source of tumor necrosis factor (TNF) and interleukin-1 (IL-1) in the destructive pannus of rheumatoid arthritis. TNF and IL-1 activate stromal expression of hematopoietic factors including CSF-1. In turn, CSF-1 recruits monocytes and promotes macrophage survival, functional activation, and in some settings, proliferation. Thus, TNF and CSF-1 interact in a perpetuating cycle that leads to inflammation and joint destruction. Macrophage numbers are also elevated in atherosclerotic plaque (Arch. Pathol. Lab. Med. 1985, 109: 445-449) where they are thought to contribute to disease progression.

Inflammatory mechanisms are also believed to play an important role in hyperalgesia resulting from nerve injury. Nerve damage can stimulate macrophage infiltration and increase the number of activated T cells (Abbadie, C., 2005, Trends Immunol. 26(1):529-534). Under these conditions, neuroinflammatory and immune responses contribute as much to the development and maintenance of pain as the initial damage itself. The role of circulating monocytes/macrophages in the development of neuropathic hyperalgesia and Wallerian degeneration due to partial nerve injury was confirmed in an animal model (Liu et al., Pain, 2000, 86: 25-32) in which macrophages were depleted following sciatic nerve ligation. In this study, treatment of nerve-injured rats with liposome-encapsulated Cl$_2$MDP (dichloromethylene diphosphonate), which is reported to effectively reduce the number of macrophages at the site of nerve transaction, alleviated thermal hyperalgesia and reduced degeneration of both myelinated and unmyelinated axons. In addition, in many instances neuropathic pain is associated with nerve inflammation (neuritis) in the absence of nerve injury. Based on an animal model of neuritis (Tal M., Curr. Rev. Pain 1999, 3(6):440-446), it has been suggested that there is a role for some cytokines in nociception and hyperalgesia by evoking peripheral sensitization, in which trauma and classical tissue inflammation are not seen. Thus, macrophage depletion by administration of a cFMS inhibitor could have clinical potential in treatment or prevention of neuropathic pain, either as a result of nerve injury and in the absence of nerve injury.

Several classes of small molecule inhibitors of cFMS said to be useful for treating cancer, autoimmune and inflammatory diseases are known (Huang, H. et al., J. Med. Chem, 2009, 52, 1081-1099; Scott, D. A. et al., Bioorg. & Med. Chem. Lett., 2009, 19, 697-700).

C-KIT receptor, also called CD117, is expressed on the surface of various cell types, including hematopoietic stem cells. This cytokine receptor is associated with certain forms of gastric cancer (Novak, C. et al., 2010 Mini Rev. Med. Chem. 10(7): 624-634). Imatinib and Sunitinib are both inhibitors of cKIT and are generally effective in treatment of patients with GIST. Eventually, however, patients develop resistance to both agents and alternative options remain limited.

There is evidence that cKIT and mast cells play a detrimental role in settings of fibrosis. For example, mast cells are concentrated in the lesional small-airway sub-epithelium in obliterative bronchiolitis (Fuehrer, N. et al., 2009, Archives Pathology Laboratory Medicine 133(9): 1420-1425). In addition, there is evidence that cKIT positive cells are involved in the pathogenesis of ureteropelvic junction obstruction (Ozel, S. et al., 2009, Journal Pediatric Urology, August 27$^{th}$).

Pulmonary arterial hypertension (PAH) involves the increase of blood pressure in the pulmonary artery and there is evidence that dysfunctional endothelial progenitors over-expressing cKIT contribute to the pathology of PAH (Toshner, M., et al., 2009, American Journal Critical Care Medicine 180(8): 780-787).

SUMMARY OF THE INVENTION

It has now been found that certain substituted N-(1H-indazol-4-yl)imidazo[1,2-a]pyridine-3-carboxamide compounds are inhibitors of type III receptor tyrosine kinases such as PDGFR, cFMS and/or cKIT, and may be useful for treating disorders and diseases sensitive to inhibition of these kinases.

Accordingly, one embodiment of this invention provides a compound of the general Formula I:

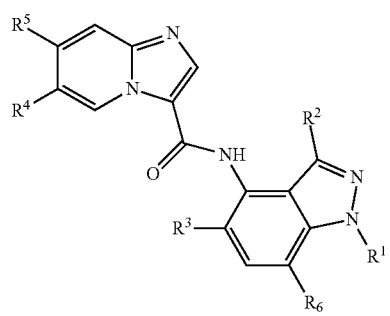

or a pharmaceutically acceptable salt thereof, wherein $R^1$, $R^2$, $R^3$, $R^4$, $R^5$ and $R^6$ are as defined herein.

In another aspect of the invention, there are provided pharmaceutical compositions comprising compounds of Formula I and a carrier, diluent or excipient.

In another aspect of the invention, there is provided a method of inhibiting type III receptor tyrosine kinases such as PGDFR, cFMS and/or cKIT in a mammal comprising administering to said mammal in need thereof a therapeutically effective amount of a compound of Formula I.

In another aspect of the invention, there is provided a method for treating a disease or disorder selected from fibrosis, bone-related diseases, cancer, autoimmune disorders, inflammatory diseases, cardiovascular diseases, pain and burns in a mammal, which comprises administering to said mammal in need thereof a therapeutically effective amount of a compound of Formula I or a pharmaceutically acceptable salt thereof.

In another aspect of the invention, there is provided a method for treating a disease or disorder selected from fibrosis, bone-related diseases, cancer, autoimmune disorders, inflammatory diseases, cardiovascular diseases and pain in a mammal, which comprises administering to said mammal in need thereof a therapeutically effective amount of a compound of Formula I or a pharmaceutically acceptable salt thereof.

In another aspect of the invention, there is provided a use of a compound of Formula I in the manufacture of a medicament for the treatment of a disease or disorder selected from fibrosis, bone-related diseases, cancer, autoimmune disorders, inflammatory diseases, cardiovascular diseases, pain and burns in a mammal, which comprises administering to said mammal in need thereof a therapeutically effective amount of a compound of Formula I or a pharmaceutically acceptable salt thereof.

In another aspect of the invention, there is provided a use of a compound of Formula I in the manufacture of a medicament for the treatment of a disease or disorder selected from fibrosis, bone-related diseases, cancer, autoimmune disorders, inflammatory diseases, cardiovascular diseases and pain in a mammal, which comprises administering to said mammal in need thereof a therapeutically effective amount of a compound of Formula I or a pharmaceutically acceptable salt thereof.

In another aspect of the invention, there is provided a use of a compound of Formula I in the treatment of a disease or disorder selected from fibrosis, bone-related diseases, cancer, autoimmune disorders, inflammatory diseases, cardiovascular diseases and pain in a mammal.

In another aspect of the invention, there is provided a compound of Formula I for use in the treatment of a disease or disorder selected from fibrosis, bone-related diseases, cancer, autoimmune disorders, inflammatory diseases, cardiovascular diseases, pain and burns in a mammal.

In another aspect of the invention, there is provided a compound of Formula I for use in the treatment of a disease or disorder selected from fibrosis, bone-related diseases, cancer, autoimmune disorders, inflammatory diseases, cardiovascular diseases and pain in a mammal.

Another aspect provides intermediates for preparing compounds of Formula I. In one embodiment, certain compounds of Formula I may be used as intermediates for the preparation of other compounds of Formula I.

Another aspect includes processes for preparing, methods of separation, and methods of purification of the compounds described herein.

DETAILED DESCRIPTION OF THE INVENTION

Accordingly to one embodiment, this invention provides a compound of the general Formula I:

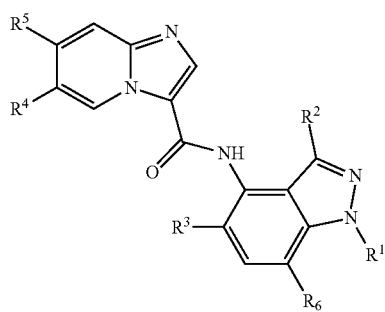

I or a pharmaceutically acceptable salt thereof, wherein:
$R^1$ is $hetAr^1(CH_2)_m$—, $hetAr^2CH_2$—, $hetAr^3CH_2$—, (3-6C cycloalkyl)-$CH_2$—, $hetCyc^1CH_2$—, $Ar^1(CH_2)_n$— or (N-1-3C alkyl)pyridinonyl-$CH_2$—;
$hetAr^1$ is a 6-membered heteroaryl having 1-2 ring N atoms and optionally substituted with one or more substituents independently selected from (1-6C)alkyl, (1-4C)alkoxy, halogen, $CF_3$, or (3-6C)cycloalkyl;
m is 0, 1 or 2;
$hetAr^2$ is a 5-membered heteroaryl ring having 2-3 ring heteroatoms independently selected from N and S where at least one of said heteroatoms is N, wherein said ring is optionally substituted with one or more substituents independently selected from (1-6C)alkyl;
$hetAr^3$ is a bicyclic 5,6-fused heteroaryl ring having two ring nitrogen atoms;
$hetCyc^1$ is a 6-membered saturated heterocyclic ring having 1-2 ring heteroatoms independently selected from N and O and optionally substituted with —C(═O)(1-6C alkyl) or —C(═O)O(1-6C alkyl);
$Ar^1$ is phenyl optionally substituted with one or more substituents independently selected from halogen, (1-6C) alkyl, CN, $CF_3$, OH, (1-6C)alkoxy, —C(═O)OH, —C(═O)O(1-6C alkyl), —C(═O)$NR^aR^b$ or benzyloxy;
$R^a$ and $R^b$ are independently H or (1-6C)alkyl;
n is 0, 1 or 2;
$R^2$ is H, F, Cl or $CH_3$;
$R^3$ is H, F or Cl;
$R^4$ is H, CN, F, Cl, Br, —OMe, —$OCF_3$, —$CF_3$, —CH(OH)$CH_2$OH or —C(═O)$NH_2$;
$R^5$ is selected from:
H,
halogen,
CN,
OH,
$hetAr^4$,
$hetAr^5$,
$hetCyc^2$,
$hetCyc^3$(1-4Calkyl)-,
$hetCyc^4$(1-4C)alkoxy,
$hetCyc^5$ (1-4C)alkoxy,
(1-3C alkoxy)(1-4C)alkoxy,
hydroxy(1-6C)alkoxy,
dihydroxy(2-6C)alkoxy,
(1-6C)alkoxy,
[hydroxy(2-4C)alkyl)amino]-(1-4C)alkyl,
[(1-4C alkoxy)(1-4C alkyl)amino](1-4C)alkyl,
[di(1-4C alkyl)amino](1-4C)alkyl,
(1-4C alkyl)C(═O)—,
hydroxy(1-6C)alkyl,
dihydroxy(2-6C)alkyl,
[di(1-3C alkyl)amino](1-4C)alkoxy,
N-(1-3C alkyl)pyridinone,
$hetAr^6$,
$hetCyc^6$C(═O)—,
($hetCyc^7$)-O—,
$hetCyc^8$(1-4C)alkoxy,
difluoroamino(1-4C)alkoxy,
[(1-4C alkoxy)carbonylamide]difluoro(1-4C)alkoxy,
(1-4C alkyl)C(═O)NH(2-4C)alkylthio-,
(1-4Calkyl)OC(═O)—, and
$R^cR^dNC$(═O)—;
$hetAr^4$ is a 5-membered heteroaryl ring having 1-3 ring heteroatoms independently selected from N, O and S, wherein said ring is optionally substituted with one or more substituents independently selected from (1-6C)alkyl and [di(1-3C alkyl)amino]$CH_2$—;
$hetAr^5$ is a 6-membered heteroaryl ring having 1-2 ring N atoms and optionally substituted with one or more substituents independently selected from (1-6C)alkyl;
$hetAr^6$ is a 9-membered partially unsaturated bicyclic heterocyclic ring having 3 ring N atoms and optionally substituted with one or more substituents independently selected from (1-6C)alkyl;

hetCyc² is a 5-7 membered saturated or partially unsaturated heterocyclic ring having 1-2 ring heteroatoms selected from N and O, wherein said ring is optionally substituted with one or more substituents independently selected from (1-6C)alkyl, hydroxy(1-6C)alkyl, OH and oxo, provided said oxo is on a carbon atom;

hetCyc³ is a 4-6 membered heterocyclic ring having 1-2 ring N atoms and optionally substituted with one or more substituents independently selected from (1-6C)alkyl, (1-6C)alkoxy and halogen;

hetCyc⁴ is a 4-7 membered heterocycle having 1-2 ring heteroatoms independently selected from N, O and S, wherein one of said ring nitrogen atoms is optionally oxidized to N(O) and wherein said S ring atom is optionally oxidized to SO or $SO_2$, wherein hetCyc⁴ is optionally substituted with one or more substituents independently selected from halogen, OH, (1-6C)alkyl, (1-4C alkoxy)(1-6C)alkyl, (1-4C)alkyl-OC(=O)— and (1-6C)alkoxy;

hetCyc⁵ is a spiro heterocycle having 2 ring heteroatoms independently selected from N and O, wherein hetCyc⁵ is optionally substituted with a group selected from (1-6C)alkyl;

hetCyc⁶ is a 6 membered heterocyclic ring having 1-2 ring N atoms and optionally substituted with one or more substituents independently selected from (1-6C)alkyl;

hetCyc⁷ is a 4-6 membered heterocyclic ring having one or two ring N atoms and optionally substituted with one or more substituents independently selected from (1-6C)alkyl and OH;

hetCyc⁸ is a bridged 8-membered heterocyclic ring having 2 ring atoms selected from N and O wherein at least one of said heteroatoms is N, wherein said ring is optionally substituted with (1-6C)alkyl;

$R^c$ is H or (1-4C)alkyl;

$R^d$ is (1-4C)alkyl, hetCyc¹⁰-, amino(1-4C)alkyl, or [di(1-4C alkyl)amino](1-4C) alkyl;

hetCyc¹⁰ is a 5 membered heterocycle having a ring N atom and optionally substituted with one or more substituents independently selected from (1-6C)alkyl; and $R^6$ is H or Cl.

Compounds of Formula I are inhibitors of type III receptor tyrosine kinases such as PDGFR, cFMS and cKIT, and are useful for treating diseases and disorders selected from fibrosis, bone-related diseases, cancer, autoimmune disorders, inflammatory diseases, cardiovascular diseases and pain in a mammal in need thereof.

In one embodiment, $R^1$ is hetAr¹$(CH_2)_m$—, hetAr²$CH_2$— or hetAr³$CH_2$—.

In one embodiment, $R^1$ is hetAr¹$(CH_2)_m$—, wherein hetAr¹ is a 6-membered heteroaryl having 1-2 ring N atoms and optionally substituted with one or more substituents independently selected from (1-6C)alkyl, (1-4C)alkoxy, halogen, $CF_3$, or (3-6C)cycloalkyl. In one embodiment, hetAr¹ is pyridyl or pyrimidyl. In one embodiment, hetAr¹ is pyridyl.

Examples of (1-6C)alkyl substituents for hetAr¹ include (1-4C)alkyl substituents such as methyl, ethyl, propyl, isopropyl, butyl, isobutyl, sec-butyl and tert-butyl.

Particular examples of (1-4C)alkoxy substituents for hetAr¹ include methoxy and ethoxy.

A particular example of a halogen substituent for hetAr¹ is fluoro.

Particular examples of (3-6C)cycloalkyl substituents for hetAr¹ include cyclopropyl, cyclobutyl, cyclopentyl and cyclohexyl.

In certain embodiments, $R^1$ is hetAr¹$(CH_2)_m$—, where hetAr¹ is a 6 membered heteroaryl ring having 1-2 ring nitrogen atoms and optionally substituted with one or more substituents independently selected from methyl, ethyl, propyl, isopropyl, isobutyl, sec-butyl, tert-butyl, methoxy, ethoxy, fluoro, $CF_3$, cyclopropyl, cyclobutyl, or cyclopentyl. In certain embodiments, hetAr¹ is optionally substituted with one or two of said substituents. In certain embodiments, hetAr¹ is pyridyl optionally substituted with one or more substituents independently selected from methyl, ethyl, propyl, isopropyl, isobutyl, sec-butyl, tert-butyl, methoxy, ethoxy, fluoro, $CF_3$, cyclopropyl, cyclobutyl, or cyclopentyl. In certain embodiments, m is 0. In certain embodiments, m is 1. In certain embodiments, m is 2.

Particular values for $R^1$ when represented by hetAr¹$(CH_2)_m$— include the structures:

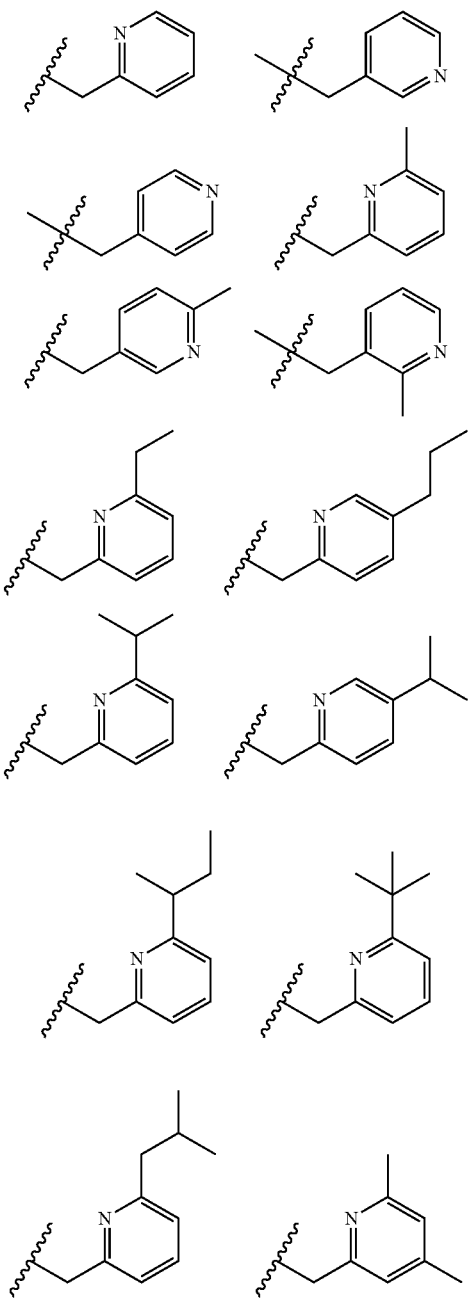

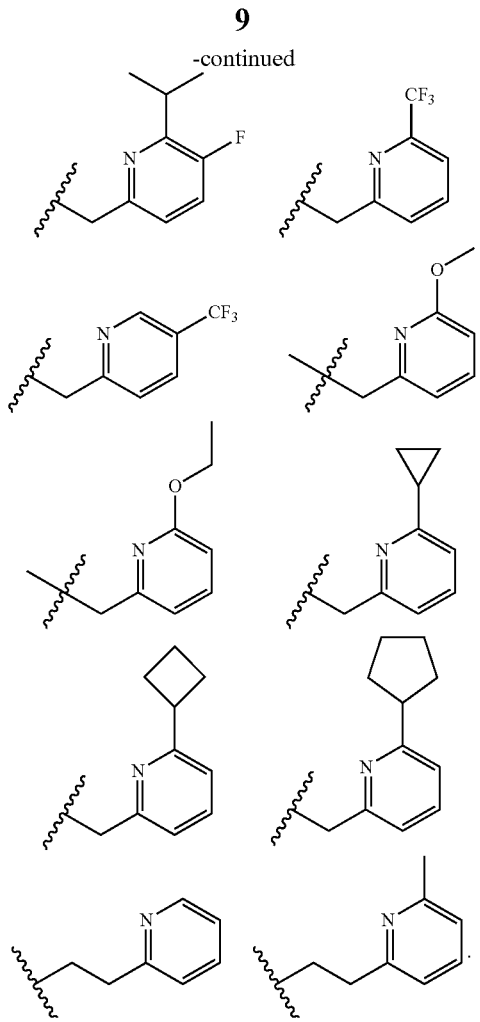

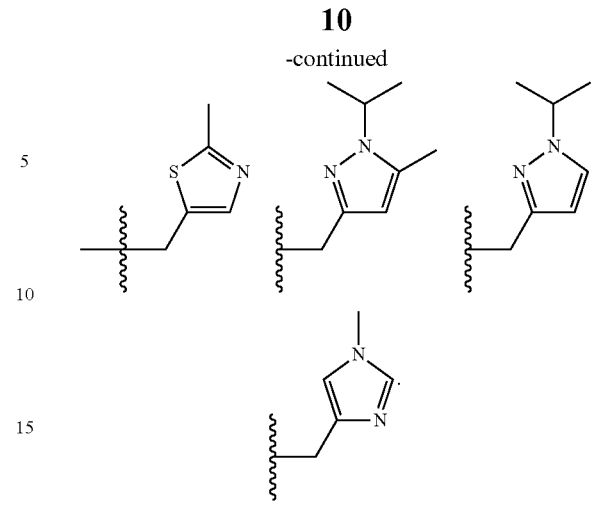

In one embodiment, R¹ is hetAr²CH₂—, where hetAr² is a 5-membered heteroaryl ring having 2-3 ring heteroatoms independently selected from N and S where at least one of said heteroatoms is N, wherein said ring is optionally substituted with one or more substituents independently selected from (1-6C)alkyl. In one embodiment, hetAr² is a 5-membered heteroaryl ring having 2 ring heteroatoms independently selected from N and S where at least one of said heteroatoms is N, wherein said ring is optionally substituted with one or more substituents independently selected from (1-6C)alkyl. Particular examples of hetAr² rings include thiazolyl, pyrazolyl, and imidazolyl. Examples of (1-6C)alkyl substituents for hetAr² include (1-4C)alkyl groups, for example methyl, ethyl, propyl and isopropyl. In one embodiment, hetAr² is optionally substituted with one or two of said substituents.

Particular examples of R¹ when represented by hetAr²CH₂ include the structures:

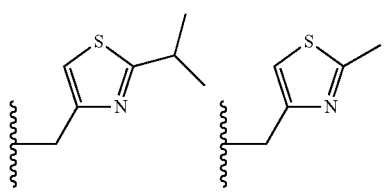

In one embodiment, R¹ is hetAr³CH₂—, where hetAr³ is a bicyclic 5,6-fused heteroaryl ring having two ring nitrogen atoms. A particular example of hetAr³CH₂— is a group having the structure:

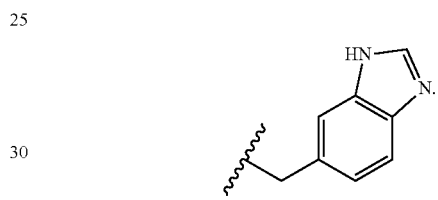

In one embodiment, R¹ is (3-6C cycloalkyl)-CH₂—. Particular example includes cyclopropylmethyl and cyclohexylmethyl having the structures:

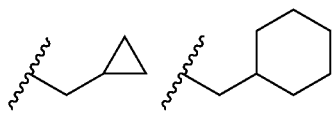

respectively.

In one embodiment, R¹ is (3-6C cycloalkyl)-CH₂—, hetCyc¹CH₂—, Ar¹(CH₂)ₙ— or (N-1-3C alkyl)pyridinonyl-CH₂—.

In one embodiment, R¹ is hetCyc¹CH₂—, where hetCyc¹ is a 6-membered saturated heterocyclic ring having 1-2 ring heteroatoms independently selected from N and O and optionally substituted with —C(=O)(1-6C alkyl) or —C(=O)O(1-6C alkyl). Examples of hetCyc¹ include tetrahydropyranyl, piperidinyl and morpholinyl rings. In one embodiment, hetCyc¹ is optionally substituted with —C(=O)CH₃ or —C(=O)OC(CH₃)₃.

Particular examples of R¹ when represented by hetCyc¹CH₂— include the structures:

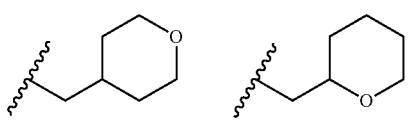

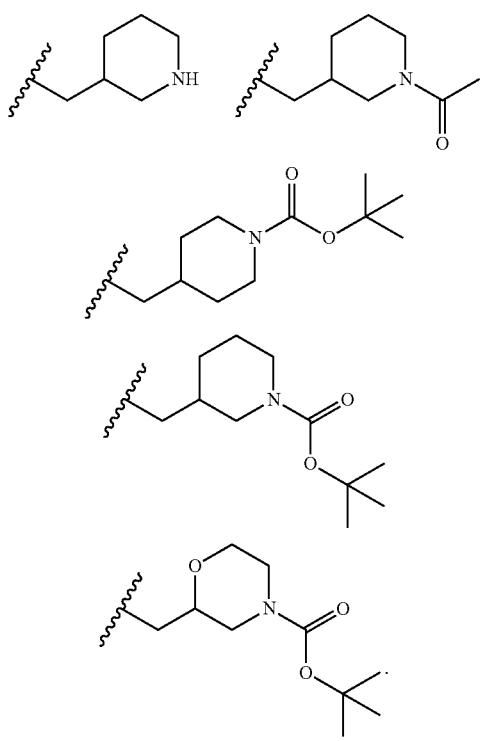

In one embodiment, R$^1$ is Ar$^1$(CH$_2$)$_n$—, where Ar$^1$ is phenyl optionally substituted with one or more substituents independently selected from halogen, (1-6C)alkyl, CN, CF$_3$, OH, (1-6C)alkoxy, —C(=O)OH, —C(=O)O(1-6C alkyl), —C(=O)NR$^a$R$^b$ or benzyloxy.

In one embodiment, R$^1$ is Ar$^1$(CH$_2$)$_n$—, where Ar$^1$ is phenyl optionally substituted with one or more substituents independently selected from F, Cl, methyl, CN, CF$_3$, OH, methoxy, —C(=O)OH, —C(=O)OCH$_3$, —C(=O)NH$_2$, —C(=O)NHCH$_3$, —C(=O)N(CH$_3$)$_2$ or benzyloxy.

In one embodiment, n is 0. In one embodiment, n is 1. In one embodiment, n is 2.

Particular examples of R$^1$ when represented by Ar$^1$(CH$_2$)$_n$— include the structures:

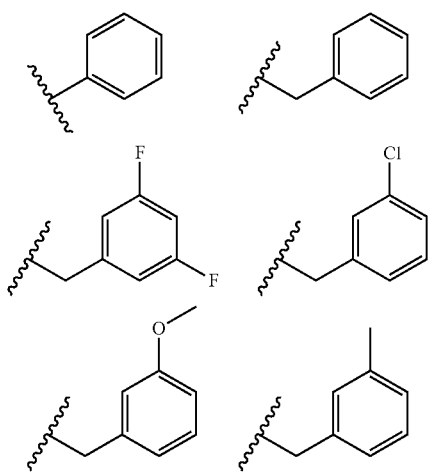

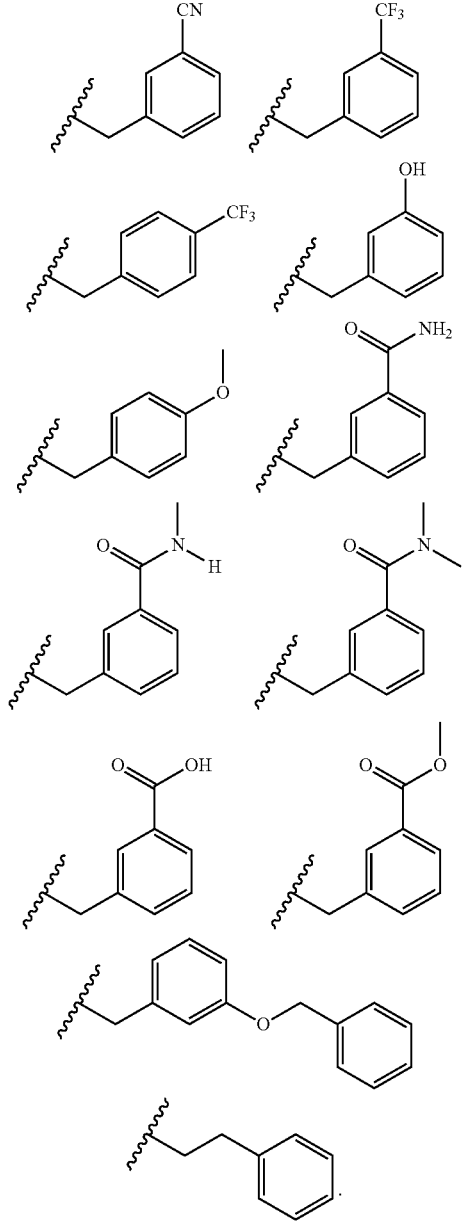

In one embodiment, R$^1$ is N-(1-3C alkyl)pyridinonyl-CH$_2$—, that is, a pyridinonyl-CH$_2$— substituent wherein the nitrogen ring atom of the pyridinonyl is substituted with (1-3C)alkyl. A particular example of R$^1$ is the structure:

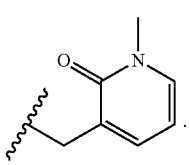

In one embodiment, R$^5$ is H.
In one embodiment, R$^5$ is halogen. In one embodiment, R$^5$ is F or Br.
In one embodiment, R$^5$ is CN.
In one embodiment, R$^5$ is OH.

In one embodiment, R⁵ is hetAr⁴, where hetAr⁴ is a 5-membered heteroaryl ring having 1-3 ring heteroatoms independently selected from N, O and S, wherein said ring is optionally substituted with one or more substituents independently selected from (1-6C)alkyl and [di(1-3C alkyl) amino]CH₂—. In one embodiment, at least one of said ring heteroatoms is nitrogen. In embodiments wherein at least one of said ring heteroatoms is nitrogen, hetAr⁴ can be a nitrogen radical (that is, hetAr⁴ is linked to the imidazopyridine ring of Formula I through a ring nitrogen atom of hetAr⁴) or a carbon radical (that is, hetAr⁴ is linked to the imidazopyridine ring of Formula I through a ring carbon atom of hetAr⁴). Examples of hetAr⁴ include pyrazolyl, triazolyl, thiadiazolyl, oxadiazolyl and furanyl rings optionally substituted with one or more substituents independently selected from (1-6C)alkyl and [di(1-3C alkyl)amino]CH₂—. In certain embodiments hetAr⁴ is optionally substituted with one or two of said substituents. In certain embodiments hetAr⁴ is optionally substituted with one or two substituents independently selected from methyl and Me₂NCH₂—. Particular examples of R⁵ when represented by hetAr⁴ include the structures:

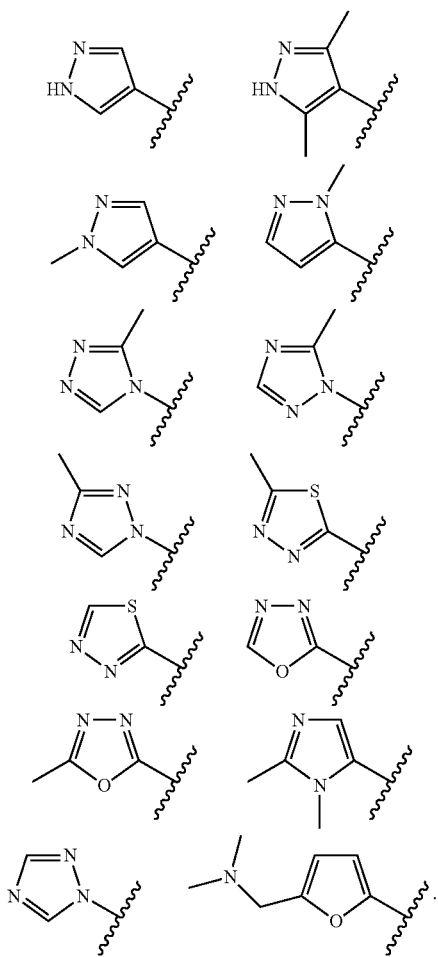

In one embodiment, R⁵ is hetAr⁴ where hetAr⁴ is a 5-membered heteroaryl ring having 2 ring nitrogen atoms, wherein said ring is optionally substituted with one or more substituents independently selected from (1-6C)alkyl, for example one or more substituents independently selected from (1-4C)alkyl, such as methyl. In one embodiment, hetAr⁴ is selected from:

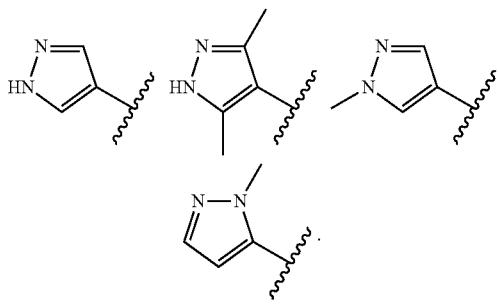

In one embodiment, R⁵ is hetAr⁵, where hetAr⁵ is a 6-membered heteroaryl ring having 1-2 ring N atoms and optionally substituted with one or more substituents independently selected from (1-6C)alkyl. Examples of hetAr⁵ include pyrimidyl and pyridyl rings optionally substituted with a substituent selected from (1-6C alkyl), for example one or more substituents independently selected from (1-4C) alkyl, for example methyl or ethyl. Particular examples of R⁵ when represented by hetAr⁵ include the structures:

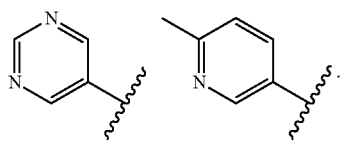

In one embodiment, R⁵ is hetAr⁵, where hetAr⁵ is pyridyl optionally substituted with one or more substituents independently selected from (1-6C)alkyl, for example one or more substituents independently selected from (1-4C)alkyl, such as methyl or ethyl. In one embodiment, hetAr⁵ is pyridyl optionally substituted with methyl. In one embodiment, hetAr⁵ is:

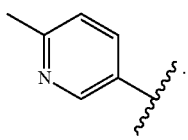 [SMILES: *c1ccc(C)nc1]

In one embodiment, R⁵ is hetCyc², where hetCyc² is a 5-7 membered saturated or partially unsaturated heterocyclic ring having 1-2 ring heteroatoms selected from N and O, wherein said ring is optionally substituted with one or more substituents independently selected from (1-6C)alkyl, hydroxy(1-4C)alkyl, OH and oxo, provided said oxo is on a carbon atom. In one embodiment, at least one of said ring heteroatoms of hetCyc² is N. In one embodiment when hetCyc² includes at least one N ring atom, hetCyc² is a nitrogen radical, that is, hetCyc² is linked to the imidazopyridine ring of Formula I through a ring nitrogen atom of hetCyc². In one embodiment when hetCyc² includes at least one N ring atom, hetCyc² is a carbon radical, that is, hetCyc² is linked to the imidazopyridine ring of Formula I through a ring carbon atom of hetCyc². Examples of hetCyc² include pyrrolidinyl, piperidinyl, piperazinyl, morpholinyl, tetrahydropyridinyl and diazepanyl rings optionally substituted with one or more substituents independently selected from (1-6C)alkyl, hydroxy(1-4C)alkyl, OH and oxo. In certain embodiments, hetCyc² is substituted with one or more substituents independently selected from methyl, ethyl, OH, HOCH₂CH₂— and oxo. In one embodiment, hetCyc² is optionally substituted with one or two of said substituents.

In one embodiment, examples of R⁵ when represented by hetCyc² include the structures:

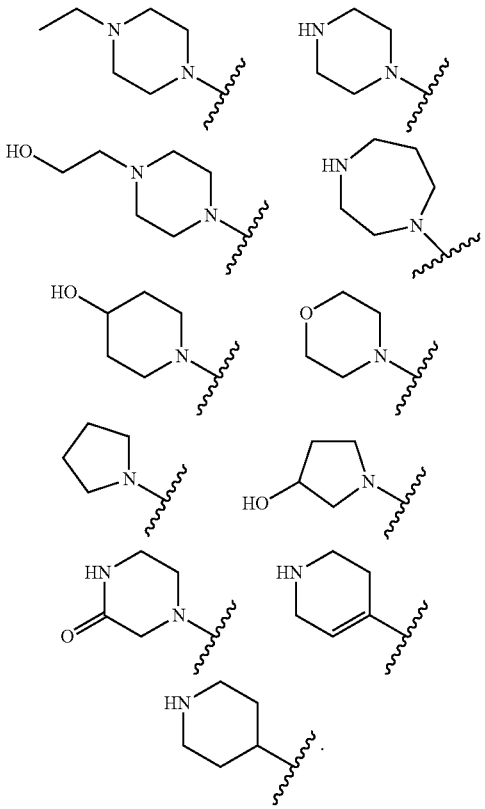

In one embodiment, R⁵ is hetCyc², where hetCyc² is a 5-6 membered saturated or partially unsaturated heterocycle having 1-2 ring nitrogen atoms. In one embodiment, hetCyc² is selected from the structures:

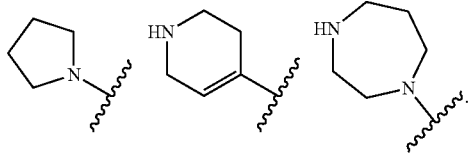 [SMILES: *N1CCCC1 ; *C1=CCNCC1 ; *N1CCCNCC1]

In one embodiment, R⁵ is hetCyc³(1-4Calkyl)-, where hetCyc³ is a 4-6 membered heterocyclic ring having 1-2 N atoms and optionally substituted with one or more substituents independently selected from (1-6C)alkyl, (1-6C)alkoxy and halogen. Examples of hetCyc³ include azetidinyl, pyrrolidinyl, piperidinyl, piperazinyl and morpholinyl rings optionally substituted with one or more substituents independently selected from (1-6C)alkyl, (1-6C)alkoxy and halogen. In one embodiment, hetCyc³ is optionally substituted with one or more substituents independently selected from (1-4C)alkyl, (1-6C)alkoxy and halogen. In certain embodiments hetCyc³ is substituted with one or more substituents independently selected from methyl, ethyl, fluoro and methoxy. In certain embodiments, hetCyc³ is substituted with one or two of said substituents. In certain embodiments, R⁵ is hetCyc³(1-3C)alkyl. Particular examples of R⁵ when represented by hetCyc³(1-4Calkyl)- include the structures:

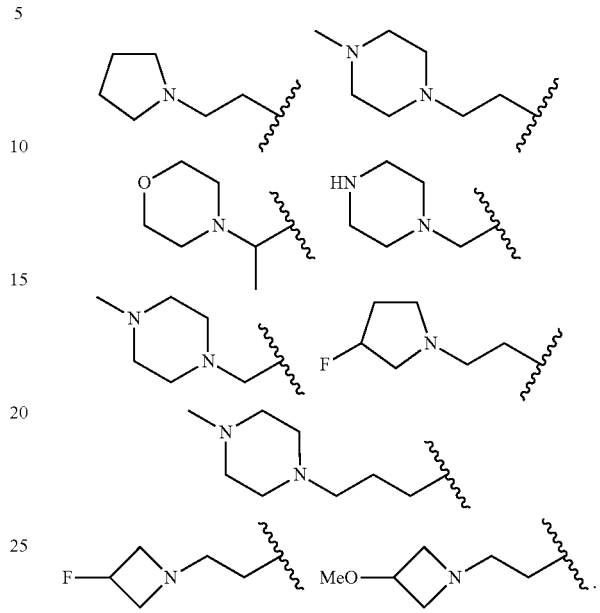

In one embodiment, R⁵ is hetCyc³(1-4Calkyl)- where hetCyc³ is a 5-6 membered heterocyclic ring having 1-2 ring heteroatoms independently selected from N and O, wherein hetCyc³ is optionally substituted with a substituent selected from (1-6C)alkyl. In one embodiment, hetCyc³(1-4Calkyl)- is selected from the structures:

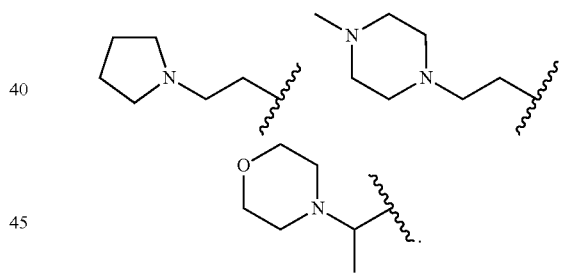

In one embodiment, R⁵ is hetCyc⁴(1-4C)alkoxy, that is, a (1-4C)alkoxy group as defined herein wherein one of the carbon atoms is substituted with hetCyc⁴, where hetCyc⁴ is a 4-7 membered heterocycle having 1-2 ring heteroatoms independently selected from N, O and S, wherein one of said ring nitrogen atoms is optionally oxidized to N(O) and wherein said S ring atom is optionally oxidized to SO or SO₂, wherein hetCyc⁴ is optionally substituted with one or more substituents independently selected from halogen, OH, (1-6C)alkyl, (1-4C alkoxy)(1-6C)alkyl, (1-4C)alkyl-OC(=O)— and (1-6C)alkoxy. Examples of hetCyc⁴ include azetidinyl, pyrrolidinyl, piperidinyl, piperazinyl, morpholinyl, diazepanyl, 1-methyl-piperazinyl-1-oxide, and thiomorpholinyl-1,1-dioxide, each of which is optionally substituted with one or more one or more substituents independently selected from halogen, OH, (1-6C)alkyl, (1-4C alkoxy)(1-6C)alkyl, (1-4C)alkyl-OC(=O)— and (1-6C)alkoxy. In certain embodiments, hetCyc⁴ is optionally substituted with one or more substituents independently selected form methyl, ethyl, isopropyl, fluoro, methoxy, $CH_2OCH_2CH_2$—, OH and $(CH_3)_3COC(=O)$—. In certain embodiments hetCyc⁴ is optionally substituted with one to three of said substituents. In certain embodiments, $R^5$ is hetCyc⁴(1-2C)alkoxy.

In one embodiment, examples of $R^5$ when represented by hetCyc⁴(1-4C)alkoxy include the structures:

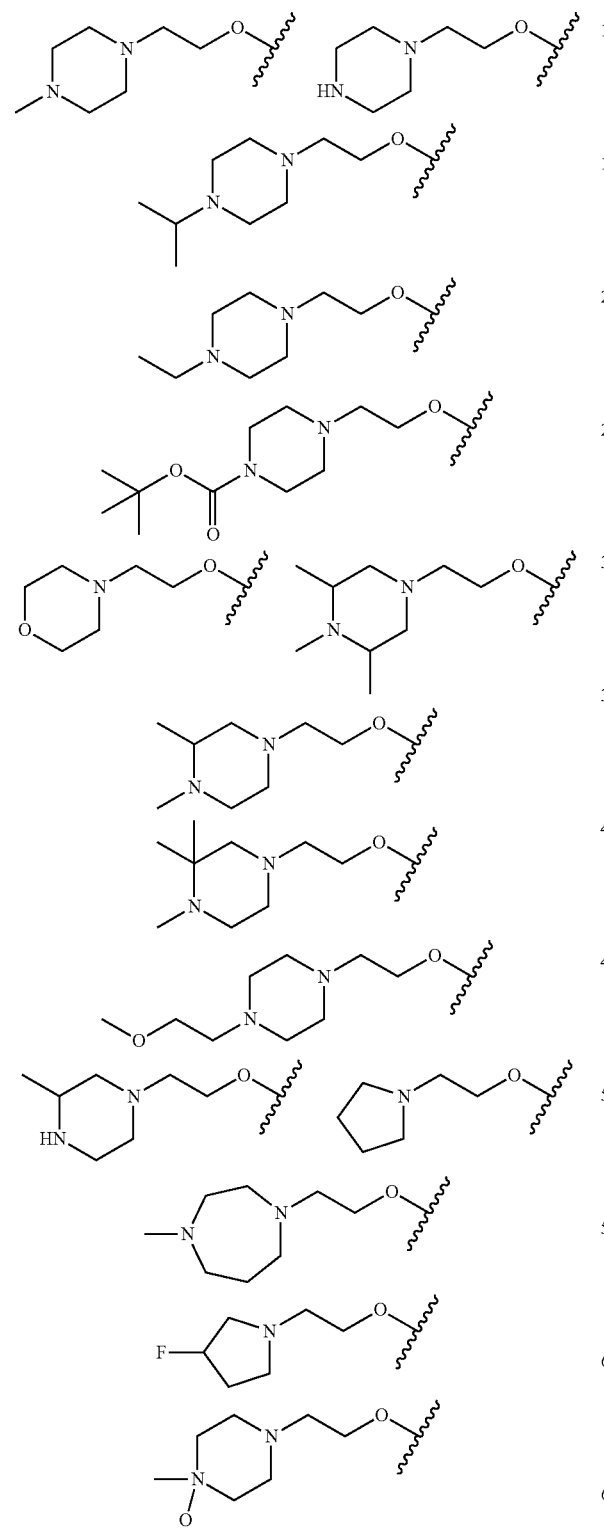

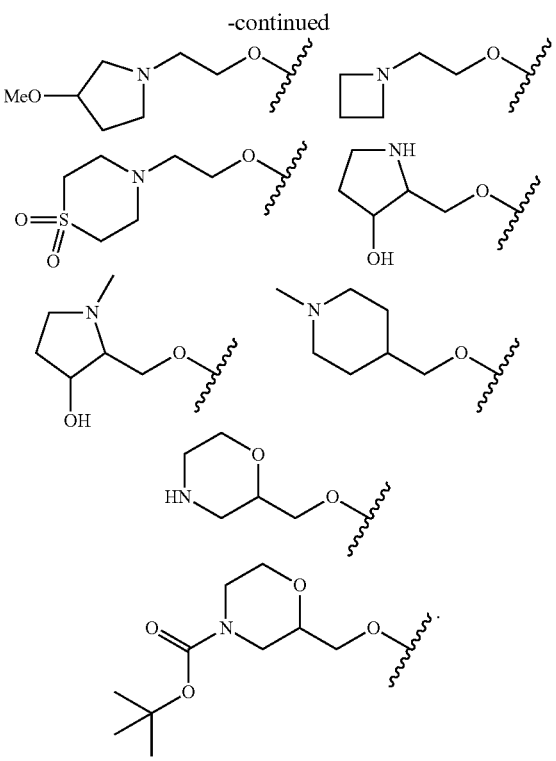

In one embodiment, $R^5$ is hetCyc⁴(1-4C)alkoxy, that is, a (1-4C)alkoxy group as defined herein wherein one of the carbon atoms is substituted with hetCyc⁴, where hetCyc⁴ is a 5-6 membered heterocycle having 1-2 ring heteroatoms independently selected form N and O, wherein said ring is optionally substituted with one or more substituents independently selected from (1-6C)alkyl, (1-4C alkoxy)(1-6C) alkyl and (1-4C)alkyl-OC(=O)—. In one embodiment, hetCyc⁴ is optionally substituted with one to three substituents independently selected from methyl, ethyl, isopropyl, $CH_3OCH_2CH_2$— and $(CH_3)_3COC(=O)$—. In one embodiment, examples of $R^5$ when represented by hetCyc⁴(1-4C) alkoxy include the structures:

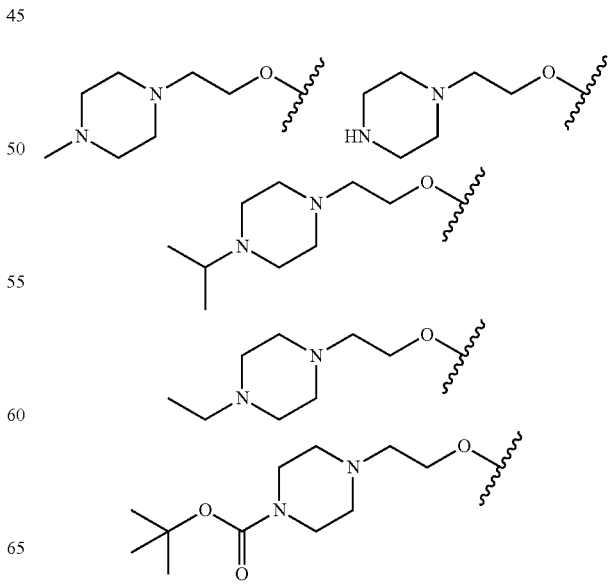

-continued

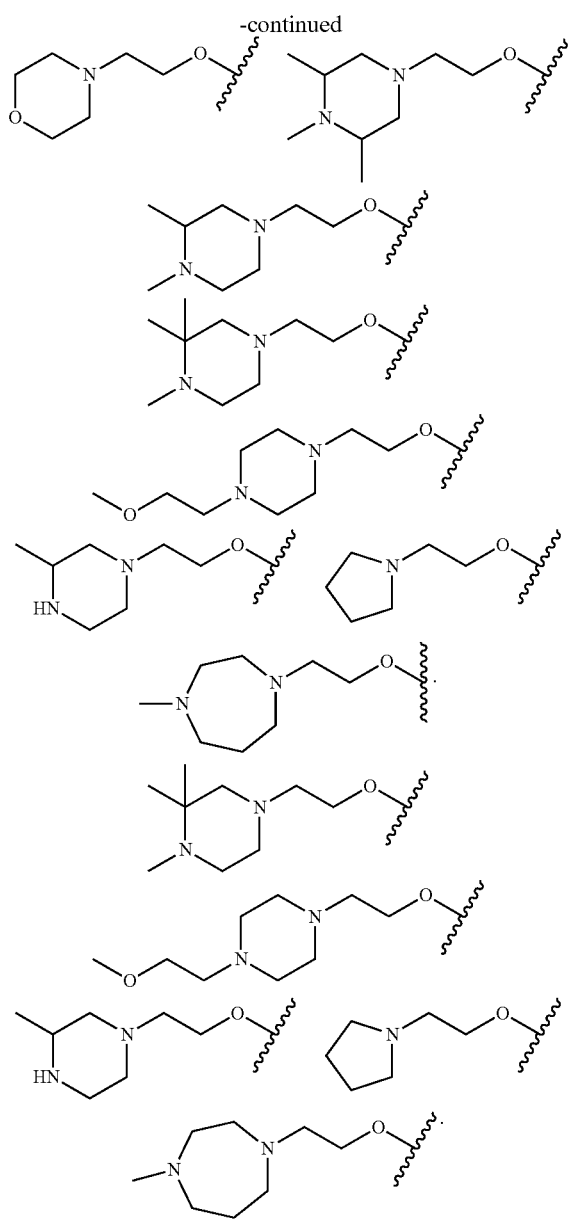

In one embodiment, R⁵ is hetCyc⁵(1-4C)alkoxy, that is, a (1-4C)alkoxy group as defined herein wherein one of the carbon atoms is substituted with hetCyc⁵, where hetCyc⁵ is a spiro heterocycle having 2 ring heteroatoms independently selected from N and O and is optionally substituted with a substituent selected from (1-6C)alkyl. As used herein, the term "spiro heterocycle" refers to a system comprising two rings, one of which being a nitrogen containing heterocycle, said rings having one carbon atom in common, such as, for instance, a 2-oxa-6-azaspiro[3.3]heptane or a 2,6-diazaspiro[3.3]heptane ring system having the structure:

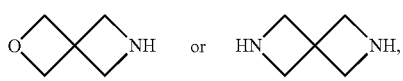

respectively. In one embodiment, hetCyc⁵ is optionally substituted with a group selected from (1-6C)alkyl, for example methyl.

In one embodiment, examples of R⁵ when represented by hetCyc⁵(1-4C)alkoxy include the structures:

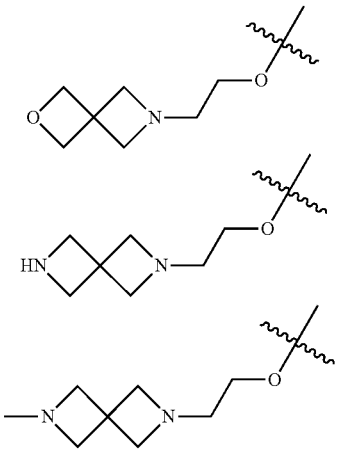

In one embodiment, R⁵ is (1-3C alkoxy)(1-4C)alkoxy, that is, a (1-4C)alkoxy group as defined herein wherein one of the carbon atoms is substituted with a (1-3C alkoxy) substituent such as methoxy. A particular example of R⁵ when represented by (1-3C alkoxy)(1-4C)alkoxy includes a methoxyethoxy substituent having the structure:

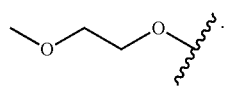 [SMILES: *OCCOC]

In one embodiment, R⁵ is hydroxy(1-6C)alkoxy, that is, a (1-6C)alkoxy group wherein one of the carbon atoms is substituted with hydroxy. In one embodiment, R⁵ is hydroxy(1-4C)alkoxy. A particular example of R⁵ when represented by hydroxy(1-6C)alkoxy includes the structure:

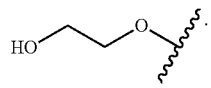

In one embodiment, R⁵ is dihydroxy(2-6C)alkoxy, that is, a (2-6C)alkoxy group wherein two of the carbon atoms are each substituted with a hydroxy group. In one embodiment, R⁵ is dihydroxy(2-4C)alkoxy. A particular example of R⁵ when represented by dihydroxy(2-6C)alkoxy is the structure:

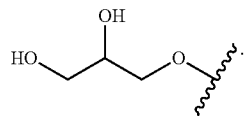

In one embodiment, R⁵ is (1-6C)alkoxy. In one embodiment, R⁵ is (1-4C)alkoxy. In one embodiment, R⁵ is methoxy or ethoxy.

In one embodiment, R⁵ is [hydroxy(2-4C)alkyl)amino](1-4C)alkyl, that is, a (1-4C)alkyl group wherein one of the carbon atoms is substituted with a [hydroxy(2-4C alkyl)]

amino substituent, for example a HOCH$_2$CH$_2$NH— substituent. A particular example of R$^5$ is the structure:

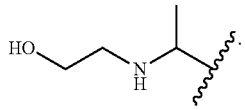

In one embodiment, R$^5$ is [(1-4C alkoxy)(1-4C alkyl)amino](1-4C)alkyl, that is, a (1-4C)alkyl group wherein one of the carbon atoms is substituted with a [(1-4C alkoxy)(1-4C alkyl)amino substituent, for example a methoxy(1-4C alkyl)NH— substituent. A particular example of R$^5$ when represented by [(1-4C alkoxy)(1-4C alkyl)]amino(1-4C)alkyl is the structure:

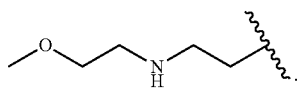 [SMILES: *CCNCCOC]

In one embodiment, R$^5$ is [di(1-4C alkyl)amino](1-4C)alkyl, that is, a (1-4C)alkyl group wherein one of the carbon atoms is substituted with a di(1-4C alkyl)amino. In one embodiment, R$^5$ is dimethylamino(1-4C alkyl). Particular examples when R$^5$ is [di(1-4C alkyl)amino](1-4C)alkyl include the structures:

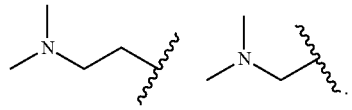

In one embodiment, R$^5$ is (1-4C alkyl)C(=O)—. A particular example of R$^5$ includes the structure:

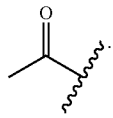

In one embodiment, R$^5$ is hydroxy(1-6C)alkyl, that is, a (1-6C)alkyl group as defined herein wherein one of the carbon atoms is substituted with hydroxy. In one embodiment, R$^5$ is hydroxy(1-4C)alkyl. Particular examples of R$^5$ include the structures:

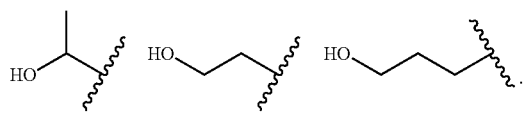

In one embodiment, R$^5$ is dihydroxy(2-6C)alkyl, that is, a (1-6C)alkyl group as defined herein wherein two of the carbon atoms are each substituted with a hydroxy group. In one embodiment, R$^5$ is dihydroxy(2-4C)alkyl. A particular example of R$^5$ is the structure:

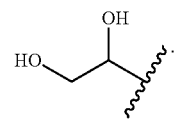

In one embodiment, R$^5$ is [di(1-3C alkyl)amino](1-4C) alkoxy, that is, a (1-4C)alkoxy group wherein one of the carbon atoms is substituted with a di(1-3C alkyl)amino, for example a dimethylamino group. A particular example of R$^5$ when represented by [di(1-3C alkyl)amino](1-4C)alkoxy includes the structure:

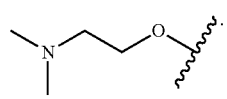 [SMILES: *OCCN(C)C]

In one embodiment, R$^5$ is N-(1-3C alkyl)pyridinone. A particular example includes N-methylpyridinone which can be represented by the structure:

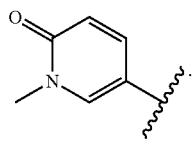

In one embodiment, R$^5$ is hetAr$^6$, where hetAr$^6$ is a 9-membered partially unsaturated bicyclic heterocyclic ring having 3 ring N atoms and optionally substituted with one or more substituents independently selected from (1-6C)alkyl. Examples of hetAr$^6$ include a 5 membered heteroaryl ring fused to a 6-membered saturated heterocyclic ring, wherein one or both of said rings are optionally substituted with a group independently selected from (1-6C alkyl). Particular examples include 5,6,7,8-tetrahydroimidazopyrazine rings optionally substituted with a substituent selected from (1-6C alkyl), for example one or more substituents independently selected from (1-4C)alkyl, for example methyl or ethyl. Particular values for R$^5$ when represented by hetAr$^6$ include the structures:

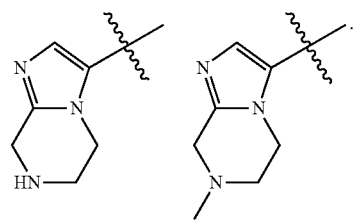 [SMILES: *c1cnc2n1CCNC2 ; *c1cnc2n1CCN(C)C2]

In one embodiment, R$^5$ is hetCyc$^6$C(=O)—, where hetCyc$^6$ is a 6 membered heterocyclic ring having 1-2 ring N atoms and optionally substituted with one or more substituents independently selected from (1-6C)alkyl. Examples of hetCyc$^6$ include piperidinyl and piperazinyl rings optionally substituted with one or more substituents independently selected from (1-6C alkyl), for example (1-4C)alkyl, such as methyl or ethyl. Particular examples of R$^5$ when represented by hetCyc$^6$C(=O)— include the structures:

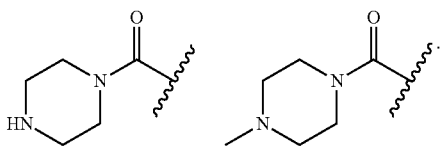

In one embodiment, R⁵ is (hetCyc⁷)-O—, where hetCyc⁷ is a 4-6 membered heterocyclic ring having one or two ring N atoms and optionally substituted with one or more substituents independently selected from (1-6C)alkyl and OH. Examples of hetCyc⁷ include azetidinyl, pyrrolidinyl, piperidinyl and piperazinyl rings optionally substituted with one or more substituents independently selected from (1-6C) alkyl and OH. In certain embodiments hetCyc⁷ is azetidinyl, pyrrolidinyl or piperidinyl optionally substituted with one or more substituents independently selected from methyl and OH. In certain embodiments hetCyc⁷ is substituted with one or two of said substituents. Particular examples of R⁵ when represented by (hetCyc⁷)-O— include the structures:

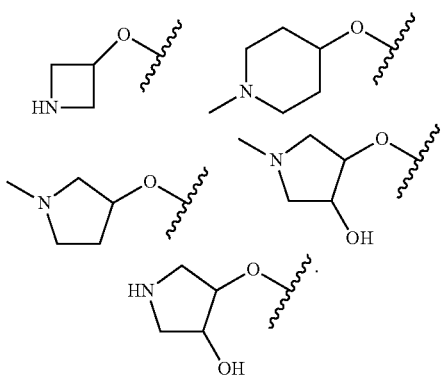

In one embodiment, R⁵ is hetCyc⁸(1-4C)alkoxy, that is, a (1-4C)alkoxy group as defined herein wherein one of the carbon atoms is substituted with hetCyc⁸, where hetCyc⁸ is a bridged 8-membered heterocyclic ring having 2 ring atoms selected from N and O wherein at least one of said heteroatoms is N, wherein said ring is optionally substituted with (1-6C)alkyl. Examples of hetCyc⁸ rings include 3,8-diazabicyclo[3.2.1]octane and 8-oxa-3-azabicyclo[3.2.1]octane rings optionally substituted with (1-6C)alkyl. Particular examples of R⁵ when represented by hetCyc⁸(1-4C)alkoxy include the structures:

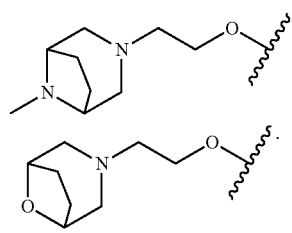

In one embodiment, R⁵ is difluoroamino(1-4C)alkoxy, that is, a (1-4C)alkoxy group as defined herein wherein one of the hydrogen atoms of the alkoxy portion as defined herein is replaced with an amino group and two of the hydrogen atoms of the alkoxy portion as defined herein are each replaced with a fluorine atom. A particular example of R⁵ when represented by difluoroamino(1-4C)alkoxy is the structure:

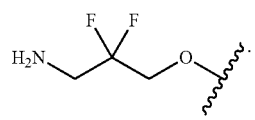

In one embodiment, R⁵ is [(1-4C alkoxy)carbonylamide] difluoro(1-4C)alkoxy, that is, a (1-4C)alkoxy group as defined herein wherein two of the carbon atoms are each substituted with a fluorine atom and one of the carbon atoms is substituted with a (1-4C alkoxy)carbonylamide, for example a (CH₃)₃OC(=O)NH— group. A particular example of R⁵ when represented by [(1-4C alkoxy)carbonylamide]difluoro(1-4C)alkoxy is the structure:

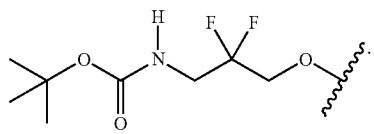 [SMILES: *OCC(F)(F)CNC(=O)OC(C)(C)C]

In one embodiment, R⁵ is (1-4C alkyl)C(=O)NH(2-4C) alkylthio-, that is, a (2-4C)alkylthio group in which the radical is on the sulfur atom, wherein one of the carbon atoms is substituted with a (1-4C alkyl)C(=O)NH— substituent. A particular example of R⁵ when represented by (1-4C alkyl)C(=O)NH(2-4C)alkylthio includes the structure:

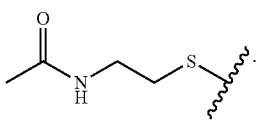 [SMILES: *SCCNC(C)=O]

In one embodiment, R⁵ is (1-4Calkyl)OC(=O)—. A particular example of R⁵ is the structure:

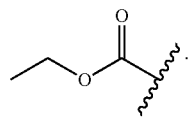

In one embodiment, R⁵ is RᶜRᵈNC(=O)—, where Rᶜ is H or methyl and Rᵈ is (1-4C)alkyl, hetCyc¹⁰-, amino(1-4C) alkyl or [di(1-4C alkyl)amino](1-4C alkyl). In one embodiment, Rᶜ is H. In one embodiment, Rᶜ is methyl.

In one embodiment, R⁵ is RᶜRᵈNC(=O)—, where Rᶜ is H or methyl and Rᵈ is hetCyc¹⁰. Examples of hetCyc¹⁰ groups include pyrrolidinyl rings optionally substituted with (1-6C)alkyl, for example (1-4C)alkyl, such as methyl or ethyl. Particular examples of R⁵ include the structures:

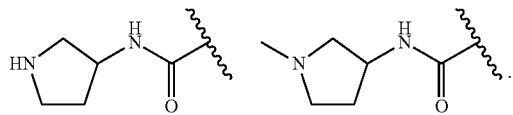

In one embodiment, $R^5$ is $R^cR^dNC(=O)-$, where $R^c$ is H or methyl and $R^d$ is amino(1-4C)alkyl. A particular example of $R^5$ is the structure:

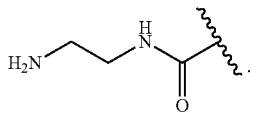

In one embodiment, $R^5$ is $R^cR^dNC(=O)-$, where $R^c$ is H or methyl and $R^d$ is [di(1-4C alkyl)amino](1-4C)alkyl-. In one embodiment $R^d$ is dimethylamino(1-4C alkyl). A particular example of $R^5$ includes the structure:

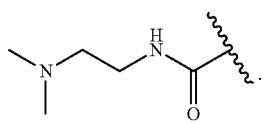 [SMILES: *C(=O)NCCN(C)C]

In one embodiment, $R^5$ is $R^cR^dNC(=O)-$, where $R^c$ is H or methyl and $R^d$ is (1-4C)alkyl. A particular example of $R^5$ includes the structures:

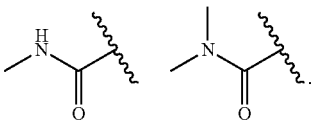

In one embodiment, $R^5$ is selected from H, halogen, CN, OH, hetAr$^4$, hetAr$^5$, hetCyc$^2$, hetCyc$^3$(1-4C alkyl)-, hetCyc$^4$(1-4C)alkoxy, hetCyc$^5$(1-4C)alkoxy, (1-3C alkoxy)(1-4C)alkoxy, hydroxy(1-6C)alkoxy, dihydroxy(2-6C)alkoxy, (1-4C)alkoxy, [hydroxy(2-4C)alkyl)amino]-(1-4C)alkyl, [(1-4C alkoxy)(1-4C alkyl)amino](1-4C)alkyl, [di(1-4C alkyl)amino](1-4C)alkyl, (1-4C alkyl)C(=O)-, hydroxy(1-6C)alkyl, dihydroxy(2-6C)alkyl, [di(1-3C alkyl)amino](1-4C)alkoxy and N-(1-3C alkyl)pyridinone.

In certain embodiments, $R^5$ is selected from H, halogen, CN and OH.

In certain embodiments, $R^5$ is selected from hetAr$^4$, hetAr$^5$, hetCyc$^2$ and hetCyc$^3$(1-4C alkyl)-.

In certain embodiments, $R^5$ is selected from hetAr$^4$ or hetAr$^5$.

In certain embodiments, $R^5$ is selected from hetCyc$^4$(1-4C)alkoxy, hetCyc$^5$(1-4C)alkoxy, (1-3C alkoxy)(1-4C)alkoxy, hydroxy(1-6C)alkoxy, dihydroxy(2-6C)alkoxy, (1-4C)alkoxy and 3C alkyl)amino](1-4C)alkoxy.

In certain embodiments, $R^5$ is selected from hetCyc$^2$ or hetCyc$^3$(1-4Calkyl)-.

In certain embodiments, $R^5$ is hetCyc$^4$(1-4C)alkoxy or hetCyc$^5$(1-4C)alkoxy.

In certain embodiments, $R^5$ is hetCyc$^4$(1-4C)alkoxy.

In certain embodiments, $R^5$ is (1-3C alkoxy)(1-4C)alkoxy.

In certain embodiments, $R^5$ is selected from (1-3C alkoxy)(1-4C)alkoxy, hydroxy(1-6C)alkoxy, dihydroxy(2-6C)alkoxy, (1-6C)alkoxy, [hydroxy(2-4C)alkyl)amino]-(1-4C)alkyl, [(1-4C alkoxy)(1-4C alkyl)amino](1-4C)alkyl, [di(1-4C alkyl)amino](1-4C)alkyl, (1-4C alkyl)C(=O)-, hydroxy(1-6C)alkyl, dihydroxy(2-6C)alkyl and [di(1-3C alkyl)amino](1-4C)alkoxy.

In certain embodiments, $R^5$ is selected from [hydroxy(2-4C)alkyl)amino]-(1-4C)alkyl, [(1-4C alkoxy)(1-4C alkyl)amino](1-4C)alkyl, [di(1-4C alkyl)amino](1-4C)alkyl, hydroxy(1-4C)alkyl and dihydroxy(2-4C)alkyl.

In certain embodiments, $R^5$ is selected from hetAr$^6$, hetCyc$^6$C(=O)-, (hetCyc$^7$)-O-, hetCyc$^8$(1-4C)alkoxy, difluoroamino(1-4C)alkoxy, [(1-4C alkoxy)carbonylamide]difluoro (1-4C)alkoxy, (1-4C alkyl)C(=O)NH(2-4C)alkyl-thio-, (1-4C alkyl)OC(=O)-, and $R^cR^dNC(=O)-$.

In certain embodiments of Formula I, $R^2$ is H.
In certain embodiments of Formula I, $R^2$ is CH$_3$.
In certain embodiments of Formula I, $R^2$ is F.
In certain embodiments of Formula I, $R^2$ is Cl.
In certain embodiments of Formula I, $R^2$ is H or CH$_3$.
In certain embodiments of Formula I, $R^3$ is H.
In certain embodiments of Formula I, $R^3$ is F.
In certain embodiments of Formula I, $R^3$ is Cl.
In certain embodiments of Formula I, $R^4$ is H.
In certain embodiments of Formula I, $R^4$ is CN.
In certain embodiments of Formula I, $R^4$ is F.
In certain embodiments of Formula I, $R^4$ is Cl.
In certain embodiments of Formula I, $R^4$ is Br.
In certain embodiments of Formula I, $R^4$ is —OMe.
In certain embodiments of Formula I, $R^4$ is —OCF$_3$.
In certain embodiments of Formula I, $R^4$ is —CF$_3$.
In certain embodiments of Formula I, $R^4$ is —CH(OH)CH$_2$OH.
In certain embodiments of Formula I, $R^4$ is —C(=O)NH$_2$.
In certain embodiments of Formula I, $R^4$ is selected from H, CN, Br, —OMe, —CH(OH)CH$_2$OH or —C(=O)NH$_2$.
In certain embodiments of Formula I, $R^6$ is H.
In certain embodiments of Formula I, $R^6$ is Cl.
In certain embodiments of Formula I, $R^3$, $R^4$, $R^5$ and $R^6$ are H.

In one embodiment of Formula I, $R^1$ is hetAr$^1$(CH$_2$)$_m$—, hetAr$^2$CH$_2$—, hetAr$^3$CH$_2$—, (3-6C cycloalkyl)-CH$_2$—, hetCyc$^1$CH$_2$—, Ar$^1$(CH$_2$)$_n$— or (N-1-3C alkyl)pyridinonyl-CH$_2$—; $R^2$ is H, F, Cl or CH$_3$; $R^3$ is H, F or Cl; $R^4$ is H, CN, Br, —OMe, —CH(OH)CH$_2$OH or —C(=O)NH$_2$; $R^5$ is selected from H, halogen, CN, OH, hetAr$^4$, hetAr$^5$, hetCyc$^2$, hetCyc$^3$(1-4C alkyl)-, hetCyc$^4$(1-4C)alkoxy, hetCyc$^5$(1-4C)alkoxy, (1-3C alkoxy)(1-4C)alkoxy, hydroxy(1-6C)alkoxy, dihydroxy(2-6C)alkoxy, (1-6C)alkoxy, [hydroxy(2-4C)alkyl)amino]-(1-4C)alkyl, [(1-4C alkoxy)(1-4C alkyl)amino](1-4C)alkyl, [di(1-4C alkyl)amino](1-4C)alkyl, (1-4C alkyl)C(=O)-, hydroxy(1-6C)alkyl, dihydroxy(2-6C)alkyl, [di(1-3C alkyl)amino](1-4C)alkoxy, and N-(1-3C alkyl)pyridinone; and $R^6$ is H or Cl; where m, hetAr$^1$, hetAr$^2$, hetAr$^3$, hetCyc$^1$, Ar$^1$, n, hetAr$^4$, hetAr$^5$, hetCyc$^2$, hetCyc$^3$, hetCyc$^4$ and hetCyc$^5$ are as defined for Formula I.

In one embodiment of Formula I, $R^1$ is hetAr$^1$(CH$_2$)$_m$—, hetAr$^2$CH$_2$— or hetAr$^3$CH$_2$—; $R^2$ is F, Cl, H or CH$_3$; $R^3$ is H; $R^4$ is H; $R^5$ is selected from H, halogen, CN, OH, hetAr$^4$, hetAr$^5$, hetCyc$^2$, hetCyc$^3$(1-4Calkyl)-, hetCyc$^4$(1-4C)alkoxy, hetCyc$^5$(1-4C)alkoxy, (1-3C alkoxy)(1-4C)alkoxy, hydroxy(1-6C)alkoxy, dihydroxy(2-6C)alkoxy, (1-6C)alkoxy, [hydroxy(2-4C)alkyl)amino]-(1-4C)alkyl, [(1-4C alkoxy)(1-4C alkyl)amino](1-4C)alkyl, [di(1-4C alkyl)amino](1-4C)alkyl, (1-4C alkyl)C(=O)-, hydroxy(1-6C)alkyl, dihydroxy(2-6C)alkyl, [di(1-3C alkyl)amino](1-4C)alkoxy, and N-(1-3C alkyl)pyridinone; and $R^6$ is H; where m, hetAr$^1$, hetAr$^2$, hetAr$^3$, hetAr$^4$, hetAr$^5$, hetCyc$^2$, hetCyc$^3$, hetCyc$^4$ and hetCyc$^5$ are as defined for Formula I.

In one embodiment of Formula I, $R^1$ is hetAr$^1$(CH$_2$)$_m$—; $R^2$ is F, Cl, H or CH$_3$; $R^3$ is H; $R^4$ is H; $R^5$ is selected from H, halogen, CN, OH, hetAr$^4$, hetAr$^5$, hetCyc$^2$, hetCyc$^3$ (1-4C alkyl)-, hetCyc$^4$(1-4C)alkoxy, hetCyc$^5$(1-4C)alkoxy, (1-3C alkoxy)(1-4C)alkoxy, hydroxy(1-6C)alkoxy, dihydroxy(2-6C)alkoxy, (1-6C)alkoxy, [hydroxy(2-4C)alkyl]amino]-(1-4C)alkyl, [(1-4C alkoxy)(1-4C alkyl)amino](1-4C)alkyl, [di(1-4C alkyl)amino](1-4C)alkyl, (1-4C alkyl)C(=O)—, hydroxy(1-6C)alkyl, dihydroxy(2-6C)alkyl, [di(1-3C alkyl)amino](1-4C)alkoxy, and N-(1-3C alkyl)pyridinone; and R$^6$ is H; where m, hetAr$^1$, hetAr$^4$, hetAr$^5$, hetCyc$^2$, hetCyc$^3$, hetCyc$^4$ and hetCyc$^5$ are as defined for Formula I.

In one embodiment of Formula I, R$^1$ is hetAr$^1$(CH$_2$)$_m$—, hetAr$^2$CH$_2$— or hetAr$^3$CH$_2$—; R$^2$ is F, Cl, H or CH$_3$; R$^3$ is H; R$^4$ is H; R$^5$ is hetCyc$^4$(1-4C)alkoxy or hetCyc$^5$(1-4C)alkoxy; and R$^6$ is H; where m, hetAr$^1$, hetAr$^2$, hetAr$^3$, hetCyc$^4$ and hetCyc$^5$ are as defined for Formula I.

In one embodiment of Formula I, R$^1$ is hetAr$^1$(CH$_2$)$_m$—, hetAr$^2$CH$_2$— or hetAr$^3$CH$_2$; R$^2$ is CH$_3$; R$^3$ is H; R$^4$ is H; R$^5$ is hetCyc$^4$(1-4C)alkoxy or hetCyc$^5$(1-4C)alkoxy; and R$^6$ is H; where m, hetAr$^1$, hetAr$^2$, hetAr$^3$, hetCyc$^4$ and hetCyc$^5$ are as defined for Formula I.

In one embodiment of Formula I, R$^1$ is hetAr$^1$(CH$_2$)$_m$—, hetAr$^2$CH$_2$— or hetAr$^3$CH$_2$; R$^2$ is F, Cl, H or CH$_3$; R$^3$ is H; R$^4$ is H; R$^5$ is hetAr$^4$ or hetAr$^5$; and R$^6$ is H; where m, hetAr$^1$, hetAr$^2$, hetAr$^3$, hetAr$^4$ and hetAr$^5$ are as defined for Formula I.

In one embodiment of Formula I, R$^1$ is hetAr$^1$(CH$_2$)$_m$—, hetAr$^2$CH$_2$— or hetAr$^3$CH$_2$; R$^2$ is F, Cl, H or CH$_3$; R$^3$ is H; R$^4$ is H; R$^5$ is hetCyc$^2$ or hetCyc$^3$(1-4Calkyl)-; and R$^6$ is H; where m, hetAr$^1$, hetAr$^2$, hetAr$^3$, hetCyc$^2$ and hetCyc$^3$ are as defined for Formula I.

In one embodiment of Formula I, R$^1$ is (3-6C cycloalkyl)-CH$_2$—, hetCyc$^1$CH$_2$—, Ar$^1$(CH$_2$)$_n$— or (N-1-3C alkyl)pyridinonyl-CH$_2$—; R$^2$ is F, Cl, H or CH$_3$; R$^3$ is H; R$^4$ is H; R$^5$ is selected from H, halogen, CN, OH, hetAr$^4$, hetAr$^5$, hetCyc$^2$, hetCyc$^3$(1-4Calkyl)-, hetCyc$^4$(1-4C)alkoxy, hetCyc$^5$ (1-4C)alkoxy, (1-3C alkoxy)(1-4C)alkoxy, hydroxy(1-6C)alkoxy, dihydroxy(2-6C)alkoxy, (1-6C)alkoxy, [hydroxy(2-4C)alkyl]amino]-(1-4C)alkyl, [(1-4C alkoxy)(1-4C alkyl)amino](1-4C)alkyl, [di(1-4C alkyl)amino](1-4C)alkyl, (1-4C alkyl)C(=O)—, hydroxy(1-6C)alkyl, dihydroxy(2-6C)alkyl, [di(1-3C alkyl)amino](1-4C)alkoxy, and N-(1-3C alkyl)pyridinone; and R$^6$ is H; where hetCyc$^1$, Ar$^1$, n, hetAr$^4$, hetAr$^5$, hetCyc$^2$, hetCyc$^3$, hetCyc$^4$ and hetCyc$^5$ are as defined for Formula I.

In one embodiment, Formula I does not include the following compounds: 3-((4-(7-(2-methoxyethoxyl)imidazo[1,2-a]pyridine-3-carboxamido)-1H-indazol-1-yl)methyl)benzoic acid and 7-(2-methoxyethoxy)-N-(1-(piperidin-4-ylmethyl)-1H-indazol-4-yl)imidazo[1,2-a]pyridine-3-carboxamide.

The terms "(1-6C)alkyl", "(1-4C)alkyl" "(2-4C)alkyl" and "(2-6C)alkyl" as used herein refers to saturated linear or branched-chain monovalent hydrocarbon radicals of one to six carbon atoms, one to four carbon atoms, two to four carbon atoms, or two to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl and hexyl.

The terms "(1-6C)alkoxy", "(1-4C)alkoxy", "(2-4C)alkoxy" and "(2-6C)alkoxy" as used herein refer to saturated linear or branched-chain monovalent alkoxy radicals of one to six carbon atoms, one to four carbon atoms, two to four carbon atoms, or two to six carbon atoms, respectively, wherein the radical is on the oxygen atom. Examples include methoxy, ethoxy, propoxy, isopropoxy, and butoxy.

When a chemical formula is used to describe a substituent, the dash on the left or the right side of the formula indicates that the free valance is on the left of the right portion, respectively, of the substituent.

The term "halogen" includes fluoro, chloro, bromo and iodo.

It will be appreciated that certain compounds according to the invention may contain one or more centers of asymmetry and may therefore be prepared and isolated as a mixture of isomers such as a racemic or diastereomeric mixture, or in an enantiomerically or diastereomerically pure form. It is intended that all stereoisomeric forms of the compounds of the invention, including but not limited to, diastereomers, enantiomers and atropisomers, as well as mixtures thereof such as racemic mixtures, form part of the present invention.

It may be advantageous to separate reaction products from one another and/or from starting materials. The desired products of each step or series of steps is separated and/or purified (hereinafter separated) to the desired degree of homogeneity by techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Enantiomers can be separated by converting the enantiomeric mixture into a diastereomeric mixture by reaction with an appropriate optically active compound (e.g., chiral auxiliary, such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column. Diastereomeric mixtures can be separated into their individual diastereomers on the basis of their physical chemical differences by methods well known to those skilled in the art, such as by chromatography and/or fractional crystallization.

A single stereoisomer, for example, an enantiomer, substantially free of its stereoisomer may be obtained by resolution of the racemic mixture using methods known in the art, such as (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: Wainer, Irving W., ed. *Drug Stereochemistry: Analytical Methods and Pharmacology*. New York: Marcel Dekker, Inc., 1993.

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid, can result in formation of the diastereomeric salts.

Alternatively, by method (2), the substrate to be resolved is reacted with one enantiomer of a chiral compound to form a diastereomeric pair (Eliel, E., and S. Wilen. *Stereochemistry of Organic Compounds*. New York: John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−)-menthyl chloroformate in the presence of base, or Mosher ester, α-methoxy-α-(trifluoromethyl)phenyl acetate (Jacob III, Peyton. "Resolution of (±)-5-Bromonornicotine. Synthesis of (R)- and (S)-Nornicotine of High Enantiomeric Purity." *J. Org. Chem.* Vol. 47, No. 21 (1982): pp. 4165-4167), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111).

By method (3), a racemic mixture of two enantiomers can be separated by chromatography using a chiral stationary phase (Lough, W. J., ed. *Chiral Liquid Chromatography*. New York: Chapman and Hall, 1989; Okamoto, Yoshio, et al. "Optical resolution of dihydropyridine enantiomers by high-performance liquid chromatography using phenylcarbamates of polysaccharides as a chiral stationary phase." *J. of Chromatogr.* Vol. 513 (1990): pp. 375-378). Enriched or purified enantiomers can be distinguished by methods used to distinguish other chiral molecules with asymmetric carbon atoms, such as optical rotation and circular dichroism.

In one embodiment, a compound of Formula I can be enriched in one enantiomer over the other by up to 80% enantiomeric excess. In one embodiment, a compound of Formula I can be enriched in one enantiomer over the other by up to 85% enantiomeric excess. In one embodiment, a compound of Formula I can be enriched in one enantiomer over the other by up to 90% enantiomeric excess. In one embodiment, a compound of Formula I can be enriched in one enantiomer over the other by up to 95% enantiomeric excess.

As used herein, the term "enantiomeric excess" means the absolute difference between the mole fraction of each enantiomer.

It will further be appreciated that an enantiomer of a compound of the invention can be prepared by starting with the appropriate chiral starting material.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

It will also be appreciated that certain compounds of Formula I may be used as intermediates for the preparation of further compounds of Formula I.

The compounds of Formula I include salts thereof. In certain embodiments, the salts are pharmaceutically acceptable salts. In addition, the compounds of Formula I include other salts of such compounds which are not necessarily pharmaceutically acceptable salts, and which may be useful as intermediates for preparing and/or purifying compounds of Formula I and/or for separating enantiomers of compounds of Formula I.

It will further be appreciated that the compounds of Formula I and their salts may be isolated in the form of solvates, and accordingly that any such solvate is included within the scope of the present invention.

Compounds of the invention may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1$H, $^2$H, $^3$H or mixtures thereof; when carbon is mentioned, it is understood to refer to $^{11}$C, $^{12}$C, $^{13}$C, $^{14}$C or mixtures thereof; when nitrogen is mentioned, it is understood to refer to $^{13}$N, $^{14}$N, $^{15}$N or mixtures thereof; when oxygen is mentioned, it is understood to refer to $^{14}$O, $^{15}$O, $^{16}$O, $^{17}$O, $^{18}$O or mixtures thereof; and when fluoro is mentioned, it is understood to refer to $^{18}$F, $^{19}$F or mixtures thereof. The compounds according to the invention therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds of the present invention, whether radioactive or not, are intended to be encompassed within the scope of the present invention.

The present invention further provides a process for the preparation of a compound of Formula I or a salt thereof as defined herein which comprises:

(a) coupling a corresponding compound of formula II

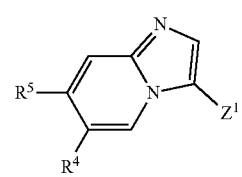

where $Z^1$ is COOH or a reactive derivative thereof with a corresponding compound of formula III

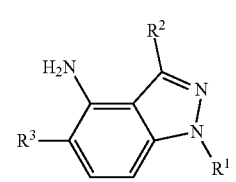

in the presence of a coupling reagent; or (b) coupling a corresponding compound of formula IV

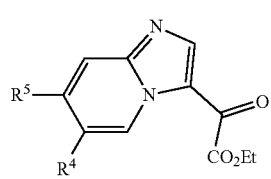

with a compound of formula III

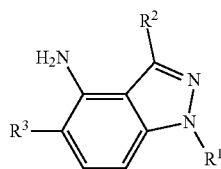

in the presence of a base; or (c) for a compound of Formula I where $R^5$ is hetCyc$^4$(1-4C)alkoxy, (hetCyc$^7$)-O—, hetCyc$^8$(1-4C)alkoxy, hydroxy (1-6C)alkoxy, difluoroamino(1-4C)alkoxy, or [(1-4C alkoxy)carbonylamide]difluoro(1-4C)alkoxy, reacting a corresponding compound of formula V

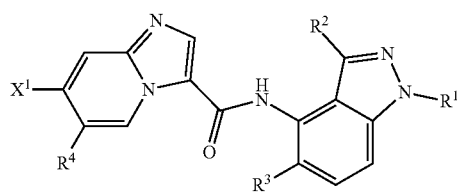

where $X^1$ is F or Cl, with a compound having the formula $R^{5a}$—O— where $R^{5a}$ is hetCyc$^4$(1-4C)alkyl-OH, hetCyc$^7$-OH, hetCyc$^8$(1-4C)alkyl-OH, P$^1$O-(1-6C)alkyl-OH, difluoroamino(1-4C)alkyl-OH or [(1-4C alkoxy)carbonyl amide]difluoro (1-4C)alkyl-OH, respectively, in the presence of a base, where $P^1$ is a hydroxyl protecting group; or (d) for a compound of Formula I where $R^5$ is hetCyc$^2$ where hetCyc$^2$ is a nitrogen radical, reacting a corresponding compound of formula V-a

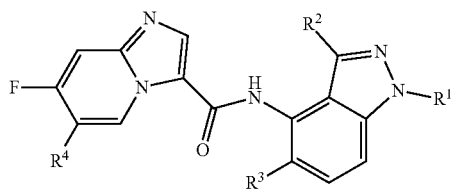

with a compound having the formula hetCyc$^2$-H; or (e) for a compound of Formula I where $R^5$ is hetAr$^4$ wherein hetAr$^4$ is a nitrogen radical, reacting a corresponding compound of formula V-a

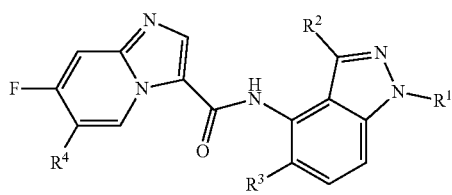

with a compound having the formula hetAr$^4$-H in the presence of a base; or (f) for a compound of Formula I where $R^5$ is a carbon linked substituent selected from hetAr$^4$, hetAr$^5$, and N-(1-3C alkyl)pyridinone, reacting a corresponding compound of formula V-b

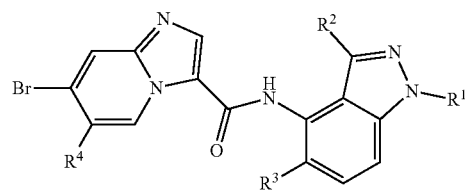

with a compound having the formula VI

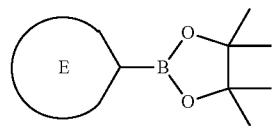

where Ring E is a carbon-linked radical selected from hetAr$^4$, hetAr$^5$, and N-(1-3C alkyl)pyridinonyl, respectively, in the presence of a palladium catalyst and a base; or (g) for a compound of Formula I where $R^5$ is hetAr$^4$ or hetAr$^6$ where hetAr$^4$ and hetAr$^6$ are carbon radicals, reacting a corresponding compound of formula V-b

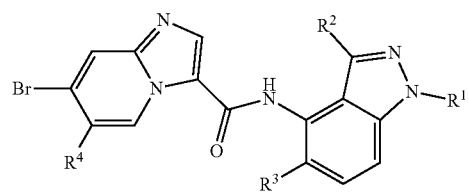

with a compound having the formula hetAr$^4$-H or hetAr$^6$-H, respectively, in the presence of a palladium catalyst and a base and optionally in the presence of a ligand; or (h) for a compound of Formula I where $R^5$ is hetCyc$^6$C (=O)—, reacting a corresponding compound having the formula VII

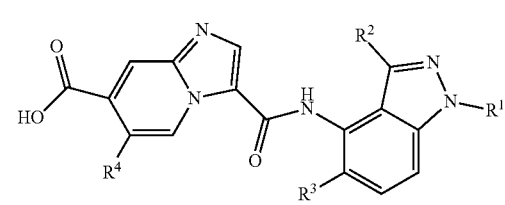

with a compound having the formula hetCyc$^6$-H in the presence of a coupling reagent; or (i) for a compound of Formula I where $R^5$ has the structure:

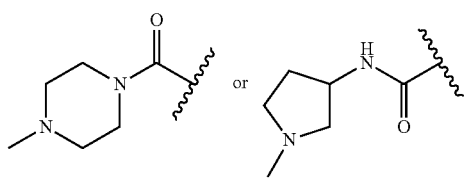

reacting a corresponding compound having the formula VIII

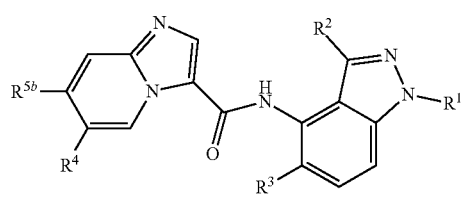

where $R^{5b}$ is

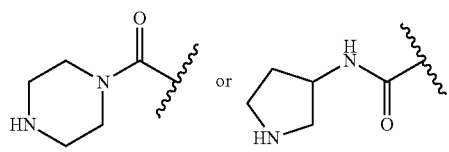 [SMILES: *C(=O)N1CCNCC1 ; "or" ; *C(=O)NC1CCNC1]

respectively, with formaldehyde in the presence of a reducing agent; or (j) for a compound of Formula I where $R^5$ is $R^cR^dNC(=O)$—, reacting a corresponding compound of formula IX

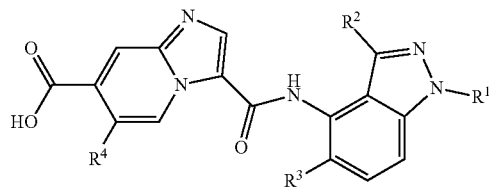

with a compound having the formula $R^cR^dNH$ in the presence of a coupling agent; or (k) for a compound of Formula I wherein $R^5$ is an oxadiazole substituent having the formula:

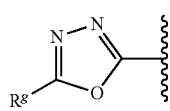

where $R^g$ is H or Me, cyclizing a corresponding compound having the formula X

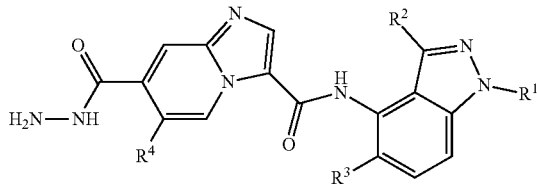

in the presence of trimethoxymethane or triethoxyethane, respectively; or (l) for a compound of Formula I wherein $R^5$ is 1,3,4-thiadiazol-2-yl, cyclizing a corresponding compound having the formula XI

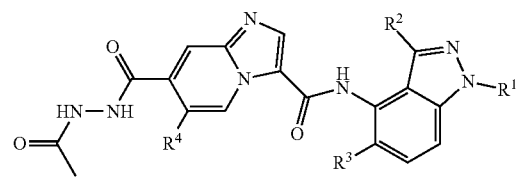

in the presence of $P_2S_5$; or (m) for a compound of Formula I wherein $R^5$ is hetCyc$^3$(1-2Calkyl)- where hetCyc$^3$ is a nitrogen radical, [(1-4C alkoxy)(1-4C alkyl)]amino(1-2C)alkyl, or [hydroxy(2-4C)alkyl)]amino-(1-2C)alkyl, reacting a corresponding compound of formula XII

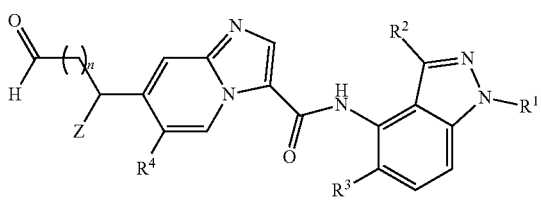

where n is 0 or 1 and Z is H or Me, with hetCyc$^3$-H, [(1-4C alkoxy)(1-4C alkyl)]NH$_2$ or [hydroxy(2-4C)alkyl)]NH$_2$, respectively, in the presence of a reducing agent; or (n) for a compound of Formula I wherein $R^1$ is hetAr$^2$CH$_2$— and hetAr$^2$ is a pyrazolyl ring having a ring N atom substituted with a substituent selected from or (1-6C) alkyl-, reacting a corresponding compound having the formula XIII

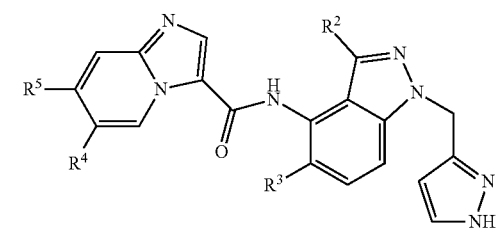

with a compound having the formula (1-6C)alkyl-X², respectively, wherein X² is a leaving group or atom, in the presence of a base; or (o) for a compound of Formula I wherein R¹ is N-(1-3C alkyl)pyridinonyl-CH₂—, coupling a corresponding compound having the formula XIV

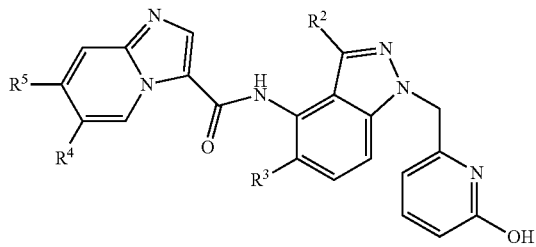

XIV with (1-3C alkyl)-L¹ where L¹ is a leaving group or atom in the presence of a base; or (p) for a compound of Formula I wherein R⁵ is hetCyc³CH₂— where hetCyc³ is a nitrogen radical, coupling a corresponding compound having the formula XV

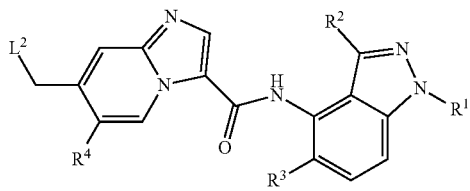

XV where L² is a leaving group with a compound having the formula hetCyc³-H in the presence of a base; or (q) for a compound of Formula I where R⁵ is hetCyc⁴(1-4C)alkoxy and hetCyc⁴ is N-methylpiperazine-1-oxide, reacting a corresponding compound of formula XVI

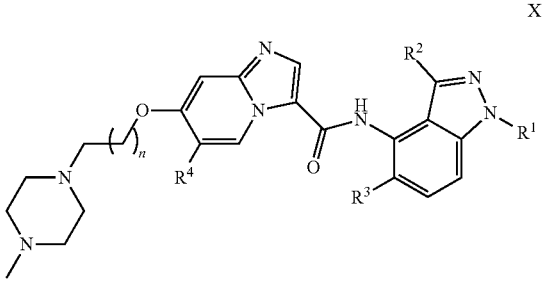

XVI where n is 0, 1, 2 or 3, with an oxidizing agent; or (r) for a compound of Formula I wherein R⁵ is hetCyc³(1-4Calkyl)- where hetCyc³ is a nitrogen radical, reacting a corresponding compound having the formula XVII

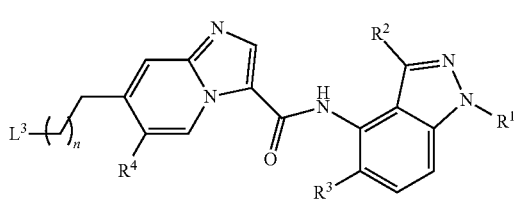

XVII where n is 0, 1, 2 or 3, and L³ is a leaving group, with a corresponding compound having the formula hetCyc³ in the presence of a base; or (s) for compound of Formula I where R⁵ is (1-4C alkyl)C(=O)NH(2-4C)alkylthio-, coupling a corresponding compound having the formula V

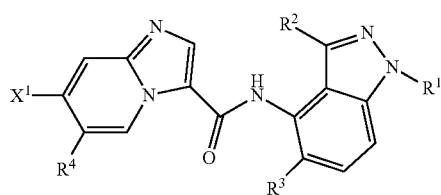

V where X¹ is F or Cl, with a compound having the formula (1-4C alkyl)C(=O)NH(2-4C)alkyl-SH in the presence of a base; or (t) for a compound of Formula I wherein R⁵ is CH₃C(=O)—, coupling a corresponding compound having the formula V-b

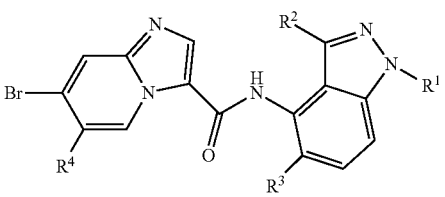

V-b with a compound having the formula

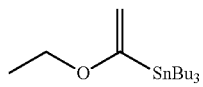

in the presence of a palladium catalyst and a ligand, followed by treatment with acid; or (u) for a compound of Formula I wherein R⁵ is HO(CH₂CH₂)—, treating a corresponding compound having the formula XVIII

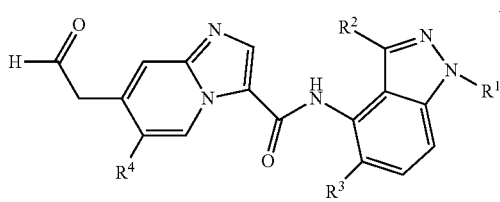

XVIII with a reducing agent; and removing any protecting groups if desired and forming a salt thereof if desired.

Referring to method (a), the coupling of the compound of formula II with a compound of formula III may be performed using conventional amide bond formation conditions, for example by treating the carboxylic acid with an activating agent, followed by addition of the amine in the presence of a base. Suitable activating agents include oxalyl chloride, thionyl chloride, EDCI, HATU, and HOBt. Suitable bases include amine bases, for example triethylamine, diisopropylethylamine, pyridine, or excess ammonia. Suitable solvents include DCM, DCE, THF, and DMF.

Alternatively, the amide bond formation can be performed by coupling a reactive derivative of a carboxylic acid of formula II, for example an acid halide such as an acid chloride, or a lithium salt thereof.

Referring to method (b), suitable bases include alkali metal hydrides such as NaH, alkali metal amine bases such as lithium diisopropylamide and silicon-containing alkali metal amides (e.g., sodium hexamethyldisilazide or lithium hexamethyldisilazide).

Referring to method (c), suitable bases include alkali metal carbonates or alkoxides, such as for example cesium carbonate or sodium tert-butoxide.

Referring to method (d), suitable solvents include toluene and THF. The reaction is conveniently performed at elevated temperatures for example at temperatures between 110-120° C.

Referring to method (e), suitable bases include alkali metal hydrides, such as sodium hydride or potassium hydride. Convenient solvents include aprotic solvents such as ethers (for example tetrahydrofuran or p-dioxane), DMF, or acetone. The reaction can be conveniently performed at elevated temperatures, for example temperatures ranging from 90 to 110° C.

Referring to method (f), suitable palladium catalysts include $Pd_2(dba)_3$, $Pd(PPh_3)_4$, and $Pd(OAc)_2$. Convenient solvents include aprotic solvents such as ethers (for example tetrahydrofuran or p-dioxane), toluene or DMF. The reaction can be conveniently performed at elevated temperatures, for example temperatures ranging from 70 to 90° C.

Referring to method (g), suitable palladium catalysts include $Pd_2(dba)_3$, $Pd(PPh_3)_4$, and $Pd(OAc)_2$. Suitable ligands include trifuran-2-ylphophine, rac-BINAP, DIPHOS and the like. The base may be, for example, an alkali metal carbonate or alkoxide, such as for example cesium carbonate or sodium tert-butoxide. Convenient solvents include aprotic solvents such as ethers (for example tetrahydrofuran or p-dioxane), toluene or DMF.

Referring to method (h), suitable coupling reagents include 1-(3-dimethylaminopropyl)-3-ethylcarbodiimide (EDCI), DCC, 1,1'-carbonyldiimidazole (CDI) and the like.

Referring to method (i), suitable reducing agents include $Na(OAc)_3BH$ and $NaCNBH_3$. Suitable solvents include neutral solvents such as acetonitrile, THF, and dichloroethane.

Referring to method (j), examples of suitable coupling agents include CDI, EDCI, phosgene, and bis(trichloromethyl) carbonate. Suitable solvents include dichloromethane, dichloroethane, THF, and DMF. The reaction is conveniently performed at ambient temperature or at elevated temperatures, e.g., at about 60-80° C.

Referring to method (k), the reaction is conveniently performed with excess trimethoxymethane or triethoxyethane at elevated temperatures, for example at 100-120° C.

Referring to method (l), suitable solvents include aprotic solvents such as ethers (for example tetrahydrofuran or p-dioxane), toluene and/or DMF. The reaction is conveniently performed at elevated temperatures, for example at 100-120° C.

Referring to methods (m) and (u), suitable reducing agents include $Na(OAc)_3BH$ and $NaCNBH_3$. Suitable solvents include methanol, ethanol, and dichloromethane or mixtures thereof. The reaction is conveniently performed at ambient temperature.

Referring to method (n), the leaving group $X^2$ may be an alkylsulfonyl or arylsulfonyl group, for example, a triflate group, or an arylsulfonyloxy group or an alkylsulfonyloxy group, such as a mesylate or a tosylate group. Alternatively, $X^2$ may be a leaving atom such as Cl or Br. The base may be, for example, an alkali metal carbonate, hydroxide or alkoxide, such as for example cesium carbonate, sodium carbonate, potassium carbonate, sodium hydroxide, cesium hydroxide or potassium tert-butoxide. Convenient solvents include aprotic solvents such as ethers (for example tetrahydrofuran or p-dioxane), toluene, DMF or DME. The reaction can be conveniently performed at ambient temperature.

Referring to method (o), the base may be, for example, an alkali metal hydride or carbonate, such as sodium hydride, potassium hydride, sodium carbonate, potassium carbonate or cesium carbonate. Convenient solvents include aprotic solvents such as ethers (for example tetrahydrofuran or p-dioxane), DMF, or acetone.

Referring to method (p), the leaving group $L^2$ may be an alkylsulfonyloxy group, such as a tosylate or a mesylate group. The base may be an alkali metal carbonate or bicarbonate, such as sodium or potassium carbonate or bicarbonate. Convenient solvents include aprotic solvents such as ethers (for example tetrahydrofuran or p-dioxane) and DMF. The reaction can be conveniently performed at a temperature ranging from ambient temperature to 50° C.

Referring to method (q), suitable oxidizing agents include organic perbenzoic acids such as metachloroperbenzoic acid. Convenient solvents include aprotic solvents such as DCM, ethers (for example tetrahydrofuran or p-dioxane) and DMF. The reaction temperature for this oxidizing step is typically in the range from −25° C. to ambient temperature, for example between −20° C. and 0° C.

Referring to method (r), the leaving group $L^3$ may be an alkylsulfonyloxy group, such as a tosylate or a mesylate group. Convenient solvents include aprotic solvents such as ethers (for example tetrahydrofuran or p-dioxane) and DMF.

Referring to method (s), suitable bases include an alkali metal carbonate or alkoxide, such as for example cesium carbonate or sodium tert-butoxide. Convenient solvents include aprotic solvents such as ethers (for example tetrahydrofuran or p-dioxane) and DMF.

Referring to method (t), suitable palladium catalysts include $Pd(PPh_3)_4$, $Pd_2(dba)_3$, $Pd(OAc)_2$, $Pd(PPh_3)_2Cl_2$ and 1,1'-bis(diphenylphosphino)ferrocene-$PdCl_2$-dichloromethane complex.

Compounds of the Formulas V, V-a, V-b, VII, VIII, IX, X, XI, XII, XIII, XIV, XV, XVI, XVII, and XVIII are also believed to be novel and are provided as further aspects of the invention.

Amine groups in compounds described in any of the above methods may be protected with any convenient amine protecting group, for example as described in Greene & Wuts, eds., "Protecting Groups in Organic Synthesis", John Wiley & Sons, Inc. Examples of amine protecting groups include acyl and alkoxycarbonyl groups, such as t-butoxycarbonyl (BOC), and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", John Wiley & Sons, Inc. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", John Wiley & Sons, Inc. Examples of alcohol protecting groups include benzyl, trityl, silyl ethers, and the like.

The compounds of Formula I represent novel potent inhibitors of protein tyrosine kinases, such as PDGFR, cFMS and/or cKIT and may be useful in the prevention and treatment of disorders resulting from actions of these kinases.

The ability of compounds of the invention to act as inhibitors of PDGFR may be demonstrated by the assays described in Examples A and/or B.

The ability of compounds of the invention to act as inhibitors of cFMS may be demonstrated by the assay described in Example C.

The ability of compounds of the invention to act as inhibitors of cKIT may be demonstrated by the assay described in Example D.

Compounds of Formula I may be of therapeutic value in the treatment of diseases or disorders selected from fibrosis, bone-related diseases, cancer, autoimmune disorders, inflammatory diseases, cardiovascular diseases, pain and burns. In one embodiment, compounds of Formula I may be of therapeutic value in the treatment of diseases or disorders selected from fibrosis, bone-related diseases, cancer, autoimmune disorders, inflammatory diseases, cardiovascular diseases and pain.

In one embodiment, the compounds of Formula I are useful for the treatment of fibrotic diseases. Examples of fibrosis include idiopathic pulmonary fibrosis (IPF), nephrogenic systemic fibrosis (NSF), cirrhosis of the liver, diabetic-induced nephropathy, cardiac fibrosis (for example, endomyocardial fibrosis), mediastinal fibrosis, myelofibrosis, retroperitoneal fibrosis, Crohn's disease, keloid formation, scleroderma and systemic sclerosis. Additional examples of fibrotic diseases include focal segmental glomerular sclerosis (FSGS), interstitial lung disease in systemic sclerosis (SSc-ILD), primary biliary cirrhosis, ethanol cirrhosis, interstitial fibrosis and tubular atrophy (CAD), proliferative vitreoretinopathy, and scarring (hypertrophic and keloid), In one embodiment, the compounds of Formula I are useful for the treatment of bone-related diseases.

Examples of bone-related diseases include metastatic bone disease, treatment-induced bone loss, osteoporosis, rheumatoid arthritis, ankylosing spondylitis, Paget's disease, and periodontal disease. The osteoporosis may be attributed to (1) menopause in women, (2) aging in men or women, (3) suboptimal bone growth during childhood and adolescence that resulted in failure to reach peak bone mass, and/or (4) bone loss secondary to other disease conditions, eating disorders, medications and/or medical treatments (for example, as a result of treatment with glucocorticoids, aromatase inhibition therapy, or anti-androgen therapy).

Other osteolytic diseases that can be treated according to the present invention are more localized. A particular example is metastatic tumor-induced osteolysis. In this condition, bone cancers or bone metastases induce localized osteolysis that causes pain, bone weakness and fractures. Such localized osteolysis also permits tumors to grow larger by creating more space for them in the bone and releasing growth factors from the bone matrix. Cancers presently known to cause tumor-induced osteolysis include hematological malignancies (e.g., myeloma and lymphoma) and solid tumors (e.g., breast, prostate, lung, renal and thyroid), all of which the present invention contemplates treating.

In one embodiment, the compounds of Formula I are useful for the treatment of cancers and proliferative disorders. Examples include multiple myeloma, acute myeloid leukemia (AML), chronic myeloid leukemia (CML), prostate cancer, breast cancer, ovarian cancer, melanoma, glioblastoma multiforme, giant cell tumor of bone (also known as osteoclastome), giant cell tumor of the tendon sheath (also known as tenosynovial giant cell tumor or TGCT), metastasis of tumors to other tissues, other chronic myeloproliferative diseases such as myelofibrosis, and pigmented villonodular synovitis (PVNS).

In one embodiment, the compounds of Formula I are useful for the treatment of autoimmune disorders and inflammatory diseases.

Examples of autoimmune disorders and inflammatory diseases include but are not limited to, rheumatoid arthritis, osteoarthritis, psoriatic arthritis, ankylosing spondylitis, Adult Still's, glomerulonephritis, osteoporosis, Sjogren's syndrome, inflammatory bowel disease, ulcerative colitis, Crohn's disease, Langerhans cell histiocytosis, hemophagocytic syndrome, multicentric reticulohistiocytosis, and Paget's disease. Additional examples of autoimmune diseases and disorders include primary sclerosing cholangitis and transplant rejection (including hepatic, renal and heart/lung transplants).

In one embodiment, the compounds of Formula I are useful for the treatment of cardiovascular diseases. Examples of cardiovascular diseases include atherosclerosis, peripheral vascular disease, coronary artery disease, ischemia/reperfusion, hypertension, restenosis, pulmonary arterial hypertension and arterial inflammation. Additional examples of cardiovascular diseases include acute respiratory distress syndrome (ARDA), arteriovenous (AV) fistula patency and veno-occlusive disease (post-HSC/BMT).

In one embodiment, the compounds of Formula I are useful for the treatment of pain. In one embodiment, the compounds of Formula I are useful for the treatment of pain as a result of nerve injury. In one embodiment, the compounds of Formula I are useful for the treatment of neuropathic pain associated with nerve inflammation (neuritis) in the absence of nerve injury. Such pain syndromes include back pain, temporomandibular joint (TMJ) disorder, and rheumatoid arthritis.

In one embodiment, the compounds of Formula I are useful for the treatment of burns.

Compounds of Formula I may be administered alone as a sole therapy or can be administered in addition with one or more other substances and/or treatments that work by the same or a different mechanism of action. Such conjoint treatment may be achieved by way of the simultaneous, sequential or separate administration of the individual components of the treatment.

Accordingly, the invention further provides methods of treating bone-related diseases in mammals, including humans, by administration to a mammal in need thereof a therapeutically effective amount of at least one compound of Formula I or a pharmaceutically acceptable salt thereof. The compounds may be administered alone or may be administered in combination with one or more drugs for the treatment of bone-related diseases that work by the same or a different mechanism of action.

The invention further provides methods of treating cancer in mammals, including humans, by administration to a mammal in need thereof a therapeutically effective amount of at least one compound of Formula I or a pharmaceutically acceptable salt thereof.

In the field of medical oncology it is normal practice to use a combination of different forms of treatment to treat each patient with cancer. In medical oncology the other component(s) of such conjoint treatment in addition to compositions of the present invention may be, for example, surgery, radiotherapy, chemotherapy, signal transduction inhibitors and/or monoclonal antibodies.

Accordingly, the compounds of Formula I may be administered in combination with one or more agents selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors.

The invention also provides methods of treating cardiovascular diseases in mammals, including humans, by administration to a mammal in need thereof at least one compound of Formula I or a pharmaceutically acceptable salt thereof. The compounds may be administered alone or may be administered in combination with one or more drugs for the treatment of cardiovascular diseases that work by the same or a different mechanism of action.

The invention also provides methods of treating inflammatory diseases in mammals, including humans, by administration of at least one compound of Formula I or a pharmaceutically acceptable salt thereof. The compounds may be administered alone for the treatment of inflammatory disease or may be administered in combination with one or more drugs for treating inflammatory diseases that work by the same or a different mechanism of action, such as gold salts or methotrexate.

The invention also provides methods of treating pain in mammals, including humans, by administration to a mammal in need thereof at least one compound of Formula I or a pharmaceutically acceptable salt thereof. The compounds may be administered alone for the treatment of pain or may be administered in combination with one or more drugs for treating pain that work by the same or a different mechanism of action.

The invention also provides methods of treating burns in mammals, including humans, by administration to a mammal in need thereof at least one compound of Formula I or a pharmaceutically acceptable salt thereof.

As used herein, the terms "treatment" or "treating" mean an alleviation, in whole or in part, of symptoms associated with a disorder or condition (e.g., bone-related diseases, fibrosis, cancer, autoimmune disorders, inflammatory diseases, cardiovascular diseases or pain as described herein), or slowing, or halting of further progression or worsening of those symptoms.

In one embodiment, compounds of Formula I are useful for preventing a disease or disorder selected from fibrosis, bone-related diseases, cancer, autoimmune disorders, inflammatory diseases, cardiovascular diseases and pain in a mammal.

As used herein, the term "preventing" means the prevention of the onset, recurrence or spread, in whole or in part, of the disease or condition (e.g., bone-related diseases, fibrosis, cancer, autoimmune disorders, inflammatory diseases, cardiovascular diseases or pain as described herein), or a symptom thereof.

As used herein, the phrase "effective amount" means an amount of compound that, when administered to a mammal in need of such treatment, is sufficient to (i) treat or prevent a particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein.

The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

The present invention further provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

The present invention further provides a compound of Formula I or a pharmaceutically acceptable salt thereof, for use in therapy. In one embodiment, the invention provides a compound of Formula I or a pharmaceutically acceptable salt thereof, for use in the treatment of a disease or disorder selected from fibrosis, bone-related diseases, cancer, autoimmune disorders, inflammatory diseases, cardiovascular diseases and pain in a mammal. In one embodiment, the disease is fibrosis. In one embodiment, the disease is a bone-related disease. In one embodiment, the disease is cancer. In one embodiment, the disease is an autoimmune disorder. In one embodiment, the disease is an inflammatory disease. In one embodiment, the disease is cardiovascular disease. In one embodiment, the disorder is pain. In one embodiment, the disorder is burns.

According to a further aspect, the present invention provides the use of a compound of Formula I or a pharmaceutically acceptable salt thereof, in the treatment of a disease or disorder selected from fibrosis, bone-related diseases, cancer, autoimmune disorders, inflammatory diseases, cardiovascular diseases and pain in a mammal. In one embodiment, the disease is fibrosis. In one embodiment, the disease is a bone-related disease. In one embodiment, the disease is cancer. In one embodiment, the disease is an autoimmune disorder. In one embodiment, the disease is an inflammatory disease. In one embodiment, the disease is cardiovascular disease. In one embodiment, the disorder is pain. In one embodiment, the disorder is burns.

According to a further aspect, the present invention provides the use of a compound of Formula I in the manufacture of a medicament for the treatment of a disease or disorder selected from fibrosis, bone-related diseases, cancer, autoimmune disorders, inflammatory diseases, cardiovascular diseases and pain in a mammal, which comprises administering to said mammal a therapeutically effective amount of a compound of Formula I or a pharmaceutically acceptable salt thereof. In one embodiment, the disease is fibrosis. In one embodiment, the disease is a bone-related disease. In one embodiment, the disease is cancer. In one embodiment, the disease is an autoimmune disorder. In one embodiment, the disease is an inflammatory disease. In one embodiment, the disease is cardiovascular disease. In one embodiment, the disorder is pain. In one embodiment, the disorder is burns.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, Alfa, Aesar, TCI, Maybridge, or other suitable suppliers, and were used without further purification unless otherwise indicated. Tetrahydrofuran (THF), dichloromethane (DCM, methylene chloride), toluene, dimethylformamide (DMF) and dioxane were purchased from DriSolve or other commercial vendors and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents by syringe. Glassware was oven dried and/or heat dried or dried under a stream of dry nitrogen.

Column chromatography was done on a Biotage system (Manufacturer: Dyax Corporation) having a silica gel or C-18 reverse phase column, or on a silica SepPak cartridge (Waters), or using conventional flash column chromatography on silica gel.

Abbreviations used herein have the following meanings:

| | |
|---|---|
| APCI | Atmospheric Pressure Chemical Ionization |
| BOC | tert-butoxycarbonyl |
| DCE | 1,2-Dichloroethane |
| DCM | Dichloromethane |
| DMA | N,N-Dimethylacetamide |
| DMF | N,N-Dimethylformamide |
| DMSO | dimethylsulfoxide |
| DPPF | 1,1'-bis(diphenylphosphino)ferrocene |
| EDCI | 1-Ethyl-3-(3'-dimethylaminopropyl)carbodiimide |
| GF/F | Glass Fiber Filter |
| HATU | (2-(7-Aza-1H-benzotriazole-1-yl)-1,1,3,3-tetramethyluronium hexafluorophosphate) |
| HOBt | Hydroxybenzotriazole |
| IPA | Isopropyl alcohol |
| LAH | Lithium Aluminum Hydride |
| LHMDS | Lithium bis(trimethylsilyl)amide (also known as lithium hexamethyldisilazide) |
| MTBE | tert-butyl-methylether |
| NMP | N-Methylpyrrolidone |
| $P_2S_5$ | Phosphorus pentasulfide |
| Pd(PPh$_3$)$_4$ | Tetrakis(triphenylphosphine)palladium(0) |
| PdCl$_2$(dppf)*dcm | 1,1'-Bis(diphenylphosphino)ferrocene-palladium(II)dichloride dichloromethane complex |
| TEA | triethylamine |
| TFA | Trifluoroacetic acid |
| THF | Tetrahydrofuran |
| X-PHOS | dicyclohexyl[2',4',6'-tris(1-methylethyl)[1,1'-biphenyl]-2-yl]-phosphine |

Example A

Phospho PDGFR Cell Assay

Compounds were screened for inhibition of PDGFR beta phosphorylation in the HS27 human fibroblast cell line. Cells were seeded into a 96 well tissue culture plate, then incubated overnight in a 37° C., 5% $CO_2$ incubator. The following day, cells were treated for one hour with test compound dilutions. After stimulation with PDGF-BB ligand for 5 minutes, cells were lysed and added to a sandwich ELISA plate from R&D Systems to detect levels of phospho PDGFR beta. A standard 4-parameter logistic model was fit to the inhibitor dose response curves, with the $IC_{50}$ being defined as the concentration of inhibitor giving 50 percent of control (POC).

Example B

Phospho PDGFR LICOR Cell Assay

Compounds were screened for inhibition of PDGFR beta phosphorylation in the HS27 human fibroblast cell line. Cells were seeded into a 96 well tissue culture plate, then incubated overnight in a 37° C./5% $CO_2$ incubator. The following day, cells were treated for one hour with test compound dilutions. After stimulation with PDGF-BB ligand for 10 minutes, cells were washed with PBS and fixed in 3.7% formaldehyde in PBS for 10 minutes. This was followed by washing in PBS/0.2% Triton X-100 and permeabilizing in 100% MeOH for 10 minutes. Cells were incubated in blocking buffer for 1 hour. Antibodies to phosphorylated PDGFRβ and total ERK were added to the cells and incubated for 3 hours. After washing with PBS/0.2% Triton X-100, the cells were incubated with fluorescently-labeled secondary antibodies for an additional hour. Cells were then washed with PBS and analyzed for fluorescence at both wavelengths using the Odyssey Infrared Imaging System (LI-COR Biosciences). Phosphorylated PDGFR signal was normalized to total ERK signal. A standard 4-parameter logistic model was fit to the inhibitor dose response curves, with the $IC_{50}$ being defined as the concentration of inhibitor giving 50 percent of control (POC).

Example C cFMS Cell-Based Assay

The ability of compounds of Formula I to inhibit cFMS activation in cells was determined by the following assay. THP-1 cells (human acute monocytic leukemia cell line) were serum-starved for 4 hours prior to treatment with compounds of Formula I for 1 hour. The concentration of compounds of Formula I was varied over a 9-point, 3-fold dilution series with 5,000 nM typically being the highest dose. Cell culture and treatment were carried out in a humidified 37° C., 5% $CO_2$ incubator. Treated cells were stimulated with 250 ng/mL recombinant human MCSF for 1 minute to induce activation of cFMS. Cells were lysed in a manner which preserves phosphoproteins, and the lysate was analyzed by ELISA (R&D Systems, Human Phospho-M-CSF R DuoSet IC DYC3268), in which total cFMS protein in the lysate is captured and phosphotyrosine residues of cFMS are detected. A standard curve, made using purified phospho-M-CSF R protein, was used to quantify phospho-c-FMS in compound-treated wells. A standard 4-parameter logistic model was fit to the inhibitor dose response curves, with the $IC_{50}$ being defined as the concentration of inhibitor giving 50 percent of control (POC).

Example D c-KIT Cell-Based Assay

The ability of compounds of Formula I to inhibit c-KIT activation in cells was determined by the following assay. M-07e cells (human acute megakaryoblastic leukemia cell line) were serum-starved for 4 hours prior to treatment with compounds of Formula I for 1 hour. The concentration of compounds of Formula I was varied over a 9-point, 3-fold dilution series with 5,000 nM typically being the highest dose. Cell culture and treatment were carried out in a humidified 37° C., 5% $CO_2$ incubator. Treated cells were stimulated with 150 ng/ml recombinant human SCF for 4 minutes to induce activation of c-KIT. Cells were lysed in a manner which preserves phosphoproteins, and the lysate was analyzed by ELISA (R&D Systems, Human Phospho-SCF R DuoSet IC DYC3527), in which total c-KIT protein in the lysate is captured and phosphotyrosine residues of c-Kit are detected. A standard curve, made using purified phospho-SCF R protein, was used to quantify phospho-c-KIT in compound-treated wells. A standard 4-parameter logistic model was fit to the inhibitor dose response curves, with the $IC_{50}$ being defined as the concentration of inhibitor giving 50 percent of control (POC).

Table A provides averaged $IC_{50}$ values for compounds of Formula I when tested in the assays described in Examples A, B, C and/or D.

TABLE A

| Ex. # | PDGFR Cell LICOR $IC_{50}$ | PDGFR Cell ELISA $IC_{50}$ | cFMS Cell ELISA $IC_{50}$ | cKIT Cell ELISA $IC_{50}$ |
| --- | --- | --- | --- | --- |
| 1 | 12.9 | 29.7 | 16.1 | 53.3 |
| 2 | 23.7 | 9.4 | 27.7 | 41.1 |
| 3 | 10.0 | 137.8 | 70.4 | 176.1 |
| 4 | 10.7 | 27.9 | 29.4 | 81.6 |
| 5 | 22.0 | 20.5 | 27.9 | 82.8 |
| 6 | 6.3 | 33.5 | 40.9 | 57.0 |
| 7 | N/A | 40.9 | 20.8 | 43.7 |
| 8 | 32.6 | N/A | 33.6 | 122.1 |
| 9 | 166.2 | N/A | 21.2 | 142.7 |
| 10 | 40.8 | N/A | 25.3 | 141.1 |
| 11 | 46.5 | N/A | 26.2 | 156.9 |
| 12 | 44.0 | N/A | 11.4 | 50.4 |
| 13 | 11.3 | N/A | 12.9 | 76.3 |
| 14 | 36.6 | 37.7 | 20.6 | 96.4 |
| 15 | 46.2 | N/A | 12.0 | 60.6 |
| 16 | 103.0 | 28.1 | 13.9 | 34.8 |
| 17 | 312.6 | 85.0 | 11.0 | 54.2 |
| 18 | 673.8 | 59.9 | 10.2 | 81.8 |
| 19 | 247.0 | 43.2 | 9.4 | 39.1 |
| 20 | N/A | 55.9 | 10.8 | 76.1 |
| 21 | N/A | 123.5 | 12.0 | 46.6 |
| 22 | N/A | 17.6 | 6.7 | 5.2 |
| 23 | N/A | 238.7 | 21.1 | 65.7 |
| 24 | N/A | 14.1 | 6.8 | 6.4 |
| 25 | 18.0 | 41.8 | 23.8 | 51.4 |
| 26 | 63.2 | 29.6 | 13.7 | 27.9 |
| 27 | 72.6 | 69.5 | 13.8 | 36.2 |
| 28 | 9.9 | 5.9 | 14.0 | 35.5 |
| 29 | 44.1 | N/A | 28.6 | 161.5 |
| 30 | 17.4 | N/A | 17.6 | 65.3 |
| 31 | N/A | 335.1 | 101.5 | 67.1 |
| 32 | N/A | 66.5 | 24.2 | 42.4 |
| 33 | N/A | 65.8 | 41.5 | 22.6 |
| 34 | 1667 | 1000 | N/A | N/A |
| 35 | N/A | 430.7 | 19.4 | 923.6 |
| 36 | N/A | 65.6 | 12.0 | 118.9 |
| 37 | N/A | 101.7 | 52.4 | 62.0 |
| 38 | N/A | 252.9 | 15.4 | 336.8 |
| 39 | N/A | 68.0 | 35.7 | 187.6 |
| 40 | N/A | 37.2 | 55.8 | 95.0 |
| 41 | N/A | 19.6 | 97.1 | 87.2 |
| 42 | 4801 | 1000 | N/A | N/A |
| 43 | N/A | 84.5 | 23.4 | 58.9 |
| 44 | 794.5 | 115.5 | 22.7 | 63.4 |
| 45 | 113.4 | 347.4 | 13.4 | 165.5 |
| 46 | N/A | 21.4 | 22.4 | 42.5 |
| 47 | 6.5 | 74.9 | 15.9 | 48.5 |
| 48 | 47.7 | N/A | 13.3 | 45.1 |
| 49 | 9.7 | N/A | 11.8 | 53.5 |
| 50 | N/A | N/A | 5.8 | N/A |
| 51 | N/A | 394 | 9.9 | 687.3 |
| 52 | N/A | 1000 | 108.2 | 5000 |
| 53 | N/A | 1000 | 73.5 | 4584.5 |
| 54 | N/A | 290.6 | 8.8 | 386.9 |
| 55 | 305.1 | N/A | 40.1 | N/A |
| 56 | N/A | 1000 | 32.1 | 1161.6 |
| 57 | N/A | 657.5 | 40.2 | 1268.0 |
| 58 | 914.8 | N/A | 21.9 | 6874.1 |
| 59 | 19.3 | N/A | 19.4 | 1493.9 |
| 60 | 5000 | N/A | 35.6 | 4562.6 |
| 61 | 222.0 | N/A | 58.1 | 527.0 |
| 62 | N/A | 885.8 | 257.1 | 2446.1 |
| 63 | N/A | 1000 | 47.0 | 5000 |
| 64 | 94.1 | N/A | 9.7 | 1007.3 |
| 65 | 212.1 | N/A | 8.5 | 646.6 |
| 66 | 4.8 | 18.3 | 10.2 | 30.7 |
| 67 | 10.3 | N/A | 10.0 | 60.6 |
| 68 | 23.2 | N/A | 5.0 | 76.9 |
| 69 | N/A | N/A | 8.2 | N/A |
| 70 | N/A | 99.2 | 5.1 | 146.0 |
| 71 | N/A | 273.7 | 7.6 | 454.6 |
| 72 | 3163.6 | N/A | 24.2 | 7013.7 |
| 73 | N/A | 1000 | 63.6 | 5000 |
| 74 | N/A | N/A | 79.5 | N/A |
| 75 | N/A | 1000 | 426.6 | 5000 |
| 76 | N/A | 1000 | 47.0 | 5000 |
| 77 | N/A | 1000 | 78.1 | 5000 |
| 78 | 3425.5 | N/A | 17.3 | 4069.4 |
| 79 | N/A | 1000 | 56.9 | 4324.1 |
| 80 | 174.0 | N/A | 8.2 | 5702.6 |
| 81 | 6444.4 | N/A | 135.9 | 4444.7 |
| 82 | N/A | 309.2 | 122.1 | 458.2 |
| 83 | N/A | 1000 | 537.9 | 5000 |
| 84 | N/A | 1000 | 734.0 | 5000 |
| 85 | 401.2 | N/A | 10.4 | 303.0 |
| 86 | 116.8 | N/A | 7.0 | 313.7 |
| 87 | 77.7 | N/A | 4.9 | 371.6 |
| 88 | 180.1 | N/A | 15.6 | 510.3 |
| 89 | 844.9 | N/A | 7.3 | 1047.5 |
| 90 | 5.0 | N/A | 9.8 | 25.8 |
| 91 | 10.9 | 22.2 | 4.4 | 30.1 |
| 92 | N/A | 137.3 | 26.0 | 204.9 |
| 93 | 6.0 | N/A | 842.3 | 6.4 |
| 94 | 65.0 | N/A | 46.9 | 94.8 |
| 95 | 74.3 | N/A | 31.4 | 78.2 |
| 96 | 14.6 | N/A | 115.0 | 3.8 |
| 97 | 9.6 | N/A | 10.4 | 25.7 |
| 98 | 5.7 | N/A | 26.3 | 4.9 |
| 99 | 6.4 | N/A | 5.6 | 11.4 |
| 100 | 6.0 | N/A | 23.6 | 3.3 |
| 101 | 23.7 | N/A | 43.6 | 30.5 |
| 102 | 17.6 | N/A | 26.0 | 94.9 |
| 103 | 2.7 | N/A | 7.3 | 7.2 |
| 104 | 78.4 | N/A | 33.7 | 397.8 |
| 105 | 2.6 | N/A | 3.3 | 2.7 |
| 106 | 557.9 | N/A | 158.5 | 747.7 |
| 107 | 158.3 | N/A | 44.8 | 123.2 |
| 108 | 142.1 | N/A | 66.7 | 181.2 |
| 109 | N/A | 26.3 | 10.5 | 8.4 |
| 110 | 1000 | N/A | 379.7 | 168.5 |
| 111 | 449.0 | N/A | 149.8 | 451.4 |

TABLE A-continued

| Ex. # | PDGFR Cell LICOR $IC_{50}$ | PDGFR Cell ELISA $IC_{50}$ | cFMS Cell ELISA $IC_{50}$ | cKIT Cell ELISA $IC_{50}$ |
|---|---|---|---|---|
| 112 | 16.7 | N/A | 33.7 | 68.9 |
| 113 | 289.1 | N/A | 120.6 | 331.4 |
| 114 | 9.3 | N/A | 24.6 | 8.7 |
| 115 | 6.8 | N/A | 24.1 | 13.4 |
| 116 | 54.0 | N/A | 184.8 | 191.7 |
| 117 | N/A | 54.8 | 167.9 | 124.6 |
| 118 | 177.6 | N/A | 309.5 | 580.9 |
| 119 | 17.4 | N/A | 26.3 | 23.0 |
| 120 | 7.7 | N/A | 34.4 | 14.5 |
| 121 | 13.3 | N/A | 20.9 | 73.1 |
| 122 | 49.5 | N/A | 131.2 | 60.9 |
| 123 | N/A | 161.9 | 378.5 | 255.0 |
| 124 | 6.9 | N/A | 8.3 | 9.5 |
| 125 | 2.1 | N/A | 12.5 | 19.8 |
| 126 | 34.5 | N/A | 27.4 | 22.2 |
| 127 | 1.7 | N/A | 14.9 | 67.8 |
| 128 | N/A | N/A | 130.9 | N/A |
| 129 | 117.5 | N/A | 80.0 | 123.6 |
| 130 | 114.0 | N/A | 441.9 | N/A |
| 131 | 681.8 | N/A | 992.6 | 5000 |
| 132 | 170.0 | N/A | 134.4 | 603.6 |
| 133 | 1000 | N/A | 99.1 | N/A |
| 134 | 2.4 | N/A | 3.1 | 11.0 |
| 135 | 362.1 | N/A | 228.0 | 395.6 |
| 136 | 1000 | N/A | 20.7 | 54.1 |
| 137 | 2.0 | N/A | 3.1 | 3.1 |
| 138 | 1.9 | N/A | 8.5 | 3.9 |
| 139 | 1.3 | N/A | 10.6 | 7.9 |
| 140 | 2.5 | N/A | 3.1 | 4.8 |
| 141 | 1.6 | N/A | 4.4 | 3.7 |
| 142 | 14.2 | N/A | 6.9 | 6.1 |
| 143 | 12.0 | N/A | 4.8 | 58.9 |
| 144 | 21.9 | N/A | 57.8 | 36.5 |
| 145 | 13.0 | N/A | 20.5 | 55.9 |
| 146 | 109.4 | N/A | 58.2 | 36.9 |
| 147 | 399.2 | N/A | 72.6 | 93.1 |
| 148 | 993.9 | N/A | 93.1 | 188.8 |
| 149 | 1.0 | N/A | 2.2 | 4.8 |
| 150 | 1.7 | N/A | 4.6 | 14.4 |
| 151 | 9.0 | N/A | 44.8 | 37.3 |
| 152 | 296.3 | N/A | 117.5 | 164.7 |
| 153 | 5.0 | N/A | 14.8 | 9.5 |
| 154 | 186.4 | N/A | 142.7 | 150.3 |
| 155 | N/A | 282.1 | 113.8 | 76.2 |
| 156 | 5.7 | N/A | 5.7 | 12.5 |
| 157 | N/A | 275.1 | 104.5 | 232.5 |
| 158 | 2403.1 | N/A | 534.8 | 2102.3 |
| 159 | 64.3 | N/A | 26.6 | 9.8 |
| 160 | 713.5 | N/A | 132.3 | 867.6 |
| 161 | N/A | 236.4 | 58.9 | 43.1 |

N/A = Not available

Preparation of Synthetic Intermediates

Preparation A

Ethyl 7-(2-(4-methylpiperazin-1-yl)ethoxy)imidazo[1,2-a]pyridine-3-carboxylate

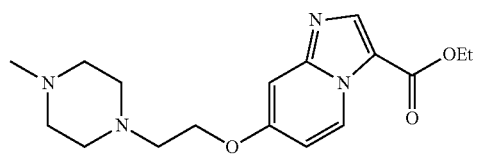 [SMILES: CCOC(=O)c1cnc2cc(OCCN3CCN(C)CC3)ccn12]

Step A: Preparation of 4-(2-(4-Methylpiperazin-1-yl)ethoxy)pyridin-2-amine

Sodium hydride (60% in mineral oil; 43.56 g; 1089 mmol) was added to a 3 L reaction flask under nitrogen. A mechanical stirrer and thermocouple was attached. Dry diglyme (400 mL) was added. A solution of 2-(4-methylpiperazin-1-yl)ethanol (157 g; 1089 mmol) in diglyme (450 mL) was added slowly with stirring. The mixture was stirred with warming to 40° C. for 1 hour. 4-Chloropyridin-2-amine (70.0 g; 544.5 mmol) was added as a solid. The mixture was heated to 80° C. with stirring until effervescence had ceased. The temperature was increased to 157° C. for 16 hours. The mixture was allowed to cool and diluted with water (500 mL). THF (1000 mL) was added followed by sodium chloride (sufficient to saturate the aqueous phase). The phases were separated and the aqueous phase was further extracted with THF (3×800 mL). Additional water was added as required to aid in phase separation. The combined organic phases were dried with sodium sulfate (1000 g) for 16 hours and filtered. The solvent was removed under vacuum to remove the majority of the THF. The solution was filtered through Celite to remove fine particulates rinsing with diglyme. The diglyme was removed under vacuum (10 mm Hg vacuum, with the bath temperature increased to 60° C.). The residue was placed under high vacuum for 1 hour and then triturated with ether (400 mL). The resulting solids were collected by filtration, washed with ether and dried under vacuum to give the product (100.4 g) as an off white solid.

Step B: Preparation of 4-(2-(4-Methylpiperazin-1-yl)ethoxy)pyridin-2-amine

Potassium 2-Chloro-3-ethoxy-3-oxoprop-1-en-1-olate (120 g, 635 mmol) was suspended (through vigorous magnetic stirring) in 1800 mL of ether and 6N sulfuric acid (53 mL, 317 mmol) was added slowly. The lower aqueous suspension was sampled periodically for acidity. Additional water (100 mL) was added to aid in phase separation. When the pH of the lower (aqueous) phase dropped below 3, the ether phase was separated. The aqueous phase was further extracted with ether (200 mL). The combined ether phases were dried over sodium sulfate and magnesium sulfate for 10 minutes. The solution was filtered and concentrated under reduced pressure, with the temperature not exceeding 20° C. An off-white semi-solid (100 g) was obtained. This was dissolved in absolute ethanol (800 mL). 4-(2-(4-Methylpiperazin-1-yl)ethoxy)pyridin-2-amine (Preparation C; 75 g, 317 mmol) was added, and the mixture was heated under nitrogen at 65° C. for 18 hours. The mixture was cooled to ambient temperature and the resulting suspension was evaporated to dryness under reduced pressure. The resulting solids were triturated with THF, collected by filtration and then dried under vacuum. The material (an HCl salt) was mixed with water (1 L) and ethanol (500 mL). Sodium bicarbonate (50 g) was added and the mixture was stirred for 18 hours. The suspension was evaporated to dryness under vacuum. The solids were extracted with a large volume of ethyl acetate (4 L) and THF (1 L) until no further product was extracted. The organic solution was further dried with sodium sulfate and magnesium sulfate, filtered and concentrated under vacuum to give a solid. The material was triturated with ether (500 mL) and the solids were collected by filtration and dried under vacuum to afford the desired product (86.2 g) as an off-white solid.

Preparation B

Potassium (E)-2-chloro-3-ethoxy-3-oxoprop-1-en-1-olate

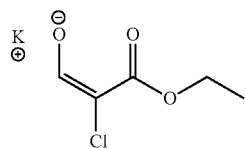

A mixture of ethyl 2-chloroacetate (220.8 g; 1802 mmol) and ethyl formate (133.5 g; 1802 mmol) was added slowly to a suspension of potassium t-butoxide (202.2 g; 1802 mmol) in diisopropyl ether (2000 mL) at 0° C. (maintaining the temperature<20° C.) with mechanical stirring. The mixture was stirred at ambient temperature for 24 hours. The solids were collected by filtration and washed with diisopropyl ether (500 mL) and acetonitrile (2×1500 mL). The material was dried under vacuum to give the product (270 g) which was used without further purification.

Preparation C ethyl 6-isopropylpicolinate

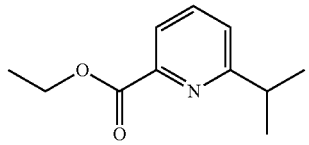

Step A: Preparation of tert-butyl 4-fluoropyridin-2-ylcarbamate

A flask was charged with 2-chloro-4-fluoropyridine (20 g, 152 mmol), tert-butyl carbamate (89 g, 760 mmol), tris(dibenzylideneacetone)dipalladium (1.39 g, 1.52 mmol), X-PHOS (1.48 g, 3.10 mmol), cesium carbonate (99 g, 588 mmol), and tetrahydrofuran (500 mL) under an atmosphere of dry nitrogen. The mixture was heated at reflux under nitrogen for 7 hours. A further 1 equivalent of cesium carbonate was added and the reaction was heated a further 7 hours. The mixture was cooled to ambient temperature, filtered through Celite and washed with ethyl acetate. The filtrate was partitioned between saturated sodium bicarbonate and ethyl acetate. The aqueous phase was extracted twice with ethyl acetate. The combined organic phases were washed with brine and dried with sodium sulfate, concentrated under vacuum, and purified by column chromatography to give tert-butyl 4-fluoropyridin-2-ylcarbamate as a pale yellow solid (22.6 g).

Step B: Preparation of 4-fluoropyridin-2-amine

A flask was charged with tert-butyl 4-fluoropyridin-2-ylcarbamate (3.5 g, 16.5 mmol) and dichloromethane (100 mL). The mixture was cooled to 0-5° C. using an ice/water bath. Trifluoroacetic acid (75 mL) was added slowly with continued stirring. The mixture was stirred at ambient temperature for 16 hours. The mixture was concentrated under vacuum before partitioning between saturated sodium bicarbonate and ethyl acetate. The aqueous layer was washed with ethyl acetate twice. The combined organic phases were washed with brine and dried with sodium sulfate before concentrating under vacuum to give 4-fluoropyridin-2-amine as a pale yellow solid (1.76 g).

Step C: Preparation of ethyl 7-fluoroimidazo[1,2-a]pyridine-3-carboxylate

4-Fluoropyridin-2-amine (10.0 g, 48.0 mmol) was mixed with ethanol (40 mL) in a reaction flask, under an atmosphere of dry nitrogen. A solution of ethyl 2-chloro-3-oxopropanoate (5% in benzene, 178 mL (commercial solution from Toronto Research Chemicals Inc.) was added. The mixture was heated to 60° C. under nitrogen for 4 hours. After allowing the mixture to cool the solvent was removed under vacuum to give a brown solid. The solid was mixed with ethyl acetate (300 mL) and sodium bicarbonate solution (75 mL) and stirred to dissolve. The phases were separated and the bicarbonate solution was extracted further with ethyl acetate (75 mL). The combined ethyl acetate extracts were dried over sodium sulfate, filtered and concentrated under vacuum to give a solid. The crude material was dissolved in ethyl acetate and passed through a short column of silica, eluting with ethyl acetate. Factions containing the desired product were concentrated to give ethyl 7-fluoroimidazo[1,2-a]pyridine-3-carboxylate as a white solid (13 g).

Step D: Preparation of ethyl 6-chloropicolinate

A flask equipped with a condenser was charged with 6-chloropicolinic acid (23.5 g, 149 mmol), 100 mL of ethanol and 400 mL of toluene. To this was added 4 mL of sulfuric acid and the mixture was warmed to reflux for three hours, and then allowed to cool to ambient temperature. The reaction mixture was concentrated under reduced pressure and the resulting oil was taken up in 200 mL of ethyl acetate, washed with 10% aqueous potassium carbonate, dried over sodium sulfate and concentrated under reduced pressure to give 26 g of ethyl 6-chloropicolinate (94%).

Step E: Preparation of ethyl 6-(prop-1-en-2-yl)picolinate

A first flask was charged with 1,4-dioxane/$H_2O$ (50 mL/10 mL). The flask was cooled to 0° C. and vacuum was applied for 20 minutes. A second flask was charged with ethyl 6-chloropicolinate (4.200 g, 22.63 mmol), potassium trifluoro(prop-1-en-2-yl)borate (4.353 g, 29.42 mmol), potassium carbonate (4.378 g, 31.68 mmol), diacetoxypalladium (0.1524 g, 0.6789 mmol) and sodium 2'-(dicyclohexylphosphino)-2,6-dimethoxybiphenyl-3-sulfonate (0.6959 g, 1.358 mmol). The second flask was also evacuated with vacuum and back filled with $N_2$ for 3 times. The cold degassed dioxane/$H_2O$ was then added to the second flask, which was evacuated with vacuum and back filled with argon 5 times. The reaction mixture was heated to 80° C. for 3 hours. The reaction was cooled to ambient temperature and concentrated under reduced pressure. The residue was then diluted with EtOAc (200 mL). The organic layer was washed with saturated $NaHCO_3$, dried ($Na_2SO_4$) and concentrated to give a quantitative yield of ethyl 6-(prop-1-en-2-yl)picolinate, which was used in the next step without further purification.

Step F: Preparation of ethyl 6-isopropylpicolinate

To ethyl 6-(prop-1-en-2-yl)picolinate (4.63 g, 24.2 mmol) in EtOH (50 mL) was added Pd/C (0.61 g, 0.573 mmol). The reaction mixture was purged with nitrogen three times and then with hydrogen three times. A hydrogen balloon was applied to the reaction for three hours. The reaction was then purged with $N_2$, filtered through Celite and washed with EtOH (100 mL). Solvent was removed under reduced pressure to give 4.36 g (93%) of ethyl 6-isopropylpicolinate.

Preparation D 1-((6-isopropylpyridin-2-yl)methyl)-3-methyl-1H-indazol-4-amine

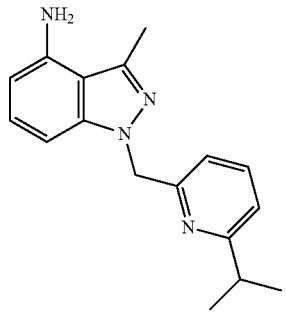 [SMILES: Cc1nn(Cc2cccc(C(C)C)n2)c2cccc(N)c12]

Step A: Preparation of (6-isopropylpyridin-2-yl)methanol

Ethyl 6-isopropylpicolinate (prepared as in Preparation C; 75 g, 0.39 mol) was dissolved in 1.5 liters of dry THF, chilled to 0° C. and lithium aluminum hydride (0.39 L, 0.39 mol, 1M in THF) was added slowly over a 20 minute period. The resulting dark solution was stirred at 0° C. for 30 minutes, then allowed to warm to ambient temperature. TLC showed complete consumption of starting material. The reaction mixture was chilled to 0° C. and quenched carefully by the addition of sodium sulfate decahydrate until no gas evolution was observed. A thick mixture resulted. Celite and ether (about 200 mL) were added and the reaction mixture was filtered. The filtrate was concentrated under reduced pressure to give 32 g of brown oil. The filter cake was slurried in IPA/EtOAc overnight and filtered to give an additional 8 g of product (68%).

Step B: Preparation of 2-(chloromethyl)-6-isopropylpyridine hydrochloride

6-Isopropylpyridin-2-yl)methanol (40 g, 0.265 mol) was dissolved in 500 mL of dry dichloromethane and chilled to 0° C. To this was added thionyl chloride (37.8 g, 0.317 mol) and the mixture was stirred for one hour. The reaction mixture was then concentrated under reduced pressure to give a quantitative yield of 2-(chloromethyl)-6-isopropylpyridine hydrochloride.

Step C: Preparation of 3-bromo-4-nitro-1H-indazole

To a flask equipped with a mechanical stirrer was added sodium acetate (26.4 g, 0.306 mol), 4-nitro-1H-indazole (50 g, 0.306 mol), 300 mL of acetic acid and 300 mL of chloroform. Bromine (51.4 g, 0.322 mol) in 60 mL of acetic acid was added to the reaction mixture over 3.5 hours, while the temperature was kept under 25° C. The reaction mixture was stirred for two hours, then concentrated under reduced pressure. Water (500 mL) was added to the resulting solids. The solids were collected by filtration, washed with 500 mL of water, and dried under vacuum to give 68 g (92%) of 3-bromo-4-nitro-1H-indazole.

Step D: Preparation of 3-bromo-1-((6-isopropylpyridin-2-yl)methyl)-4-nitro-1H-indazole A flask was charged with 3-bromo-4-nitro-1H-indazole (64 g, 0.264 mol), 2-(chloromethyl)-6-isopropylpyridine hydrochloride (55 g, 0.264 mol), powdered potassium carbonate (91 g, 0.661 mol), and 500 mL of DMF. This mixture was warmed to 35° C. for 72 hours, then poured into 2 liters of cold water, upon which a tan solid precipitated. After stirring for 20 minutes, the solids were collected by filtration and dried under vacuum to give 91 g (92%) of 3-bromo-1-((6-isopropylpyridin-2-yl)methyl)-4-nitro-1H-indazole.

Step E: Preparation of 1-((6-isopropylpyridin-2-yl)methyl)-3-methyl-4-nitro-1H-indazole A 3 liter heavy walled reaction flask was charged with dioxane (1 liter), 3-bromo-1-((6-isopropylpyridin-2-yl)methyl)-4-nitro-1H-indazole (90 g, 0.24 mol), methyl boronic acid (72 g, 1.20 mol), $Pd(PPh_3)_4$ (9.7 g, 0.0084 mol), potassium carbonate (99.5 g, 0.719 mol), followed by 200 mL of water. This mixture was purged with argon for 10 minutes, flask sealed and heated to 120° C. for 16 hours. Another 1.5 mol % of $Pd(PPh_3)_4$ was added followed by another 2 equivalents of methyl boronic acid, and the mixture warmed to 120° C. for 24 hours. The mixture was diluted with water and extracted with EtOAc. The combined organic extracts were dried over sodium sulfate and concentrated. Column chromatography (5% ethyl acetate/hexane to 10% ethyl acetate/hexane) gave 54 g (73%) of 1-((6-isopropylpyridin-2-yl)methyl)-3-methyl-4-nitro-1H-indazole as an orange/yellow solid.

Step F: Preparation of 1-((6-isopropylpyridin-2-yl)methyl)-3-methyl-1H-indazol-4-amine A flask equipped with an overhead stirrer and condenser was charged with 1-((6-isopropylpyridin-2-yl)methyl)-3-methyl-4-nitro-1H-indazole (25 g, 0.081 mol) and 150 mL of ethanol, followed by 45 g (0.805 mol) of iron powder. An equal amount of saturated ammonium chloride solution was added and the mixture was brought to 80° C. After 5 hours of heating, the mixture was allowed to cool to ambient temperature, diluted with water (500 mL) and filtered through GF/F filter paper multiple times to remove the iron and iron salts. The filtrate was extracted with EtOAc, dried over sodium sulfate and concentrated under reduced pressure. Column chromatography (1:1 ethyl acetate/hexane to 100% ethyl acetate) afforded 12.6 g (56%) of 1-((6-isopropylpyridin-2-yl)methyl)-3-methyl-1H-indazol-4-amine.

EXAMPLES

Example 1

N-(1-((6-isopropylpyridin-2-yl)methyl)-3-methyl-1H-indazol-4-yl)-7-(2-morpholinoethoxy)imidazo[1,2-a]pyridine-3-carboxamide

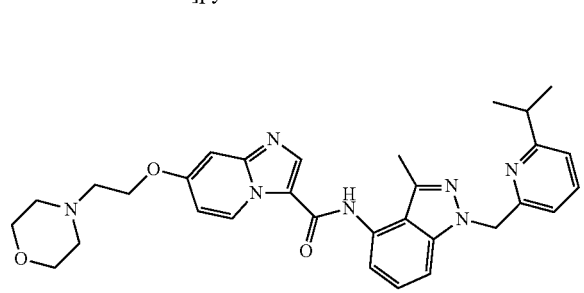

Step A: Preparation of 7-fluoro-N-(1-((6-isopropylpyridin-2-yl)methyl)-3-methyl-1H-indazol-4-yl)imidazo[1,2-a]pyridine-3-carboxamide 1-((6-Isopropylpyridin-2-yl)methyl)-3-methyl-1H-indazol-4-amine (Preparation D; 0.673 g, 2.40 mmol) and ethyl 7-fluoroimidazo[1,2-a]pyridine-3-carboxylate (Step C, 0.500 g, 2.40 mmol) were dissolved in dry THF (24 mL) and chilled to 0° C. LiHMDS (5.28 mL, 5.28 mmol, 1M in THF) was added by syringe over a five-minute period. Once the addition was complete, the reaction mixture was removed from the cooling bath and allowed to warm to ambient temperature. The mixture was quenched with saturated ammonium chloride solution and extracted with EtOAc. The combined organic extracts were washed with saturated sodium bicarbonate solution, dried over sodium sulfate and concentrated. The crude material was purified by column chromatography (100% ethyl acetate) to afford 775 mg (73%) of 7-fluoro-N-(1-((6-isopropylpyridin-2-yl)methyl)-3-methyl-1H-indazol-4-yl)imidazo[1,2-a]pyridine-3-carboxamide.

Step B: Preparation of N-(1-((6-isopropylpyridin-2-yl)methyl)-3-methyl-1H-indazol-4-yl)-7-(2-morpholinoethoxy)imidazo[1,2-a]pyridine-3-carboxamide 7-Fluoro-N-(1-((6-isopropylpyridin-2-yl)methyl)-3-methyl-1H-indazol-4-yl)imidazo[1,2-a]pyridine-3-carboxamide (0.250 g, 0.565 mmol), 2-morpholinoethanol (0.371 g, 2.82 mmol), and potassium t-butoxide were combined in t-BuOH in a reaction tube. The tube was sealed and heated to 95° C. for 16 hours. After cooling to ambient temperature, the mixture was diluted with water and extracted with EtOAc. The combined organic extracts were with 10% aqueous potassium carbonate, dried over sodium sulfate, and concentrated. The resulting crude product was triturated with ether to give 165 mg (53%) of N-(1-((6-isopropylpyridin-2-yl)methyl)-3-methyl-1H-indazol-4-yl)-7-(2-morpholinoethoxy)imidazo[1,2-a]pyridine-3-carboxamide as a tan solid. MS (APCI), positive scan, m/z=554.1 (M+H).

Example 2

7-(2-(4-Ethylpiperazin-1-yl)ethoxy)-N-(1-((6-isopropylpyridin-2-yl)methyl)-3-methyl-1H-indazol-4-yl)imidazo[1,2-a]pyridine-3-carboxamide

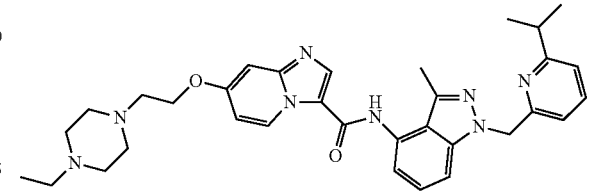

Step A: Preparation of 2-(4-ethylpiperazin-1-yl)ethanol

1-Ethylpiperazine (5.0 g, 43.8 mmol) was dissolved in 90 mL of acetonitrile, followed by the addition of powdered potassium carbonate (18.2 g, 131 mmol), and 2-bromoethanol (10.9 g, 87.6 mmol). This mixture was warmed to reflux for 16 hours, cooled to ambient temperature, and filtered. The filtrate was concentrated under reduced pressure and purified by column chromatography (10% MeOH/DCM/0.5% $NH_4OH$) to give 5.4 g (78%) of 2-(4-ethylpiperazin-1-yl)ethanol as a light yellow oil.

Step B: Preparation of 7-(2-(4-ethylpiperazin-1-yl)ethoxy)-N-(1-((6-isopropylpyridin-2-yl)methyl)-3-methyl-1H-indazol-4-yl)imidazo[1,2-a]pyridine-3-carboxamide Prepared as in Example 1, Step B, substituting 2-(4-ethylpiperazin-1-yl)ethanol for 2-morpholinoethanol, to give the title compound (22%). MS (APCI), positive scan, m/z=581.1 (M+H).

Example 3

7-(2-(2,6-diazaspiro[3.3]heptan-2-yl)ethoxy)-N-(1-((6-isopropylpyridin-2-yl)methyl)-3-methyl-1H-indazol-4-yl)imidazo[1,2-a]pyridine-3-carboxamide trihydrochloride

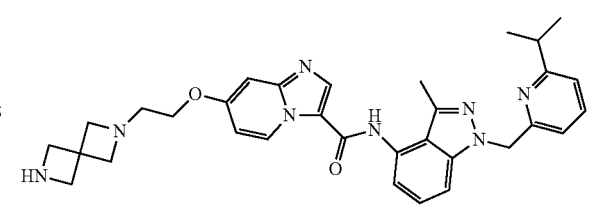

Step A: Preparation of tert-butyl 6-(2-hydroxyethyl)-2,6-diazaspiro[3.3]heptane-2-carboxylate Prepared as in Example 2, Step A, substituting tert-butyl 2,6-diazaspiro[3.3]heptane-2-carboxylate hemioxalate for 1-ethylpiperazine to give the title compound (36%).

Step B: Preparation of tert-butyl 6-(2-(3-(1-((6-isopropylpyridin-2-yl)methyl)-3-methyl-1H-indazol-4-ylcarbamoyl)imidazo[1,2-a]pyridin-7-yloxy)ethyl)-2,6-diazaspiro[3.3]heptane-2-carboxylate Prepared as in Example 1, Step B, substituting tert-butyl 6-(2-hydroxyethyl)-2,6-diazaspiro[3.3]heptane-2-carboxylate for 2-morpholinoethanol, to give 0.8 g (33%) of the title compound.

Step C: Preparation of 7-(2-(2,6-diazaspiro[3.3]heptan-2-yl)ethoxy)-N-(1-((6-isopropylpyridin-2-yl)methyl)-3-methyl-1H-indazol-4-yl)imidazo[1,2-a]pyridine-3-carboxamide trihydrochloride tert-Butyl 6-(2-(3-(1-((6-isopropylpyridin-2-yl)methyl)-3-methyl-1H-indazol-4-ylcarbamoyl)imidazo[1,2-a]pyridin-7-yloxy)ethyl)-2,6-diazaspiro[3.3]heptane-2-carboxylate (0.075 g, 0.113 mmol) was dissolved in 2 mL of 1:1 DCM/MeOH and 4M HCl/dioxane (0.282 mL, 1.13 mmol) was added. The mixture was stirred at ambient temperature for 4 hours, then concentrated under reduced pressure. The resulting residue was triturated with DCM and the solids were collected by filtration to give 57 mgs (75%) of the title compound. MS (APCI), positive scan, m/z=567.1 (M+H).

Example 4

N-(1-((6-isopropylpyridin-2-yl)methyl)-3-methyl-1H-indazol-4-yl)-7-(2-(6-methyl-2,6-diazaspiro[3.3]heptan-2-yl)ethoxy)imidazo[1,2-a]pyridine-3-carboxamide

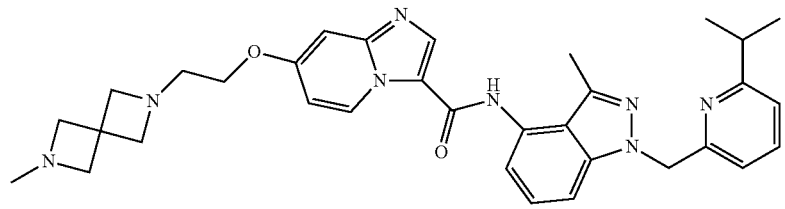 [SMILES: Cc1nn(Cc2cccc(C(C)C)n2)c2cccc(NC(=O)c3cnc4cc(OCCN5CC6(CN(C)C6)C5)ccn34)c12]

Step A: Preparation of 2-(6-methyl-2,6-diazaspiro[3.3]heptan-2-yl)ethanol tert-Butyl-6-(2-hydroxyethyl)-2,6-diazaspiro[3.3]heptane-2-carboxylate (0.620 g, 2.56 mmol) was dissolved in dry THF (13 mL) and chilled to 0° C. Lithium aluminum hydride (7.68 mL, 7.68 mmol, 1M in THF) was added by syringe. Once addition was complete, the mixture was brought to reflux for 16 hours. The reaction was cooled to 0° C., quenched with 291 µL of water, 291 µL of 15% aq. NaOH, and 873 µL of water, stirred vigorously for two hours, and then filtered. The filtrate was concentrated under reduced pressure to give 268 mgs (67%) of the title compound.

Step B: Preparation of N-(1-((6-isopropylpyridin-2-yl)methyl)-3-methyl-1H-indazol-4-yl)-7-(2-(6-methyl-2,6-diazaspiro[3.3]heptan-2-yl)ethoxy)imidazo[1,2-a]pyridine-3-carboxamide Prepared as in Example 1, Step B, substituting 2-(6-methyl-2,6-diazaspiro[3.3]heptan-2-yl)ethanol for 2-morpholinoethanol, to give the title compound (20%). MS (APCI), positive scan, m/z=580.6, 581.7 (M+H).

Example 5

7-(2-(2-oxa-6-azaspiro[3.3]heptan-6-yl)ethoxy)-N-(1-((6-isopropylpyridin-2-yl)methyl)-3-methyl-1H-indazol-4-yl)imidazo[1,2-a]pyridine-3-carboxamide

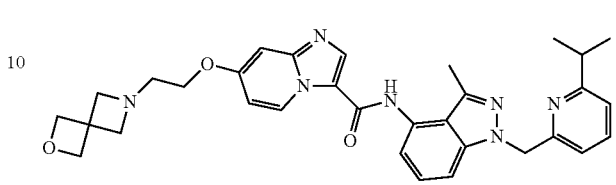

Step A: Preparation of 2-(2-oxa-6-azaspiro[3.3]heptan-6-yl)ethanol

Prepared as in Example 2, Step A, substituting 2-oxa-6-azaspiro[3.3]heptane oxalate for 1-ethylpiperazine to give the title compound (17%).

Step B: Preparation of 7-(2-(2-oxa-6-azaspiro[3.3]heptan-6-yl)ethoxy)-N-(1-((6-isopropylpyridin-2-yl)methyl)-3-methyl-1H-indazol-4-yl)imidazo[1,2-a]pyridine-3-carboxamide Prepared as in Example 1, Step B, substituting 2-(2-oxa-6-azaspiro[3.3]heptan-6-yl)ethanol for 2-morpholinoethanol, to give the title compound (50%). MS (APCI), positive scan, m/z=566.1 (M+H).

Example 6

7-(2-(4-Isopropylpiperazin-1-yl)ethoxy)-N-(1-((6-isopropylpyridin-2-yl)methyl)-3-methyl-1H-indazol-4-yl)imidazo[1,2-a]pyridine-3-carboxamide

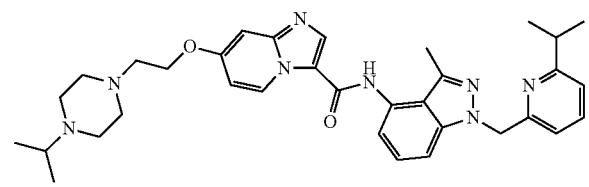 [SMILES: Cc1nn(Cc2cccc(C(C)C)n2)c2cccc(NC(=O)c3cnc4cc(OCCN5CCN(C(C)C)CC5)ccn34)c12]

Prepared as in Example 1, Step B, substituting 2-(4-isopropylpiperazin-1-yl)ethanol for 2-morpholinoethanol, to give the title compound (55%). MS (APCI), positive scan, m/z=595.2 (M+H).

Example 7

N-(1-((6-Isopropylpyridin-2-yl)methyl)-3-methyl-1H-indazol-4-yl)-7-(2-((3S,5R)-3,4,5-trimethylpiperazin-1-yl)ethoxy)imidazo[1,2-a]pyridine-3-carboxamide

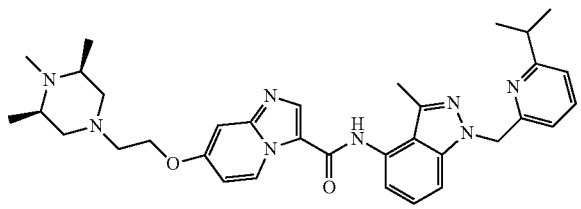 [SMILES: Cc1nn(Cc2cccc(C(C)C)n2)c2cccc(NC(=O)c3cnc4cc(OCCN5C[C@@H](C)N(C)[C@@H](C)C5)ccn34)c12]

Step A: Preparation of (3R,5S)-tert-butyl 3,4,5-trimethylpiperazine-1-carboxylate (3R,5S)-tert-Butyl 3,5-dimethylpiperazine-1-carboxylate (1.50 g, 7.00 mmol) was dissolved in 70 mL of methanol. To this was added 37% aqueous formaldehyde (1.17 mL, 14.0 mmol) and formic acid (1.14 mL, 24.5 mmol). The reaction mixture was heated to 70° C. for 24 hours, then concentrated under reduced pressure. The resulting oil was taken up in EtOAc, washed with 10% aqueous potassium carbonate, dried over sodium sulfate and concentrated to give 1.17 g (73%) of the title compound.

Step B: Preparation of (2S,6R)-1,2,6-trimethylpiperazine dihydrochloride (3R,5S)-tert-butyl 3,4,5-trimethylpiperazine-1-carboxylate (1.17 g, 5.12 mmol) was dissolved in 50 mL of EtOAc and chilled to 0° C. HCl gas was bubbled through the solution for 20 minutes, and then the reaction flask capped securely and the mixture stirred at ambient temperature for 16 hours. The excess HCl gas was purged from the mixture with a steady stream of nitrogen gas and the reaction mixture was concentrated under reduced pressure to give 1 g (97%) of the title compound.

Step C: Preparation of 2-((3R,5S)-3,4,5-trimethylpiperazin-1-yl)ethanol

Prepared according to Example 2, Step A, substituting (2S,6R)-1,2,6-trimethylpiperazine di-hydrochloride for 1-ethylpiperazine to give 0.856 g (100%) of the title compound.

Step D: Preparation of ethyl 7-chloroimidazo[1,2-a]pyridine-3-carboxylate

To a flask equipped with a reflux condenser, mechanical stirring, and internal temperature probe was added potassium 2-chloro-3-ethoxy-3-oxoprop-1-en-1-olate (58.70 g, 311.1 mmol) followed by 200 mL of EtOH. Aqueous hydrogen chloride (4.862 ml, 15.56 mmol) in EtOH was added to the slurry. The slurry was stirred for about 15 minutes, and then 4-chloropyridin-2-amine (20.00 g, 155.6 mmol) was added, and the mixture was warmed to 70° C. After about one hour, an additional 2 equivalents of 3.2 M aqueous HCl were added and the mixture stirred at 70° C. for 16 hours. An additional 30 g of potassium 2-chloro-3-ethoxy-3-oxoprop-1-en-1-olate were added and the mixture was stirred at 70° C. for 2 hours. The mixture was cooled to ambient temperature and 500 mL of water added, followed by pH adjustment to 11 with 10% aqueous sodium carbonate. After stirring for several hours, the precipitated solids were collected by filtration and dried under vacuum to give 31 g (88%) of the title compound.

Step E: Preparation of 7-chloro-N-(1-((6-isopropylpyridin-2-yl)methyl)-3-methyl-1H-indazol-4-yl)imidazo[1,2-a]pyridine-3-carboxamide Prepared according to Example 1, Step A, substituting ethyl 7-chloroimidazo[1,2-a]pyridine-3-carboxylate for ethyl 7-fluoroimidazo[1,2-a]pyridine-3-carboxylate to give the title compound (56%).

Step F: Preparation of N-(1-((6-isopropylpyridin-2-yl)methyl)-3-methyl-1H-indazol-4-yl)-7-(2-((3S,5R)-3,4,5-trimethylpiperazin-1-yl)ethoxy)imidazo[1,2-a]pyridine-3-carboxamide A pressure tube was charged with 7-chloro-N-(1-((6-isopropylpyridin-2-yl)methyl)-3-methyl-1H-indazol-4-yl)imidazo[1,2-a]pyridine-3-carboxamide (0.500 g, 1.09 mmol), 2-((3R,5S)-3,4,5-trimethylpiperazin-1-yl)ethanol (0.375 g, 2.18 mmol), crushed potassium hydroxide (0.306 g, 5.45 mmol) in 10 mL of DMSO. The tube was sealed and heated to 95° C. for 16 hours, then allowed to cool to ambient temperature. The mixture was diluted with water and extracted with EtOAc. The combined organic extracts were washed with brine, dried over sodium sulfate, and concentrated under reduced pressure. Column chromatography (10% MeOH/DCM/0.5% NH$_4$OH) followed by trituration with methyl t-butyl ether afforded 42 mgs (6%) of the title compound. MS (APCI), positive scan, m/z=595.1 (M+H).

Example 8

N-(1-((1-Isopropyl-5-methyl-1H-pyrazol-3-yl)methyl)-3-methyl-1H-indazol-4-yl)-7-(2-(6-methyl-2,6-diazaspiro[3.3]heptan-2-yl)ethoxy)imidazo[1,2-a]pyridine-3-carboxamide

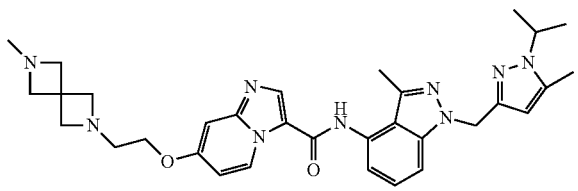

Step A: Preparation of ethyl 1-isopropyl-5-methyl-1H-pyrazole-3-carboxylate

To ethyl 2,4-dioxopentanoate (20.1 g, 127 mmol) in acetic acid (100 mL) at 0° C. was added isopropylhydrazine (9.42 g, 127 mmol) dropwise. The cold bath was removed and the reaction mixture was stirred for 2 hours. The reaction mixture was diluted with EtOAc/H$_2$O (300 mL/100 mL). The organic layer was washed with saturated NaHCO$_3$ aqueous solution (100 mL), H$_2$O (50 mL) and brine (50 mL). The organic layer was dried (Na$_2$SO$_4$) and concentrated. The residue was purified by silica gel flash chromatography (1:2 EtOAc/hexane) to give 7.8 g (31%) of the title compound.

Step B: Preparation of (1-isopropyl-5-methyl-1H-pyrazol-3-yl)methanol

To ethyl 1-isopropyl-5-methyl-1H-pyrazole-3-carboxylate (7.68 g, 39.1 mmol) in THF (50 mL) at 0° C. was added LAH (1.49 g, 39.1 mmol). The cold bath was removed, and the reaction mixture was stirred for 2 hours, and then quenched carefully with sodium sulfate decahydrate. The reaction mixture was filtered through Celite and washed with Et$_2$O. The filtrate was concentrated under reduced pressure to give 5.3 g (88%) of the title compound.

Step C: Preparation of 3-(chloromethyl)-1-isopropyl-5-methyl-1H-pyrazole hydrochloride Prepared according to Preparation D, Step B, substituting (1-isopropyl-5-methyl-1H-pyrazol-3-yl)methanol for isopropylpyridin-2-yl)methanol to give 7.1 g (99%) of the title compound.

Step D: Preparation of 3-bromo-1-((1-isopropyl-5-methyl-1H-pyrazol-3-yl)methyl)-4-nitro-1H-indazole Prepared according to Preparation D, Step D, substituting 3-(chloromethyl)-1-isopropyl-5-methyl-1H-pyrazole hydrochloride for 2-(chloromethyl)-6-isopropylpyridine hydrochloride to give 9.12 g (71%) of the title compound.

Step E: Preparation of 1-((1-isopropyl-5-methyl-1H-pyrazol-3-yl)methyl)-3-methyl-4-nitro-1H-indazole A flask was charged with 1,4-dioxane/H$_2$O (30 mL/5 mL). The flask was cooled to 0° C. and vacuum was applied for 20 minutes. A second flask was charged with 3-bromo-1-((1-isopropyl-5-methyl-1H-pyrazol-3-yl)methyl)-4-nitro-1H-indazole (1.95 g, 5.16 mmol), K$_2$CO$_3$ (2.85 g, 20.6 mmol), diacetoxypalladium (0.0579 g, 0.258 mmol), methylboronic acid (0.926 g, 15.5 mmol) and sodium 2'-(dicyclohexylphosphino)-2,6-dimethoxybiphenyl-3-sulfonate (0.264 g, 0.516 mmol). The second flask was evacuated with and back filled with nitrogen three times. The cold degassed dioxane/H$_2$O was added to the second flask, which was evacuated and back filled with argon 5 times. The reaction mixture was heated to 80° C. for 3 hours. The reaction was cooled to ambient temperature and filtered, and concentrated under reduced pressure. The residue was diluted with EtOAc (200 mL). The organic layer was washed with saturated NaHCO$_3$ (30 mL), dried (Na$_2$SO$_4$) and concentrated to give 1.34 g (83%) of the title compound, which was used in the next step without further purification.

Step F: Preparation of 1-((1-isopropyl-5-methyl-1H-pyrazol-3-yl)methyl)-3-methyl-1H-indazol-4-amine Prepared according to Preparation D, Step F, substituting 1-((1-isopropyl-5-methyl-1H-pyrazol-3-yl)methyl)-3-methyl-4-nitro-1H-indazole for 1-((6-isopropylpyridin-2-yl)methyl)-3-methyl-4-nitro-1H-indazole to give 0.86 g (72%) of the title compound.

Step G: Preparation of 7-fluoro-N-(1-((1-isopropyl-5-methyl-1H-pyrazol-3-yl)methyl)-3-methyl-1H-indazol-4-yl)imidazo[1,2-a]pyridine-3-carboxamide Prepared according to Example 1, Step A, substituting 1-((1-isopropyl-5-methyl-1H-pyrazol-3-yl)methyl)-3-methyl-1H-indazol-4-amine for 1-((6-isopropylpyridin-2-yl)methyl)-3-methyl-1H-indazol-4-amine, to give 0.245 g (60%) of the title compound.

Step H: Preparation of N-(1-((1-Isopropyl-5-methyl-1H-pyrazol-3-yl)methyl)-3-methyl-1H-indazol-4-yl)-7-(2-(6-methyl-2,6-diazaspiro[3.3]heptan-2-yl)ethoxy)imidazo[1,2-a]pyridine-3-carboxamide Prepared according Example 1, Step B, substituting 7-fluoro-N-(1-((1-isopropyl-5-methyl-1H-pyrazol-3-yl)methyl)-3-methyl-1H-indazol-4-yl)imidazo[1,2-a]pyridine-3-carboxamide for 7-fluoro-N-(1-((6-isopropylpyridin-2-yl)methyl)-3-methyl-1H-indazol-4-yl)imidazo[1,2-a]pyridine-3-carboxamide and 2-(6-methyl-2,6-diazaspiro[3.3]heptan-2-yl)ethanol for 2-morpholinoethanol to give 23 mg (25%) of the title compound. MS (APCI), positive scan, m/z=583.3 (M+H).

Example 9

N-(1-((1-isopropyl-5-methyl-1H-pyrazol-3-yl)methyl)-3-methyl-1H-indazol-4-yl)-7-(2-((3S,5R)-3,4,5-trimethylpiperazin-1-yl)ethoxy)imidazo[1,2-a]pyridine-3-carboxamide

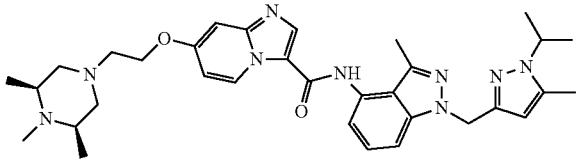

Prepared according Example 1, Step B, substituting 7-fluoro-N-(1-((1-isopropyl-5-methyl-1H-pyrazol-3-yl)methyl)-3-methyl-1H-indazol-4-yl)imidazo[1,2-a]pyridine-3-carboxamide (Example 8, Steps A-G) for 7-fluoro-N-(1-((6-isopropylpyridin-2-yl)methyl)-3-methyl-1H-indazol-4-yl)imidazo[1,2-a]pyridine-3-carboxamide and 2-((3R,5S)-3,4,5-trimethylpiperazin-1-yl)ethanol for 2-morpholinoethanol to give 11 mg (6%) of the title compound. MS (APCI), positive scan, m/z=598.2 (M+H).

Example 10

N-(1-((1-Isopropyl-5-methyl-1H-pyrazol-3-yl)methyl)-3-methyl-1H-indazol-4-yl)-7-(2-(4-isopropylpiperazin-1-yl)ethoxy)imidazo[1,2-a]pyridine-3-carboxamide

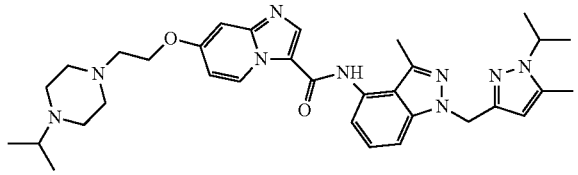 [SMILES: Cc1nn(Cc2cc(C)n(C(C)C)n2)c2cccc(NC(=O)c3cnc4cc(OCCN5CCN(C(C)C)CC5)ccn34)c12]

61

Prepared according Example 1, Step B, substituting 7-fluoro-N-(1-((1-isopropyl-5-methyl-1H-pyrazol-3-yl)methyl)-3-methyl-1H-indazol-4-yl)imidazo[1,2-a]pyridine-3-carboxamide (Example 8, Steps A-G) for 7-fluoro-N-(1-((6-isopropylpyridin-2-yl)methyl)-3-methyl-1H-indazol-4-yl)imidazo[1,2-a]pyridine-3-carboxamide and 2-(4-isopropylpiperazin-1-yl)ethanol for 2-morpholinoethanol to give 15 mg (11%) of the title compound. MS (APCI), positive scan, m/z=598.1 (M+H).

Example 11

N-(1-((1-isopropyl-5-methyl-1H-pyrazol-3-yl)methyl)-3-methyl-1H-indazol-4-yl)-7-(2-(4-methyl-1,4-diazepan-1-yl)ethoxy)imidazo[1,2-a]pyridine-3-carboxamide

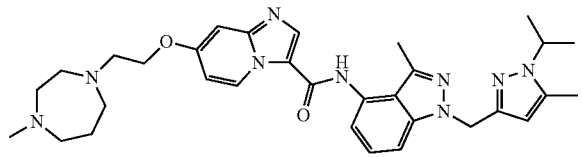

Step A: Preparation of tert-butyl 4-(2-hydroxyethyl)-1,4-diazepane-1-carboxylate Prepared according to Example 2, Step A, substituting tert-butyl 1,4-diazepane-1-carboxylate for 1-ethylpiperazine to give 0.845 g (46%) of the title compound.

Step B: Preparation of 2-(4-methyl-1,4-diazepan-1-yl)ethanol

Prepared according to Example 4, Step A, substituting tert-butyl 4-(2-hydroxyethyl)-1,4-diazepane-1-carboxylate for tert-Butyl 6-(2-hydroxyethyl)-2,6-diazaspiro[3.3]heptane-2-carboxylate to give 0.220 g (40%) of the title compound.

Step C: Preparation of N-(1-((1-isopropyl-5-methyl-1H-pyrazol-3-yl)methyl)-3-methyl-1H-indazol-4-yl)-7-(2-(4-methyl-1,4-diazepan-1-yl)ethoxy)imidazo[1,2-a]pyridine-3-carboxamide Prepared according Example 1, Step B, substituting 7-fluoro-N-(1-((1-isopropyl-5-methyl-1H-pyrazol-3-yl)methyl)-3-methyl-1H-indazol-4-yl)imidazo[1,2-a]pyridine-3-carboxamide (Example 8, Steps A-G) for 7-fluoro-N-(1-((6-isopropylpyridin-2-yl)methyl)-3-methyl-1H-indazol-4-yl)imidazo[1,2-a]pyridine-3-carboxamide and 2-(4-methyl-1,4-diazepan-1-yl)ethanol for 2-morpholinoethanol to give 18 mgs (11%) of the title compound. MS (APCI), positive scan, m/z=584.1 (M+H).

62

Example 12

N-(1-((2-isopropylthiazol-4-yl)methyl)-3-methyl-1H-indazol-4-yl)-7-(2-(4-methylpiperazin-1-yl)ethoxy)imidazo[1,2-a]pyridine-3-carboxamide

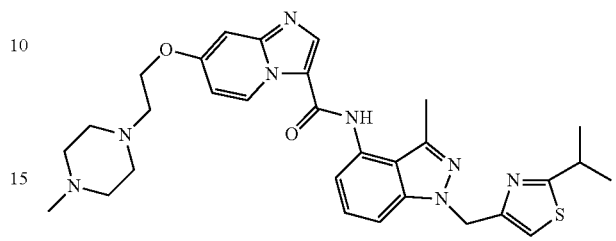

Step A: Preparation of 4-(chloromethyl)-2-isopropylthiazole hydrochloride

Prepared according to Preparation D, Step B, substituting (2-isopropylthiazol-4-yl)methanol for isopropylpyridin-2-yl)methanol to give (81%) of the title compound (81%).

Step B: Preparation of 4-((3-bromo-4-nitro-1H-indazol-1H-indazol-1-yl)methyl)-2-isopropylthiazole Prepared according to Preparation D, Step D, substituting 4-(chloromethyl)-2-isopropylthiazole hydrochloride for 2-(chloromethyl)-6-isopropylpyridine hydrochloride to give the final product (78%).

Step C: Preparation of 2-isopropyl-4-((3-methyl-4-nitro-1H-indazol-1-yl)methyl)thiazole Prepared according to Preparation D, Step E, substituting 4-((3-bromo-4-nitro-1H-indazol-1-yl)methyl)-2-isopropylthiazole for 3-bromo-1-((6-isopropylpyridin-2-yl)methyl)-4-nitro-1H-indazole to give the title compound (79%).

Step D: Preparation of 1-((2-isopropylthiazol-4-yl)methyl)-3-methyl-1H-indazol-4-amine Prepared according to Preparation D, Step F, substituting 2-isopropyl-4-((3-methyl-4-nitro-1H-indazol-1-yl)methyl)thiazole for 1-((6-isopropylpyridin-2-yl)methyl)-3-methyl-4-nitro-1H-indazole to give the title compound (76%).

Step E: Preparation of 7-fluoro-N-(1-((2-isopropylthiazol-4-yl)methyl)-3-methyl-1H-indazol-4-yl)imidazo[1,2-a]pyridine-3-carboxamide Prepared according to Example 1, Step A, substituting 1-((2-isopropylthiazol-4-yl)methyl)-3-methyl-1H-indazol-4-amine for 1-((6-isopropylpyridin-2-yl)methyl)-3-methyl-1H-indazol-4-amine, to give the title compound (53%).

Step F: Preparation of N-(1-((2-isopropylthiazol-4-yl)methyl)-3-methyl-1H-indazol-4-yl)-7-(2-(4-methylpiperazin-1-yl)ethoxy)imidazo[1,2-a]pyridine-3-carboxamide Prepared according Example 1, Step B, substituting 7-fluoro-N-(1-((2-isopropylthiazol-4-yl)methyl)-3-methyl-1H-indazol-4-yl) imidazo[1,2-a]pyridine-3-carboxamide (Example 12, Steps A-E) for 7-fluoro-N-(1-((6-isopropylpyridin-2-yl)methyl)-3-methyl-1H-indazol-4-yl)imidazo[1,2-a]pyridine-3-carboxamide and 2-(4-methyl-1,4-diazepan-1-yl)ethanol for 2-morpholinoethanol to give the title compound (78%). MS (APCI), positive scan, m/z=573.1 (M+H).

Example 13

N-(1-((2-isopropylthiazol-4-yl)methyl)-3-methyl-1H-indazol-4-yl)-7-(2-(6-methyl-2,6-diazaspiro[3.3]heptan-2-yl)ethoxy)imidazo[1,2-a]pyridine-3-carboxamide

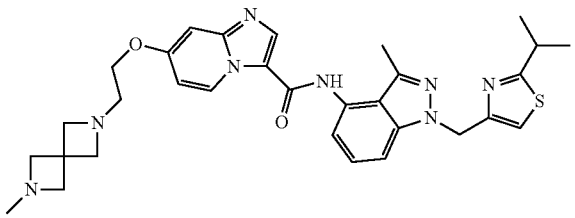 [SMILES: Cc1nn(Cc2csc(C(C)C)n2)c2cccc(NC(=O)c3cnc4cc(OCCN5CC6(CN(C)C6)C5)ccn34)c12]

Prepared according Example 1, Step B, substituting 7-fluoro-N-(1-((2-isopropylthiazol-4-yl)methyl)-3-methyl-1H-indazol-4-yl)imidazo[1,2-a]pyridine-3-carboxamide (Example 12, Steps A-E) for 7-fluoro-N-(1-((6-isopropylpyridin-2-yl)methyl)-3-methyl-1H-indazol-4-yl)imidazo[1,2-a]pyridine-3-carboxamide and 2-(6-methyl-2,6-diazaspiro[3.3]heptan-2-yl)ethanol (Example 4) for 2-morpholinoethanol to give the title compound (41%). MS (APCI), positive scan, m/z=585.1 (M+H).

Example 14

7-(2-(2-oxa-6-azaspiro[3.3]heptan-6-yl)ethoxy)-N-(1-((2-isopropylthiazol-4-yl)methyl)-3-methyl-1H-indazol-4-yl)imidazo[1,2-a]pyridine-3-carboxamide

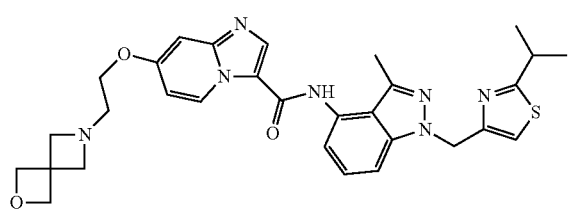 [SMILES: Cc1nn(Cc2csc(C(C)C)n2)c2cccc(NC(=O)c3cnc4cc(OCCN5CC6(COC6)C5)ccn34)c12]

Prepared according Example 1, Step B, substituting 7-fluoro-N-(1-((2-isopropylthiazol-4-yl)methyl)-3-methyl-1H-indazol-4-yl)imidazo[1,2-a]pyridine-3-carboxamide (Example 12, Steps A-E) for 7-fluoro-N-(1-((6-isopropylpyridin-2-yl)methyl)-3-methyl-1H-indazol-4-yl)imidazo[1,2-a]pyridine-3-carboxamide and 2-(2-oxa-6-azaspiro[3.3]heptan-6-yl)ethanol (Example 5) for 2-morpholinoethanol to give the title compound (53%). MS (APCI), positive scan, m/z=572.0 (M+H).

Example 15

7-(2-(4-isopropylpiperazin-1-yl)ethoxy)-N-(1-((2-isopropylthiazol-4-yl)methyl)-3-methyl-1H-indazol-4-yl)imidazo[1,2-a]pyridine-3-carboxamide

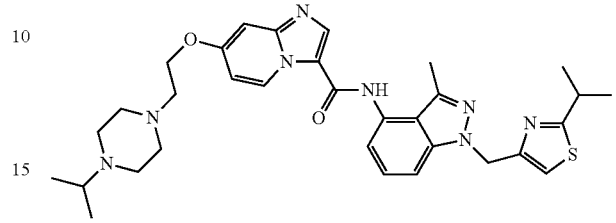

Prepared according Example 1, Step B, substituting 7-fluoro-N-(1-((2-isopropylthiazol-4-yl)methyl)-3-methyl-1H-indazol-4-yl)imidazo[1,2-a]pyridine-3-carboxamide (Example 12, Steps A-E) for 7-fluoro-N-(1-((6-isopropylpyridin-2-yl)methyl)-3-methyl-1H-indazol-4-yl)imidazo[1,2-a]pyridine-3-carboxamide and substituting 2-(4-isopropylpiperazin-1-yl)ethanol for 2-morpholinoethanol to give the title compound (68%). MS (APCI), positive scan, m/z=601.1 (M+H).

Example 16

N-(1-((6-cyclopropylpyridin-2-yl)methyl)-3-methyl-1H-indazol-4-yl)-7-(2-(4-isopropylpiperazin-1-yl)ethoxy)imidazo[1,2-a]pyridine-3-carboxamide

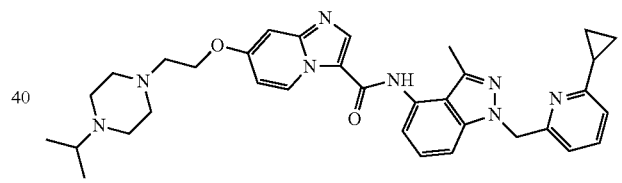

Step A: Preparation of 6-cyclopropylpicolinaldehyde

A flame dried flask was charged with dry THF (75 mL) and chilled to −78° C. To this was added n-BuLi (9.90 mL, 24.7 mmol, 2.5 M in hexanes), followed by the slow addition of a THF (25 mL) solution of the 2-bromo-6-cyclopropylpyridine (4.90 g, 24.7 mmol) over a 15 minute period). The mixture was stirred at −78° C. for 15 minutes, and neat DMF (2.87 mL, 37.1 mmol) was added. The mixture was stirred for 15 minutes at −78° C., then quenched with saturated ammonium chloride solution (50 mL) and allowed to warm to ambient temperature. The mixture was diluted with water, extracted with EtOAc, dried over sodium sulfate and concentrated to 3.5 g (96%) of an orange oil/liquid.

Step B: Preparation of (6-cyclopropylpyridin-2-yl)methanol

To 6-cyclopropylpicolinaldehyde (3.5 g, 23.8 mmol) in methanol (95 mL) chilled to 0° C. was added sodium borohydride (2.70 g, 37.8 mmol). Once addition was complete, the cooling bath was removed and the reaction mixture was allowed to warm to ambient temperature. The mixture was concentrated under reduced pressure and the resulting residue was taken up in water, extracted with EtOAc, dried over sodium sulfate and concentrated under reduced pressure. Column chromatography (100% EtOAc as the eluent) of the crude material afforded 2.20 g (62%) of the title compound.

Step C: Preparation of 2-(chloromethyl)-6-cyclopropylpyridine hydrochloride

Prepared according to Preparation D, Step B, substituting (6-cyclopropylpyridin-2-yl)methanol for 6-isopropylpyridin-2-yl)methanol, to give the title compound (100%).

Step D: Preparation of 3-bromo-1-((6-cyclopropylpyridin-2-yl)methyl)-4-nitro-1H-indazole Prepared according to Preparation D, Step D, substituting 2-(chloromethyl)-6-cyclopropylpyridine hydrochloride for 2-(chloromethyl)-6-isopropylpyridine hydrochloride to give the final product (87%).

Step E: Preparation of 1-((6-cyclopropylpyridin-2-yl)methyl)-3-methyl-4-nitro-1H-indazole Prepared according to Preparation D, Step E, substituting 3-bromo-1-((6-cyclopropylpyridin-2-yl)methyl)-4-nitro-1H-indazole (Example 16, Steps A-D) for 3-bromo-1-((6-isopropylpyridin-2-yl)methyl)-4-nitro-1H-indazole to give the title compound (70%).

Step F: Preparation of 1-((6-cyclopropylpyridin-2-yl)methyl)-3-methyl-1H-indazol-4-amine Prepared according to Preparation D, Step F, substituting 1-((6-cyclopropylpyridin-2-yl)methyl)-3-methyl-4-nitro-1H-indazole for 1-((6-isopropylpyridin-2-yl)methyl)-3-methyl-4-nitro-1H-indazole to give the title compound (70%).

Step G: Preparation of N-(1-((6-cyclopropylpyridin-2-yl)methyl)-3-methyl-1H-indazol-4-yl)-7-fluoroimidazo[1,2-a]pyridine-3-carboxamide Prepared according to Example 1, Step A, substituting 1-((6-cyclopropylpyridin-2-yl)methyl)-3-methyl-1H-indazol-4-amine for 1-((6-isopropylpyridin-2-yl)methyl)-3-methyl-1H-indazol-4-amine, to give the title compound (83%).

Step H: Preparation of N-(1-((6-cyclopropylpyridin-2-yl)methyl)-3-methyl-1H-indazol-4-yl)-7-(2-(4-isopropylpiperazin-1-yl)ethoxy)imidazo[1,2-a]pyridine-3-carboxamide Prepared according Example 1, Step B, substituting N-(1-((6-cyclopropylpyridin-2-yl)methyl)-3-methyl-1H-indazol-4-yl)-7-fluoroimidazo[1,2-a]pyridine-3-carboxamide for 7-fluoro-N-(1-((6-isopropylpyridin-2-yl)methyl)-3-methyl-1H-indazol-4-yl)imidazo[1,2-a]pyridine-3-carboxamide and substituting 2-(4-isopropylpiperazin-1-yl)ethanol for 2-morpholinoethanol to give the title compound (48%). MS (APCI), positive scan, m/z=593.8 (M+H).

Example 17

N-(1-((6-cyclopropylpyridin-2-yl)methyl)-3-methyl-1H-indazol-4-yl)-7-(2-(4-ethylpiperazin-1-yl)ethoxy)imidazo[1,2-a]pyridine-3-carboxamide

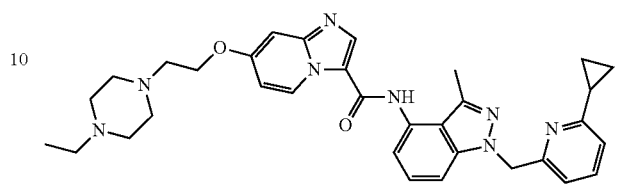

Prepared according Example 1, Step B, substituting N-(1-((6-cyclopropylpyridin-2-yl)methyl)-3-methyl-1H-indazol-4-yl)-7-fluoroimidazo[1,2-a]pyridine-3-carboxamide (Example 16, Steps A-G) for 7-fluoro-N-(1-((6-isopropylpyridin-2-yl)methyl)-3-methyl-1H-indazol-4-yl)imidazo[1,2-a]pyridine-3-carboxamide and substituting 2-(4-ethylpiperazin-1-yl)ethanol for 2-morpholinoethanol to give the title compound (8%). MS (APCI), positive scan, m/z=579.1 (M+H).

Example 18

N-(1-((6-cyclopropylpyridin-2-yl)methyl)-3-methyl-1H-indazol-4-yl)-7-(2-morpholinoethoxy)imidazo[1,2-a]pyridine-3-carboxamide

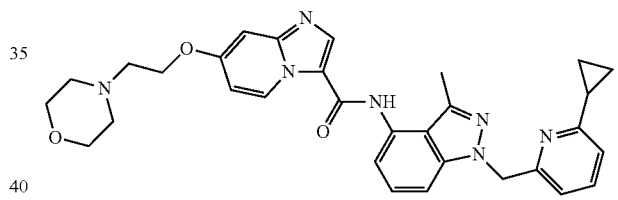

Prepared according Example 1, Step B, substituting N-(1-((6-cyclopropylpyridin-2-yl)methyl)-3-methyl-1H-indazol-4-yl)-7-fluoroimidazo[1,2-a]pyridine-3-carboxamide (Example 16, Steps A-G) for 7-fluoro-N-(1-((6-isopropylpyridin-2-yl)methyl)-3-methyl-1H-indazol-4-yl)imidazo[1,2-a]pyridine-3-carboxamide to give the title compound (64%). MS (APCI), positive scan, m/z=552.1 (M+H).

Example 19

N-(1-((6-cyclopropylpyridin-2-yl)methyl)-3-methyl-1H-indazol-4-yl)-7-(2-(3,3,4-trimethylpiperazin-1-yl)ethoxy)imidazo[1,2-a]pyridine-3-carboxamide

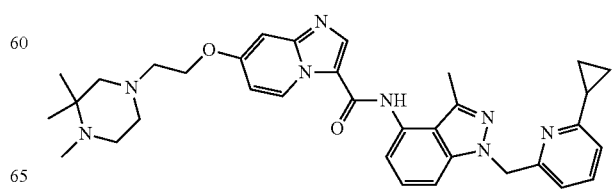

Step A: Preparation of tert-butyl 4-(2-hydroxy-ethyl)-2,2-dimethylpiperazine-1-carboxylate Prepared as in Example 2, Step A, substituting tert-butyl 2,2-dimethylpiperazine-1-carboxylate for 1-ethylpiperazine to give the title compound (85%).

Step B: Preparation of 2-(3,3,4-trimethylpiperazin-1-yl)ethanol

Prepared according to Example 4, Step A, substituting tert-butyl 4-(2-hydroxyethyl)-2,2-dimethylpiperazine-1-carboxylate for tert-Butyl 6-(2-hydroxyethyl)-2,6-diazaspiro[3.3]heptane-2-carboxylate, to give the title compound (100%).

Step C: Preparation of N-(1-((6-cyclopropylpyridin-2-yl)methyl)-3-methyl-1H-indazol-4-yl)-7-(2-(3,3,4-trimethylpiperazin-1-yl)ethoxy)imidazo[1,2-a]pyridine-3-carboxamide Prepared according Example 1, Step B, substituting N-(1-((6-cyclopropylpyridin-2-yl)methyl)-3-methyl-1H-indazol-4-yl)-7-fluoroimidazo[1,2-a]pyridine-3-carboxamide (Example 16, Steps A-G) for 7-fluoro-N-(1-((6-isopropylpyridin-2-yl)methyl)-3-methyl-1H-indazol-4-yl)imidazo[1,2-a]pyridine-3-carboxamide and 2-(3,3,4-trimethylpiperazin-1-yl)ethanol for 2-morpholinoethanol to give the title compound (19%). MS (APCI), positive scan, m/z=593.1 (M+H).

Example 20

N-(1-((6-cyclopropylpyridin-2-yl)methyl)-3-methyl-1H-indazol-4-yl)-7-(2-(4-(2-methoxyethyl)piperazin-1-yl)ethoxy)imidazo[1,2-a]pyridine-3-carboxamide

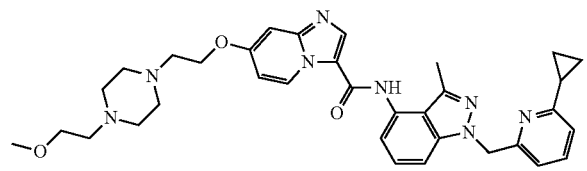 [SMILES: COCCN1CCN(CCOc2ccn3c(C(=O)Nc4cccc5c4c(C)nn5Cc4cccc(C5CC5)n4)cnc3c2)CC1]

Step A: Preparation of 2-(4-(2-methoxyethyl)piperazin-1-yl)ethanol

Prepared as in Example 2, Step A, substituting 2-(piperazin-1-yl)ethanol for 1-ethylpiperazine to give the title compound (71%).

Step B: Preparation of N-(1-((6-cyclopropylpyridin-2-yl)methyl)-3-methyl-1H-indazol-4-yl)-7-(2-(4-(2-methoxyethyl)piperazin-1-yl)ethoxy)imidazo[1,2-a]pyridine-3-carboxamide Prepared according Example 1, Step B, substituting N-(1-((6-cyclopropylpyridin-2-yl)methyl)-3-methyl-1H-indazol-4-yl)-7-fluoroimidazo[1,2-a]pyridine-3-carboxamide (Example 16, Steps A-G) for 7-fluoro-N-(1-((6-isopropylpyridin-2-yl)methyl)-3-methyl-1H-indazol-4-yl)imidazo[1,2-a]pyridine-3-carboxamide and 2-(4-(2-methoxyethyl)piperazin-1-yl)ethanol for 2-morpholinoethanol to give the title compound (41%). MS (APCI), positive scan, m/z=609.1 (M+H).

Example 21

N-(3-chloro-1-((6-cyclopropylpyridin-2-yl)methyl)-1H-indazol-4-yl)-7-(2-(4-isopropylpiperazin-1-yl)ethoxy)imidazo[1,2-a]pyridine-3-carboxamide

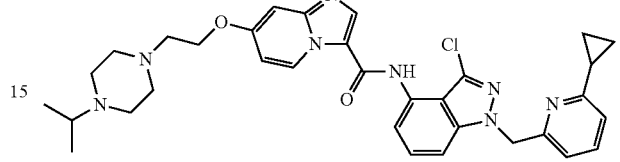

Step A: Preparation of 3-chloro-4-nitro-1H-indazole

To a solution of sodium hydroxide (2.94 g, 73.6 mmol) in 100 mL of water was added 4-nitro-1H-indazole (3.00 g, 18.39 mmol), followed by sodium hypochlorite (33.4 g, 6.15% aqueous solution). This mixture was allowed to stir at ambient temperature overnight. The mixture was acidified to pH 2 with 10% aqueous HCl and extracted with 25% IPA/DCM. The combined organic extracts were washed with water, dried over sodium sulfate and concentrated under reduced pressure. The resulting solids were triturated with ether to give 1.5 g (41%) of the title compound.

Step B: Preparation of 3-chloro-1-((6-cyclopropylpyridin-2-yl)methyl)-4-nitro-1H-indazole Prepared according to Preparation D, Step D, substituting 3-chloro-4-nitro-1H-indazole for 3-bromo-4-nitro-1H-indazole and 2-(chloromethyl)-6-cyclopropylpyridine hydrochloride for 2-(chloromethyl)-6-isopropylpyridine hydrochloride, to give the title compound (72%).

Step C: Preparation of 3-chloro-1-((6-cyclopropylpyridin-2-yl)methyl)-1H-indazol-4-amine Prepared according to Preparation D, Step F, substituting 3-chloro-1-((6-cyclopropylpyridin-2-yl)methyl)-4-nitro-1H-indazole for 1-((6-isopropylpyridin-2-yl)methyl)-3-methyl-4-nitro-1H-indazole to give the title compound (63%).

Step D: Preparation of N-(3-chloro-1-((6-cyclopropylpyridin-2-yl)methyl)-1H-indazol-4-yl)-7-fluoroimidazo[1,2-a]pyridine-3-carboxamide Prepared according to Example 1, Step A, substituting 3-chloro-1-((6-cyclopropylpyridin-2-yl)methyl)-1H-indazol-4-amine for 1-((6-isopropylpyridin-2-yl)methyl)-3-methyl-1H-indazol-4-amine to give the title compound (19%).

Step E: Preparation of N-(3-chloro-1-((6-cyclopropylpyridin-2-yl)methyl)-1H-indazol-4-yl)-7-(2-(4-isopropylpiperazin-1-yl)ethoxy)imidazo[1,2-a]pyridine-3-carboxamide Prepared according Example 1, Step B, substituting N-(3-chloro-1-((6-cyclopropylpyridin-2-yl)methyl)-1H-indazol- 4-yl)-7-fluoroimidazo[1,2-a]pyridine-3-carboxamide for 7-fluoro-N-(1-((6-isopropylpyridin-2-yl)methyl)-3-methyl-1H-indazol-4-yl)imidazo[1,2-a]pyridine-3-carboxamide and 2-(4-isopropylpiperazin-1-yl)ethanol for 2-morpholinoethanol to give the title compound (25%). MS (APCI), positive scan, m/z=613.1 (M+H).

Example 22

N-(1-((6-cyclopropylpyridin-2-yl)methyl)-3-fluoro-1H-indazol-4-yl)-7-(2-(4-isopropylpiperazin-1-yl)ethoxy)imidazo[1,2-a]pyridine-3-carboxamide

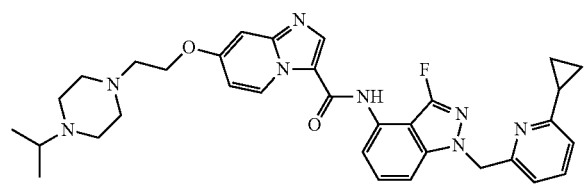 [SMILES: CC(C)N1CCN(CCOc2ccn3c(C(=O)Nc4cccc5c4c(F)nn5Cc4cccc(C5CC5)n4)cnc3c2)CC1]

Step A: Preparation of 3-fluoro-4-nitro-1H-indazole

A microwave vial equipped with a stir bar was charged with the 4-nitro-1H-indazole (1.00 g, 6.13 mmol), and Select Fluor (2.82 g, 7.97 mmol) in 10 mL of acetonitrile. The mixture was heated in a microwave at 100° C. for 2 hours. The mixture was diluted with EtOAc, washed with 10% aqueous potassium carbonate, dried over sodium sulfate and concentrated under reduced pressure. Column chromatography (EtOAc) of the crude material afforded 820 mg (74%) of the title compound.

Step B: Preparation of 1-((6-cyclopropylpyridin-2-yl)methyl)-3-fluoro-4-nitro-1H-indazole Prepared according to Preparation D, Step D, substituting 3-fluoro-4-nitro-1H-indazole for 3-bromo-4-nitro-1H-indazole and 2-(chloromethyl)-6-cyclopropylpyridine hydrochloride for 2-(chloromethyl)-6-isopropylpyridine hydrochloride to give the title compound (35%).

Step C: Preparation of 1-((6-cyclopropylpyridin-2-yl)methyl)-3-fluoro-1H-indazol-4-amine Prepared according to Preparation D, Step F, substituting 1-((6-cyclopropylpyridin-2-yl)methyl)-3-fluoro-4-nitro-1H-indazole for 1-((6-isopropylpyridin-2-yl)methyl)-3-methyl-4-nitro-1H-indazole to give the title compound (91%).

Step D: Preparation of N-(1-((6-cyclopropylpyridin-2-yl)methyl)-3-fluoro-1H-indazol-4-yl)-7-fluoroimidazo[1,2-a]pyridine-3-carboxamide Prepared according to Example 1, Step A, substituting 1-((6-cyclopropylpyridin-2-yl)methyl)-3-fluoro-1H-indazol-4-amine for 1-((6-isopropylpyridin-2-yl)methyl)-3-methyl-1H-indazol-4-amine to give the title compound (38%).

Step E: Preparation of N-(1-((6-cyclopropylpyridin-2-yl)methyl)-3-fluoro-1H-indazol-4-yl)-7-(2-(4-isopropylpiperazin-1-yl)ethoxy)imidazo[1,2-a]pyridine-3-carboxamide Prepared according Example 1, Step B, substituting N-(1-((6-cyclopropylpyridin-2-yl)methyl)-3-fluoro-1H-indazol-4-yl)-7-fluoroimidazo[1,2-a]pyridine-3-carboxamide for 7-fluoro-N-(1-((6-isopropylpyridin-2-yl)methyl)-3-methyl-1H-indazol-4-yl)imidazo[1,2-a]pyridine-3-carboxamide and 2-(4-isopropylpiperazin-1-yl)ethanol for 2-morpholinoethanol to give the title compound (35%). MS (APCI), positive scan, m/z=597.0 (M+H).

Example 23

(S)—N-(3-chloro-1-((6-cyclopropylpyridin-2-yl)methyl)-1H-indazol-4-yl)-7-(2-(3,4-dimethylpiperazin-1-yl)ethoxy)imidazo[1,2-a]pyridine-3-carboxamide

Step A: Preparation of (S)-tert-butyl 3,4-dimethylpiperazine-1-carboxylate

To a solution of (S)-tert-butyl 3-methylpiperazine-1-carboxylate (50 g, 0.250 mol) in 500 mL of methanol was added formaldehyde (41.6 mL, 0.5 mol, 37% aqueous solution) and formic acid (33 mL, 0.874 mol) and the mixture was heated to 70° C. for 16 hours, then concentrated under reduced pressure. The resulting residue was taken up in EtOAc (500 mL), washed with 10% aqueous potassium carbonate, dried over sodium sulfate and concentrated under reduced pressure to give 54 g (100%) of the title compound.

Step B: Preparation of (S)-1,2-dimethylpiperazine dihydrochloride (S)-tert-Butyl 3,4-dimethylpiperazine-1-carboxylate (54 g, 0.252 mol) was dissolved in 500 mL of EtOAc and the mixture was chilled to 0° C. HCl gas was bubbled through the solution for 20 minutes, during which time a white solid formed and then dissolved. The reaction vessel was capped and allowed to stir at ambient temperature for 16 hours, during which a white precipitate had formed. The mixture was purged with nitrogen for 10 minutes and the solids were collected by filtration to give 45 g (96%) of the title compound.

Step C: Preparation of (S)-2-(3,4-dimethylpiperazin-1-yl)ethanol

Prepared according to Example 2, Step A, substituting (S)-1,2-dimethylpiperazine di-hydrochloride for 1-ethylpiperazine and sodium bicarbonate for potassium carbonate to give the title compound (64%).

Step D: (S)—N-(3-chloro-1-((6-cyclopropylpyridin-2-yl)methyl)-1H-indazol-4-yl)-7-(2-(3,4-dimethyl-piperazin-1-yl)ethoxy)imidazo[1,2-a]pyridine-3-carboxamide Prepared according Example 1, Step B, substituting N-(3-chloro-1-((6-cyclopropylpyridin-2-yl)methyl)-1H-indazol-4-yl)-7-fluoroimidazo[1,2-a]pyridine-3-carboxamide (Example 21, Steps A-D) for 7-fluoro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-morpholinoethanol to give the title compound (5%). MS (APCI), positive scan, m/z=599.0 (M+H).

Example 24

(S)—N-(1-((6-cyclopropylpyridin-2-yl)methyl)-3-fluoro-1H-indazol-4-yl)-7-(2-(3,4-dimethylpiperazin-1-yl)ethoxy)imidazo[1,2-a]pyridine-3-carboxamide

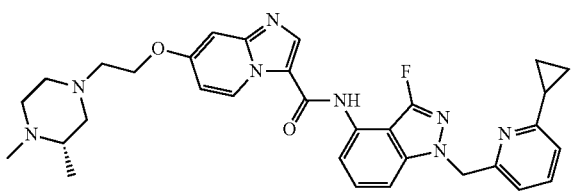 [SMILES: C[C@H]1CN(CCOc2ccn3c(C(=O)Nc4cccc5c4c(F)nn5Cc4cccc(C5CC5)n4)cnc3c2)CCN1C]

Prepared according Example 1, Step B, substituting N-(1-((6-cyclopropylpyridin-2-yl)methyl)-3-fluoro-1H-indazol-4-yl)-7-fluoroimidazo[1,2-a]pyridine-3-carboxamide (Example 22, Steps A-D) for 7-fluoro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-morpholinoethanol to give the title compound (15%). MS (APCI), positive scan, m/z=583.1 (M+H).

Example 25

(S)-7-(2-(3,4-dimethylpiperazin-1-yl)ethoxy)-N-(1-((6-isopropylpyridin-2-yl)methyl)-3-methyl-1H-indazol-4-yl)imidazo[1,2-a]pyridine-3-carboxamide

Step A: Preparation of ethyl 7-chloroimidazo[1,2-a]pyridine-3-carboxylate

A flask equipped with a reflux condenser, mechanical stirring, and an internal temperature probe, was charged with potassium 2-chloro-3-ethoxy-3-oxoprop-1-en-1-olate (58.70 g, 311.1 mmol) followed by addition 200 mL of EtOH to form a slurry. Aqueous hydrogen chloride (4.862 mL, 15.56 mmol) in EtOH was then added to the slurry. The slurry was stirred for about 15 minutes, and then 4-chloro-pyridin-2-amine (20.00 g, 155.6 mmol) was added, and the mixture was warmed to 70° C. After about one hour, an additional 2 equivalents of 3.2 M aqueous HCl were added and the mixture stirred at 70° C. for 16 hours. At this point, an additional 30 g of potassium 2-chloro-3-ethoxy-3-oxo-prop-1-en-1-olate were added and the mixture stirred at 70° C. for 2 hours to facilitate completion of the reaction. The mixture was cooled to ambient temperature and 500 mL of water were added, followed by adjustment of the pH to 11 with 10% aqueous sodium carbonate. After stirring for several hours, the precipitated solids were collected by filtration and dried under vacuum to give 31 g (88%) of the desired compound.

Step B: Preparation of 7-chloro-N-(1-((6-isopropylpyridin-2-yl)methyl)-3-methyl-1H-indazol-4-yl)imidazo[1,2-a]pyridine-3-carboxamide A round bottom flask containing ethyl 7-chloroimidazo[1,2-a]pyridine-3-carboxylate (15.22 g, 67.8 mmol) and 1-((6-isopropylpyridin-2-yl)methyl)-3-methyl-1H-indazol-4-amine (Preparation D; 19.0 g, 67.8 mmol,) in 130 mls of THF was chilled to 0° C. LiHMDS (1M in THF, 149 mls, 149 mmol) was then added by syringe over a 15 minute period. Once the addition was complete, the reaction mixture was stirred at 0° C. for 15 minutes, and then quenched with saturated ammonium chloride (250 mls). This mixture was then extracted two times with EtOAc, the extracts were dried over sodium sulfate and concentrated under reduced pressure. Column chromatography (100% EtOAc) afforded 18.6 g (60%) of the title compound.

Step C: Preparation of (S)-7-(2-(3,4-dimethylpiperazin-1-yl)ethoxy)-N-(1-((6-isopropylpyridin-2-yl)methyl)-3-methyl-1H-indazol-4-yl)imidazo[1,2-a]pyridine-3-carboxamide A flask equipped with a condenser was charged with the 7-chloro-N-(1-((6-isopropylpyridin-2-yl)methyl)-3-methyl-1H-indazol-4-yl)imidazo[1,2-a]pyridine-3-carboxamide (15.0 g, 32.68 mmol), (S)-2-(3,4-dimethylpiperazin-1-yl)ethanol (10.34 g, 65.37 mmol, Example 23), crushed KOH (9.17 g, 163.4 mmol) and 100 mL of DMSO. The mixture was heated to 95° C. for 22 hours. The mixture was allowed to cool to ambient temperature, 350 mL of water were added and the mixture stirred vigorously for 30 minutes. The mixture was extracted with EtOAc, and the combined organic extracts were washed with brine and 10% aqueous potassium carbonate, dried and concentrated. The resulting material was purified by column chromatography (10% MeOH/DCM/0.5% NH$_4$OH to 15% MeOH/DCM/0.5% NH$_4$OH) and then triturated with ether. The resulting solid was collected to give 10 g (53%) of the title compound. MS (APCI), positive scan, m/z=581.1 (M+H). [α]$_D$=+5.6° (c=1.0, CHCl$_3$).

Example 26

(S)—N-(1-((6-cyclopropylpyridin-2-yl)methyl)-3-methyl-1H-indazol-4-yl)-7-(2-(3,4-dimethylpiperazin-1-yl)ethoxy)imidazo[1,2-a]pyridine-3-carboxamide dihydrochloride

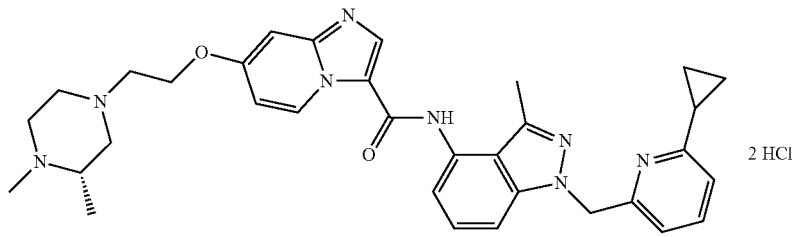 [SMILES: Cc1nn(Cc2cccc(C3CC3)n2)c2cccc(NC(=O)c3cnc4cc(OCCN5CCN(C)[C@@H](C)C5)ccn34)c12]

2 HCl

Step A: Preparation of (S)—N-(1-((6-cyclopropylpyridin-2-yl)methyl)-3-methyl-1H-indazol-4-yl)-7-(2-(3,4-dimethylpiperazin-1-yl)ethoxy)imidazo[1,2-a]pyridine-3-carboxamide N-(1-((6-cyclopropylpyridin-2-yl)methyl)-3-methyl-1H-indazol-4-yl)-7-fluoroimidazo[1,2-a]pyridine-3-carboxamide (Example 16, Step G; 0.250 g, 0.568 mmol), (S)-2-(3,4-dimethylpiperazin-1-yl)ethanol (0.449 g, 2.84 mmol), and potassium t-butoxide (0.382 g, 3.41 mmol) were combined in t-butanol in a pressure tube. The tube was sealed and warmed to 95° C. for 16 hours, then allowed to cool to ambient temperature. The mixture was diluted with water and extracted with EtOAc. The combined organic extracts were washed with 10% aqueous potassium carbonate, dried over sodium sulfate and concentrated under reduced pressure. Column chromatography (10% MeOH/DCM/0.5% NH$_4$OH) of the crude material followed by trituration with ether gave 102 mg (31%) of the title compound. MS (APCI), positive scan, m/z=579.1 (M+H).

Step B: Preparation of (S)—N-(1-((6-cyclopropylpyridin-2-yl)methyl)-3-methyl-1H-indazol-4-yl)-7-(2-(3,4-dimethylpiperazin-1-yl)ethoxy)imidazo[1,2-a]pyridine-3-carboxamide di-hydrochloride (S)—N-(1-((6-cyclopropylpyridin-2-yl)methyl)-3-methyl-1H-indazol-4-yl)-7-(2-(3,4-dimethylpiperazin-1-yl)ethoxy)imidazo[1,2-a]pyridine-3-carboxamide (81.6 mg, 0.141 mmol) was taken up in 2 mL of 4:1 DCM/MeOH-4M HCl/dioxane (0.071 mL, 0.282 mmol) was added and the mixture stirred at ambient temperature for one hour, then concentrated under reduced pressure and dried under vacuum for 16 hours to give 91.9 mgs (100%) of the HCl salt. [α]$_D$=−3.6° (c=1.0, CHCl$_3$).

Example 27

(R)—N-(1-((6-cyclopropylpyridin-2-yl)methyl)-3-methyl-1H-indazol-4-yl)-7-(2-(3,4-dimethylpiperazin-1-yl)ethoxy)imidazo[1,2-a]pyridine-3-carboxamide dihydrochloride

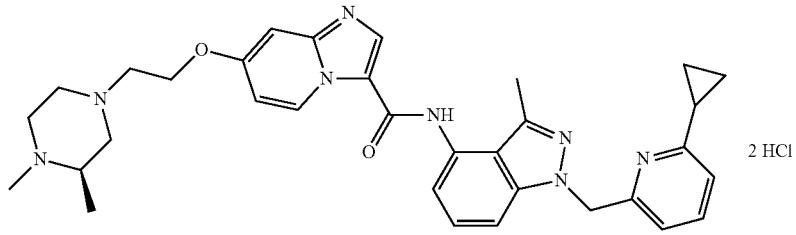 [SMILES: Cc1nn(Cc2cccc(C3CC3)n2)c2cccc(NC(=O)c3cnc4cc(OCCN5CCN(C)[C@H](C)C5)ccn34)c12]

2 HCl

Step A: Preparation of (R)-tert-butyl 4-(2-hydroxyethyl)-2-methylpiperazine-1-carboxylate Prepared according to Example 2, Step A, substituting (R)-tert-butyl 2-methylpiperazine-1-carboxylate for 1-ethylpiperazine to give the final product (70%).

Step B: Preparation of (R)-2-(3,4-dimethylpiperazin-1-yl)ethanol

Prepared according to Example 4, Step A, substituting (R)-tert-butyl 4-(2-hydroxyethyl)-2-methylpiperazine-1-carboxylate for tert-Butyl 6-(2-hydroxyethyl)-2,6-diazaspiro[3.3]heptane-2-carboxylate, to give the final product (81%).

Step C: Preparation of (R)—N-(1-((6-cyclopropylpyridin-2-yl)methyl)-3-methyl-1H-indazol-4-yl)-7-(2-(3,4-dimethylpiperazin-1-yl)ethoxy)imidazo[1,2-a]pyridine-3-carboxamide Prepared according Example 1, Step B, substituting N-(1-((6-cyclopropylpyridin-2-yl)methyl)-3-methyl-1H-indazol-4-yl)-7-fluoroimidazo[1,2-a]pyridine-3-carboxamide (Example 16, Steps A-G) for 7-fluoro-N-(1-((6-isopropylpyridin-2-yl)methyl)-3-methyl-1H-indazol-4-yl)imidazo[1,2-a]pyridine-3-carboxamide and substituting (R)-2-(3,4-dimethylpiperazin-1-yl)ethanol for 2-morpholinoethanol to give the title compound (34%). MS (APCI), positive scan, m/z=579.1 (M+H).

Step D: Preparation of (R)—N-(1-((6-cyclopropylpyridin-2-yl)methyl)-3-methyl-1H-indazol-4-yl)-7-(2-(3,4-dimethylpiperazin-1-yl)ethoxy)imidazo[1,2-a]pyridine-3-carboxamide di-hydrochloride (R)—N-(1-((6-cyclopropylpyridin-2-yl)methyl)-3-methyl-1H-indazol-4-yl)-7-(2-(3,4-dimethylpiperazin-1-yl)ethoxy)imidazo[1,2-a]pyridine-3-carboxamide (79.3 mg, 0.139 mmol) was taken up in 2 mL of 4:1 DCM/MeOH. 4M HCl/dioxane (0.069 mL, 0.278 mmol) was added and the

Example 28

(R)-7-(2-(3,4-dimethylpiperazin-1-yl)ethoxy)-N-(1-((6-isopropylpyridin-2-yl)methyl)-3-methyl-1H-indazol-4-yl)imidazo[1,2-a]pyridine-3-carboxamide

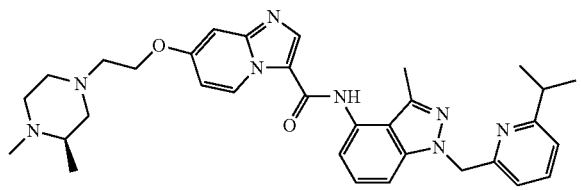 [SMILES: Cc1nn(Cc2cccc(C(C)C)n2)c2cccc(NC(=O)c3cnc4cc(OCCN5CCN(C)[C@H](C)C5)ccn34)c12]

7-Fluoro-N-(1-((6-isopropylpyridin-2-yl)methyl)-3-methyl-1H-indazol-4-yl)imidazo[1,2-a]pyridine-3-carboxamide (Example 1, Step A), 0.300 g, 0.678 mmol), (R)-2-(3,4-dimethylpiperazin-1-yl)ethanol (0.536 g, 3.39 mmol), and potassium t-butoxide (0.456 g, 4.07 mmol) were combined in t-butanol in a pressure tube. The tube was sealed and warmed to 95° C. for 16 hours, then allowed to cool to ambient temperature. The mixture was diluted with water and extracted with EtOAc. The combined organic extracts were washed with 10% aqueous potassium carbonate, dried over sodium sulfate and concentrated under reduced pressure. Column chromatography (10% MeOH/DCM/0.5% NH₄OH) of the crude material followed by trituration with ether gave 136 mg (33%) of the title compound. MS (APCI), positive scan, m/z=581.1 (M+H). [α]$_D$=-5.3° (c=1.0, CHCl₃).

Example 29

(S)-7-(2-(3,4-dimethylpiperazin-1-yl)ethoxy)-N-(1-((1-isopropyl-5-methyl-1H-pyrazol-3-yl)methyl)-3-methyl-1H-indazol-4-yl)imidazo[1,2-a]pyridine-3-carboxamide

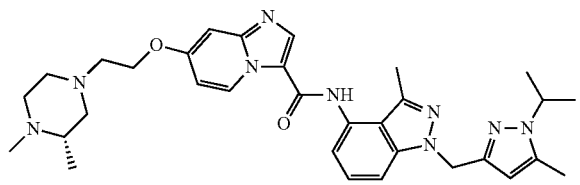 [SMILES: Cc1nn(Cc2cc(C)n(C(C)C)n2)c2cccc(NC(=O)c3cnc4cc(OCCN5CCN(C)[C@@H](C)C5)ccn34)c12]

Prepared according Example 1, Step B, substituting 7-fluoro-N-(1-((1-isopropyl-5-methyl-1H-pyrazol-3-yl)methyl)-3-methyl-1H-indazol-4-yl)imidazo[1,2-a]pyridine-3-carboxamide (Example 8, Steps A-G) for 7-fluoro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-morpholinoethanol to give the title compound (50%). MS (APCI), positive scan, m/z=585.4 (M+H).

Example 30

(S)-7-(2-(3,4-dimethylpiperazin-1-yl)ethoxy)-N-(1-((2-isopropylthiazol-4-yl)methyl)-3-methyl-1H-indazol-4-yl)imidazo[1,2-a]pyridine-3-carboxamide

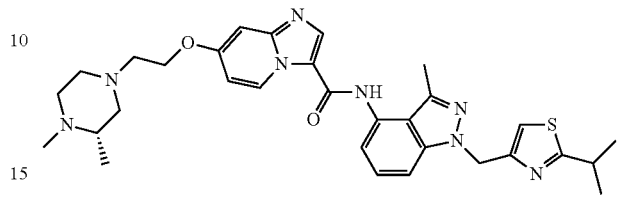

Prepared according Example 1, Step B, substituting 7-fluoro-N-(1-((2-isopropylthiazol-4-yl)methyl)-3-methyl-1H-indazol-4-yl)imidazo[1,2-a]pyridine-3-carboxamide (Example 12, Steps A-E) for 7-fluoro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-morpholinoethanol to give the title compound (22%). MS (APCI), positive scan, m/z=587.2 (M+H).

Example 31

(S)—N-(1-((6-tert-butylpyridin-2-yl)methyl)-3-methyl-1H-indazol-4-yl)-7-(2-(3,4-dimethylpiperazin-1-yl)ethoxy)imidazo[1,2-a]pyridine-3-carboxamide

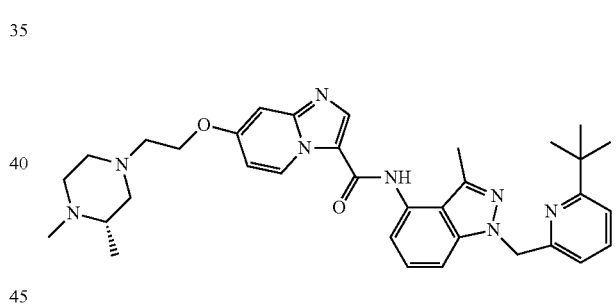

Step A: Preparation of (6-tert-butylpyridin-2-yl)methanol

Prepared according to Example 16, Step B, substituting 6-tert-butylpicolinaldehyde for 6-cyclopropylpicolinaldehyde, to give the title compound (60%).

Step B: Preparation of 2-tert-butyl-6-(chloromethyl)pyridine hydrochloride

Prepared according to Preparation D, Step B, substituting (6-tert-butylpyridin-2-yl)methanol for 6-isopropylpyridin-2-yl)methanol, to give the title compound (100%).

Step C: Preparation of 3-bromo-1-((6-tert-butylpyridin-2-yl)methyl)-4-nitro-1H-indazole Prepared according to Preparation D, Step D, substituting 2-tert-butyl-6-(chloromethyl)pyridine hydrochloride for 2-(chloromethyl)-6-isopropylpyridine hydrochloride, to give the title compound (55%).

(Text cut off at top left: mixture stirred at ambient temperature for one hour, then concentrated under reduced pressure and dried under vacuum for 16 hours to give 89 mg (100%) of the HCl salt. [α]$_D$=+3.3° (c=1.0, CHCl₃).)

Step D: Preparation of 1-((6-tert-butylpyridin-2-yl)methyl)-3-methyl-4-nitro-1H-indazole Prepared according to Preparation D, Step E, substituting 3-bromo-1-((6-tert-butylpyridin-2-yl)methyl)-4-nitro-1H-indazole for 3-bromo-1-((6-isopropylpyridin-2-yl)methyl)-4-nitro-1H-indazole, to give the title compound (64%).

Step E: Preparation of 1-((6-tert-butylpyridin-2-yl)methyl)-3-methyl-1H-indazol-4-amine Prepared according to Preparation D, Step F, substituting 1-((6-tert-butylpyridin-2-yl)methyl)-3-methyl-4-nitro-1H-indazole for 1-((6-isopropylpyridin-2-yl)methyl)-3-methyl-4-nitro-1H-indazole, to give the title compound (73%).

Step F: Preparation of N-(1-((6-tert-butylpyridin-2-yl)methyl)-3-methyl-1H-indazol-4-yl)-7-fluoroimidazo[1,2-a]pyridine-3-carboxamide Prepared according to Example 1, Step A, substituting 1-((6-tert-butylpyridin-2-yl)methyl)-3-methyl-1H-indazol-4-amine for 1-((6-isopropylpyridin-2-yl)methyl)-3-methyl-1H-indazol-4-amine, to give the title compound (55%).

Step G: Preparation of S)—N-(1-((6-tert-butylpyridin-2-yl)methyl)-3-methyl-1H-indazol-4-yl)-7-(2-(3,4-dimethylpiperazin-1-yl)ethoxy)imidazo[1,2-a]pyridine-3-carboxamide Prepared according Example 1, Step B, substituting N-(1-((6-tert-butylpyridin-2-yl)methyl)-3-methyl-1H-indazol-4-yl)-7-fluoroimidazo[1,2-a]pyridine-3-carboxamide for 7-fluoro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-morpholinoethanol to give the title compound (54%). MS (APCI), positive scan, m/z=595.1 (M+H).

Example 32

(S)—N-(1-((6-cyclobutylpyridin-2-yl)methyl)-3-methyl-1H-indazol-4-yl)-7-(2-(3,4-dimethylpiperazin-1-yl)ethoxy)imidazo[1,2-a]pyridine-3-carboxamide

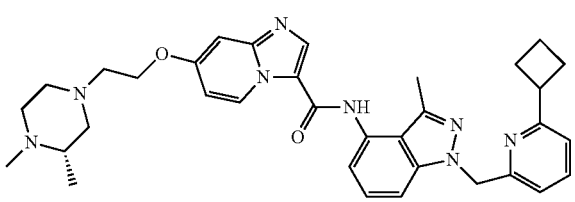 [SMILES: Cc1nn(Cc2cccc(C3CCC3)n2)c2cccc(NC(=O)c3cnc4cc(OCCN5CCN(C)[C@@H](C)C5)ccn34)c12]

Step A: Preparation of 2-bromo-6-cyclobutylpyridine

A round bottom flask was charged with dry THF (50 mL), 2,6-dibromopyridine (3.00 g, 12.7 mmol), copper iodide (0.555 g, 2.91 mmol) and PdCl$_2$(dppf):dichloromethane adduct (1.09 g, 1.33 mmol). The mixture was purged with argon for 10 minutes, and then cyclobutyl zinc bromide (0.5 M in THF, 30.4 mL, 15.2 mmol) was added and the mixture stirred at ambient temperature for 2 hours. The mixture was quenched with saturated ammonium chloride solution and extracted with EtOAc. The combined organic extracts were dried over sodium sulfate and concentrated under reduced pressure. Column chromatography (5% ethyl acetate/hexane) afforded 1.48 g (55%) of the title compound as an orange oil.

Step B: Preparation of 6-cyclobutylpicolinaldehyde

Prepared according to Example 16, Step A, substituting 2-bromo-6-cyclobutylpyridine for 2-bromo-6-cyclopropylpyridine, to give the title compound (52%).

Step C: Preparation of (6-cyclobutylpyridin-2-yl)methanol

Prepared according to Example 16, Step B, substituting 6-cyclobutylpicolinaldehyde for 6-cyclopropylpicolinaldehyde, to give the title compound (82%).

Step D: Preparation of 2-(chloromethyl)-6-cyclobutylpyridine hydrochloride

Prepared according to Preparation D, Step B, substituting (6-cyclobutylpyridin-2-yl)methanol for 6-isopropylpyridin-2-yl)methanol, to give the title compound (100%).

Step E: Preparation of 3-bromo-1-((6-cyclobutylpyridin-2-yl)methyl)-4-nitro-1H-indazole Prepared according to Preparation D, Step D, substituting 2-(chloromethyl)-6-cyclobutylpyridine hydrochloride for 2-(chloromethyl)-6-isopropylpyridine hydrochloride, to give the title compound (68%).

Step F: Preparation of 1-((6-cyclobutylpyridin-2-yl)methyl)-3-methyl-4-nitro-1H-indazole Prepared according to Preparation D, Step E, substituting 3-bromo-1-((6-cyclobutylpyridin-2-yl)methyl)-4-nitro-1H-indazole for 3-bromo-1-((6-isopropylpyridin-2-yl)methyl)-4-nitro-1H-indazole, to give the title compound (72%).

Step G: Preparation of 1-((6-cyclobutylpyridin-2-yl)methyl)-3-methyl-1H-indazol-4-amine Prepared according to Preparation D, Step F, substituting 1-((6-cyclobutylpyridin-2-yl)methyl)-3-methyl-4-nitro-1H-indazole for 1-((6-isopropylpyridin-2-yl)methyl)-3-methyl-4-nitro-1H-indazole, to give the title compound (50%).

Step H: Preparation of N-(1-((6-cyclobutylpyridin-2-yl)methyl)-3-methyl-1H-indazol-4-yl)-7-fluoroimidazo[1,2-a]pyridine-3-carboxamide Prepared according to Example 1, Step A, substituting 1-((6-cyclobutylpyridin-2-yl)methyl)-3-methyl-1H-indazol-4-amine for 1-((6-isopropylpyridin-2-yl)methyl)-3-methyl-1H-indazol-4-amine, to give the title compound (40%).

Step I: Preparation of (S)—N-(1-((6-cyclobutylpyridin-2-yl)methyl)-3-methyl-1H-indazol-4-yl)-7-(2-(3,4-dimethylpiperazin-1-yl)ethoxy)imidazo[1,2-a]pyridine-3-carboxamide Prepared according Example 1, Step B, substituting N-(1-((6-cyclobutylpyridin-2-yl)methyl)-3-methyl-1H-indazol-4- yl)-7-fluoroimidazo[1,2-a]pyridine-3-carboxamide for 7-fluoro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-morpholinoethanol to give the title compound (29%). MS (APCI), positive scan, m/z=593.1 (M+H).

Example 33

(S)—N-(1-((6-cyclopentylpyridin-2-yl)methyl)-3-methyl-1H-indazol-4-yl)-7-(2-(3,4-dimethylpiperazin-1-yl)ethoxy)imidazo[1,2-a]pyridine-3-carboxamide

Step A: Preparation of 2-bromo-6-cyclopentylpyridine

Prepared according to Example 32, Step A, substituting cyclopentyl zinc bromide for cyclobutyl zinc bromide, to give the title compound (45%).

Step B: Preparation of (6-cyclopentylpyridin-2-yl)methanol

A flame dried flask was charged with dry THF (88 mL) and chilled to −78° C. To this was added n-BuLi (3.54 mL, 8.85 mmol, 2.5 M in hexanes), followed by the slow addition of a THF (10 mL) solution of 2-bromo-6-cyclopentylpyridine (2.00 g, 8.85 mmol) over a 15 minute period. The mixture was stirred at −78° C. for 15 minutes, and neat DMF (1.03 mL, 13.3 mmol) was added. The mixture was stirred for 15 minutes at −78° C., then quenched with saturated ammonium chloride solution and allowed to warm up to ambient temperature. The mixture was diluted with water and extracted with EtOAc. The combined organic extracts were dried over sodium sulfate and concentrated under reduced pressure to give 1.6 g of a brown oil. The crude material was then taken up in methanol (50 mL), chilled to 0° C. and NaBH$_4$ (1.00 g, 26.5 mmol) was then added. After 10 minutes, the mixture was allowed to warm to ambient temperature and stirred for 2 hours. The mixture was concentrated under reduced pressure, and the residue was taken up in saturated ammonium chloride solution, extracted with EtOAc, extracts dried over sodium sulfate and concentrated. Column Chromatography (100% ethyl acetate) of the crude material afforded 0.549 g (35%) of the title compound as an orange oil.

Step C: Preparation of 2-(chloromethyl)-6-cyclopentylpyridine hydrochloride

Prepared according to Preparation D, Step B, substituting (6-cyclopentylpyridin-2-yl)methanol for 6-isopropylpyridin-2-yl)methanol, to give the title compound (100%).

Step D: Preparation of 3-bromo-1-((6-cyclopentylpyridin-2-yl)methyl)-4-nitro-1H-indazole Prepared according to Preparation D, Step D, substituting 2-(chloromethyl)-6-cyclopentylpyridine hydrochloride for 2-(chloromethyl)-6-isopropylpyridine hydrochloride, to give the title compound (69%).

Step E: Preparation of 1-((6-cyclopentylpyridin-2-yl)methyl)-3-methyl-4-nitro-1H-indazole Prepared according to Preparation D, Step E, substituting 3-bromo-1-((6-cyclopentylpyridin-2-yl)methyl)-4-nitro-1H-indazole for 3-bromo-1-((6-isopropylpyridin-2-yl)methyl)-4-nitro-1H-indazole, to give the title compound (67%).

Step F: Preparation of 1-((6-cyclopentylpyridin-2-yl)methyl)-3-methyl-1H-indazol-4-amine 1-((6-cyclopentylpyridin-2-yl)methyl)-3-methyl-4-nitro-1H-indazole (0.470 g, 1.40 mmol) was dissolved in 14 mL of methanol. To this solution was added 20% Pd(OH)$_2$ (0.470 g, 50% water content) and the reaction mixture was stirred under a hydrogen balloon for 2 hours. This mixture was filtered through GF/F filter paper and the filtrate was concentrated to 0.340 g (79%) of the title compound.

Step G: Preparation of 7-chloro-N-(1-((6-cyclopentylpyridin-2-yl)methyl)-3-methyl-1H-indazol-4-yl)imidazo[1,2-a]pyridine-3-carboxamide Prepared according to Example 1, Step A, substituting ethyl 7-chloroimidazo[1,2-a]pyridine-3-carboxylate for ethyl 7-fluoroimidazo[1,2-a]pyridine-3-carboxylate and 1-((6-cyclopentylpyridin-2-yl)methyl)-3-methyl-1H-indazol-4-amine for 1-((6-isopropylpyridin-2-yl)methyl)-3-methyl-1H-indazol-4-amine to give the title compound (56%).

Step H: Preparation of (S)—N-(1-((6-cyclopentylpyridin-2-yl)methyl)-3-methyl-1H-indazol-4-yl)-7-(2-(3,4-dimethylpiperazin-1-yl)ethoxy)imidazo[1,2-a]pyridine-3-carboxamide Prepared according to Example 7, Step F, substituting 7-chloro-N-(1-((6-cyclopentylpyridin-2-yl)methyl)-3-methyl-1H-indazol-4-yl)imidazo[1,2-a]pyridine-3-carboxamide for 7-chloro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-((3R,5S)-3,4,5-trimethylpiperazin-1-yl)ethanol to give the title compound (17%). MS (APCI), positive scan, m/z=607.1 (M+H).

Example 34

(S)-7-(2-(3,4-dimethylpiperazin-1-yl)ethoxy)-N-(1-((4,6-dimethylpyridin-2-yl)methyl)-3-methyl-1H-indazol-4-yl)imidazo[1,2-a]pyridine-3-carboxamide

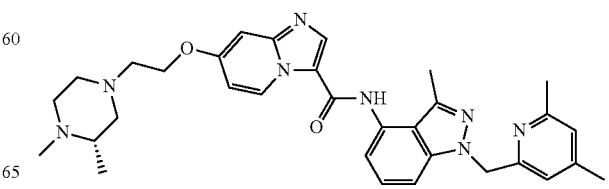

Step A: Preparation of (4,6-dimethylpyridin-2-yl)methanol

Prepared according to Example 16, Step B, substituting 4,6-dimethylpicolinaldehyde for 6-cyclopropylpicolinaldehyde, to give the title compound (71%).

Step B: Preparation of 2-(chloromethyl)-4,6-dimethylpyridine hydrochloride

Prepared according to Preparation D, Step B, substituting (4,6-dimethylpyridin-2-yl)methanol for 6-isopropylpyridin-2-yl)methanol, to give the title compound (100%).

Step C: 3-bromo-1-((4,6-dimethylpyridin-2-yl)methyl)-4-nitro-1H-indazole

Prepared according to Preparation D, Step D, substituting 2-(chloromethyl)-4,6-dimethylpyridine hydrochloride for 2-(chloromethyl)-6-isopropylpyridine hydrochloride, to give the title compound (100%).

Step D: Preparation of 1-((4,6-dimethylpyridin-2-yl)methyl)-3-methyl-4-nitro-1H-indazole Prepared according to Preparation D, Step E, substituting 3-bromo-1-((4,6-dimethylpyridin-2-yl)methyl)-4-nitro-1H-indazole for 3-bromo-1-((6-isopropylpyridin-2-yl)methyl)-4-nitro-1H-indazole, to give the title compound (59%).

Step E: Preparation of 1-((4,6-dimethylpyridin-2-yl)methyl)-3-methyl-1H-indazol-4-amine Prepared according to Example 33, Step F, substituting 1-((4,6-dimethylpyridin-2-yl)methyl)-3-methyl-4-nitro-1H-indazole for 1-((6-cyclopentylpyridin-2-yl)methyl)-3-methyl-4-nitro-1H-indazole, to give the title compound (88%).

Step F: Preparation of 7-chloro-N-(1-((4,6-dimethylpyridin-2-yl)methyl)-3-methyl-1H-indazol-4-yl)imidazo[1,2-a]pyridine-3-carboxamide Prepared according to Example 1, Step A, substituting ethyl 7-chloroimidazo[1,2-a]pyridine-3-carboxylate for ethyl 7-fluoroimidazo[1,2-a]pyridine-3-carboxylate and 1-((4,6-dimethylpyridin-2-yl)methyl)-3-methyl-1H-indazol-4-amine for 1-((6-isopropylpyridin-2-yl)methyl)-3-methyl-1H-indazol-4-amine to give the title compound (54%).

Step G: Preparation of (S)-7-(2-(3,4-dimethylpiperazin-1-yl)ethoxy)-N-(1-((4,6-dimethylpyridin-2-yl)methyl)-3-methyl-1-indazol-4-yl)imidazo[1,2-a]pyridine-3-carboxamide Prepared according to Example 7, Step F, substituting 7-chloro-N-(1-((4,6-dimethylpyridin-2-yl)methyl)-3-methyl-1H-indazol-4-yl)imidazo[1,2-a]pyridine-3-carboxamide for 7-chloro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-((3R,5S)-3,4,5-trimethylpiperazin-1-yl)ethanol to give the title compound (42%). MS (APCI), positive scan, m/z=567.1 (M+H).

Example 35

(S)-7-(2-(3,4-dimethylpiperazin-1-yl)ethoxy)-N-(3-methyl-1-((6-methylpyridin-2-yl)methyl)-1H-indazol-4-yl)imidazo[1,2-a]pyridine-3-carboxamide

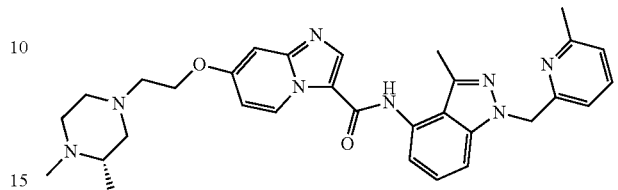

Step A: Preparation of 2-(chloromethyl)-6-methylpyridine hydrochloride

Prepared according to Preparation D, Step B, substituting (6-methylpyridin-2-yl)methanol for 6-isopropylpyridin-2-yl)methanol, to give the title compound (100%).

Step B: Preparation of 3-bromo-1-((6-methylpyridin-2-yl)methyl)-4-nitro-1H-indazole Prepared according to Preparation D, Step D, substituting 2-(chloromethyl)-6-methylpyridine hydrochloride for 2-(chloromethyl)-6-isopropylpyridine hydrochloride, to give the title compound (56%).

Step C: Preparation of 3-methyl-1-((6-methylpyridin-2-yl)methyl)-4-nitro-1H-indazole Prepared according to Preparation D, Step E, substituting 3-bromo-1-((6-methylpyridin-2-yl)methyl)-4-nitro-1H-indazole for 3-bromo-1-((6-isopropylpyridin-2-yl)methyl)-4-nitro-1H-indazole, to give the title compound (67%).

Step D: Preparation of 3-methyl-1-((6-methylpyridin-2-yl)methyl)-1H-indazol-4-amine Prepared according to Example 33, Step F, substituting 3-methyl-1-((6-methylpyridin-2-yl)methyl)-4-nitro-1H-indazole for 1-((6-cyclopentylpyridin-2-yl)methyl)-3-methyl-4-nitro-1H-indazole, to give the title compound (84%).

Step E: Preparation of 7-chloro-N-(3-methyl-1-((6-methylpyridin-2-yl)methyl)-1H-indazol-4-yl)imidazo[1,2-a]pyridine-3-carboxamide Prepared according to Example 1, Step A, substituting ethyl 7-chloroimidazo[1,2-a]pyridine-3-carboxylate for ethyl 7-fluoroimidazo[1,2-a]pyridine-3-carboxylate and 3-methyl-1-((6-methylpyridin-2-yl)methyl)-1H-indazol-4-amine for 1-((6-isopropylpyridin-2-yl)methyl)-3-methyl-1H-indazol-4-amine to give the title compound (38%).

Step F: Preparation of (S)-7-(2-(3,4-dimethylpiperazin-1-yl)ethoxy)-N-(3-methyl-1-((6-methylpyridin-2-yl)methyl)-1H-indazol-4-yl)imidazo[1,2-a]pyridine-3-carboxamide Prepared according to Example 7, Step F, substituting 7-chloro-N-(3-methyl-1-((6-methylpyridin-2-yl)methyl)-1H-indazol-4-yl)imidazo[1,2-a]pyridine-3-carboxamide for 7-chloro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-((3R,5S)-3,4,5-trimethylpiperazin-1-yl)ethanol to give the title compound (11%). MS (APCI), positive scan, m/z=553.1 (M+H).

Example 36

(S)-7-(2-(3,4-dimethylpiperazin-1-yl)ethoxy)-N-(1-((6-ethylpyridin-2-yl)methyl)-3-methyl-1H-indazol-4-yl)imidazo[1,2-a]pyridine-3-carboxamide

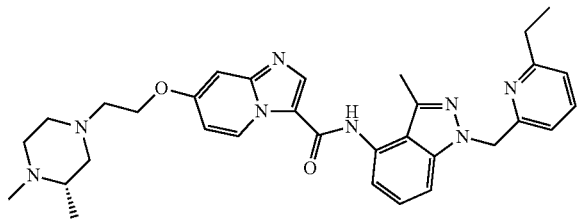 [SMILES: CCc1cccc(Cn2nc(C)c3c(NC(=O)c4cnc5cc(OCCN6CCN(C)[C@@H](C)C6)ccn45)cccc32)n1]

Step A: Preparation of ethyl 6-vinylpicolinate

Prepared according to Preparation C, Step E, substituting potassium trifluoro(vinyl)borate for potassium trifluoro(prop-1-en-2-yl)borate to give the title compound (99%).

Step B: Preparation of ethyl 6-ethylpicolinate

Ethyl 6-vinylpicolinate (4.70 g, 26.5 mmol) was dissolved in 100 mL of ethanol. To this was added 20% Pd(OH)$_2$ on carbon (1 g, 50% water) and the mixture was stirred under a hydrogen balloon for 2 hours. The mixture was purged with nitrogen, filtered through GF/F filter paper, and the filtrate concentrated under reduced pressure to give 4.5 g (95%) of the title compound.

Step C: Preparation of (6-ethylpyridin-2-yl)methanol

Prepared according to Preparation D, Step A, substituting ethyl 6-ethylpicolinate for Ethyl 6-isopropylpicolinate, to give the title compound (41%).

Step D: Preparation of 2-(chloromethyl)-6-ethylpyridine hydrochloride

Prepared according to Preparation D, Step B, substituting (6-ethylpyridin-2-yl)methanol for 6-isopropylpyridin-2-yl)methanol, to give the title compound (100%).

Step E: Preparation of 3-bromo-1-((6-ethylpyridin-2-yl)methyl)-4-nitro-1H-indazole Prepared according to Preparation D, Step D, substituting 2-(chloromethyl)-6-ethylpyridine hydrochloride for 2-(chloromethyl)-6-isopropylpyridine hydrochloride, to give the title compound (72%).

Step F: Preparation of 1-((6-ethylpyridin-2-yl)methyl)-3-methyl-4-nitro-1H-indazole Prepared according to Preparation D, Step E, substituting 3-bromo-1-((6-ethylpyridin-2-yl)methyl)-4-nitro-1H-indazole for 3-bromo-1-((6-isopropylpyridin-2-yl)methyl)-4-nitro-1H-indazole, to give the title compound (70%).

Step G: Preparation of 1-((6-ethylpyridin-2-yl)methyl)-3-methyl-1H-indazol-4-amine Prepared according to Example 33, Step F, substituting 1-((6-ethylpyridin-2-yl)methyl)-3-methyl-4-nitro-1H-indazole for 1-((6-cyclopentylpyridin-2-yl)methyl)-3-methyl-4-nitro-1H-indazole, to give the title compound (93%).

Step H: Preparation of 7-chloro-N-(1-((6-ethylpyridin-2-yl)methyl)-3-methyl-1H-indazol-4-yl)imidazo[1,2-a]pyridine-3-carboxamide Prepared according to Example 1, Step A, substituting ethyl 7-chloroimidazo[1,2-a]pyridine-3-carboxylate for ethyl 7-fluoroimidazo[1,2-a]pyridine-3-carboxylate and 1-((6-ethylpyridin-2-yl)methyl)-3-methyl-1H-indazol-4-amine for 1-((6-isopropylpyridin-2-yl)methyl)-3-methyl-1H-indazol-4-amine to give the title compound (45%).

Step I: Preparation of (S)-7-(2-(3,4-dimethylpiperazin-1-yl)ethoxy)-N-(1-((6-ethylpyridin-2-yl)methyl)-3-methyl-1H-indazol-4-yl)imidazo[1,2-a]pyridine-3-carboxamide Prepared according to Example 7, Step F, substituting 7-chloro-N-(1-((6-ethylpyridin-2-yl)methyl)-3-methyl-1H-indazol-4-yl)imidazo[1,2-a]pyridine-3-carboxamide for 7-chloro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-((3R,5S)-3,4,5-trimethylpiperazin-1-yl)ethanol to give the title compound (27%). MS (APCI), positive scan, m/z=567.1 (M+H).

Example 37

N-(1-((6-sec-butylpyridin-2-yl)methyl)-3-methyl-1H-indazol-4-yl)-7-(2-((S)-3,4-dimethylpiperazin-1-yl)ethoxy)imidazo[1,2-a]pyridine-3-carboxamide

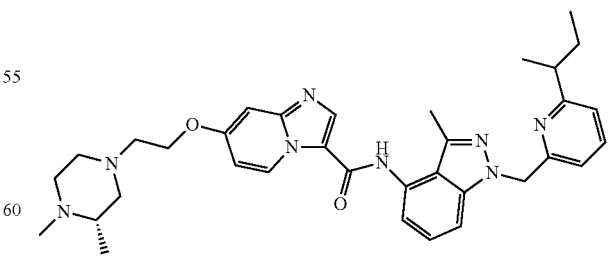

Prepared according to the method of Example 33, Steps A through H, starting with sec-butyl zinc bromide instead of cyclopentyl zinc bromide in Step A. MS (APCI), positive scan, m/z=595.1 (M+H).

Example 38

(S)-7-(2-(3,4-dimethylpiperazin-1-yl)ethoxy)-N-(3-methyl-1-((5-propylpyridin-2-yl)methyl)-1H-indazol-4-yl)imidazo[1,2-a]pyridine-3-carboxamide

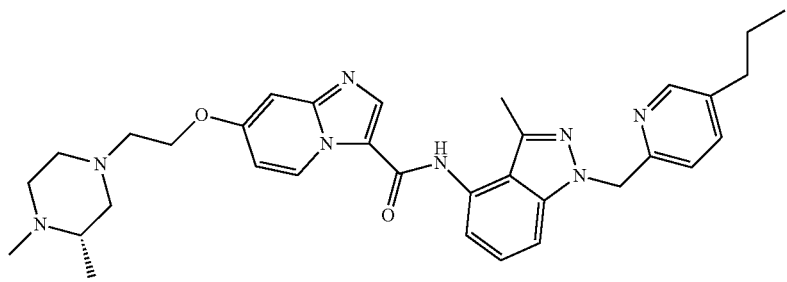 [SMILES: CCCc1ccc(Cn2nc(C)c3c(NC(=O)c4cnc5cc(OCCN6CCN(C)[C@@H](C)C6)ccn45)cccc32)nc1]

Prepared according to the method of Example 33, Steps B through H, using 2-bromo-5-propylpyridine instead of 2-bromo-6-cyclopentylpyridine in Step B. MS (APCI), positive scan, m/z=581.1 (M+H).

Example 39

(S)-7-(2-(3,4-dimethylpiperazin-1-yl)ethoxy)-N-(1-((5-isopropylpyridin-2-yl)methyl)-3-methyl-1H-indazol-4-yl)imidazo[1,2-a]pyridine-3-carboxamide

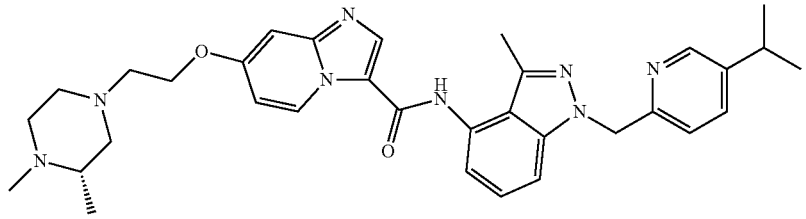 [SMILES: Cc1nn(Cc2ccc(C(C)C)cn2)c2cccc(NC(=O)c3cnc4cc(OCCN5CCN(C)[C@@H](C)C5)ccn34)c12]

Step A: Preparation of 5-(prop-1-en-2-yl)picolinaldehyde

Prepared according to Preparation C, Step E, substituting 5-bromopicolinaldehyde for ethyl 6-chloropicolinate to give the title compound (77%).

Step B: Preparation of (5-isopropylpyridin-2-yl)methanol 5-(prop-1-en-2-yl)picolinaldehyde (0.600 g, 4.08 mmol) was dissolved in methanol (15 mL). To this was added Pd(OH)$_2$ (0.600 mgs, 20% catalyst on carbon, 50% water by weight) and the mixture was hydrogenated under a balloon of hydrogen for 2 hours. The mixture was then filtered through GF/F filter paper and the filtrate was concentrated under reduced pressure to give the title compound (84%).

Step C: Preparation of (S)-7-(2-(3,4-dimethylpiperazin-1-yl)ethoxy)-N-(1-((5-isopropylpyridin-2-yl)methyl)-3-methyl-1H-indazol-4-yl)imidazo[1,2-a]pyridine-3-carboxamide Example 39 was prepared according to Example 33, Steps C through H, using (5-isopropylpyridin-2-yl)methanol instead of (6-cyclopentylpyridin-2-yl)methanol in Step C. MS (APCI), positive scan, m/z=581.1 (M+H).

Example 40

(S)-7-(2-(3,4-dimethylpiperazin-1-yl)ethoxy)-N-(1-((6-isobutylpyridin-2-yl)methyl)-3-methyl-1H-indazol-4-yl)imidazo[1,2-a]pyridine-3-carboxamide

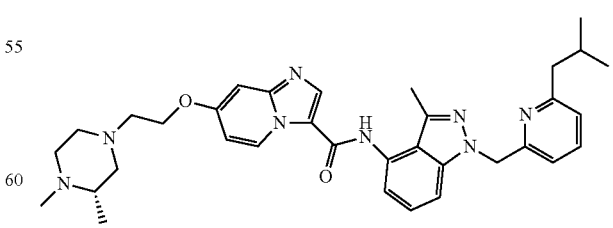

Prepared according to the method of Example 33, Steps A through H, using isobutyl zinc bromide instead of cyclopentyl zinc bromide in Step A. MS (APCI), positive scan, m/z=595.2 (M+H).

Example 41

(S)-7-(2-(3,4-dimethylpiperazin-1-yl)ethoxy)-N-(1-((5-fluoro-6-isopropylpyridin-2-yl)methyl)-3-methyl-1H-indazol-4-yl)imidazo[1,2-a]pyridine-3-carboxamide

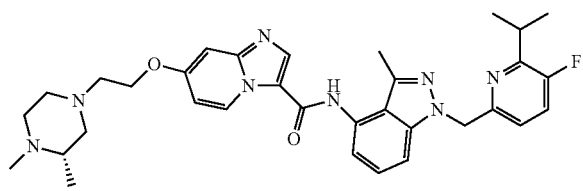 [SMILES: Cc1nn(Cc2ccc(F)c(C(C)C)n2)c2cccc(NC(=O)c3cnc4cc(OCCN5CCN(C)[C@@H](C)C5)ccn34)c12]

Step A: Preparation of 6-bromo-5-fluoropicolinic acid

2-Bromo-3-fluoro-6-methylpyridine (3.60 g, 18.9 mmol) was dissolved in 10 mL of pyridine in pressure tube. To this was added 50 mL of water, and the mixture was warmed to 85° C. Potassium permanganate (5.99 g, 37.9 mmol) was added, the tube was capped, and the mixture was stirred at 85° C. for 48 hours. The mixture was filtered through GF/F filter paper, and the filtrate was concentrated to about half volume under reduced pressure. The remaining material was acidified to pH 4 with 1M aqueous HCl and extracted with EtOAc. The combined organic extracts were dried over sodium sulfate and concentrated under reduced pressure to give 0.70 g of the title compound (17%).

Step B: Preparation of 1-((5-fluoro-6-isopropylpyridin-2-yl)methyl)-3-methyl-4-nitro-1H-indazole Prepared according to Preparation C, Steps D through F and Preparation D, Steps B, D and E, starting with 6-bromo-5-fluoropicolinic acid instead of 6-chloropicolinic acid in Preparation C, Step D, to give the title compound.

Step C: Preparation of 1-((5-fluoro-6-isopropylpyridin-2-yl)methyl)-3-methyl-1H-indazol-4-amine Prepared according to Example 33, Step F, substituting 1-((5-fluoro-6-isopropylpyridin-2-yl)methyl)-3-methyl-4-nitro-1H-indazole for 1-((6-cyclopentylpyridin-2-yl)methyl)-3-methyl-4-nitro-1H-indazole, to give the title compound (87%).

Step D: Preparation of (S)-4-(2-(3,4-dimethylpiperazin-1-yl)ethoxy)pyridin-2-amine 4-Chloropyridin-2-amine (0.500 g, 3.89 mmol), (S)-2-(3,4-dimethylpiperazin-1-yl)ethanol (1.23 g, 7.78 mmol), and crushed potassium hydroxide (0.546 g, 9.72 mmol) were combined in 8 mL of DMSO in a pressure tube and heated to 95° C. for 16 hours. The mixture was then diluted with water (100 mL), extracted 2 times with EtOAc, extracts washed with brine, dried and concentrated under reduced pressure. Column chromatography (5% MeOH/DCM) afforded 0.484 g (50%) of the title compound.

Step E: Preparation of (S)-ethyl 7-(2-(3,4-dimethylpiperazin-1-yl)ethoxy)imidazo[1,2-a]pyridine-3-carboxylate Prepared according to Preparation C, Step C, substituting (S)-4-(2-(3,4-dimethylpiperazin-1-yl)ethoxy)pyridin-2-amine for 4-fluoropyridin-2-amine, to give the title compound (25%).

Step F: Preparation of (S)-7-(2-(3,4-dimethylpiperazin-1-yl)ethoxy)-N-(1-((5-fluoro-6-isopropylpyridin-2-yl)methyl)-3-methyl-1H-indazol-4-yl)imidazo[1,2-a]pyridine-3-carboxamide Prepared according to Example 1, Step A, substituting (S)-ethyl 7-(2-(3,4-dimethylpiperazin-1-yl)ethoxy)imidazo[1,2-a]pyridine-3-carboxylate for ethyl 7-fluoroimidazo[1,2-a]pyridine-3-carboxylate and 1-((5-fluoro-6-isopropylpyridin-2-yl)methyl)-3-methyl-1H-indazol-4-amine for 1-((6-isopropylpyridin-2-yl)methyl)-3-methyl-1H-indazol-4-amine, to give the title compound (46%). MS (APCI), positive scan, m/z=599.2 (M+H).

Example 42

(S)-7-(2-(3,4-dimethylpiperazin-1-yl)ethoxy)-N-(3-methyl-1-(2-(6-methylpyridin-2-yl)ethyl)-1H-indazol-4-yl)imidazo[1,2-a]pyridine-3-carboxamide

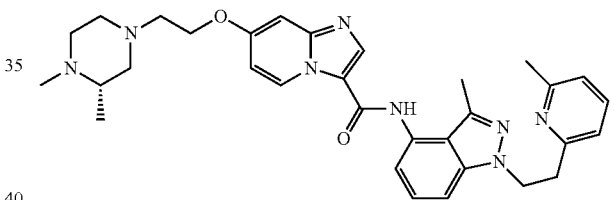

Step A: Preparation of 3-bromo-1-(2-(6-methylpyridin-2-yl)ethyl)-4-nitro-1H-indazole Prepared according to Preparation D, Step D, substituting 2-(2-bromoethyl)-6-methylpyridine hydrobromide for 2-(chloromethyl)-6-isopropylpyridine hydrochloride, to give the title compound (31%).

Step B: Preparation of 3-methyl-1-(2-(6-methylpyridin-2-yl)ethyl)-4-nitro-1H-indazole Prepared according to Preparation D, Step E, substituting 3-bromo-1-(2-(6-methylpyridin-2-yl)ethyl)-4-nitro-1H-indazole for), 3-bromo-1-((6-isopropylpyridin-2-yl)methyl)-4-nitro-1H-indazole, to give the title compound (83%).

Step C: Preparation of 3-methyl-1-(2-(6-methylpyridin-2-yl)ethyl)-1H-indazol-4-amine Prepared according to Example 33, Step F, substituting 3-methyl-1-(2-(6-methylpyridin-2-yl)ethyl)-4-nitro-1H-indazole for 1-((6-cyclopentylpyridin-2-yl)methyl)-3-methyl-4-nitro-1H-indazole, to give the title compound (68%).

Step D: Preparation of 7-chloro-N-(3-methyl-1-(2-(6-methylpyridin-2-yl)ethyl)-1H-indazol-4-yl)imidazo[1,2-a]pyridine-3-carboxamide Prepared according to Example 1, Step A, substituting ethyl 7-chloroimidazo[1,2-a]pyridine-3-carboxylate for ethyl 7-fluoroimidazo[1,2-a]pyridine-3-carboxylate and 3-methyl-1-(2-(6-methylpyridin-2-yl)ethyl)-1H-indazol-4-amine for 1-((6-isopropylpyridin-2-yl)methyl)-3-methyl-1H-indazol-4-amine to give the title compound (100%).

Step E: Preparation of (S)-7-(2-(3,4-dimethylpiperazin-1-yl)ethoxy)-N-(3-methyl-1-(2-(6-methylpyridin-2-yl)ethyl)-1H-indazol-4-yl)imidazo[1,2-a]pyridine-3-carboxamide Prepared according to Example 7, Step F, substituting 7-chloro-N-(3-methyl-1-(2-(6-methylpyridin-2-yl)ethyl)-1H-indazol-4-yl)imidazo[1,2-a]pyridine-3-carboxamide for 7-chloro-N-(1-((6-isopropylpyridin-2-yl)methyl)-3-methyl-1H-indazol-4-yl)imidazo[1,2-a]pyridine-3-carboxamide and (S)-2-(3,4-dimethylpiperazin-1-yl)ethanol for 2-((3R,5S)-3,4,5-trimethylpiperazin-1-yl)ethanol to give the title compound (6%). MS (APCI), positive scan, m/z=567.1 (M+H).

Example 43

(S)—N-(1-((6-cyclopropylpyridin-2-yl)methyl)-5-fluoro-3-methyl-1H-indazol-4-yl)-7-(2-(3,4-dimethylpiperazin-1-yl)ethoxy)imidazo[1,2-a]pyridine-3-carboxamide

Step A: Preparation of 6-fluoro-2-methyl-3-nitrobenzoic acid

2-Fluoro-6-methylbenzoic acid (40 g, 0.26 mol) was dissolved in 320 mL of sulfuric acid and chilled to −15° C. To this was added 14 mL of fuming nitric acid in 60 mL of sulfuric acid over a 10 minute period. Once the addition was complete, the mixture was stirred at 0° C. for 1 hour, then poured into ice water, and stirred. The resulting solids were collected and then dissolved in EtOAc, which was washed with water, dried over sodium sulfate and concentrated to 50 g (97%) of the title compound.

Step B: Preparation of methyl 6-fluoro-2-methyl-3-nitrobenzoate

To a mixture of 6-fluoro-2-methyl-3-nitrobenzoic acid (21.2 g, 0.107 mol), powdered potassium carbonate (36.8, 0.266 mol) in DMF (200 mL) was added methyl iodide (37.8 g, 0.266 mol). The mixture was stirred at ambient temperature for 16 hours, then diluted with water and extracted with EtOAc. The combined organic extracts were washed with brine, dried over sodium sulfate and concentrated under reduced pressure. Column chromatography (20% ethyl acetate/hexane) afforded 12.6 g (56%) of the title compound.

Step C: Preparation of methyl 3-amino-6-fluoro-2-methylbenzoate

Prepared according to Example 33, Step F, substituting methyl 6-fluoro-2-methyl-3-nitrobenzoate for 1-((6-cyclopentylpyridin-2-yl)methyl)-3-methyl-4-nitro-1H-indazole, to give the title compound (95%).

Step D: Preparation of methyl-5-fluoro-1H-indazole-4-carboxylate

Methyl 3-amino-6-fluoro-2-methylbenzoate (7.50 g, 0.041 mol) was dissolved in 150 mL of acetic acid. To this was added acetic anhydride (14.6 g, 0.143 mol) and the mixture was warmed to 75° C. Sodium nitrite (11.3 g, 0.164 mol) was added in portions to the reaction mixture (evolution of an gas observed). The mixture was stirred at 75° C. for 16 hours, then allowed to cool to ambient temperature, and then poured into cold 10% aqueous potassium carbonate solution. This material was extracted twice with EtOAc, the extracts dried over sodium sulfate and concentrated under reduced pressure. Column chromatography (1:1 EtOAc/Hexanes) afforded 0.48 g of methyl 1-acetyl-5-fluoro-1H-indazole-4-carboxylate. The crude material was then added to 5 mL of 4M HCl/dioxane and 15 mL of methanol in a pressure tube and heated to 60° C. for 2 hours. The mixture was concentrated under reduced pressure and the resulting solids were taken up in 10% aqueous potassium carbonate/EtOAc. The organic layer was isolated, dried over sodium sulfate and concentrated under reduced pressure to give 0.483 g (5%) of the title compound.

Step E: Preparation of methyl 3-bromo-5-fluoro-1H-indazole-4-carboxylate

To a solution of methyl-5-fluoro-1H-indazole-4-carboxylate (0.475 g, 2.45 mmol) in 25 mL of DMF was added N-bromosuccinimide (0.566 g, 3.18 mmol). This mixture was stirred at ambient temperature for one hour, then quenched with water. This mixture was extracted with EtOAc, and the combined organic extracts washed with brine, dried over sodium sulfate and concentrated under reduced pressure. Column chromatography (1:1 EtOAc/Hexane) afforded 0.459 g (69%) of the title compound.

Step F: Preparation of methyl 3-bromo-1-((6-cyclopropylpyridin-2-yl)methyl)-5-fluoro-1H-indazole-4-carboxylate Prepared according to Preparation D, Step D, substituting methyl 3-bromo-5-fluoro-1H-indazole-4-carboxylate for 3-bromo-4-nitro-1H-indazole and 2-(chloromethyl)-6-cyclopropylpyridine hydrochloride for 2-(chloromethyl)-6-isopropylpyridine hydrochloride, to give the title compound (77%).

Step G: Preparation of methyl 1-((6-cyclopropylpyridin-2-yl)methyl)-5-fluoro-3-methyl-1H-indazole-4-carboxylate Prepared according to Preparation D, Step E, substituting methyl 3-bromo-1-((6-cyclopropylpyridin-2-yl)methyl)-5- fluoro-1H-indazole-4-carboxylate for 3-bromo-1-((6-isopropylpyridin-2-yl)methyl)-4-nitro-1H-indazole, to give the title compound (73%).

Step H: Preparation of 1-((6-cyclopropylpyridin-2-yl)methyl)-5-fluoro-3-methyl-1H-indazole-4-carboxylic acid Methyl 1-((6-cyclopropylpyridin-2-yl)methyl)-5-fluoro-3-methyl-1H-indazole-4-carboxylate (0.310 g, 0.913 mmol) was subjected to 1M aqueous lithium hydroxide (1.83 mL, 1.83 mmol) in 10 mL of THF for 16 hours at reflux. The mixture was then diluted with 1M aqueous HCl (to pH 4), and extracted twice with EtOAc. The combined organic extracts were dried over sodium sulfate and concentrated to give 0.206 g (69%) of the title compound.

Step I: Preparation of 1-((6-cyclopropylpyridin-2-yl)methyl)-5-fluoro-3-methyl-1H-indazol-4-amine 1-((6-Cyclopropylpyridin-2-yl)methyl)-5-fluoro-3-methyl-1H-indazole-4-carboxylic acid (0.205 g, 0.630 mmol) was dissolved in 6 mL of DMF. To this was added diphenylphosphoryl azide (0.260 g, 0.945 mmol) and TEA (0.263 mL, 1.89 mmol) and the mixture was stirred at ambient temperature for 1.5 hours. Water (5 mL) was added and the mixture was warmed to 80° C. for 2 hours, then allowed to stir at ambient temperature for 16 hours. The reaction mixture was diluted with water and extracted twice with EtOAc. The combined organic extracts washed with brine, dried over sodium sulfate, and concentrated under reduced pressure. Column chromatography (1:1 EtOAc: Hexanes) of the crude material afforded 0.107 g (57%) of the title compound.

Step J: Preparation of N-(1-((6-cyclopropylpyridin-2-yl)methyl)-5-fluoro-3-methyl-1H-indazol-4-yl)-7-fluoroimidazo[1,2-a]pyridine-3-carboxamide Prepared according to Example 1, Step A, substituting 1-((6-cyclopropylpyridin-2-yl)methyl)-5-fluoro-3-methyl-1H-indazol-4-amine for 1-((6-isopropylpyridin-2-yl)methyl)-3-methyl-1H-indazol-4-amine, to give the title compound (6.5%).

Step K: Preparation of (S)—N-(1-((6-cyclopropylpyridin-2-yl)methyl)-5-fluoro-3-methyl-1H-indazol-4-yl)-7-(2-(3,4-dimethylpiperazin-1-yl)ethoxy)imidazo[1,2-a]pyridine-3-carboxamide Prepared according Example 1, Step B, substituting N-(1-((6-cyclopropylpyridin-2-yl)methyl)-5-fluoro-3-methyl-1H-indazol-4-yl)-7-fluoroimidazo[1,2-a]pyridine-3-carboxamide for 7-fluoro-N-(1-((6-isopropylpyridin-2-yl)methyl)-3-methyl-1H-indazol-4-yl)imidazo[1,2-a]pyridine-3-carboxamide and substituting (S)-2-(3,4-dimethylpiperazin-1-yl)ethanol for 2-morpholinoethanol to give the title compound (20%). MS (APCI), positive scan, m/z=597.1 (M+H).

Example 44

7-(2-(4-isopropylpiperazin-1-yl)ethoxy)-N-(3-methyl-1-((5-(trifluoromethyl)pyridin-2-yl)methyl)-1H-indazol-4-yl)imidazo[1,2-a]pyridine-3-carboxamide

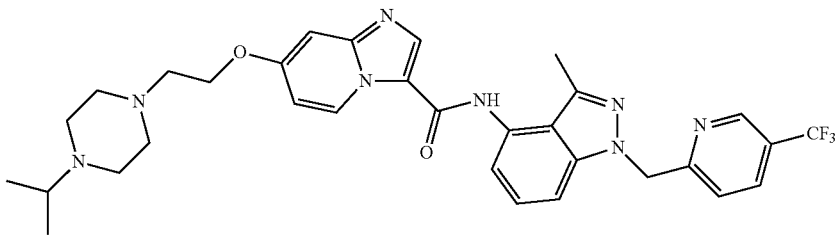 [SMILES: Cc1nn(Cc2ccc(C(F)(F)F)cn2)c2cccc(NC(=O)c3cnc4cc(OCCN5CCN(C(C)C)CC5)ccn34)c12]

Step A: Step A: Preparation of ethyl 7-(2-(4-isopropylpiperazin-1-yl)ethoxy)imidazo[1,2-a]pyridine-3-carboxylate Potassium (E)-2-chloro-3-ethoxy-3-oxoprop-1-en-1-olate (Preparation B; 41.32 g, 219.0 mmol) was suspended (through vigorous magnetic stirring) in anhydrous ether (0.3M, 365 mL) and 6 N sulfuric acid (18.25 ml, 109.5 mmol) was added. More water (about 100 mL) was added to aid in phase separation. When the pH of the bottom (aqueous) layer dropped below 3, the ether layer was separated. The aqueous layer was further extracted with ether (400 mL). The combined ether phases were dried over sodium sulfate and magnesium sulfate for 10 minutes. The solution was filtered and concentrated under reduced pressure, with the temperature of the water bath not exceeding 20° C. An oil was obtained, which solidified upon drying under high vacuum overnight. The solid was dissolved in absolute EtOH (0.3M, 360 mL), 4-(2-(4-isopropylpiperazin-1-yl)ethoxy)pyridin-2-amine (28.95 g, 109.5 mmol) was added, and the mixture was heated under nitrogen at 65° C. for 18 hours. After allowing the mixture to cool, the resulting suspension was evaporated to dryness. The resulting solids were shaken with THF and collected by filtration, then dried under vacuum. The crude material (isolated as the HCl salt) was mixed with water (400 mL) and ethanol (200 mL). Sodium bicarbonate (20 g) was added and stirred overnight. The suspension was evaporated to dryness under vacuum. The solids were shaken in EtOAc/THF and isolated by filtration. The solids were then washed with a large volume of ethyl acetate and THF under gravity. The filtrate was further dried with sodium sulfate and magnesium sulfate, filtered and evaporated to an amber gum. This material was triturated with 2:1 ether-hexanes, and the resulting solids were collected by filtration to afford ethyl 7-(2-(4-isopropylpiperazin-1-yl)ethoxy)imidazo[1,2-a]pyridine-3-carboxylate (23.46 g, 59% yield).

Step B: Preparation of lithium 7-(2-(4-isopropylpiperazin-1-yl)ethoxy)imidazo[1,2-a]pyridine-3-carboxylate To ethyl 7-(2-(4-isopropylpiperazin-1-yl)ethoxy)imidazo[1,2-a]pyridine-3-carboxylate (5.68 g, 15.8 mmol) in water (30 mL) was added lithium hydroxide hydrate (0.67 g, 16.0 mmol). The reaction was heated to 95° C. for 4 hours. The reaction was cooled to ambient temperature and hydrogen chloride (0.0394 mL, 4M in dioxane) was added to the reaction mixture, which was stirred for 10 minutes. Water was removed under vacuum for overnight to give the title compound (5.43 g).

Step C: Preparation of 2-(chloromethyl)-5-(trifluoromethyl)pyridine hydrochloride Prepared according to Preparation D, Step B, substituting (5-(trifluoromethyl)pyridin-2-yl)methanol for isopropylpyridin-2-yl)methanol, to give the title compound (100%).

Step D: Preparation of 3-bromo-4-nitro-1-((5-(trifluoromethyl)pyridin-2-yl)methyl)-1H-indazole Prepared according to Preparation D, Step D, substituting 2-(chloromethyl)-5-(trifluoromethyl)pyridine hydrochloride for 2-(chloromethyl)-6-isopropylpyridine hydrochloride, to give the title compound (59%).

Step E: Preparation of 3-methyl-4-nitro-1-((5-(trifluoromethyl)pyridin-2-yl)methyl)-1H-indazole Prepared according to Preparation D, Step E, substituting 3-bromo-4-nitro-1-((5-(trifluoromethyl)pyridin-2-yl)methyl)-1H-indazole for 3-bromo-1-((6-isopropylpyridin-2-yl)methyl)-4-nitro-1H-indazole, to give the title compound (42%).

Step F: Preparation of 3-methyl-1-((5-(trifluoromethyl)pyridin-2-yl)methyl)-1H-indazol-4-amine Prepared according to Preparation D, Step F, substituting 3-methyl-4-nitro-1-((5-(trifluoromethyl)pyridin-2-yl)methyl)-1H-indazole for 1-((6-isopropylpyridin-2-yl)methyl)-3-methyl-4-nitro-1H-indazole, to give the title compound (91%).

Step G: Preparation of 7-(2-(4-isopropylpiperazin-1-yl)ethoxy)-N-(3-methyl-1-((5-(trifluoromethyl)pyridin-2-yl)methyl)-1H-indazol-4-yl)imidazo[1,2-a]pyridine-3-carboxamide Lithium 7-(2-(4-isopropylpiperazin-1-yl)ethoxy)imidazo[1,2-a]pyridine-3-carboxylate (0.746 g, 2.204 mmol) was dissolved in 16 mL of dry NMP. To this was added 2,4,6-trichlorobenzoyl chloride (0.538 g, 2.20 mmol) and this mixture was stirred at ambient temperature for 30 minutes. 3-Methyl-1-((5-(trifluoromethyl)pyridin-2-yl)methyl)-1H-indazol-4-amine (0.500 g, 1.63 mmol) was added and the mixture was warmed to 90° C. for 16 hours, then allowed to cool to ambient temperature. Water (50 mL) was added and the mixture extracted with EtOAc. The extracts were then washed with 10% aqueous potassium carbonate solution and brine, dried over sodium sulfate, and concentrated under reduced pressure. Column chromatography (7% MeOH/DCM/0.5% NH$_4$OH) afforded 0.112 g (11%) of the final compound. MS (APCI), positive scan, m/z=622.2 (M+H).

Example 45

7-(2-(4-isopropylpiperazin-1-yl)ethoxy)-N-(3-methyl-1-((6-(trifluoromethyl)pyridin-2-yl)methyl)-1H-indazol-4-yl)imidazo[1,2-a]pyridine-3-carboxamide

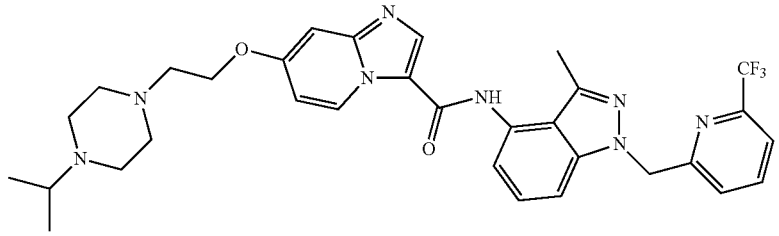 [SMILES: Cc1nn(Cc2cccc(C(F)(F)F)n2)c2cccc(NC(=O)c3cnc4cc(OCCN5CCN(C(C)C)CC5)ccn34)c12]

Step A: Preparation of 2-(chloromethyl)-6-(trifluoromethyl)pyridine hydrochloride Prepared according to Preparation D, Step B, substituting (6-(trifluoromethyl)pyridin-2-yl)methanol for isopropylpyridin-2-yl)methanol to give the title compound (100%).

Step B: Preparation of 3-bromo-4-nitro-1-((6-(trifluoromethyl)pyridin-2-yl)methyl)-1H-indazole Prepared according to Preparation D, Step D, substituting 2-(chloromethyl)-6-(trifluoromethyl)pyridine hydrochloride for 2-(chloromethyl)-6-isopropylpyridine hydrochloride, to give the title compound (81%).

Step C: Preparation of 3-methyl-4-nitro-1-((5-(trifluoromethyl)pyridin-2-yl)methyl)-1H-indazole Prepared according to Preparation D, Step E, substituting 3-bromo-4-nitro-1-((5-(trifluoromethyl)pyridin-2-yl)methyl)-1H-indazole for 3-bromo-1-((6-isopropylpyridin-2-yl)methyl)-4-nitro-1H-indazole, to give the title compound (42%).

Step D: Preparation of 3-methyl-1-((6-(trifluoromethyl)pyridin-2-yl)methyl)-1H-indazol-4-amine Prepared according to Preparation D, Step F, substituting 3-methyl-4-nitro-1-((6-(trifluoromethyl)pyridin-2-yl)methyl)-1H-indazole for 1-((6-isopropylpyridin-2-yl)methyl)-3-methyl-4-nitro-1H-indazole to give the title compound.

Step E: Preparation of 7-fluoroimidazo[1,2-a]pyridine-3-carboxylic acid

Ethyl 7-fluoroimidazo[1,2-a]pyridine-3-carboxylate (8 g; 44.4 mmol) was mixed with tetrahydrofuran (225 mL), ethanol (110 mL) and water (55 mL). Lithium hydroxide monohydrate (0.962 g; 22.9 mmol) was added. The mixture was stirred at ambient temperature overnight. The mixture concentrated under reduced pressure to remove tetrahydrofuran and ethanol. 2 N hydrochloric acid was added to aqueous mixture to adjust to pH 3. A white precipitate formed and was filtered off with drying under high vacuum overnight to give 7-fluoroimidazo[1,2-a]pyridine-3-carboxylic acid as a white solid (6.3 g).

Step F: Preparation of 7-fluoro-N-(3-methyl-1-((6-(trifluoromethyl)pyridin-2-yl)methyl)-1H-indazol-4-yl)imidazo[1,2-a]pyridine-3-carboxamide Prepared according to Example 44, Step G, substituting 7-fluoroimidazo[1,2-a]pyridine-3-carboxylic acid for lithium 7-(2-(4-isopropylpiperazin-1-yl)ethoxy)imidazo[1,2-a]pyridine-3-carboxylate and substituting 3-methyl-1-((6-(trifluoromethyl)pyridin-2-yl)methyl)-1H-indazol-4-amine for 3-methyl-1-((5-(trifluoromethyl)pyridin-2-yl)methyl)-1H-indazol-4-amine, to give the title compound (20%).

Step G: Preparation of 7-(2-(4-isopropylpiperazin-1-yl)ethoxy)-N-(3-methyl-1-((6-(trifluoromethyl)pyridin-2-yl)methyl)-1H-indazol-4-yl)imidazo[1,2-a]pyridine-3-carboxamide Prepared according to Example 1, Step B, substituting 7-fluoro-N-(3-methyl-1-((6-(trifluoromethyl)pyridin-2-yl)methyl)-1H-indazol-4-yl)imidazo[1,2-a]pyridine-3-carboxamide for 7-fluoro-N-(1-((6-isopropylpyridin-2-yl)methyl)-3-methyl-1H-indazol-4-yl)imidazo[1,2-a]pyridine-3-carboxamide and 2-(4-isopropylpiperazin-1-yl)ethanol for 2-morpholinoethanol, to give the final compound (41%). MS (APCI), negative scan, m/z=620.4 (M−H).

Example 46

(S)—N-(1-((6-isopropylpyridin-2-yl)methyl)-3-methyl-1H-indazol-4-yl)-7-(2-(3-methylpiperazin-1-yl)ethoxy)imidazo[1,2-a]pyridine-3-carboxamide

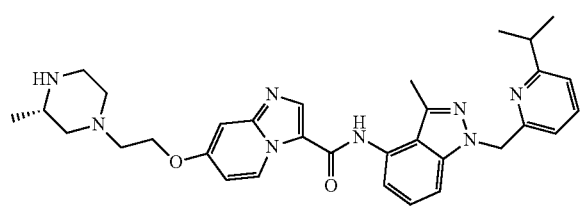 [SMILES: Cc1nn(Cc2cccc(C(C)C)n2)c2cccc(NC(=O)c3cnc4cc(OCCN5CCN[C@@H](C)C5)ccn34)c12]

Step A: Preparation of (S)-benzyl 4-(2-hydroxyethyl)-2-methylpiperazine-1-carboxylate Prepared according to Example 2, Step A, substituting (S)-benzyl 2-methylpiperazine-1-carboxylate for 1-ethylpiperazine and sodium bicarbonate for potassium carbonate to give the title compound (61%).

Step B: Preparation of (S)-2-(3-methylpiperazin-1-yl)ethanol

Prepared according to Example 33, Step F, substituting (S)-benzyl 4-(2-hydroxyethyl)-2-methylpiperazine-1-carboxylate for 1-((6-cyclopentylpyridin-2-yl)methyl)-3-methyl-4-nitro-1H-indazole, to give the title compound (77%).

Step C: Preparation of (S)—N-(1-((6-isopropylpyridin-2-yl)methyl)-3-methyl-1H-indazol-4-yl)-7-(2-(3-methylpiperazin-1-yl)ethoxy)imidazo[1,2-a]pyridine-3-carboxamide Prepared according to Example 7, Step F, substituting (S)-2-(3-methylpiperazin-1-yl)ethanol for 2-((3R,5S)-3,4,5-trimethylpiperazin-1-yl)ethanol, to give the final compound (19%). MS (APCI), positive scan, m/z=567.1 (M+H).

Example 47

N-(1-((6-cyclopropylpyridin-2-yl)methyl)-3-methyl-1H-indazol-4-yl)-7-(2-(4-methylpiperazin-1-yl)ethoxy)imidazo[1,2-a]pyridine-3-carboxamide

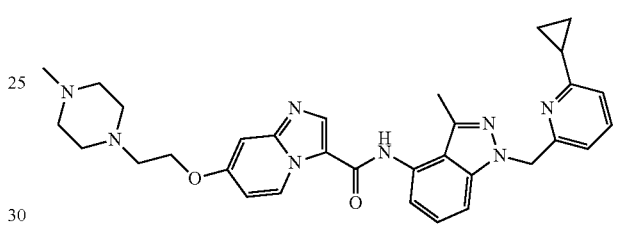

Prepared according to Example 1, Step B, substituting N-(1-((6-cyclopropylpyridin-2-yl)methyl)-3-methyl-1H-indazol-4-yl)-7-fluoroimidazo[1,2-a]pyridine-3-carboxamide for 7-fluoro-N-(1-((6-isopropylpyridin-2-yl)methyl)-3-methyl-1H-indazol-4-yl)imidazo[1,2-a]pyridine-3-carboxamide and 2-(4-methylpiperazin-1-yl)ethanol for 2-morpholinoethanol, to give the final product (45%). MS (APCI), positive scan, m/z=565.3 (M+H).

Example 48

N-(1-((1-isopropyl-1H-pyrazol-3-yl)methyl)-3-methyl-1H-indazol-4-yl)-7-(2-(4-methylpiperazin-1-yl)ethoxy)imidazo[1,2-a]pyridine-3-carboxamide bis hydrochloride

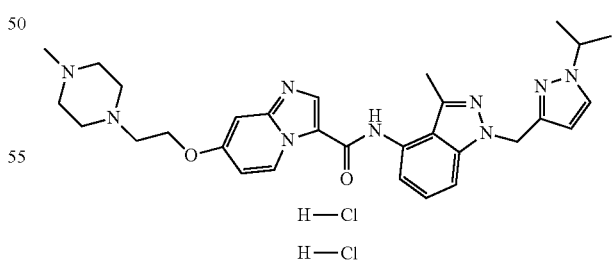

Step A: Preparation of (1-Isopropyl-1H-pyrazol-3-yl)methanol

Commercially available ethyl 1-isopropyl-1H-pyrazole-3-carboxylate was dissolved in diethyl ether, the solution was cooled to 0° C., and a 1M lithium aluminum solution in tetrahydrofuran was added. After stirring for 3 hours, the reaction mixture was poured into a cold 30% aqueous Rochelle's salt solution and was allowed to stir for one hour. The resulting mixture was extracted twice with diethyl ether. The combined organic extracts were washed with 10% aqueous potassium carbonate solution and brine, dried over sodium sulfate, and concentrated under reduced pressure to yield the desired compound (54% yield).

Step B: Preparation of 3-(chloromethyl)-1-isopropyl-1H-pyrazole hydrochloride (1-Isopropyl-1H-pyrazol-3-yl)methanol was dissolved into dichloromethane and $SOCl_2$ (2 equivalents) was added. The resulting mixture was allowed to stir overnight, then concentrated under vacuum to yield the desired compound (quantitative yield).

Step C: Preparation of 3-bromo-1-((1-isopropylpyrazole-3-yl)methyl)-4-nitro-1H-indazole Prepared according to Example 1, Step J, substituting 3-(chloromethyl)-1-isopropyl-1H-pyrazole Hydrochloride for 2-(chloromethyl)-6-isopropylpyridine hydrochloride to yield the desired compound (75% yield).

Step D: Preparation of 3-methyl-1-((1-isopropylpyrazole-3-yl)methyl)-4-nitro-1H-indazole Prepared according to Example 1, Step K, substituting 3-Bromo-1-((1-isopropylpyrazole-3-yl)methyl)-4-nitro-1H-indazole for 3-bromo-1-((6-isopropylpyridin-2-yl)methyl)-4-nitro-1H-indazole to yield the desired compound (56%).

Step E: Preparation of 3-methyl-1-((1-isopropylpyrazole-3-yl)methyl)-4-amino-1H-indazole Prepared according to Example 1, Step L, substituting 3-methyl-1-((1-isopropylpyrazole-3-yl)methyl)-4-nitro-1H-indazole for 3-methyl-1-((6-isopropylpyridin-2-yl)methyl)-4-nitro-1H-indazole to yield the desired compound (77%).

Step F: Preparation of 7-chloro-N-(1-((1-isopropyl-1H-pyrazol-3-yl)methyl)-3-methyl-1H-indazol-4-yl)imidazo[1,2-a]pyridine-3-carboxamide 3-Methyl-1-((1-isopropylpyrazole-3-yl)methyl)-4-amino-1H-indazole (1 equivalent) and ethyl 7-chloroimidazo[1,2-a]pyridine-3-carboxylate (Example 7 step D; 1 equivalent) were dissolved in dry THF (0.2 M) and the resulting solution was cooled to 0° C. Lithium bis(trimethylsilyl)amide (2.3 equivalents) was slowly added and the resulting mixture was allowed to warm to ambient temperature overnight. THF was removed under vacuum and the remaining material was partitioned between water and ethyl acetate. The bottom aqueous layer was extracted twice with ethyl acetate. The combined organic extracts were combined, dried over sodium sulfate, filtered and \ concentrated to give desired compound (52% yield).

Step G: Preparation of N-(1-((1-isopropyl-1H-pyrazol-3-yl)methyl)-3-methyl-1H-indazol-4-yl)-7-(2-(4-methylpiperazin-1-yl)ethoxy)imidazo[1,2-a]pyridine-3-carboxamide bis hydrochloride Prepared according to Example 7, Step F, substituting 7-chloro-N-(1-((1-isopropyl-1H-pyrazol-3-yl)methyl)-3-methyl-1H-indazol-4-yl)imidazo[1,2-a]pyridine-3-carboxamide for 7-chloro-N-(1-((6-isopropylpyridin-2-yl)methyl)-3-methyl-1H-indazol-4-yl)imidazo[1,2-a]pyridine-3-carboxamide and 2-(4-methylpiperazin-1-yl)ethanol for 2-((3R,5S)-3,4,5-trimethylpiperazin-1-yl)ethanol. The HCl salt was prepared by subjecting the compound to 4M HCl/ether (20 equivalents) in methanol and concentrating under reduced pressure to give the bis-HCl salt (45%). MS (APCI), positive scan, m/z=556.3 (M+H).

Example 49

N-(1-((1-isopropyl-1H-pyrazol-3-yl)methyl)-3-methyl-1H-indazol-4-yl)-7-(2-(4-isopropylpiperazin-1-yl)ethoxy)imidazo[1,2-a]pyridine-3-carboxamide

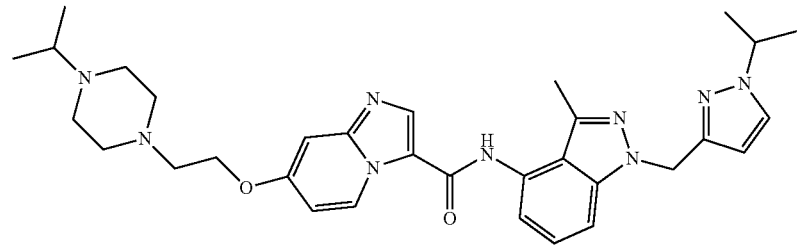 [SMILES: Cc1nn(Cc2ccn(C(C)C)n2)c2cccc(NC(=O)c3cnc4cc(OCCN5CCN(C(C)C)CC5)ccn34)c12]

Prepared according to Example 48, Step G, substituting 2-(4-isopropylpiperazin-1-yl)ethanol for 2-(4-methylpiperazin-1-yl)ethanol, to give the final product (17%). MS (APCI), positive scan, m/z=584.3 (M+H).

Example 50

N-(3-methyl-1-((6-methylpyridin-2-yl)methyl)-1H-indazol-4-yl)-7-(6-methylpyridin-3-yl)imidazo[1,2-a]pyridine-3-carboxamide di-hydrochloride

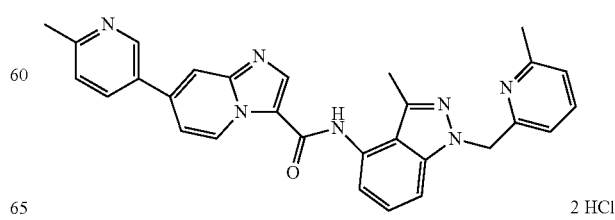

2 HCl

Step A: Preparation of methyl 7-bromoimidazo[1,2-a]pyridine-3-carboxylate 7-bromoimidazo[1,2-a]pyridine-3-carboxylic acid (4.93 g, 20.5 mmol) was dissolved in 80 mL of dry dichloromethane. To this solution was added oxalyl chloride (20.5 mL, 40.9 mmol, 2M in dichloromethane) followed by a few drops of DMF. The mixture was stirred at ambient temperature for 16 hours, then concentrated under reduced pressure. The resulting material was taken up in 100 mL of methanol and stirred at ambient temperature for 6 hours, then concentrated under reduced pressure. The resulting material was suspended in saturated aqueous sodium bicarbonate, extracted with dichloromethane and EtOAc. The organics were combined, dried over sodium sulfate and concentrated under reduced pressure to give 4.63 g (89%) of the title compound.

Step B: Preparation of 7-bromo-N-(3-methyl-1-((6-methylpyridin-2-yl)methyl)-1H-indazol-4-yl)imidazo[1,2-a]pyridine-3-carboxamide Prepared according to Example 1, Step A, substituting 3-methyl-1-((6-methylpyridin-2-yl)methyl)-1H-indazol-4-amine for 1-((6-isopropylpyridin-2-yl)methyl)-3-methyl-1H-indazol-4-amine and methyl 7-bromoimidazo[1,2-a]pyridine-3-carboxylate for ethyl 7-fluoroimidazo[1,2-a]pyridine-3-carboxylate, to give the title compound (62%).

Step C: Preparation of N-(3-methyl-1-((6-methylpyridin-2-yl)methyl)-1H-indazol-4-yl)-7-(6-methylpyridin-3-yl)imidazo[1,2-a]pyridine-3-carboxamide di-hydrochloride 7-Bromo-N-(3-methyl-1-((6-methylpyridin-2-yl)methyl)-1H-indazol-4-yl)imidazo[1,2-a]pyridine-3-carboxamide (0.0486 g, 0.102 mmol) was dissolved in 2 mL of 1:1 DME:DMF. To this was added 6-methylpyridin-3-ylboronic acid (0.0210 g, 0.153 mmol), Pd(dppf)Cl$_2$ (5 mol %), and 2M aqueous sodium carbonate (153 µL, 0.306 mmol). Nitrogen was bubbled through the mixture for 5 minutes and the mixture was then heated to 90° C. for 16 hours. The reaction mixture was diluted with EtOAc and the resulting precipitate was removed by filtration. The filtrate was washed with water and brine, dried over sodium sulfate and concentrated under reduced pressure. Reverse phase chromatography of the crude material, followed by treatment with 4M HCl/dioxane gave the final product. MS (APCI), positive scan, m/z=488.2 (M+H).

Example 51

N-(3-methyl-1-((6-methylpyridin-2-yl)methyl)-1H-indazol-4-yl)-7-(1,2,3,6-tetrahydropyridin-4-yl)imidazo[1,2-a]pyridine-3-carboxamide hydrochloride

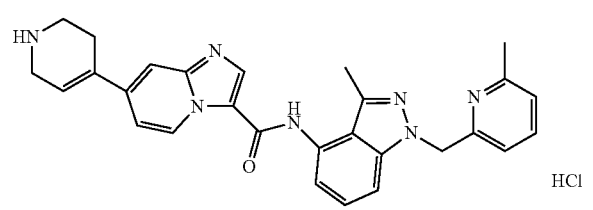 [SMILES: Cc1cccc(Cn2nc(C)c3c(NC(=O)c4cnc5cc(C6=CCNCC6)ccn45)cccc32)n1 ; Cl]

HCl

7-Bromo-N-(3-methyl-1-((6-methylpyridin-2-yl)methyl)-1H-indazol-4-yl)imidazo[1,2-a]pyridine-3-carboxamide (Example 50, Steps A-B; 0.0815 g, 0.171 mmol) was dissolved in 2 mL of 1:1 (DME:DMF). To this was added tert-butyl 4-(4,4,5,5-tetramethyl-1,3,2-dioxaborolan-2-yl)-5,6-dihydropyridine-1(2H)-carboxylate (0.0795 g, 0.257 mmol), Pd(dppf)Cl$_2$ (5 mol %), and 2M aqueous sodium carbonate (256 µL, 0.513 mmol). Nitrogen was bubbled through the solution for 5 minutes and the reaction mixture was then heated to 90° C. for 16 hours. The reaction mixture was then diluted with EtOAc and the precipitate formed was filtered and the filtrate was washed with water and brine, dried over sodium sulfate and concentrated under reduced pressure. The crude material was purified by reverse phase chromatography to provided tert-butyl 4-(3-(3-methyl-1-((6-methylpyridin-2-yl)methyl)-1H-indazol-4-ylcarbamoyl)imidazo[1,2-a]pyridin-7-yl)-5,6-dihydropyridine-1(2H)-carboxylate, which was treated 4M HCl/dioxane to give the title product. MS (APCI), positive scan, m/z=478.2 (M+H).

Example 52

N-(3-methyl-1-((6-methylpyridin-2-yl)methyl)-1H-indazol-4-yl)-7-(piperidin-4-yl)imidazo[1,2-a]pyridine-3-carboxamide tri-hydrochloride

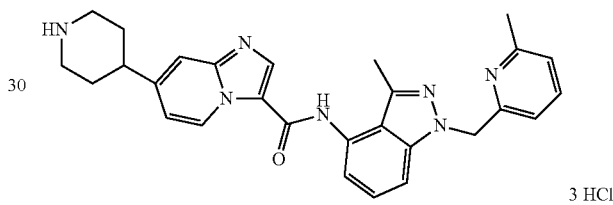

3 HCl tert-Butyl 4-(3-(3-methyl-1-((6-methylpyridin-2-yl)methyl)-1H-indazol-4-ylcarbamoyl)imidazo[1,2-a]pyridin-7-yl)-5,6-dihydropyridine-1(2H)-carboxylate (Example 51; 0.037 g, 0.064 mmol) was dissolved in 6 mL of methanol and 1.3 mL of 6N HCl in isopropyl alcohol. 10% Pd/C (0.075 g) was added and the mixture hydrogenated under a balloon of hydrogen for 2 hours. Celite was added and the mixture was then filtered through GF/F filter paper and the filtrate concentrated under reduced pressure. The crude material was purified by reverse phase chromatography, followed by treatment of the isolated material with 4M HCl/dioxane to provide the title compound (17% yield). MS (APCI), positive scan, m/z=480.3 (M+H).

Example 53

7-fluoro-N-(3-methyl-1-((6-methylpyridin-2-yl)methyl)-1H-indazol-4-yl)imidazo[1,2-a]pyridine-3-carboxamide

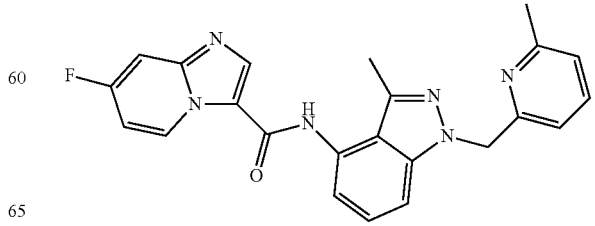

7-Fluoroimidazo[1,2-a]pyridine-3-carboxylic acid (0.081 g, 0.449 mmol) was dissolved in thionyl chloride (2 mL). To this was added a few drops of DMF and the mixture stirred at ambient temperature for 1 hour. The mixture was concentrated under reduced pressure and the resulting solid was dissolved in 3 mL of 1:2 DCM:DMF. To this was added 3-methyl-1-((6-methylpyridin-2-yl)methyl)-1H-indazol-4-amine (0.114 g, 0.451 mmol) followed by diisopropylethylamine (235 µL, 1.35 mmol). This mixture was stirred at ambient temperature for 2 hours, then diluted with water (22 mL), forming a beige precipitate with stirring for several hours. The solids were collected to give 0.100 g (54%) of the title compound. MS (APCI), positive scan, m/z=415.2 (M+H).

Example 54

N-(3-methyl-1-((6-methylpyridin-2-yl)methyl)-1H-indazol-4-yl)-7-(pyrrolidin-1-yl)imidazo[1,2-a]pyridine-3-carboxamide dihydrochloride

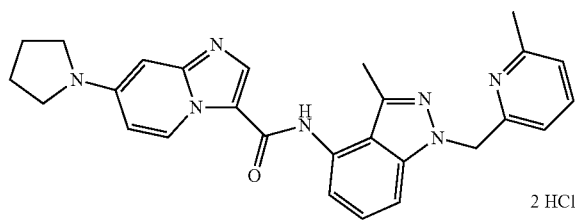 [SMILES: Cc1cccc(Cn2nc(C)c3c(NC(=O)c4cnc5cc(N6CCCC6)ccn45)cccc32)n1]

2 HCl

7-Fluoro-N-(3-methyl-1-((6-methylpyridin-2-yl)methyl)-1H-indazol-4-yl)imidazo[1,2-a]pyridine-3-carboxamide (Example 53; 0.0144 g, 0.0347 mmol) was suspended in n-butanol (0.2 mL). To this was added pyrrolidine (7.25 µL, 0.0869 mmol) and the mixture was heated to 120° C. for 12 hours. The mixture was concentrated under reduced pressure and the resulting material was taken up in THF and concentrated three times to give a brown solid. This material was taken up in dichloromethane, washed with water and brine, dried over sodium sulfate and concentrated under reduced pressure (0.0127 g, 79%). The resulting material was treated with 2M HCl in diethyl ether to provide N-(3-methyl-1-((6-methylpyridin-2-yl)methyl)-1H-indazol-4-yl)-7-(pyrrolidin-1-yl)imidazo[1,2-a]pyridine-3-carboxamide dihydrochloride. MS (APCI), positive scan, m/z=466.3 (M+H).

Example 55

N-(3-methyl-1-((6-methylpyridin-2-yl)methyl)-1H-indazol-4-yl)-7-(2-(pyrrolidin-1-yl)ethoxy)imidazo[1,2-a]pyridine-3-carboxamide dihydrochloride

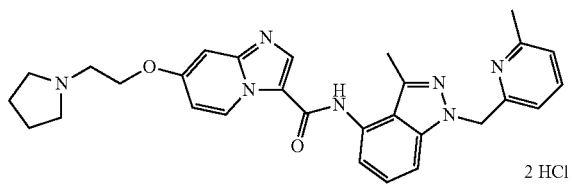 [SMILES: Cc1cccc(Cn2nc(C)c3c(NC(=O)c4cnc5cc(OCCN6CCCC6)ccn45)cccc32)n1]

2 HCl

Prepared according to Example 1, Step B, substituting 7-fluoro-N-(3-methyl-1-((6-methylpyridin-2-yl)methyl)-1H-indazol-4-yl)imidazo[1,2-a]pyridine-3-carboxamide (Example 53) for 7-fluoro-N-(1-((6-isopropylpyridin-2-yl)methyl)-3-methyl-1H-indazol-4-yl)imidazo[1,2-a]pyridine-3-carboxamide and 2-(pyrrolidin-1-yl)ethanol for 2-morpholinoethanol. Purification of the crude material by reverse phase chromatography gave 71 mg (41%) of the product, which was treated with 2M HCl/ether to give the dihydrochloride salt. MS (APCI), positive scan, m/z=510.0 (M+H).

Example 56 tert-Butyl 4-(2-(3-(3-methyl-1-((6-methylpyridin-2-yl)methyl)-1H-indazol-4-ylcarbamoyl)imidazo[1,2-a]pyridin-7-yloxy)ethyl)piperazine-1-carboxylate

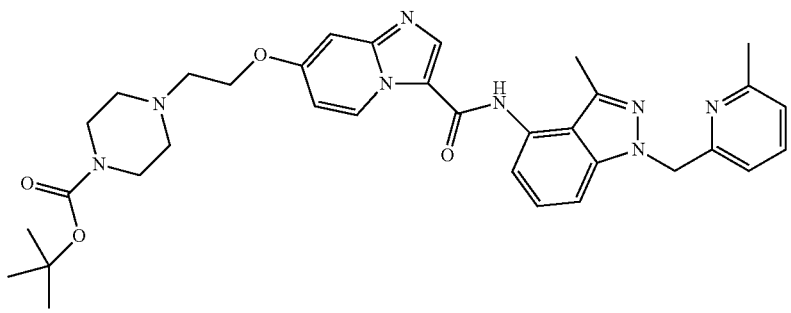 [SMILES: Cc1cccc(Cn2nc(C)c3c(NC(=O)c4cnc5cc(OCCN6CCN(C(=O)OC(C)(C)C)CC6)ccn45)cccc32)n1]

To a 0.4 M solution of potassium tert-butoxide (0.068 g, 0.606 mmol) in THF cooled in an ice-water bath was added tert-butyl 4-(2-hydroxyethyl)piperazine-1-carboxylate 0.278 g, 1.21 mmol). The reaction was stirred for 10 minutes before adding 7-fluoro-N-(3-methyl-1-((6-methylpyridin-2-yl)methyl)-1H-indazol-4-yl)imidazo[1,2-a]pyridine-3-carboxamide (Example 53; 0.100 g 0.241 mmol) in 2 mL of NMP. The reaction was warmed to ambient temperature and stirred for 1 hour, then heated to 60° C. and stirred for 12 hours. THF was removed by rotary evaporation and the mixture was heated to 120° C. for 5 hours. Another equivalent of potassium t-butoxide was added and the mixture was heated for another 3 hours. The reaction was quenched with water and extracted with EtOAc. The extracts were dried over sodium sulfate and concentrated under reduced pressure. Purification by preparative thin layer chromatography and reverse phase chromatography gave the title compound. MS (APCI), positive scan, m/z=625.0 (M+H).

Example 57

7-(2-hydroxyethoxy)-N-(3-methyl-1-((6-methylpyridin-2-yl)methyl)-1H-indazol-4-yl)imidazo[1,2-a]pyridine-3-carboxamide di-hydrochloride salt

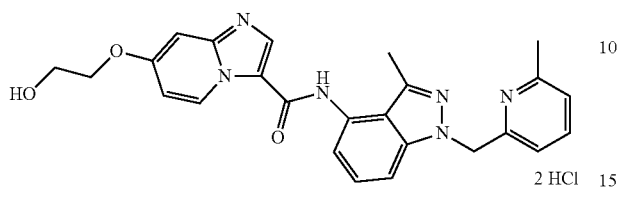

Prepared according to Example 57, substituting 2-tert-butoxyethanol for tert-butyl 4-(2-hydroxyethyl)piperazine-1-carboxylate to give 7-(2-tert-butoxyethoxy)-N-(3-methyl-1-((6-methylpyridin-2-yl)methyl)-1H-indazol-4-yl)imidazo[1,2-a]pyridine-3-carboxamide. This material was treated with TFA, followed by treatment with 2M HCl/ether to give the title compound (20 mg, 65%). MS (APCI), positive scan, m/z=457.2 (M+H).

Example 58

7-(2,3-dihydroxypropoxy)-N-(3-methyl-1-((6-methylpyridin-2-yl)methyl)-1H-indazol-4-yl)imidazo[1,2-a]pyridine-3-carboxamide

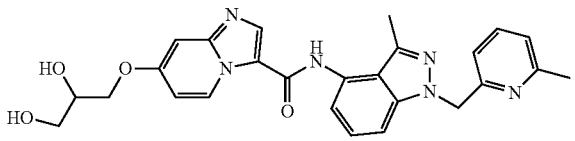 [SMILES: Cc1cccc(Cn2nc(C)c3c(NC(=O)c4cnc5cc(OCC(O)CO)ccn45)cccc32)n1]

Step A: Preparation of 4-((2,2-dimethyl-1,3-dioxolan-4-yl)methoxy)pyridin-2-amine A sealed tube containing 4-chloro-2-pyridinamine (4 g, 31.2 mmol), (2,2-dimethyl-1,3-dioxolan-4-yl)methanol (8.4 g, 60.6 mmol), and sodium (1.46 g, 63.5 mmol) was heated at 145° C. for 8 hours. The mixture was cooled to ambient temperature, and water (25 mL) and dichloromethane (50 mL) were added. The organic phase was separated, dried with sodium sulfate, and concentrated under reduced pressure. The residue was purified by chromatography by silica gel chromatography to give 4-((2,2-dimethyl-1,3-dioxolan-4-yl)methoxy)pyridin-2-amine as a pale yellow solid (5.6 g).

Step B: Preparation of ethyl 7-((2,2-dimethyl-1,3-dioxolan-4-yl)methoxy)imidazo[1,2-a]pyridine-3-carboxylate 4-((2,2-Dimethyl-1,3-dioxolan-4-yl)methoxy)pyridin-2-amine (5.6 g, 0.025 mol) was mixed with ethanol (60 mL) in a reaction flask under an atmosphere of dry nitrogen. A solution of ethyl 2-chloro-3-oxopropanoate (5% in benzene; 93 mL; Commercial solution from Toronto Research Chemicals Inc.) was added. The mixture was heated to 60° C. under nitrogen for 2 hours. After allowing the mixture to cool the solvent was removed under vacuum to give a brown solid. The solid was mixed with ethyl acetate (200 mL) and sodium bicarbonate solution (100 mL) and stirred to dissolve. The phases were separated and the bicarbonate solution was extracted further with ethyl acetate (50 mL). The combined ethyl acetate extracts were dried over sodium sulfate, filtered and concentrated under vacuum to give a solid. The crude material was dissolved in ethyl acetate and passed through a short column of silica gel, eluting with ethyl acetate to give ethyl 7-((2,2-dimethyl-1,3-dioxolan-4-yl)methoxy)imidazo[1,2-a]pyridine-3-carboxylate as a pale yellow solid (5.76 g).

Step C: Preparation of 7-((2,2-dimethyl-1,3-dioxolan-4-yl)methoxy)imidazo[1,2-a]pyridine-3-carboxylic acid Ethyl 7-((2,2-dimethyl-1,3-dioxolan-4-yl)methoxy)imidazo[1,2-a]pyridine-3-carboxylate (1.8 g, 5.63 mmol) and lithium hydroxide monohydrate (0.284 g, 6.75 mmol) were combined in a flask containing tetrahydrofuran/ethanol/water (1:2:1, 56 mL). After stirring overnight at ambient temperature, the solvent was removed under vacuum to give a yellow gum. Water (20 mL) and dichloromethane were added. The aqueous layer was separated and cooled in an ice-water bath before adjusting to pH 4 with 20% citric acid. A precipitate formed and was collected by filtration. The solids were washed with a small amount of water (5 mL) and dried under vacuum to give 7-((2,2-dimethyl-1,3-dioxolan-4-yl)methoxy)imidazo[1,2-a]pyridine-3-carboxylic acid as a white solid (1.3 g).

Step D: Preparation of 7-((2,2-dimethyl-1,3-dioxolan-4-yl)methoxy)-N-(3-methyl-1-((6-methylpyridin-2-yl)methyl)-1H-indazol-4-yl)imidazo[1,2-a]pyridine-3-carboxamide 7-((2,2-Dimethyl-1,3-dioxolan-4-yl)methoxy)imidazo[1,2-a]pyridine-3-carboxylic acid (66 mg, 0.23 mmol) was dissolved in dichloromethane (1 mL) and 2 M oxalyl chloride in dichloromethane (0.12 mL, 0.25 mmol) was added with a drop of dimethylformamide. The mixture was stirred at ambient temperature for 1 hour before addition of 3-methyl-1-((6-methylpyridin-2-yl)methyl)-1H-indazol-4-amine (57 mg, 0.23 mmol) and diisopropylethylamine (0.08 mL, 0.46 mmol), and then the mixture was stirred overnight. The crude mixture was purified using preparative thin layer chromatography (silica, 20×20 cm, 1 mm) developed in a chamber with 10% methanol/dichloromethane to give 7-((2,2-dimethyl-1,3-dioxolan-4-yl)methoxy)-N-(3-methyl-1-((6-methylpyridin-2-yl)methyl)-1H-indazol-4-yl)imidazo[1,2-a]pyridine-3-carboxamide (12 mg).

Step E: Preparation of 7-(2,3-dihydroxypropoxy)-N-(3-methyl-1-((6-methylpyridin-2-yl)methyl)-1H-indazol-4-yl)imidazo[1,2-a]pyridine-3-carboxamide 7-((2,2-Dimethyl-1,3-dioxolan-4-yl)methoxy)-N-(3-methyl-1-((6-methylpyridin-2-yl)methyl)-1H-indazol-4-yl)imidazo[1,2-a]pyridine-3-carboxamide (11 mg, 0.02 mmol) was taken up in 50% trifluoroacetic acid/water and stirred at ambient temperature for 1 hour. Concentrated and dried under high vacuum for an hour before treating with excess 2 M hydrochloric acid in diethyl ether. The solution was stirred for an hour and then concentrated to give 7-(2,3-dihydroxypropoxy)-N-(3-methyl-1-((6-methylpyridin-2-yl)

methyl)-1H-indazol-4-yl)imidazo[1,2-a]pyridine-3-carboxamide as a colorless residue (8 mg). MS m/z 487.2 (M+1, APCI+).

Example 59

N-(3-methyl-1-((6-methylpyridin-2-yl)methyl)-1H-indazol-4-yl)-7-(2-morpholinoethoxyl)imidazo[1,2-a]pyridine-3-carboxamide

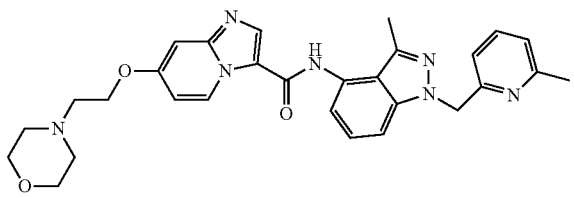

Step A: Preparation of 4-(2-morpholinoethoxyl)pyridin-2-amine

2-Morpholinoethanol (2.2 g, 16.8 mmol) was treated with sodium (116 mg, 5.0 mmol) in a sealed tube and stirred at ambient temperature until homogeneous. 4-Chloropyridin-2-amine (1.1 g, 8.9 mmol) was added and reaction heated to 145° C. and stirred in sealed tube for 10 hours. The mixture was cooled to ambient temperature before diluting with ethyl acetate and water. After separation of layers, the aqueous was extracted twice more with ethyl acetate. Concentration of the reaction mixture afforded a viscous oil which was purified on a Biotage 40+ Silica column, eluting with 10% methanol/dichloromethane, to give 4-(2-morpholinoethoxyl)pyridin-2-amine as a viscous oil which solidified upon further drying under high vacuum (1.4 g).

Step B: Preparation of ethyl 7-(2-morpholinoethoxyl)imidazo[1,2-a]pyridine-3-carboxylate 4-(2-Morpholinoethoxy)pyridin-2-amine (1.37 g, 6.14 mmol) was dissolved in ethanol (20 mL) in round bottom flask. Ethyl 2-chloro-3-oxopropanoate (5% in benzene; 30 mL; Commercial solution from Toronto Research Chemicals Inc.) was added and the mixture was heated to reflux with stirring overnight. The reaction was concentrated to give a beige solid (1.31 g). The solid was purified on a silica column eluting with a gradient from 50-100% ethyl acetate/hexanes over 800 mL followed by elution with 10% methanol/dichloromethane to give ethyl 7-(2-morpholinoethoxyl)imidazo[1,2-a]pyridine-3-carboxylate as a white solid (1 g).

Step C: Preparation of lithium 7-(2-morpholinoethoxyl)imidazo[1,2-a]pyridine-3-carboxylate Ethyl 7-(2-morpholinoethoxyl)imidazo[1,2-a]pyridine-3-carboxylate (1 g, 3.13 mmol) was dissolved in tetrahydrofuran/water (4:1, 0.5 M). Lithium hydroxide monohydrate (131 mg, 3.13 mmol) was added and the mixture stirred at ambient temperature overnight. The mixture was then further diluted with tetrahydrofuran and concentrated. The resulting material was dried under high vacuum for 6 hours to give lithium 7-(2-morpholinoethoxyl)imidazo[1,2-a]pyridine-3-carboxylate as a pale yellow solid (979 mg).

Step D: Preparation of N-(3-methyl-1-((6-methylpyridin-2-yl)methyl)-1H-indazol-4-yl)-7-(2-morpholinoethoxyl)imidazo[1,2-a]pyridine-3-carboxamide Lithium 7-(2-morpholinoethoxyl)imidazo[1,2-a]pyridine-3-carboxylate (0.055 g, 0.186 mmol) was dissolved in dimethylformamide (0.6 mL), O-(7-Azabenzotriazol-1-yl)-N,N,N',N'-tetramethyluroniumhexafluorophosphate (53 mL, 0.17 mmol), 3-methyl-1-((6-methylpyridin-2-yl)methyl)-1H-indazol-4-amine (Example 35, Steps A-D; 0.042 g, 0.167 mmol), and diisopropylethylamine (0.058 mL, 0.334 mmol) were combined in a 1 dram vial. The mixture stirred at ambient temperature overnight. The crude mixture was purified using preparative thin layer chromatography (silica, 20×20 cm, 1 mm) developed in a chamber with 10% Methanol/dichloromethane to give N-(3-methyl-1-((6-methylpyridin-2-yl)methyl)-1H-indazol-4-yl)-7-(2-morpholinoethoxyl)imidazo[1,2-a]pyridine-3-carboxamide (6 mg). MS m/z 526.1 (M+, APCI+).

Example 60

7-(2-(dimethylamino)ethoxy)-N-(3-methyl-1-((6-methylpyridin-2-yl)methyl)-1H-indazol-4-yl)imidazo[1,2-a]pyridine-3-carboxamide

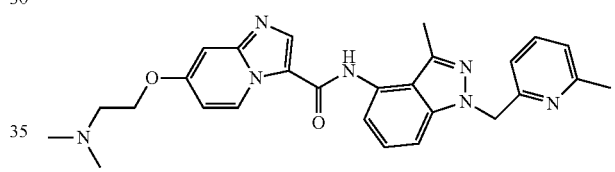

Step A: Preparation of 4-(2-(dimethylamino)ethoxy)pyridin-2-amine

2-Dimethylaminoethanol (34.8 g, 39.0 mmol) was treated with sodium (2.7 g, 11.7 mmol) in a sealed tube and stirred at ambient temperature until homogeneous. 4-Chloropyridin-2-amine (5 g, 3.9 mmol) was added and reaction heated to 150° C. and stirred in sealed tube for 8 hours. The mixture was cooled to ambient temperature before concentrating and triturating with dichloromethane (50 mL) four times. The combined triturates were concentrated and purified by column chromatography to give 4-(2-(dimethylamino)ethoxy)pyridin-2-amine as a yellow solid (3.8 g).

Step B: Preparation of ethyl 7-(2-(dimethylamino)ethoxy)imidazo[1,2-a]pyridine-3-carboxylate 4-(2-(Dimethylamino)ethoxy)pyridin-2-amine (0.87 g, 4.8 mmol) was dissolved in ethanol (15 mL) in round bottom flask. Ethyl 2-chloro-3-oxopropanoate (5% in benzene; 23 mL; Commercial solution from Toronto Research Chemicals Inc.) was added and the mixture refluxed for 10 hours. The reaction mixture was concentrated to give a beige solid (1.31 g). The solid was purified using a Biotage silica column (25+) eluting with a gradient from 50-100% ethyl acetate/hexanes over 600 mL followed by 10% methanol/dichloromethane to give ethyl 7-(2(dimethylamino)ethoxy) imidazo[1,2-a]pyridine-3-carboxylate as a yellow solid (1.2 g).

107

Step C: Preparation of 7-(2-(dimethylamino)
ethoxy)-N-(3-methyl-1-((6-methylpyridin-2-yl)
methyl)-1H-indazol-4-yl)imidazo[1,2-a]pyridine-3-
carboxamide 3-Methyl-1-((6-methylpyridin-2-yl)methyl)-1H-indazol-4-amine (59 mg, 0.24 mmol) was dissolved in tetrahydropyran (DriSolve; 1.2 mL) and degassed before back-filling with nitrogen. The solution was cooled in an ice water bath for 15 minutes before dropwise addition of lithium bis(trimethylsilyl)amide (0.25 mL, 1 M in tetrahydrofuran). The reaction stirred for 10 minutes before dropwise addition into a solution of ethyl 7-(2-(dimethylamino)ethoxy)imidazo[1,2-a]pyridine-3-carboxylate (31 mg, 0.12 mmol) in tetrahydrofuran (DriSolve; 1.2 mL) cooled in an ice-water bath. The reaction was then stirred while being cooled in the ice-water bath for 1.5 hours. The reaction was quenched with water and concentrated. Purification using reverse phase chromatography, eluting with a gradient from 10% to 60% ACN/water, gave 7-(2-(dimethylamino)ethoxy)-N-(3-methyl-1-((6-methylpyridin-2-yl)methyl)-1H-indazol-4-yl)imidazo[1,2-a]pyridine-3-carboxamide (30 mg). MS m/z 484.1 (M+1, APCI+).

Example 61

N-(3-methyl-1-((6-methylpyridin-2-yl)methyl)-1H-indazol-4-yl)imidazo[1,2-a]pyridine-3-carboxamide

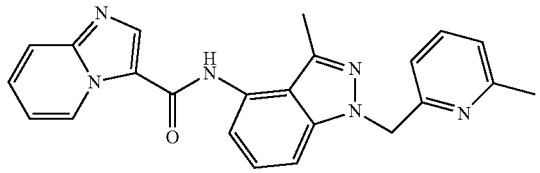 [SMILES: Cc1cccc(Cn2nc(C)c3c(NC(=O)c4cnc5ccccn45)cccc32)n1]

Imidazo[1,2-a]pyridine-3-carboxylic acid (62 mg, 0.38 mmol) was dissolved neat in thionyl chloride (112 mL, 1.5 mmol). The reaction mixture was stirred at ambient temperature for 1 hour before concentrating and drying under high vacuum for 16 hours. The resulting solid was dissolved in tetrahydrofuran (2 mL). 3-Methyl-1-((6-methylpyridin-2-yl)methyl)-1H-indazol-4-amine (97 mg, 0.38 mmol) was added and the reaction was stirred at 70° C. in a sand bath for 6 hours. The mixture was concentrated and partitioned between ethyl acetate and saturated sodium bicarbonate. The ethyl acetate layer was washed with water and brine before drying over sodium sulfate and concentrating. Preparative Thin Layer Chromatography (Silica, 1 mm) of the crude material, eluting with 10% MeOH/DCM, gave N-(3-methyl-1-((6-methylpyridin-2-yl)methyl)-1H-indazol-4-yl)imidazo[1,2-a]pyridine-3-carboxamide (48 mg) in a band with Rf=0.6. MS m/z 397.3 (M+1, APCI+).

Example 62

6-cyano-N-(3-methyl-1-((6-methylpyridin-2-yl)
methyl)-1H-indazol-4-yl)imidazo[1,2-a]pyridine-3-
carboxamide

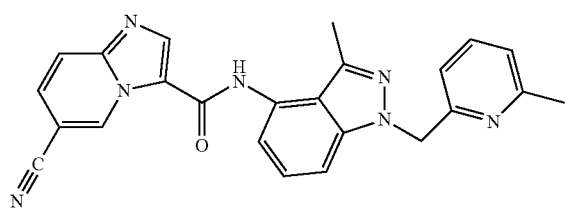 [SMILES: Cc1cccc(Cn2nc(C)c3c(NC(=O)c4cnc5ccc(C#N)cn45)cccc32)n1]

108

Step A: Preparation of ethyl
6-cyanoimidazo[1,2-a]pyridine-3-carboxylate

2-Amino-5-cyanopyridine (15.5 g, 152 mmol) was dissolved in ethanol (500 mL) in 2 L round bottom flask. Ethyl 2-chloro-3-oxopropanoate (5% in benzene; 730 mL; Commercial solution from Toronto Research Chemicals Inc.) was added and the mixture was heated at reflux for 10 hours. The mixture was concentrated under reduced pressure and the residue was purified by silica-gel chromatography to give ethyl 6-cyanoimidazo[1,2-a]pyridine-3-carboxylate as a pale yellow solid (13.9 g).

Step B: Preparation of lithium
6-cyanoimidazo[1,2-a]pyridine-3-carboxylate

Ethyl 6-cyanoimidazo[1,2-a]pyridine-3-carboxylate (13.9 g, 65 mmol) and lithium hydroxide monohydrate (2.7 g, 65 mmol) were dissolved in tetrahydrofuran/ethanol/water (1:2:1, 150 mL:300 mL:150 mL). After stirring for 16 hours at ambient temperature, the solvent was removed under vacuum to give lithium 6-cyanoimidazo[1,2-a]pyridine-3-carboxylate (12.6 g).

Step C: Lithium 6-cyanoimidazo[1,2-a]pyridine-3-carboxylate (138 mg, 0.7 mmol) was dissolved in anhydrous NMP (3.6 mL) and 2,4,6-trichlorobenzoyl chloride (115 mL, 0.7 mmol) added drop-wise. The mixture was stirred at ambient temperature for 30 minutes. 3-methyl-1-((6-methylpyridin-2-yl)methyl)-1H-indazol-4-amine (186 mg, 0.7 mmol) was then added in one portion and the reaction heated to 80° C. in a sand bath for 6 hours. Saturated sodium bicarbonate was added until precipitate formed and allowed to stir at ambient temperature for an hour. The precipitate was filtered off and dried under high vacuum for 2 hours to give 6-cyano-N-(3-methyl-1-((6-methylpyridin-2-yl)methyl)-1H-indazol-4-yl)imidazo[1,2-a]pyridine-3-carboxamide as a beige solid (140 mg). MS m/z 422.3 (M+1, APCI+).

Example 63

7-hydroxy-N-(3-methyl-1-((6-methylpyridin-2-yl)
methyl)-1H-indazol-4-yl)imidazo[1,2-a]pyridine-3-
carboxamide

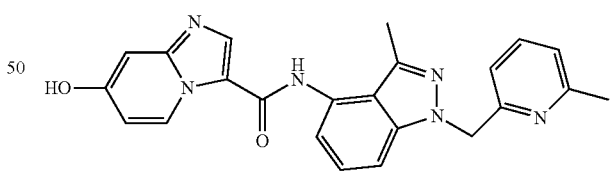

Step A: Preparation of ethyl
7-hydroxyimidazo[1,2-a]pyridine-3-carboxylate

2-Aminopyridin-4-ol (3 g, 27 mmol) was dissolved in ethanol (90 mL) in 250 mL round bottom flask. Ethyl 2-chloro-3-oxopropanoate (5% in benzene; 130 mL; Commercial solution from Toronto Research Chemicals Inc.) was added and the mixture refluxed for 10 hours. Reaction was concentrated and triturated with ethyl acetate before drying under high vacuum to give ethyl 7-hydroxyimidazo[1,2-a]pyridine-3-carboxylate as a beige solid (829 mg).

Step B: Preparation of ethyl 7-(ethoxymethoxy) imidazo[1,2-a]pyridine-3-carboxylate Ethyl 7-hydroxyimidazo[1,2-a]pyridine-3-carboxylate (100 mg, 0.38 mmol) was dissolved in DMF (3 mL) and treated with potassium carbonate (79 mg, 0.57 mmol). The mixture was stirred at ambient temperature for 30 minutes before adding chloromethylethyl ether (40 mg, 0.42 mmol) and heating mixture to 60° C. for 1 hour. The crude mixture was purified by reverse phase chromatography to give ethyl 7-(ethoxymethoxy)imidazo[1,2-a]pyridine-3-carboxylate (11 mg).

Step C: Preparation of 7-(ethoxymethoxy)-N-(3-methyl-1-((6-methylpyridin-2-yl)methyl)-1H-indazol-4-yl)imidazo[1,2-a]pyridine-3-carboxamide 3-Methyl-1-((6-methylpyridin-2-yl)methyl)-1H-indazol-4-amine (22 mg, 0.09 mmol) was dissolved in tetrahydropyran (DriSolve; 0.5 mL) and degassed before back-filling with nitrogen gas. The solution was then cooled in an ice water bath for 15 minutes before drop-wise addition of lithium bis(trimethylsilyl)amide (0.09 mL, 1 M in tetrahydrofuran). The reaction stirred for 10 minutes before drop-wise addition into a solution of ethyl 7-(ethoxymethoxy) imidazo[1,2-a]pyridine-3-carboxylate (11 mg, 0.04 mmol) in tetrahydrofuran (DriSolve; 0.2 mL) cooled in an ice-water bath. The reaction was then stirred while being cooled in the ice-water bath for 1.5 hours. The reaction was quenched with water and concentrated. The resulting crude material was purified by reverse phase chromatography, eluting with a gradient from 10% to 70% ACN/water over 25 column volumes, to give 7-(ethoxymethoxy)-N-(3-methyl-1-((6-methylpyridin-2-yl)methyl)-1H-indazol-4-yl)imidazo[1,2-a]pyridine-3-carboxamide (11.2 mg).

Step D: Preparation of 7-hydroxy-N-(3-methyl-1-((6-methylpyridin-2-yl)methyl)-1H-indazol-4-yl) imidazo[1,2-a]pyridine-3-carboxamide 7-(Ethoxymethoxy)-N-(3-methyl-1-((6-methylpyridin-2-yl)methyl)-1H-indazol-4-yl)imidazo[1,2-a]pyridine-3-carboxamide (11.2 mg, 0.02 mmol) was dissolved in dichloromethane (0.9 mL) and treated with trifluoroacetic acid (0.1 mL). The mixture was stirred at ambient temperature for 2 hours. The mixture was concentrated and dried under high vacuum to give 7-hydroxy-N-(3-methyl-1-((6-methylpyridin-2-yl)methyl)-1H-indazol-4-yl)imidazo[1,2-a]pyridine-3-carboxamide (8 mg). MS m/z 413.2 (M+1, APCI+).

Example 64

N-(3-methyl-1-((6-methylpyridin-2-yl)methyl)-1H-indazol-4-yl)-7-(2-(piperazin-1-yl)ethoxy)imidazo[1,2-a]pyridine-3-carboxamide

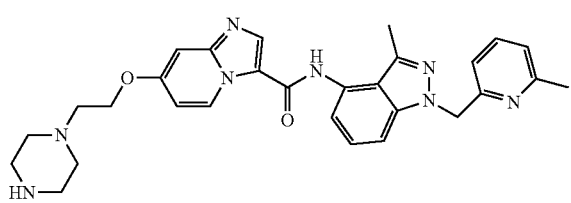 [SMILES: Cc1cccc(Cn2nc(C)c3c(NC(=O)c4cnc5cc(OCCN6CCNCC6)ccn45)cccc32)n1]

Step A: Preparation of tert-butyl 4-fluoropyridin-2-ylcarbamate

A flask was charged with 2-chloro-4-fluoropyridine (20 g, 152 mmol), tert-butyl carbamate (89 g, 760 mmol), tris(dibenzylideneacetone)dipalladium (1.39 g, 1.52 mmol), X-PHOS (1.48 g, 3.10 mmol), cesium carbonate (99 g, 588 mmol), and tetrahydrofuran (500 mL) under an atmosphere of dry nitrogen. This mixture was refluxed under nitrogen for 7 hours. An additional equivalent of cesium carbonate was added to drive reaction to completion. The mixture was cooled to ambient temperature and filtered through Celite, and the Celite was washed with ethyl acetate. The filtrate was partitioned between saturated sodium bicarbonate and ethyl acetate. The aqueous layer was washed with ethyl acetate twice. The combined organics were washed with brine and dried with sodium sulfate, concentrated under vacuum, and purified by column chromatography to give tert-butyl 4-fluoropyridin-2-ylcarbamate as a pale yellow solid (22.6 g).

Step B: Preparation of 4-fluoropyridin-2-amine

A flask was charged with tert-butyl 4-fluoropyridin-2-ylcarbamate (3.5 g, 16.5 mmol) and dichloromethane (100 mL). The mixture was cooled to 0-5° C. using an ice/water bath. Trifluoroacetic acid (75 mL) was added slowly down the side of the flask with continued stirring. The mixture was stirred at ambient temperature overnight. The mixture was concentrated before partitioning between saturated sodium bicarbonate and ethyl acetate. The aqueous layer was washed with ethyl acetate twice. The combined organic layers were washed with brine and dried with sodium sulfate before concentrating to give 4-fluoropyridin-2-amine as a pale yellow solid (1.76 g).

Step C: Preparation of ethyl 7-fluoroimidazo[1,2-a]pyridine-3-carboxylate

4-Fluoropyridin-2-amine (10.0 g, 48.0 mmol) was mixed with ethanol (40 mL) in a reaction flask under an atmosphere of dry nitrogen. A solution of ethyl 2-chloro-3-oxopropanoate (5% in benzene, 178 mL; commercial solution from Toronto Research Chemicals Inc.) was added. The mixture was heated to 60° C. under nitrogen for 4 hours. After allowing the mixture to cool the solvent was removed under vacuum to give a brown solid. The solid was mixed with ethyl acetate (300 mL) and sodium bicarbonate solution (75 mL) and stirred to dissolve. The phases were separated and the bicarbonate solution was extracted further with ethyl acetate (75 mL). The combined ethyl acetate extracts were dried over sodium sulfate, filtered and concentrated under vacuum to give a solid. The crude material was dissolved in ethyl acetate and passed through a short column of silica, eluting with ethyl acetate to give ethyl 7-fluoroimidazo[1,2-a]pyridine-3-carboxylate as a white solid (13 g).

Step D: Preparation of 7-fluoroimidazo[1,2-a]pyridine-3-carboxylic acid

Ethyl 7-fluoroimidazo[1,2-a]pyridine-3-carboxylate (8 g; 44.4 mmol) was mixed with tetrahydrofuran (225 mL), ethanol (110 mL) and water (55 mL). Lithium hydroxide monohydrate (0.962 g; 22.9 mmol) was added. The mixture was stirred at ambient temperature overnight. The mixture concentrated under reduced pressure to remove tetrahydrofuran and ethanol. Hydrochloric acid (2N) was added to aqueous mixture to adjust to pH 3. White precipitate formed and was filtered off with drying under high vacuum overnight to give 7-fluoroimidazo[1,2-a]pyridine-3-carboxylic acid as a white solid (6.3 g).

Step E: Preparation of 7-fluoro-N-(3-methyl-1-((6-methylpyridin-2-yl)methyl)-1H-indazol-4-yl)imidazo[1,2-a]pyridine-3-carboxamide A solution of 7-fluoroimidazo[1,2-a]pyridine-3-carboxylic acid (0.15 g, 0.84 mmol) in anhydrous 1-methyl-2-pyrrolidinone (4 mL) and treated with anhydrous triethylamine (0.3 mL, 2.11 mmol) allowing to stir until the reaction mixture became homogeneous. 2,4,6-Trichlorobenzoyl chloride (0.22 g, 0.89 mmol) was added dropwise and the reaction mixture was allowed to stir for 30 minutes at ambient temperature. Within 5 minutes, the anhydride precipitate formed and vigorous stirring was required. 3-Methyl-1-((6-methylpyridin-2-yl)methyl)-1H-indazol-4-amine (Example 35, Steps A-D; 0.19 g, 0.75 mmol) was added as a 0.5 M solution in anhydrous 1-methyl-2-pyrrolidinone. The reaction was heated in a sand bath at 80° C. and stirred overnight. The reaction mixture was cooled to ambient temperature and solids were removed by filtration. The filter cake was washed with ethyl acetate and the filtrate was concentrated. The resulting material was diluted with saturated sodium bicarbonate and a dark brown precipitate formed. The precipitate was isolated by filtration to give 7-fluoro-N-(3-methyl-1-((6-methylpyridin-2-yl)methyl)-1H-indazol-4-yl)imidazo[1,2-a]pyridine-3-carboxamide as a brown solid (170 mg).

Step F: Preparation of tert-butyl 4-(2-(3-(3-methyl-1-((6-methylpyridin-2-yl)methyl)-1H-indazol-4-ylcarbamoyl)imidazo[1,2-a]pyridin-7-yloxy)ethyl)piperazine-1-carboxylate A flask was charged with solid potassium tert-butoxide (0.07 g, 0.64 mmol), tert-butyl 4-(2-hydroxyethyl)piperazine-1-carboxylate (0.17 g, 0.74 mmol), and tert-butanol (0.6 mL). The mixture was heated to 60° C. for 20 minutes before adding N-(3-methyl-1-((6-methylpyridin-2-yl)methyl)-1H-indazol-4-yl)-7-fluoroimidazo[1,2-a]pyridine-3-carboxamide (0.045 g, 0.105 mmol) in one portion. The mixture was heated in a sand bath at 80° C. with stirring overnight. The reaction mixture was quenched with water and concentrated before purifying by reverse phase chromatography on a Biotage 25+C18 column, eluting with a gradient from 0-65% acetonitrile/water over 12 column volumes, to give tert-butyl 4-(2-(3-(3-methyl-1-((6-methylpyridin-2-yl)methyl)-1H-indazol-4-ylcarbamoyl)imidazo[1,2-a]pyridin-7-yloxy)ethyl)piperazine-1-carboxylate (40 mg) as a beige solid. MS (APCI), positive scan, m/z=639.1 (M+).

Step G: Preparation of N-(3-methyl-1-((6-methyl-pyridin-2-yl)methyl)-1H-indazol-4-yl)-7-(2-(piperazin-1-yl)ethoxy)imidazo[1,2-a]pyridine-3-carboxamide tert-Butyl 4-(2-(3-(3-methyl-1-((6-methylpyridin-2-yl)methyl)-1H-indazol-4-ylcarbamoyl)imidazo[1,2-a]pyridin-7-yloxy)ethyl)piperazine-1-carboxylate (0.04 g, 0.1 mmol) was dissolved in methanol and treated with concentrated hydrogen chloride. This mixture was stirred at ambient temperature for 2 hours before concentrating and drying under high vacuum overnight to give N-(3-methyl-1-((6-methylpyridin-2-yl)methyl)-1H- indazol-4-yl)-7-(2-(piperazin-1-yl)ethoxy)imidazo[1,2-a]pyridine-3-carboxamide as a white solid (38 mg). MS (APCI), positive scan, m/z=539.1 (M+).

Example 65

N-(3-methyl-1-((6-methylpyridin-2-yl)methyl)-1H-indazol-4-yl)-7-(1-methyl-6-oxo-1,6-dihydropyridin-3-yl)imidazo[1,2-a]pyridine-3-carboxamide

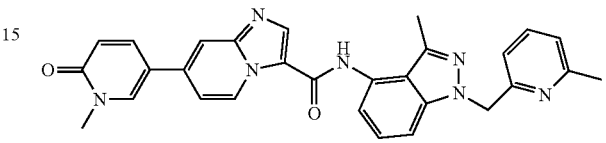

Step A: Preparation of 1-methyl-5-(4,4,5,5-tetramethyl-1,3,2-dioxaborolan-2-yl)pyridin-2(1H)-one A flask was charged with 4,4,4',4',5,5,5',5'-octamethyl-2,2'-bi(1,3,2-dioxaborolane) (4.204 g, 16.56 mmol), potassium acetate (4.432 g, 45.15 mmol), DPPF (0.2502 g, 0.4515 mmol), PdCl$_2$(DPPF)*dcm (0.3733 g, 0.4515 mmol), and dioxane (37 mL). The mixture was degassed with house nitrogen and heated at an oil bath temperature of 80° C. with stirring overnight. The mixture was cooled to ambient temperature, diluted with ethyl acetate and saturated sodium bicarbonate. The organic layer was dried over sodium sulfate and concentrated. Purification using flash chromatography eluting with a gradient from 0-50% ethyl acetate/hexanes to give 1-methyl-5-(4,4,5,5-tetramethyl-1,3,2-dioxaborolan-2-yl)pyridin-2(1H)-one as a colorless oil that solidifies to off-white solid under high vacuum (331 mg). MS (APCI), positive scan, m/z=504.2 (M+).

Step B: Preparation of N-(3-methyl-1-((6-methyl-pyridin-2-yl)methyl)-1H-indazol-4-yl)-7-(1-methyl-6-oxo-1,6-dihydropyridin-3-yl)imidazo[1,2-a]pyridine-3-carboxamide 7-Bromo-N-(3-methyl-1-((6-methylpyridin-2-yl)methyl)-1H-indazol-4-yl)imidazo[1,2-a]pyridine-3-carboxamide (0.05 g, 0.12 mmol) was dissolved in dimethoxyethane:dimethylformamide (1:1, 0.8 mL) in a 2 dram vial, and 1-Methyl-5-(4,4,5,5-tetramethyl-1,3,2-dioxaborolan-2-yl)pyridin-2(1H)-one (0.04 g, 0.17 mmol), PdCl$_2$(dppf)*dcm (0.005 g, 0.006 mmol), and 2 M sodium carbonate (0.17 mL, 0.34 mmol) were added. Nitrogen was bubbled through the reaction mixture for 5 minutes before capping the vial and heating in a sand bath at 90° C. overnight. The reaction mixture was diluted with ethyl acetate and water. A greenish precipitate formed and was collected. The crude material was purified by preparatory thin layer chromatography (silica, 20×20 cm, 0.5 mm) developed in a chamber with 10% MeOH/DCM. The UV active band with R$_f$=0.1 was isolated and the silica washed with 10% MeOH/DCM. The filtrate was concentrated to give N-(3-methyl-1-((6-methyl-pyridin-2-yl)methyl)-1H-indazol-4-yl)-7-(1-methyl-6-oxo-1,6-dihydropyridin-3-yl)imidazo[1,2-a]pyridine-3-carboxamide as a beige solid (31 mg).

Example 66

N-(1-((6-isopropylpyridin-2-yl)methyl)-3-methyl-1H-indazol-4-yl)-7-(2-(4-methylpiperazin-1-yl)ethoxy)imidazo[1,2-a]pyridine-3-carboxamide

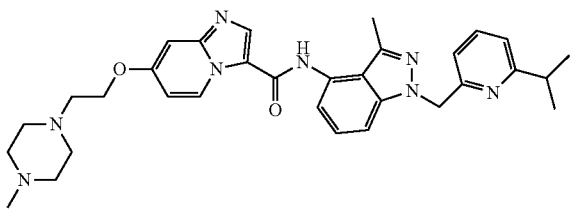 [SMILES: Cc1nn(Cc2cccc(C(C)C)n2)c2cccc(NC(=O)c3cnc4cc(OCCN5CCN(C)CC5)ccn34)c12]

Step A: Preparation of 1-((6-isopropylpyridin-2-yl)methyl)-3-methyl-4-nitro-1H-indazole A first flask was charged with 1,4-dioxane/H₂O (30 mL/5 mL). The flask was cooled to 0° C. and vacuum was applied for 20 minutes. A second flask was charged with K₂CO₃ (2.92 g, 21.1 mmol), 3-bromo-1-((6-isopropylpyridin-2-yl)methyl)-4-nitro-1H-indazole (1.98 g, 5.28 mmol), diacetoxypalladium (0.0592 g, 0.264 mmol), methylboronic acid (0.948 g, 15.8 mmol) and sodium 2'-(dicyclohexylphosphino)-2,6-dimethoxybiphenyl-3-sulfonate (0.270 g, 0.528 mmol). The second flask was evacuated with vacuum and back filled with N₂ for 3 times. The cold degassed dioxane/H₂O was then added to the second flask, which was again evacuated with vacuum and back filled with argon 5 times. The reaction mixture was heated to 80° C. for 3 hours. The reaction was cooled to ambient temperature, filtered and concentrated under reduced pressure. The residue was diluted with EtOAc (200 mL). The organic layer was washed with saturated NaHCO₃, dried (Na₂SO₄) and concentrated to give the desired product, which was used without further purification.

Step B: Preparation of 1-((6-isopropylpyridin-2-yl)methyl)-3-methyl-1H-indazol-4-amine To a suspension of 1-((6-isopropylpyridin-2-yl)methyl)-3-methyl-4-nitro-1H-indazole (1.51 g, 4.87 mmol) in EtOH/H₂O (40 mL/10 mL) was added iron (5.43 g, 97.3 mmol) and ammonium chloride (0.260 g, 4.87 mmol). The reaction mixture was heated to reflux for three hours, then cooled to 60° C. and filtered through a pad of Celite®. The filter cake was washed with EtOH/Et₃N (20:1, 200 mL) and MeOH/DCM (1:1, 100 mL). The filtrate was concentrated, and the residue was dissolved in EtOAc (200 mL). The ethyl acetate was washed with NaHCO₃, dried (Na₂SO₄), filtered and concentrated to give the desired product (57%).

Step C: Preparation of N-(1-((6-isopropylpyridin-2-yl)methyl)-3-methyl-1H-indazol-4-yl)-7-(2-(4-methylpiperazin-1-yl)ethoxy)imidazo[1,2-a]pyridine-3-carboxamide Prepared according to the method of Example 138. MS (ES+APCI) m/z=567.1 (M+H).

Example 67

N-(1-((1-isopropyl-5-methyl-1H-pyrazol-3-yl)methyl)-3-methyl-1H-indazol-4-yl)-7-(2-(4-methylpiperazin-1-yl)ethoxy)imidazo[1,2-a]pyridine-3-carboxamide

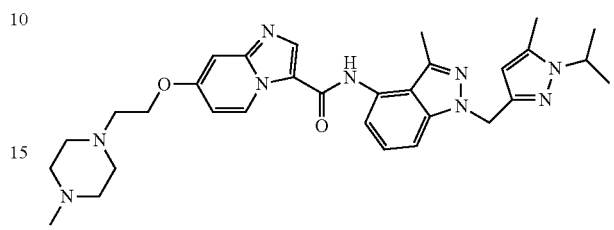

Prepared according to the method of Example 66, replacing 1-((6-isopropylpyridin-2-yl)methyl)-3-methyl-4-nitro-1H-indazole in Step B with 1-((1-isopropyl-5-methyl-1H-pyrazol-3-yl)methyl)-3-methyl-4-nitro-1H-indazole. MS (ES+APCI) m/z=570.2 (M+H).

Example 68

N-(3-methyl-1-((6-methylpyridin-2-yl)methyl)-1H-indazol-4-yl)-7-(1-methyl-1H-pyrazol-4-yl)imidazo[1,2-a]pyridine-3-carboxamide

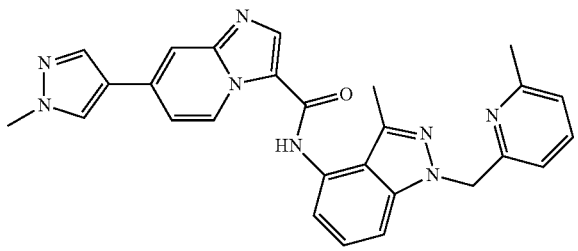 [SMILES: Cc1cccc(Cn2nc(C)c3c(NC(=O)c4cnc5cc(-c6cnn(C)c6)ccn45)cccc32)n1]

Step A: Preparation of 7-bromo-N-(3-methyl-1-((6-methylpyridin-2-yl)methyl)-1H-indazol-4-yl)imidazo[1,2-a]pyridine-3-carboxamide To a solution of 3-methyl-1-((6-methylpyridin-2-yl)methyl)-1H-indazol-4-amine (197.8 mg, 0.784 mmol) in anhydrous THF (3 ml) was added lithium bis(trimethylsilyl)amide (1.0 M in THF, 1.6 mL) under a nitrogen atmosphere at ambient temperature. The resulting mixture was stirred at ambient temperature for 10 minutes, then added dropwise to a chilled (ice-water bath) solution of methyl 7-bromoimidazo[1,2-a]pyridine-3-carboxylate (200 mg, 0.784 mmol) in anhydrous THF (3 mL). The cold bath was removed, and the reaction mixture was allowed to warm to ambient temperature, and quenched with water. The resulting suspension was extracted with DCM. The combined organic extracts were dried over anhydrous sodium sulfate and concentrated to afford the crude product. The crude product was subjected to preparative thin-layer chromatography on silica with 8% MeOH/DCM as the eluent to afford 255.6 mg of desired product as a yellow solid.

Step B: Preparation of N-(3-methyl-1-((6-methylpyridin-2-yl)methyl)-1H-indazol-4-yl)-7-(1-methyl-1H-pyrazol-4-yl)imidazo[1,2-a]pyridine-3-carboxamide A dried flask equipped with a reflux condenser and a nitrogen line was charged with 1-methyl-4-(4,4,5,5-tetramethyl-1,3,2-dioxaborolan-2-yl)-1H-pyrazole (14.4 mg, 0.069 mmol), 7-bromo-N-(3-methyl-1-((6-methylpyridin-2-yl)methyl)-1H-indazol-4-yl)imidazo[1,2-a]pyridine-3-carboxamide (Example 50, Steps A-B; 30 mg, 0.063 mmol), Pd(PPh$_3$)$_4$ (3.7 mg, 0.003 mmol), and potassium carbonate (44 mg, 0.32 mmol). To the flask was added a water:DMF:CH$_3$CN (1:1:4.5; 0.16:0.16:1.0 mL) mixture, and the reaction mixture was degassed under nitrogen and heated at 80° C. for 5 hours. The reaction mixture was cooled and diluted with water. The resulting suspension was extracted with EtOAc and DCM. The combined organic extracts were dried over anhydrous sodium sulfate and concentrated to afford the crude product. The crude product was subjected to preparative thin-layer chromatography on silica with 8% MeOH/DCM as eluent to afford 12.7 mg of product as a yellow solid. MS (ES+APCI) m/z=477 (M+H) detected.

Example 69

7-(3,5-dimethyl-1H-pyrazol-4-yl)-N-(3-methyl-1-((6-methylpyridin-2-yl)methyl)-1H-indazol-4-yl)imidazo[1,2-a]pyridine-3-carboxamide

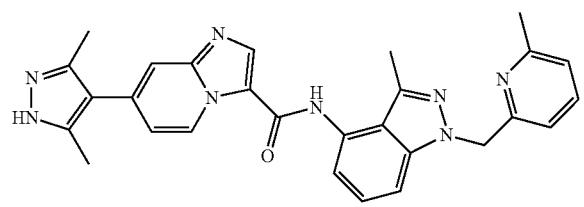 [SMILES: Cc1cccc(Cn2nc(C)c3c(NC(=O)c4cnc5cc(-c6c(C)n[nH]c6C)ccn45)cccc32)n1]

Prepared according to procedure of Example 68, using 7-bromo-N-(3-methyl-1-((6-methylpyridin-2-yl)methyl)-1H-indazol-4-yl)imidazo[1,2-a]pyridine-3-carboxamide and 3,5-dimethyl-4-(4,4,5,5-tetramethyl-1,3,2-dioxaborolan-2-yl)-1H-pyrazole. $^1$H NMR (CDCl$_3$, δ) 9.55 (d, 1H), 8.40 (s, 1H), 8.24 (s, 1H), 7.78 (d, 1H), 7.62 (s, 1H), 7.42 (t, 1H), 7.34 (t, 1H), 7.15 (d, 1H), 7.06 (t, 2H), 6.52 (d, 1H), 5.64 (s, 2H), 2.87 (s, 3H), 2.58 (s, 3h), 2.40 (s, 6H).

Example 70

N-(3-methyl-1-((6-methylpyridin-2-yl)methyl)-1H-indazol-4-yl)-7-(1H-pyrazol-4-yl)imidazo[1,2-a]pyridine-3-carboxamide

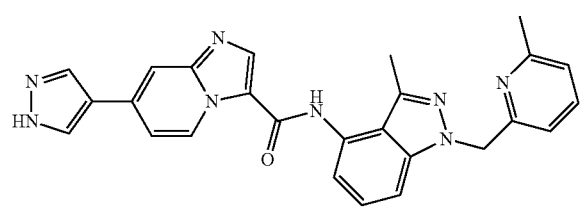 [SMILES: Cc1cccc(Cn2nc(C)c3c(NC(=O)c4cnc5cc(-c6cn[nH]c6)ccn45)cccc32)n1]

Prepared according to procedure of Example 68 using 7-bromo-N-(3-methyl-1-((6-methylpyridin-2-yl)methyl)-1H-indazol-4-yl)imidazo[1,2-a]pyridine-3-carboxamide and tert-butyl 4-(4,4,5,5-tetramethyl-1,3,2-dioxaborolan-2-yl)-1H-pyrazole-1-carboxylate. MS (ES+APCI) m/z=463 (M+H) detected.

Example 71

N-(3-methyl-1-((6-methylpyridin-2-yl)methyl)-1H-indazol-4-yl)-7-(1-methyl-1H-pyrazol-5-yl)imidazo[1,2-a]pyridine-3-carboxamide

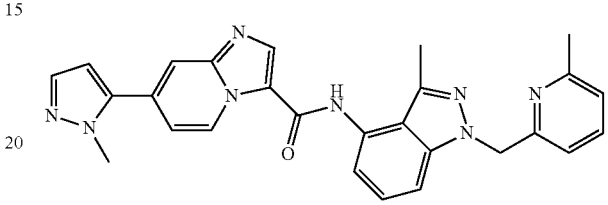

Step A: Preparation of 3-methyl-1-((6-methylpyridin-2-yl)methyl)-4-nitro-1H-indazole A flask equipped with a reflux condenser and a nitrogen line was charged with 3-iodo-1-((6-methylpyridin-2-yl)methyl)-4-nitro-1H-indazole (Example 89, Steps A-B; 100 mg, 0.254 mmol), trio-tolylphosphine (15.4 mg, 0.051 mmol), and tris(dibenzylideneacetone)dipalladium (0) (23 mg, 0.025 mmol). The flask was purged with nitrogen and anhydrous DMF (30 mL), and tetramethylstannane (0.04 ml, 0.28 mmol) were added, followed by triethylamine (0.04 mL, 0.30 mmol). The flask was degassed under nitrogen and heated at 80° C. for 6 hours. The reaction mixture was cooled to ambient temperature, diluted with water, and extracted with DCM and EtOAc. The combined organic extracts were dried over anhydrous sodium sulfate, and concentrated. The crude product was subjected to preparative thin-layer chromatography on silica with 2% MeOH/DCM as eluent to afford 56.8 mg of desired product as a yellow solid.

Step B: Preparation of 3-methyl-1-((6-methylpyridin-2-yl)methyl)-1H-indazol-4-amine A suspension of 3-methyl-1-((6-methylpyridin-2-yl)methyl)-4-nitro-1H-indazole (54 mg, 0.19 mmol) in absolute EtOH (1.5 mL) was treated at ambient temperature with dihydroxypalladium (27 mg, 0.019 mmol). The mixture was stirred at ambient temperature under a hydrogen atmosphere for 16 hours, then filtered through a Celite® pad and concentrated to afford 36 mg of the desired product as a clear yellow oil.

Step C: Preparation of methyl 7-bromoimidazo[1,2-a]pyridine-3-carboxylate

A 50 mL flask equipped with a reflux condenser and a nitrogen line was charged with 7-bromoimidazo[1,2-a]pyridine-3-carboxylic acid (1.00 g, 4.15 mmol), DCM (20 mL), oxalyl chloride (0.72 mL, 1.46 mmol), and chilled in a ice-water bath. Four drops of DMF were added to the reaction, and the flask was stirred at ambient temperature overnight. The reaction mixture was concentrated to dryness, chilled in an ice water bath, and 30 mL MeOH were added under a nitrogen atmosphere. The reaction mixture was stirred at ambient temperature overnight, concentrated to dryness, and re-suspended in saturated, aqueous sodium bicarbonate solution. The suspension was extracted with DCM and EtOAc, the combined organic extracts were dried over anhydrous sodium sulfate, and concentrated to afford the desired product (0.918 g) as a tan solid.

Step D: Preparation of methyl 7-(1-methyl-1H-pyrazol-5-yl)imidazo[1,2-a]pyridine-3-carboxylate A dried flask equipped with a reflux condenser and a nitrogen line was charged with methyl 7-bromoimidazo[1,2-a]pyridine-3-carboxylate (200 mg, 0.784 mmol), 1-methyl-5-(4,4,5,5-tetramethyl-1,3,2-dioxaborolan-2-yl)-1H-pyrazole (180 mg, 0.869 mmol) and PdCl$_2$(dppf) dichloromethane adduct (64 mg, 0.078 mmol). To the flask was added 3 mL 1,2-dimethoxyethane containing 1% absolute ethanol, followed by addition of triethylamine (0.22 mL, 1.57 mmol). The flask was degassed under nitrogen and heated at 85° C. for 10 hours. The reaction mixture was allowed to cool to ambient temperature and then diluted with water. The resulting suspension was extracted with DCM. The combined organic extracts were dried over anhydrous sodium sulfate, and concentrated to afford the crude product. The crude product was subjected to preparative thin-layer chromatography on silica with 4% MeOH/DCM as eluent to afford 47.4 mg of pure, desired product as a pale yellow solid.

Step E: Preparation of N-(3-methyl-1-((6-methylpyridin-2-yl)methyl)-1H-indazol-4-yl)-7-(1-methyl-1H-pyrazol-5-yl)imidazo[1,2-a]pyridine-3-carboxamide To a solution of 3-methyl-1-((6-methylpyridin-2-yl)methyl)-1H-indazol-4-amine (46.7 mg, 0.185 mmol) in anhydrous THF (2 ml) was added under a nitrogen atmosphere at ambient temperature lithium bis(trimethylsilyl)amide (1.0 M in THF, 0.38 mL). The resulting mixture was stirred at ambient temperature for 10 minutes, then added dropwise to a chilled (ice-water bath) solution of methyl 7-(1-methyl-1H-pyrazol-5-yl)imidazo[1,2-a]pyridine-3-carboxylate (47.4 mg, 0.185 mmol) in anhydrous THF (2 mL). The cold bath was removed, and the reaction mixture was allowed to warm to ambient temperature, and quenched with water. The resulting suspension was extracted with DCM. The combined organic extracts were dried over anhydrous sodium sulfate and concentrated to afford the dried product. The crude product was subjected to preparative thin-layer chromatography on silica with 8% MeOH/DCM as eluent to afford 45.7 mg of pure, desired product as a yellow-brown solid. MS (ES+APCI) m/z=477 (M+H) detected.

Example 72

7-(2-(dimethylamino)ethyl)-N-(3-methyl-1-((6-methylpyridin-2-yl)methyl)-1H-indazol-4-yl)imidazo[1,2-a]pyridine-3-carboxamide

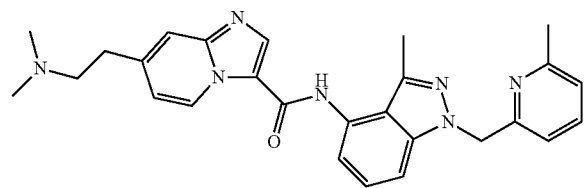 [SMILES: Cc1cccc(Cn2nc(C)c3c(NC(=O)c4cnc5cc(CCN(C)C)ccn45)cccc32)n1]

Step A: Preparation of (Z)-7-(2-ethoxyvinyl)-N-(3-methyl-1-((6-methylpyridin-2-yl)methyl)-1H-indazol-4-yl)imidazo[1,2-a]pyridine-3-carboxamide A flask was charged with 7-bromo-N-(3-methyl-1-((6-methylpyridin-2-yl)methyl)-1H-indazol-4-yl)imidazo[1,2-a]pyridine-3-carboxamide (Example 50, Steps A-B; 100 mg, 0.21 mmol), tri-O-tolylphosphine (12.8 mg, 0.042 mmol) and tris(dibenzylideneacetone)dipalladium (19.3 mg, 0.021 mmol). To the flask was added DMF (3 mL), followed by (Z)-tributyl(2-ethoxyvinyl)stannane (114 mg, 0.316 mmol) and triethylamine (0.04 mL, 0.30 mmol). The reaction mixture was degassed under nitrogen, and stirred at 100° C. for 10 hours. The reaction mixture was cooled, diluted with water, and extracted with DCM and EtOAc. The combined organic extracts were dried over anhydrous sodium sulfate and concentrated. The crude product was subjected to preparative thin-layer chromatography on silica with 5% MeOH/DCM as eluent to afford 82.8 mg of product as a yellow solid.

Step B: Preparation of N-(3-methyl-1-((6-methylpyridin-2-yl)methyl)-1H-indazol-4-yl)-7-(2-oxoethyl)imidazo[1,2-a]pyridine-3-carboxamide A solution of (Z)-7-(2-ethoxyvinyl)-N-(3-methyl-1-((6-methylpyridin-2-yl)methyl)-1H-indazol-4-yl)imidazo[1,2-a]pyridine-3-carboxamide (82.8 mg, 0.177 mmol) in 1:1 dioxane/water (2 mL) was treated with 45 equivalents of 4.0 M hydrochloric acid in dioxane solution at ambient temperature. The reaction mixture was stirred at ambient temperature for 1.5 hours, quenched with saturated aqueous sodium bicarbonate solution, and extracted with DCM and EtOAc. The combined organic extracts were dried over anhydrous sodium sulfate, concentrated, and subjected to preparative thin-layer chromatography on silica with a 10% MeOH in DCM solution as eluent to afford 37 mg of the impure desired product as a yellow solid. The crude product was used in the next step without further purification.

Step C: Preparation of 7-(2-(dimethylamino)ethyl)-N-(3-methyl-1-((6-methylpyridin-2-yl)methyl)-1H-indazol-4-yl)imidazo[1,2-a]pyridine-3-carboxamide A solution of N-(3-methyl-1-((6-methylpyridin-2-yl)methyl)-1H-indazol-4-yl)-7-(2-oxoethyl)imidazo[1,2-a]pyridine-3-carboxamide (33 mg, 0.068 mmol) and dimethylamine (0.34 mL, 0.68 mmol) in 1.4 mL of a 1:1 MeOH/EtOH mixture was treated at ambient temperature with excess (10 equivalents) sodium triacetoxyborohydride. The reaction mixture was stirred overnight at ambient temperature. Another 10 equivalents of sodium triacetoxyborohydride were added, and stirring was continued for a few more hours. The reaction mixture was quenched with an equal volume of saturated, aqueous sodium bicarbonate, and extracted with DCM and EtOAc. The combined organic extracts were dried over anhydrous sodium sulfate, concentrated, and subjected to preparative thin-layer chromatography on silica, with an 8% MeOH-2% 7N NH$_3$/MeOH/DCM mixture as eluent, to afford 6.6 mg of desired product. MS (ES+APCI) m/z=468 (M+H) detected.

Example 73

7-(2-hydroxyethyl)-N-(3-methyl-1-((6-methylpyridin-2-yl)methyl)-1H-indazol-4-yl)imidazo[1,2-a]pyridine-3-carboxamide

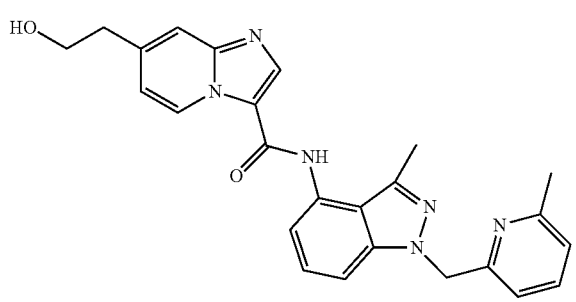 [SMILES: Cc1cccc(Cn2nc(C)c3c(NC(=O)c4cnc5cc(CCO)ccn45)cccc32)n1]

A solution of N-(3-methyl-1-((6-methylpyridin-2-yl)methyl)-1H-indazol-4-yl)-7-(2-oxoethyl)imidazo[1,2-a]pyridine-3-carboxamide (5 mg, 0.011 mmol) in 0.5 mL absolute EtOH was treated at ambient temperature with 3 equivalents of sodium triacetoxyborohydride. The reaction mixture was stirred overnight at ambient temperature, after which another 10 equivalents reducing agent were added. Stirring was continued until starting material was consumed. The reaction was quenched with excess saturated aqueous sodium bicarbonate solution, and extracted with DCM and EtOAc. The combined organic extracts were dried over anhydrous sodium sulfate, and concentrated. The crude product was subjected to preparative thin-layer chromatography on silica with 5% MeOH/DCM as eluent to afford 3.7 mg of product as a white solid. MS (ES+APCI) m/z=441 (M+H) detected.

Example 74

7-(2-(2-methoxyethylamino)ethyl)-N-(3-methyl-1-((6-methylpyridin-2-yl)methyl)-1H-indazol-4-yl)imidazo[1,2-a]pyridine-3-carboxamide

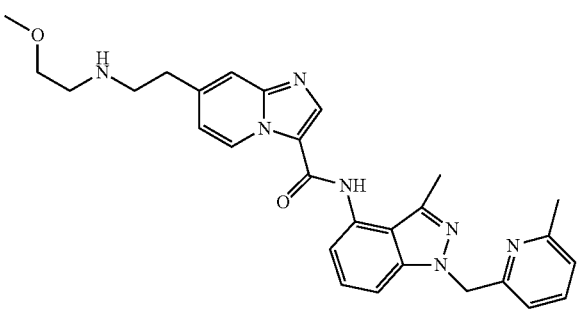 [SMILES: COCCNCCc1ccn2c(C(=O)Nc3cccc4c3c(C)nn4Cc3cccc(C)n3)cnc2c1]

Prepared according to procedure for Example 72 from N-(3-ethyl-1-((6-methylpyridin-2-yl)methyl)-1H-indazol-4-yl)-7-(2-oxoethyl)imidazo[1,2-a]pyridine-3-carboxamide and 2-methoxyethanamine. MS (ES+APCI) m/z=498 (M+H) detected.

Example 75

7-(1-(2-hydroxyethylamino)ethyl)-N-(3-methyl-1-((6-methylpyridin-2-yl)methyl)-1H-indazol-4-yl)imidazo[1,2-a]pyridine-3-carboxamide

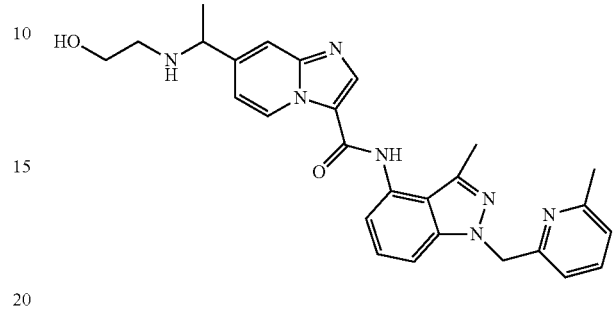

Prepared from 7-acetyl-N-(3-methyl-1-((6-methylpyridin-2-yl)methyl)-1H-indazol-4-yl)imidazo[1,2-a]pyridine-3-carboxamide (Example 79) and ethanolamine following procedure in Example 72, Step C. MS (ES+APCI) m/z=484 (M+H) detected.

Example 76

7-(1-hydroxyethyl)-N-(3-methyl-1-((6-methylpyridin-2-yl)methyl)-1H-indazol-4-yl)imidazo[1,2-a]pyridine-3-carboxamide

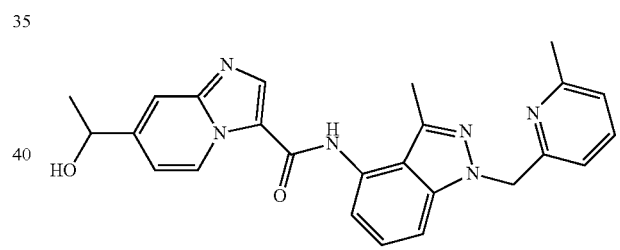

Isolated as a by-product from preparation of Example 75. MS (ES+APCI) m/z=441 (M+H) detected.

Example 77

N-(3-methyl-1-((6-methylpyridin-2-yl)methyl)-1H-indazol-4-yl)-7-(2-(pyrrolidin-1-yl)ethyl)imidazo[1,2-a]pyridine-3-carboxamide

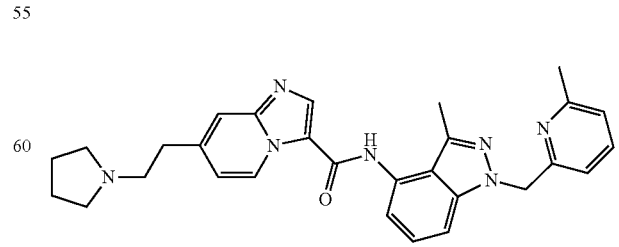

Prepared according to procedure of Example 72 from N-(3-methyl-1-((6-methylpyridin-2-yl)methyl)-1H-indazol- 4-yl)-7-(2-oxoethyl)imidazo[1,2-a]pyridine-3-carboxamide (Example 72, Steps A-B) and pyrrolidine. MS (ES+APCI) m/z=494 (M+H) detected.

Example 78

N-(3-methyl-1-((6-methylpyridin-2-yl)methyl)-1H-indazol-4-yl)-7-(2-(4-methylpiperazin-1-yl)ethyl)imidazo[1,2-a]pyridine-3-carboxamide

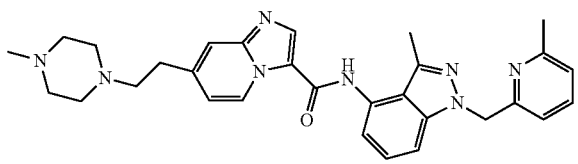 [SMILES: Cc1cccc(Cn2nc(C)c3c(NC(=O)c4cnc5cc(CCN6CCN(C)CC6)ccn45)cccc32)n1]

Prepared according to procedure for Example 72 from N-(3-methyl-1-((6-methylpyridin-2-yl)methyl)-1H-indazol-4-yl)-7-(2-oxoethyl)imidazo[1,2-a]pyridine-3-carboxamide and 1-methylpiperazine. MS (ES+APCI) m/z=523 (M+H) detected.

Example 79

7-acetyl-N-(3-methyl-1-((6-methylpyridin-2-yl)methyl)-1H-indazol-4-yl)imidazo[1,2-a]pyridine-3-carboxamide

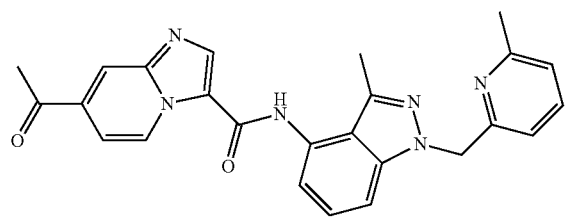 [SMILES: CC(=O)c1ccn2c(C(=O)Nc3cccc4c3c(C)nn4Cc3cccc(C)n3)cnc2c1]

Step A: Preparation of 7-(1-ethoxyvinyl)-N-(3-methyl-1-((6-methylpyridin-2-yl)methyl)-1H-indazol-4-yl)imidazo[1,2-a]pyridine-3-carboxamide A flask equipped with a reflux condenser and a nitrogen line was charged with 7-bromo-N-(3-methyl-1-((6-methylpyridin-2-yl)methyl)-1H-indazol-4-yl)imidazo[1,2-a]pyridine-3-carboxamide (Example 50, Steps A-B; 74.8 mg, 0.157 mmol), tri-O-tolylphosphine (9.6 mg, 0.031 mmol), and tris(dibenzylideneacetone)dipalladium (0) (14.4 mg, 0.015 mmol). Anhydrous DMF (2 mL), tributyl(1-ethoxyvinyl)tin (0.07 mL, 0.22 mmol) and triethylamine (0.03 mL, 0.22 mmol) were added to the flask, and the reaction mixture was degassed under nitrogen and stirred at 100° C. for 6 hours. The reaction mixture was cooled, diluted with excess water and extracted with DCM and EtOAc. The combined organics were dried over anhydrous sodium sulfate and concentrated. The crude product was purified by preparative thin-layer chromatography (silica, 5% MeOH/DCM as eluent) to afford 56.4 mg of desired product as a yellow solid.

Step B: Preparation 7-acetyl-N-(3-methyl-1-((6-methylpyridin-2-yl)methyl)-1H-indazol-4-yl)imidazo[1,2-a]pyridine-3-carboxamide A solution of 7-(1-ethoxyvinyl)-N-(3-methyl-1-((6-methylpyridin-2-yl)methyl)-1H-indazol-4-yl)imidazo[1,2-a]pyridine-3-carboxamide (56.4 mg, 0.121 mmol) in DCM (1 mL) was treated at ambient temperature with a 4.0 M solution of HCl in dioxane (10 equivalents). The reaction mixture was stirred at ambient temperature for 0.5 hours, then quenched with saturated aqueous sodium bicarbonate. The resulting suspension was extracted with DCM and EtOAc. The combined organic extracts were dried over anhydrous sodium sulfate and concentrated. The crude product was purified by preparative thin-layer chromatography (silica, 5% MeOH/DCM as eluent) to afford 24 mg of desired product as a solid. MS (ES+APCI) m/z=439 (M+H) detected.

Example 80

N-(1-benzyl-3-methyl-1H-indazol-4-yl)-7-(2-methoxyethoxyl)imidazo[1,2-a]pyridine-3-carboxamide

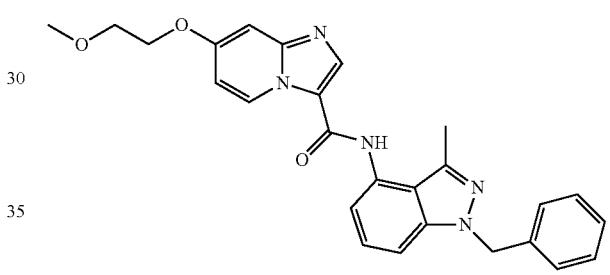

Step A: Preparation of 3-iodo-4-nitro-1H-indazole

Prepared according to the method of Example 89.

Step B: Preparation of 3-methyl-4-nitro-1H-indazole

A solution of dimethyl zinc (1.73 ml, 3.46 mmol) was added dropwise to a mixture of 3-iodo-4-nitro-1H-indazole (0.500 g, 1.73 mmol) and (1,1'-bis(diphenylphosphino)ferrocene)dichloropalladium (0.427 g, 0.519 mmol) in dioxane (0.2M, 9 mL) under argon. The mixture was heated under reflux for 2 hours. After cooling, MeOH (<1 mL) was added, followed by 2N HCl (1 mL) and DCM (5 mL). After stirring mixture for 30 minutes, the organic layer was separated, washed with saturated aqueous sodium bicarbonate, water, and brine. The combined organic extracts were dried (phase separator silicone treated filter paper), concentrated and purified on silica gel (1-10% EtOAc in DCM to provide 3-methyl-4-nitro-1H-indazole (0.082 g, 27% yield) as a brown residue.

Step C: Preparation of 1-benzyl-3-methyl-4-nitro-1H-indazole

To a solution of 3-methyl-4-nitro-1H-indazole (0.100 g, 0.564 mmol) in acetone (0.4M, 1.4 mL) cooled to 0° C. was added potassium hydroxide (0.0475 g, 0.847 mmol). After 15 minutes at 0° C., (bromomethyl)benzene (0.0737 ml, 0.621 mmol) was added. The mixture was allowed to stir at ambient temperature overnight and then concentrated. The residue was purified on silica gel (10-50% EtOAc in hexanes) to provide 1-benzyl-3-methyl-4-nitro-1H-indazole (0.052 g, 34% yield) as a yellow gum.

Step D: Preparation of 1-benzyl-3-methyl-1H-indazol-4-amine

A solution of 1-benzyl-3-methyl-4-nitro-1H-indazole (0.052 g, 0.19 mmol), ammonium chloride (0.0052 g, 0.097 mmol) in 4:1 EtOH/water (5 mL) was treated with iron (0.11 g, 1.9 mmol) and refluxed for 2 hours. The mixture was concentrated and residue shaken in EtOAc/water, filtered through GF/F paper, and concentrated to provide 1-benzyl-3-methyl-1H-indazol-4-amine (0.46 g, 82% yield) as a yellow gum.

Step E: Preparation of N-(1-benzyl-3-methyl-1H-indazol-4-yl)-7-(2-methoxyethoxy) imidazo[1,2-a]pyridine-3-carboxamide A mixture of 7-(2-methoxyethoxyl)imidazo[1,2-a]pyridine-3-carboxylic acid (0.035 g, 0.148 mmol) in dichloromethane (10 mL) was added oxalyl chloride in dichloromethane (2M, 0.081 mL, 0.163 mmol) with a catalytic (drop) amount of DMF. After stirring at ambient temperature for 30 minutes, 1-benzyl-3-methyl-1H-indazol-4-amine (0.0387 g, 0.163 mmol) was added (as a solution in 1 mL methylene chloride), followed by diisopropylethylamine (0.0310 mL, 0.178 mmol). The mixture was stirred overnight and then partitioned between water and DCM. The combined organic extracts were dried (phase separator silicone treated filter paper), evaporated in vacuum and purified on silica gel (10-50% EtOAc in hexanes) to afford N-(1-benzyl-3-methyl-1H-indazol-4-yl)-7-(2-methoxyethoxyl)imidazo[1,2-a]pyridine-3-carboxamide (0.022 g, 33% yield) as a white solid, 22 mg. MS (APCI) m/z=456 (M+H).

Example 81

N-(3-methyl-1-((6-methylpyridin-3-yl)methyl)-1H-indazol-4-yl)imidazo[1,2-a]pyridine-3-carboxamide

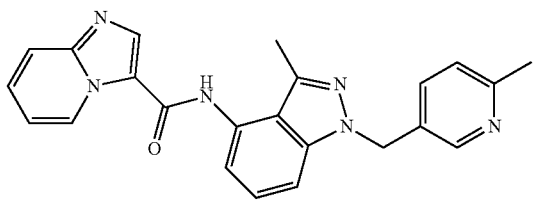 [SMILES: Cc1ccc(Cn2nc(C)c3c(NC(=O)c4cnc5ccccn45)cccc32)cn1]

Step A: Preparation of (6-methylpyridin-3-yl)methanol

A solution of methyl 6-methylnicotinate (16.3 g, 108 mmol) in MeOH (150 mL) was treated with sodium borohydride (12.2 g, 323 mmol) at ambient temperature in portions. The mixture was quenched with water (100 mL) and concentrated. This mixture was diluted with water (300 mL) and extracted with EtOAc. The combined organic extracts were dried (phase separator silicone treated filter paper) and concentrated to give (6-methylpyridin-3-yl)methanol (8.5 g, 64% yield) as a light yellow oil.

Step B: Preparation of 5-(chloromethyl)-2-methylpyridine hydrochloride (6-Methylpyridin-3-yl)methanol (8.54 g, 69.34 mmol) was dissolved in toluene (0.5M, 125 mL). Thionyl chloride (10.12 mL, 138.7 mmol) was added dropwise, during which a white solid began to precipitate out of solution. The mixture was heated to 65° C. and stirred for 1 hour. The mixture was concentrated, shaken in ether and collected by filtration to provide 5-(chloromethyl)-2-methylpyridine hydrochloride (11.3 g, 92% yield) as a beige solid.

Step C: Preparation of 3-methyl-1-((6-methylpyridin-3-yl)methyl)-4-nitro-1H-indazole Prepared according to the method of Example 80, replacing (bromomethyl)benzene with 5-(chloromethyl)-2-methylpyridine hydrochloride.

Step D: Preparation of 3-methyl-1-((6-methylpyridin-3-yl)methyl)-1H-indazol-4-amine Prepared according to the method of Example 80, replacing 1-benzyl-3-methyl-4-nitro-1H-indazole with 3-methyl-1-((6-methylpyridin-3-yl)methyl)-4-nitro-1H-indazole.

Step E: Preparation of N-(3-methyl-1-((6-methylpyridin-3-yl)methyl)-1H-indazol-4-yl)imidazo[1,2-a]pyridine-3-carboxamide Prepared according to the method of Example 80, replacing 7-(2-methoxyethoxyl)imidazo[1,2-a]pyridine-3-carboxylic acid and 1-benzyl-3-methyl-1H-indazol-4-amine with imidazo[1,2-a]pyridine-3-carboxylic acid and 3-methyl-1-((6-methylpyridin-3-yl)methyl)-1H-indazol-4-amine (8 mg, 11% yield). MS (APCI) m/z=397 (M+H).

Example 82

7-(2-methoxyethoxy)-N-(3-methyl-1-((tetrahydro-2H-pyran-2-yl)methyl)-1H-indazol-4-yl)imidazo[1,2-a]pyridine-3-carboxamide

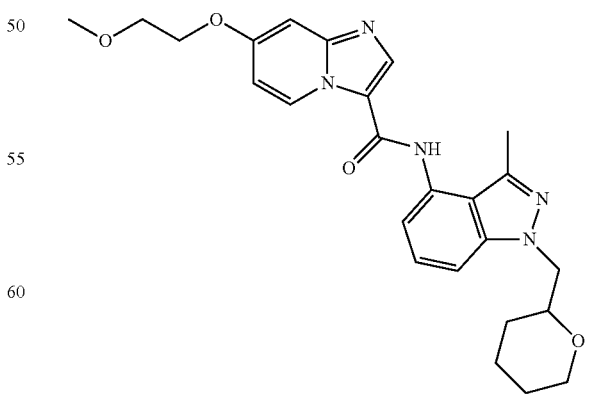

Prepared according to the method of Example 80, replacing 1-benzyl-3-methyl-1H-indazol-4-amine with 3-methyl- 1-((tetrahydro-2H-pyran-2-yl)methyl)-1H-indazol-4-amine. MS (APCI) m/z=464 (M+H).

Example 83

7-(2-methoxyethoxy)-N-(3-methyl-1-((tetrahydro-2H-pyran-4-yl)methyl)-1H-indazol-4-yl)imidazo[1,2-a]pyridine-3-carboxamide

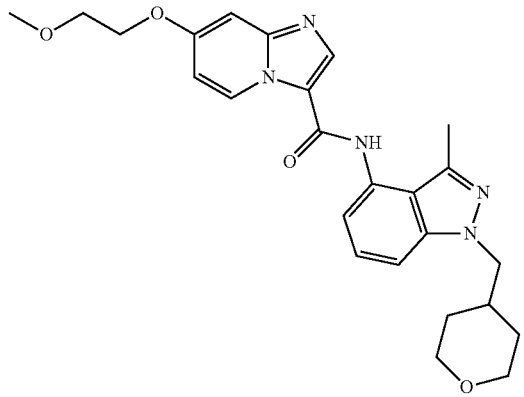 [SMILES: COCCOc1ccn2c(C(=O)Nc3cccc4c3c(C)nn4CC3CCOCC3)cnc2c1]

Prepared according to the method of Example 80, replacing 1-benzyl-3-methyl-1H-indazol-4-amine with 3-methyl-1-((tetrahydro-2H-pyran-4-yl)methyl)-1H-indazol-4-amine. MS (APCI) m/z=464 (M+H).

Example 84

N-(1-(cyclopropylmethyl)-3-methyl-1H-indazol-4-yl)-7-(2-methoxyethoxy)imidazo[1,2-a]pyridine-3-carboxamide

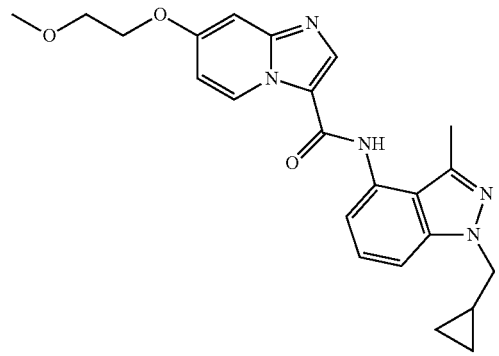 [SMILES: COCCOc1ccn2c(C(=O)Nc3cccc4c3c(C)nn4CC3CC3)cnc2c1]

Prepared according to the method of Example 80, replacing 1-benzyl-3-methyl-1H-indazol-4-amine with 1-(cyclopropylmethyl)-3-methyl-1H-indazol-4-amine. MS (APCI) m/z=420 (M+H).

Example 85

N-(3-methyl-1-((6-methylpyridin-3-yl)methyl)-1H-indazol-4-yl)-7-(2-(4-methylpiperazin-1-yl)ethoxy)imidazo[1,2-a]pyridine-3-carboxamide

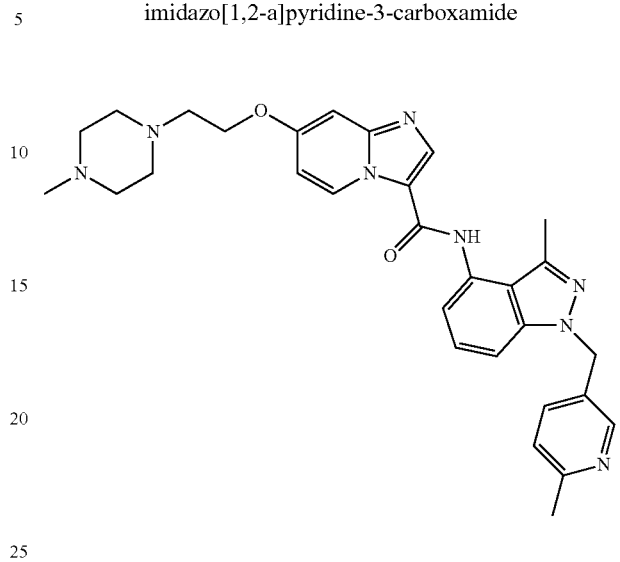

Prepared according to the method of Example 80, replacing 7-(2-methoxyethoxyl)imidazo[1,2-a]pyridine-3-carboxylic acid and 1-benzyl-3-methyl-1H-indazol-4-amine with 3-methyl-1-((6-methylpyridin-3-yl)methyl)-1H-indazol-4-amine and lithium 7-(2-(4-methylpiperazin-1-yl)ethoxy)imidazo[1,2-a]pyridine-3-carboxylate, respectively. MS (APCI) m/z=539 (M+H).

Example 86

N-(1-((6-ethoxypyridin-2-yl)methyl)-3-methyl-1H-indazol-4-yl)-7-(2-(4-methylpiperazin-1-yl)ethoxy)imidazo[1,2-a]pyridine-3-carboxamide

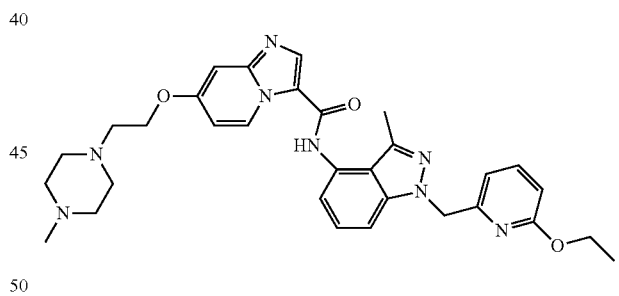

Step A: Preparation of ethyl 6-ethoxypicolinate

Iodoethane (6.90 mL, 86.3 mmol) was added to a suspension of 6-hydroxypicolinic acid (3.0 g, 21.6 mmol) and silver carbonate (11.9 g, 43.1 mmol) in chloroform (0.1M, 200 mL). The mixture was allowed to stir at ambient temperature for 18 hours. Insoluble material was removed by filtration and the solid was washed with chloroform. The filtrate was concentrated to give ethyl 6-ethoxypicolinate (4.14 g, 98% yield) as reddish oil.

Step B: Preparation of (6-ethoxypyridin-2-yl)methanol

Sodium borohydride (16.0 g, 424 mmol) was added in portions over 35 minutes to ethyl 6-ethoxypicolinate (4.14 g, 21.2 mmol) in EtOH (0.2M, 200 mL). The resulting mixture was stirred at ambient temperature for two days. The mixture was concentrated and the residue was distributed between water and DCM. The organic layer was dried (phase separator silicone treated filter paper), and concentrated to give (6-ethoxypyridin-2-yl)methanol (3.05 g, 94% yield) as a pale yellow oil.

Step C: Preparation of 2-(chloromethyl)-6-ethoxypyridine hydrochloride (6-Ethoxypyridin-2-yl)methanol (3.00 g, 19.6 mmol) was dissolved in toluene (0.5M, 40 mL). Thionyl chloride (2.86 ml, 39.2 mmol) was added dropwise, during which a white solid began to precipitate out of solution. The mixture was heated to 65° C. with stirring for 1 hour. The mixture was concentrated and the residue shaken with ether and collected by filtration to afford 2-(chloromethyl)-6-ethoxypyridine hydrochloride (1.2 g, 29% yield).

Step D: Preparation of 3-bromo-1-((6-ethoxypyridin-2-yl)methyl)-4-nitro-1H-indazole To a solution of 3-bromo-4-nitro-1H-indazole (1.5 g, 6.20 mmol) in DMF (0.5M, 12 mL) was added potassium carbonate (1.71 g, 12.4 mmol) at ambient temperature. After 15 minutes, 2-(chloromethyl)-6-ethoxypyridine hydrochloride (1.29 g, 6.20 mmol) was added. The mixture was allowed to stir at ambient temperature for 18 hours. The mixture was concentrated and diluted with ice-water (300 mL). Precipitated solids were collected by filtration, washed with water and dried under high vacuum overnight to provide 3-bromo-1-((6-ethoxypyridin-2-yl)methyl)-4-nitro-1H-indazole (1.21 g, 52% yield).

Step E: Preparation of 1-((6-ethoxypyridin-2-yl)methyl)-3-methyl-4-nitro-1H-indazole A solution of 3-bromo-1-((6-ethoxypyridin-2-yl)methyl)-4-nitro-1H-indazole (0.500 g, 1.33 mmol) in dioxane (0.2M, 7 mL) was treated with potassium carbonate (0.916 g, 6.63 mmol), methylboronic acid (0.793 g, 13.3 mmol), water (0.239 mL, 13.3 mmol), followed by tetrakis(triphenylphosphine)palladium (0) (0.0766 g, 0.0663 mmol) at ambient temperature, purging under argon. The mixture was refluxed overnight, cooled to ambient temperature, filtered through glass fiber filter paper, concentrated and purified on silica (10-75% EtOAc in hexanes) to give 1-((6-ethoxypyridin-2-yl)methyl)-3-methyl-4-nitro-1H-indazole (0.118 g, 28% yield).

Step F: Preparation of 1-((6-ethoxypyridin-2-yl)methyl)-3-methyl-1H-indazol-4-amine A solution of 1-((6-ethoxypyridin-2-yl)methyl)-3-methyl-4-nitro-1H-indazole (0.118 g, 0.378 mmol), ammonium chloride (0.0101 g, 0.189 mmol) in 4:1 EtOH/water (2 mL) was treated with iron (0.211 g, 3.78 mmol) and refluxed for 2 hours. The solvent was removed and the residue taken in EtOAc-water and filtered through glass fiber filter paper. The organic phase was separated, dried (phase separator silicone treated filter paper), and concentrated to provide 1-((6-ethoxypyridin-2-yl)methyl)-3-methyl-1H-indazol-4-amine (0.076 g, 71% yield) as a yellow gum.

Step G: Preparation of N-(1-((6-ethoxypyridin-2-yl)methyl)-3-methyl-1H-indazol-4-yl)-7-(2-(4-methylpiperazin-1-yl)ethoxy)imidazo[1,2-a]pyridine-3-carboxamide Prepared according to the method of Example 85, replacing 3-methyl-1-((6-methylpyridin-3-yl)methyl)-1H-indazol-4-amine with 1-((6-ethoxypyridin-2-yl)methyl)-3-methyl-1H-indazol-4-amine. MS (APCI) m/z=569 (M+H).

Example 87

N-(1-((6-methoxypyridin-2-yl)methyl)-3-methyl-1H-indazol-4-yl)-7-(2-(4-methylpiperazin-1-yl)ethoxy)imidazo[1,2-a]pyridine-3-carboxamide

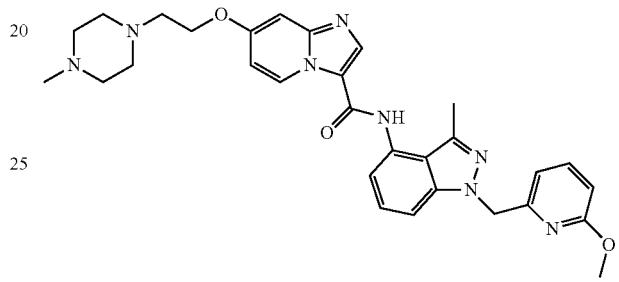

Step A: Preparation of (6-methoxypyridin-2-yl)methanol

A cold solution of 6-methoxypicolinic acid (1.8 g, 11.8 mmol) in tetrahydrofuran (0.3M, 40 mL) was treated with lithium aluminum hydride (11.8 mL, 11.8 mmol) at 0° C. This mixture was stirred at 0° C. for 30 minutes, poured into a beaker containing aqueous saturated Rochelle's salt and stirring at ambient temperature continued for 1 hour. The product was extracted from EtOAc, dried (phase separator silicone treated filter paper) paper, concentrated (1.13 g, 69% yield) as a clear oil.

Step B: Preparation of 2-(chloromethyl)-6-methoxypyridine hydrochloride

Prepared according to Example 86, Step C, replacing (6-Ethoxypyridin-2-yl)methanol with (6-methoxypyridin-2-yl)methanol.

Step C: Preparation of 3-bromo-1-((6-methoxypyridin-2-yl)methyl)-4-nitro-1H-indazole Prepared according to Example 86, Step D, replacing 2-(chloromethyl)-6-ethoxypyridine hydrochloride with 2-(chloromethyl)-6-methoxypyridine hydrochloride.

Step D: Preparation of 1-((6-methoxypyridin-2-yl)methyl)-3-methyl-4-nitro-1H-indazole Prepared according to Example 86, Step E, replacing 3-bromo-1-((6-ethoxypyridin-2-yl)methyl)-4-nitro-1H-indazole with 3-bromo-1-((6-methoxypyridin-2-yl)methyl)-4-nitro-1H-indazole.

Step E: Preparation of 1-((6-methoxypyridin-2-yl)methyl)-3-methyl-1H-indazol-4-amine Prepared according to Example 86, Step F, replacing 1-((6-ethoxypyridin-2-yl)methyl)-3-methyl-4-nitro-1H-indazole with 1-((6-methoxypyridin-2-yl)methyl)-3-methyl-4-nitro-1H-indazole.

Step F: Preparation of N-(1-((6-methoxypyridin-2-yl)methyl)-3-methyl-1H-indazol-4-yl)-7-(2-(4-methylpiperazin-1-yl)ethoxy)imidazo[1,2-a]pyridine-3-carboxamide Prepared according to Example 86, Step G, replacing 1-((6-ethoxypyridin-2-yl)methyl)-3-methyl-1H-indazol-4-amine with 1-((6-methoxypyridin-2-yl)methyl)-3-methyl-1H-indazol-4-amine. MS (APCI) m/z=555 (M+H).

Example 88

N-(3-methyl-1-((2-methylthiazol-4-yl)methyl)-1H-indazol-4-yl)-7-(2-(4-methylpiperazin-1-yl)ethoxy)imidazo[1,2-a]pyridine-3-carboxamide

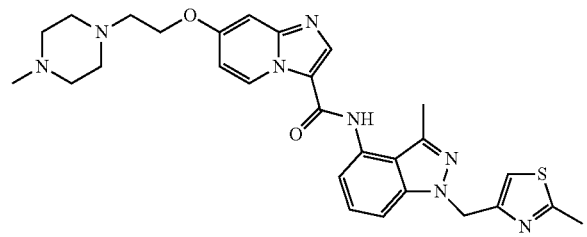

Prepared according to the method of Example 86, replacing 1-((6-ethoxypyridin-2-yl)methyl)-3-methyl-1H-indazol-4-amine in Step F with 3-methyl-1-((2-methylthiazol-4-yl)methyl)-1H-indazol-4-amine. MS (APCI) m/z=545 (M+H).

Example 89

N-(3-methyl-1-((6-methylpyridin-2-yl)methyl)-1H-indazol-4-yl)-7-(2-(4-methylpiperazin-1-yl)ethoxy)imidazo[1,2-a]pyridine-3-carboxamide tetrahydrochloride

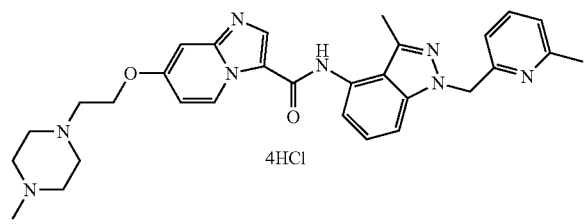 [SMILES: Cc1cccc(Cn2nc(C)c3c(NC(=O)c4cnc5cc(OCCN6CCN(C)CC6)ccn45)cccc32)n1]

Step A: Preparation of 3-iodo-4-nitro-1H-indazole

A solution of 4-nitro-1H-indazole (50.0 g; 306 mmol) in DMF (600 mL) was cooled to 5° C. under a nitrogen atmosphere with stirring. Powdered potassium hydroxide (68.8 g; 1226 mmol) was added. A solution of iodine (156 g; 613 mmol) in DMF (200 mL) was added slowly to the reaction mixture over 2 hours maintaining the temperature between 5 and 10° C. The mixture was stirred at 25° C. for 24 hours. Additional iodine (39.0 g; 153.2 mmol) and potassium hydroxide (17.2 g; 306.5 mmol) were added. The mixture was stirred at 25° C. for an additional 12 hours. The reaction mixture was added to an aqueous solution of sodium bisulfite (10% solution; 3300 mL) with stirring. The resulting precipitate was collected by filtration and washed with water. The material was dried in a vacuum oven at 40° C. The material was dissolved in methylene chloride/methanol (10:1; 1.5 L) and filtered through Celite® to remove inorganic impurities. Concentration of the solution under vacuum gave 3-iodo-4-nitro-1H-indazole as a yellow solid (75 g).

Step B: Preparation of 3-iodo-1-((6-methylpyridin-2-yl)methyl)-4-nitro-1H-indazole To a solution of 3-iodo-4-nitro-1H-indazole (172 mg, 0.596 mmol) in dry DMF (3 mL) under an atmosphere of dry nitrogen was added 2-(bromomethyl)-6-methylpyridine (122 mg, 0.656 mmol) and potassium carbonate (165 mg, 1.19 mmol) with stirring. The mixture was stirred at ambient temperature for 3 days. The reaction mixture was diluted with water (20 mL) and extracted into ethyl acetate. The organic phases were combined, washed with saturated sodium chloride solution, dried over sodium sulfate, filtered and concentrated under reduced pressure. The resulting material was purified using preparative chromatography on silica, eluting with hexane/ethyl acetate (3:1) to give 3-iodo-1-((6-methylpyridin-2-yl)methyl)-4-nitro-1H-indazole (213 mg).

Step C: Preparation of 3-methyl-1-((6-methylpyridin-2-yl)methyl)-4-nitro-1H-indazole A dried flask equipped with a reflux condenser and a nitrogen line was charged with 3-iodo-1-((6-methylpyridin-2-yl)methyl)-4-nitro-1H-indazole (100 mg, 0.254 mmol), tri-o-tolylphosphine (15.4 mg, 0.051 mmol), and tris(dibenzylideneacetone)dipalladium (0) (23 mg, 0.025 mmol). The flask was purged with nitrogen and anhydrous DMF (30 mL) and tetramethylstannane (0.04 mL, 0.28 mmol) were added, followed by triethylamine (0.04 mL, 0.30 mmol). The flask was degassed under nitrogen and heated at 80° C. for 6 hours. The reaction mixture was cooled to ambient temperature, diluted with water, and extracted multiple times with DCM and EtOAc. The combined organic extracts were dried over anhydrous sodium sulfate and concentrated under reduced pressure. The crude product was subjected to preparative thin-layer chromatography on silica with 2% MeOH/DCM as eluent to afford 56.8 mg of desired product as a yellow solid.

Step D: Preparation of 3-methyl-1-((6-methylpyridin-2-yl)methyl)-1H-indazol-4-amine A suspension of 3-methyl-1-((6-methylpyridin-2-yl)methyl)-4-nitro-1H-indazole (54 mg, 0.19 mmol) in absolute EtOH (1.5 mL) was treated at ambient temperature with 10% palladium hydroxide on carbon (27 mg, 0.019 mmol). The mixture was stirred at ambient temperature under a hydrogen atmosphere for 16 hours, and then filtered through a Celite® pad, washing with EtOH. The filtrate was concentrated under reduced pressure to afford the product (36 mg) as a yellow oil.

Step E: Preparation of N-(3-methyl-1-((6-methyl-pyridin-2-yl)methyl)-1H-indazol-4-yl)-7-(2-(4-methylpiperazin-1-yl)ethoxy)imidazo[1,2-a]pyridine-3-carboxamide tetrahydrochloride To a cooled (0° C.) solution of 3-methyl-1-((6-methyl-pyridin-2-yl)methyl)-1H-indazol-4-amine (1.67 g; 6.62 mmol) in anhydrous THF (10 mL) under nitrogen was added lithium bis(trimethylsilyl)amide (6.50 mL; 1.0M solution in THF; 6.50 mmol) dropwise over 3 minutes with vigorous stirring. The reaction mixture was stirred with ice/water cooling for 10 minutes. A solution of ethyl 7-(2-(4-methyl-piperazin-1-yl)ethoxy)imidazo[1,2-a]pyridine-3-carboxylate (Preparation A; 1.00 g; 3.01 mmol) in anhydrous THF (10 mL) was added dropwise by syringe over 8 minutes, and the syringe was rinsed with THF (1 mL). The mixture was stirred in an ice/water bath for 30 minutes. The mixture was quenched with water (50 mL) and saturated aqueous ammonium chloride solution (50 mL). The mixture was extracted with DCM (150 mL). Brine solution was added to the aqueous phase (150 mL) which was then further extracted with DCM (100 mL). The pH of the aqueous phase was then adjusted to pH 10-11 with 2N NaOH solution. The aqueous layer was then further extracted with DCM (50 mL) and ethyl acetate (50 mL). The combined organic phases were washed with brine (100 mL). The brine solution was back extracted with DCM (25 mL). The combined organic phases were dried over sodium sulfate (50 g), filtered and concentrated under reduced pressure. The residue was purified by silica gel chromatography, eluting with 7N ammonium hydroxide in methanol/Methanol/DCM (20/80/900) to give a yellow solid which was triturated with ether (2×25 mL). The material was then precipitated from a minimal volume of DCM (cooling to 4° C. to precipitate) to give a pale yellow solid which was dried under vacuum at 38° C. for 16 hours). This material (1.05 g) was dissolved in methanol and an excess of HCl (2M in ether) was added. The solvent was removed under vacuum and dried under high vacuum for 16 hours to give N-(3-methyl-1-((6-methylpyridin-2-yl)methyl)-1H-indazol-4-yl)-7-(2-(4-methylpiperazin-1-yl)ethoxy)imidazo[1,2-a]pyridine-3-carboxamide tetrahydrochloride as an off white solid (1.20 g). $^1$H NMR CD$_3$OD δ 9.61 (d, 1H), 8.81 (s, 1H), 8.34 (t, 1H), 7.86 (d, 1H), 7.64 (d, 1H), 7.54 (m, 2H), 7.44 (dd, 1H), 7.32 (d, 1H), 7.25 (d, 1H), 5.97 (s, 2H), 4.81 (t, 2H), 3.91 (t, 2H), 3.81 (bs, 8H), 3.04 (s, 3H), 2.87 (s, 3H), 2.61 (s, 3H).

Example 90

N-(1-benzyl-1H-indazol-4-yl)-7-(2-morpholinoethoxy)imidazo[1,2-a]pyridine-3-carboxamide

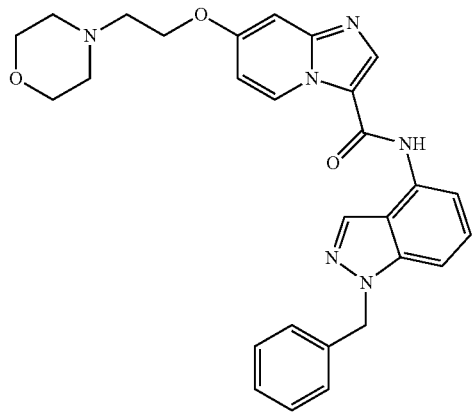 [SMILES: O=C(Nc1cccc2c1cnn2Cc1ccccc1)c1cnc2cc(OCCN3CCOCC3)ccn12]

Step A: Preparation of 4-(2-morpholinoethoxyl)pyridin-2-amine

2-Morpholinoethanol (2.21 g, 16.8 mmol) was treated with sodium (0.407 g, 17.7 mmol) until a homogeneous suspension was obtained. 4-Chloropyridin-2-amine (1.14 g, 8.86 mmol) was added and the mixture was heated with magnetic stirring at 145° C. in a sealed tube for 10 hours. The reaction mixture was cooled and diluted with water and EtOAc. The layers were separated, and the aqueous phase was extracted twice with EtOAc. The combined organic extracts were concentrated to afford a viscous oil which was subjected to chromatographic purification on silica with 10% MeOH/DCM as eluent to provide 1.37 g of desired product as a low-melting solid.

Step B: Preparation of ethyl 7-(2-morpholinoethoxyl)imidazo[1,2-a]pyridine-3-carboxylate 4-(2-Morpholinoethoxy)pyridin-2-amine (1.37 g, 6.14 mmol) was dissolved in ethanol (20 ml) and treated with ethyl 2-chloro-3-oxopropanoate (5% solution in benzene, 30 mL). The mixture was refluxed overnight. The reaction mixture was cooled and concentrated to afford a beige solid (1.31 g), which was purified by chromatography on silica, eluting with a gradient from 50% EtOAc/Hexanes to 100% EtOAc, followed by 10% MeOH/DCM to provide 1.0 g of the desired product as a white solid.

Step C: Preparation of lithium 7-(2-morpholinoethoxyl)imidazo[1,2-a]pyridine-3-carboxylate ethyl 7-(2-morpholinoethoxyl)imidazo[1,2-a]pyridine-3-carboxylate Ethyl 7-(2-morpholinoethoxyl)imidazo[1,2-a]pyridine-3-carboxylate 4-(2-morpholinoethoxyl)pyridin-2-amine (1.0 g, 3.13 mmol) was dissolved in a 4:1 THF/water mixture (to a 0.5 M concentration). Lithium hydroxide monohydrate (75 mg, 3.13 mmol) was added and the resulting mixture was stirred overnight at ambient temperature, followed by heating at 65° C. for eight hours. An additional 0.1 equivalents of lithium hydroxide monohydrate was added, and heating at 65° C. was continued overnight. The reaction mixture was diluted with THF, filtered, concentrated, and dried under high vacuum to afford the crude product (0.979 g) as a pale yellow, free flowing solid.

Step D: Preparation of N-(1-benzyl-1H-indazol-4-yl)-7-(2-morpholinoethoxyl)imidazo[1,2-a]pyridine-3-carboxamide To a suspension of lithium 7-(2-morpholinoethoxyl)imidazo[1,2-a]pyridine-3-carboxylate (42 mg, 0.142 mmol) in DCM were added oxalyl chloride (1.1 equivalents) and a drop of DMF. The mixture was stirred until gas evolution stopped. To the reaction mixture were then added 1-benzyl-1H-indazol-4-amine (31.6 mg, 0.142 mmol) and Hunig's base (1.2 equivalents). The reaction was stirred at ambient temperature for two hours and then concentrated. The residue was triturated with diethyl ether followed by chromatographic purification on silica with 10% MeOH/DCM as eluent to provide 8.6 mg of the desired product as a white solid. MS (ES+APCI) m/z=497 (M+H) detected.

Example 91

N-(1-benzyl-1H-indazol-4-yl)-7-(2,3-dihydroxy-propoxy)imidazo[1,2-a]pyridine-3-carboxamide

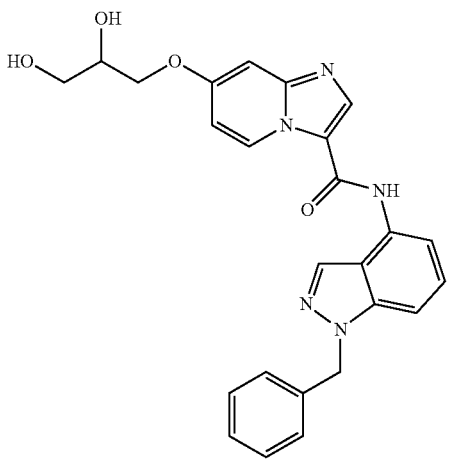 [SMILES: O=C(Nc1cccc2c1cnn2Cc1ccccc1)c1cnc2cc(OCC(O)CO)ccn12]

A DCM solution of 7-((2,2-dimethyl-1,3-dioxolan-4-yl)methoxy)imidazo[1,2-a]pyridine-3-carboxylic acid (Example 58, Steps A-C; 109.7 mg, 0.375 mmol) was treated at ambient temperature with oxalyl chloride (1.1 equivalents) and a drop of DMF. After gas evolution ceased, 1-benzyl-1H-indazol-4-amine (83.8 mg, 0.375 mmol) and Hunig's base (1.2 equivalents) were added, and stirring continued overnight. The resulting mixture was concentrated, and triturated with diethyl ether, followed by chromatographic purification on silica with 10% MeOH/DCM as eluent to provide 25.2 mg of the desired product. MS (ES+APCI) m/z=458 (M+H) detected.

Example 92

N-(1-benzyl-1H-indazol-4-yl)-7-hydroxyimidazo[1,2-a]pyridine-3-carboxamide

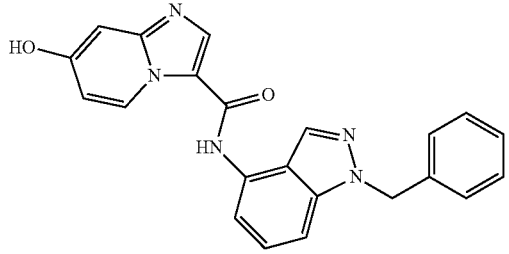 [SMILES: O=C(Nc1cccc2c1cnn2Cc1ccccc1)c1cnc2cc(O)ccn12]

Step A: Preparation of ethyl 7-hydroxyimidazo[1,2-a]pyridine-3-carboxylate

To a chilled (0° C.) solution of potassium 2-chloro-3-ethoxy-3-oxoprop-1-en-1-olate (16.4 g, 86.3 mmol) in concentrated sulfuric acid (43.5 mmol) and ethanol (50 mL) was added 2-aminopyridin-4-ol (3 g, 27 mmol). The resulting mixture was warmed to ambient temperature and refluxed for 10 hours. The reaction was concentrated and suspended in EtOAc. The solids were isolated to afford 829 mg of pure product. The supernatant was concentrated, and subjected to chromatography on silica with 30% EtOAc/Hexanes as eluent to afford a second batch of desired product (5.8 g, 80% purity) as a brown, viscous oil.

Step B: Preparation of 7-hydroxyimidazo[1,2-a]pyridine-3-carboxylic acid

A solution of 7-hydroxyimidazo[1,2-a]pyridine-3-carboxylate (414 mg, 2.01 mmol) in a 2:1:1 THF/ethanol/water mixture (36 mL) was treated at ambient temperature with lithium hydroxide monohydrate (2.1 equivalents). The reaction mixture was stirred at ambient temperature overnight. To the reaction were then added another 2.1 equivalents of lithium hydroxide monohydrate and stirring continued for 72 hours. After removal of the volatiles the mixture was diluted with water, cooled in an ice bath, and the pH adjusted to 4 with aqueous 6N hydrochloric acid. The resulting white precipitate was isolated and dried to afford the desired product (358 mg).

Step C: Preparation of N-(1-benzyl-1H-indazol-4-yl)-7-hydroxyimidazo[1,2-a]pyridine-3-carboxamide A suspension of EDCI (192 mg, 0.679 mmol), 2,4,6-trimethylpyridine (224 mg, 1.85 mmol), and 7-hydroxyimidazo[1,2-a]pyridine-3-carboxylic acid (110 mg, 0.617 mmol) in DMF (2 mL) was stirred at ambient temperature for two hours. A solution of 1-benzyl-1H-indazol-4-amine (138 mg, 0.617 mmol) in DMF (2 mL) was added, and the resulting mixture was sonicated for 5 minutes. The heterogeneous mixture was stirred at ambient temperature overnight, then diluted with EtOAc, and washed twice with 1M aqueous hydrochloric acid, followed by brine. The organic layer was concentrated and subjected to chromatography on silica with 10% MeOH/DCM as eluent to provide 1.5 mg of desired product. MS (ES+APCI) m/z=384 (M+H) detected.

Example 93

Methyl 3-((4-(7-(2-methoxyethoxy)imidazo[1,2-a]pyridine-3-carboxamido)-1H-indazol-1-yl)methyl)benzoate

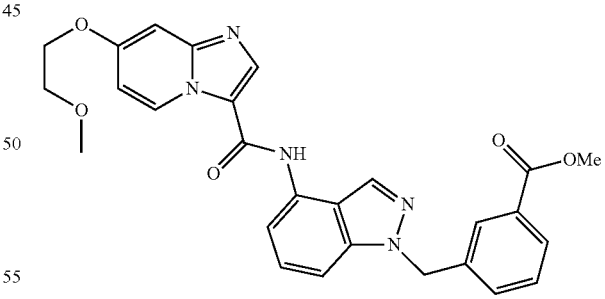

Step A: Preparation of methyl 3-((3-iodo-4-nitro-1H-indazol-1-yl)methyl)benzoate To a slurry of 3-iodo-4-nitro-1H-indazole (1.0 g, 3.46 mmol) and methyl 3-(bromomethyl)benzoate (1.59 g, 6.92 mmol) and CH$_3$CN (12 mL) was added 2-tert-butyl-1,1,3,3-tetramethylguanidine (0.697 mL, 3.46 mmol) dropwise, and the mixture was allowed to stir overnight at ambient temperature. The mixture was then concentrated and diluted with saturated aqueous NH$_4$Cl (40 mL) and EtOAc (70 mL).

The organic layer was separated and the aqueous phase was extracted with EtOAc (25 mL). The combined organic extracts were washed with brine, then dried over Na₂SO₄, filtered and concentrated. The crude product was purified by column chromatography (50% EtOAc/hexane) to provide 1.04 g (68%) of the product as a yellow/orange solid.

Step B: Preparation of methyl 3-((4-amino-1H-indazol-1-yl)methyl)benzoate

A suspension of methyl 3-((3-iodo-4-nitro-1H-indazol-1-yl)methyl)benzoate (1.00 g, 2.29 mmol) and MeOH (45 mL) was cooled to 0° C. Zinc dust (0.748 g, 11.4 mmol) was added followed by saturated aqueous NH₄Cl (23 mL). The mixture was stirred at 0° C. for 2 hours, then warmed to ambient temperature and stirred for an additional 3 hours. The mixture was diluted with MeOH and filtered. To the filtrate was added saturated aqueous NH₄OAc and the mixture was concentrated to remove bulk MeOH. The concentrated mixture was extracted with EtOAc and the combined organic extracts were washed with saturated aqueous NaHCO₃ and brine, then dried over Na₂SO₄, filtered and concentrated. The product was purified by column chromatography (25 to 100% EtOAc/hexane) to afford 0.398 g (61%) of the title compound as a sticky orange foam.

Step C: Preparation of methyl 3-((4-(7-(2-methoxyethoxyl)imidazo[1,2-a]pyridine-3-carboxamido)-1H-indazol-1-yl)methyl)benzoate To a vial was added 7-(2-methoxyethoxyl)imidazo[1,2-a]pyridine-3-carboxylic acid (0.260 g, 1.05 mmol) and NMP (3.5 mL). Triethylamine (0.243 mL, 1.74 mmol) was added and the mixture was stirred until homogeneous. 2,4,6-Trichlorobenzoyl chloride (0.153 mL, 0.975 mmol) was added and the mixture was stirred at ambient temperature for 0.5 hours. Methyl 3-((4-amino-1H-indazol-1-yl)methyl)benzoate (0.196 g, 0.697 mmol) was added as a NMP solution (1.2 mL), and the reaction mixture was sealed in the vial and warmed to 80° C. with stirring overnight. The reaction mixture was cooled and diluted with EtOAc (20 mL), and then filtered to remove white solids. The solids were washed with EtOAc and the filtrate was concentrated under vacuum until only DMA was left. The concentrated solution diluted with water/saturated aqueous NaHCO₃ (25 mL, 1:1) forming a precipitate. The precipitate was isolated by filtration and the solid was washed with water, Et₂O, and hexanes, then dried under vacuum at 40° C. for 4 hours to provide 0.279 g (74%) of the title compound. MS (ES+APCI) m/z=500 (M+H).

Example 94

N-(1-(3-carbamoylbenzyl)-1H-indazol-4-yl)-7-(2-methoxyethoxyl)imidazo[1,2-a]pyridine-3-carboxamide

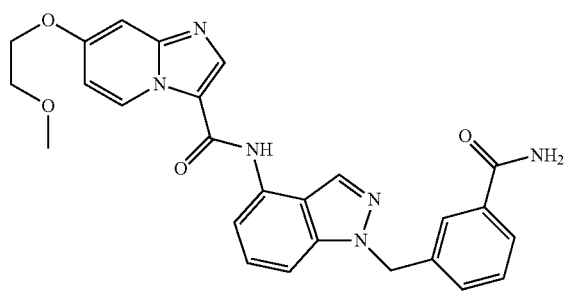 [SMILES: COCCOc1ccn2c(C(=O)Nc3cccc4c3cnn4Cc3cccc(C(N)=O)c3)cnc2c1]

To a vial was added 34(4-(7-(2-methoxyethoxyl)imidazo[1,2-a]pyridine-3-carboxamido)-1H-indazol-1-yl)methyl)benzoic acid (0.020 g, 0.0412 mmol), HOBT (0.00612 g, 0.0453 mmol) and EDCI (0.00869 g, 0.0453 mmol) followed by THF (0.500 mL). Diisopropylethylamine (0.00789 mL, 0.0453 mmol) was added and the mixture was stirred for 15 minutes. Ammonium carbonate (0.0119 g, 0.124 mmol) was added in one portion and the mixture was stirred vigorously overnight. The mixture was diluted with water and the resulting precipitate was isolated by vacuum filtration and washed with water. The solid was isolated and slurried in Et₂O and filtered and the solid was washed with Et₂O and hexanes, then dried under vacuum (0.025 g). The crude solid was purified by preparative TLC (10% MeOH/CH₂Cl₂) which provided 0.003 g (15%) of the desired product. MS (ES+APCI) m/z=485 (M+H).

Example 95

7-(2-Methoxyethoxy)-N-(1-(3-(methylcarbamoyl)benzyl)-1H-indazol-4-yl)imidazo[1,2-a]pyridine-3-carboxamide

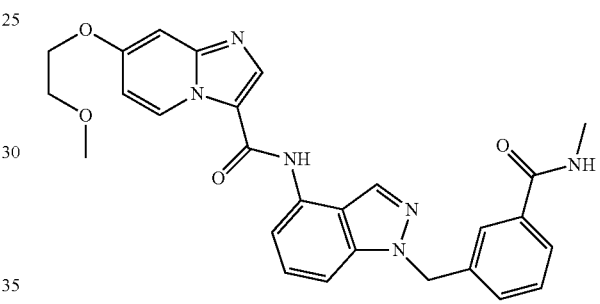

To a vial was added methyl 3-((4-(7-(2-methoxyethoxyl)imidazo[1,2-a]pyridine-3-carboxamido)-1H-indazol-1-yl)methyl)benzoate (Example 93; 0.026 g, 0.0521 mmol) followed by methylamine (0.972 mL, 7.81 mmol, 33% in EtOH) and the mixture was sealed and heated to 50° C. with stirring for 8 hours. Additional methyl amine (0.972 mL, 7.81 mmol) was added and the mixture was stirred at 50° C. overnight. The mixture was cooled to ambient temperature and purified directly by preparative TLC (10% MeOH/CH₂Cl₂), providing 0.014 g (54%) of the product as a tan powder. MS (ES+APCI) m/z=499 (M+H).

Example 96

Methyl 3-((4-(7-(2-(4-methylpiperazin-1-yl)ethoxy)imidazo[1,2-a]pyridine-3-carboxamido)-1H-indazol-1-yl)methyl)benzoate dihydrochloride

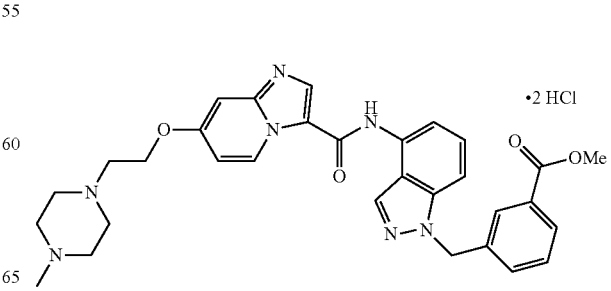

Step A: Preparation of methyl 3-((3-iodo-4-nitro-1H-indazol-1-yl)methyl)benzoate To a slurry of 3-iodo-4-nitro-1H-indazole (1.0 g, 3.46 mmol) and methyl 3-(bromomethyl)benzoate (1.59 g, 6.92 mmol) and CH₃CN (12 mL) was added 2-tert-butyl-1,1,3,3-tetramethylguanidine (0.697 mL, 3.46 mmol) dropwise and the mixture was allowed to stir overnight at ambient temperature. The mixture was concentrated and diluted with saturated aqueous NH₄Cl (40 mL) and EtOAc (70 mL). The layers were mixed and separated and the aqueous phase was extracted with EtOAc (25 mL). The combined organic extracts were washed with brine, dried over Na₂SO₄, filtered and concentrated. The crude product was purified by column chromatography (50% EtOAc/hexane) to provide 1.04 g (68%) of the product as a yellow/orange solid.

Step B: Preparation of methyl 3-((4-amino-1H-indazol-1-yl)methyl)benzoate

A suspension of methyl 3-((3-iodo-4-nitro-1H-indazol-1-yl)methyl)benzoate (1.00 g, 2.29 mmol) and MeOH (45 mL) was cooled to 0° C. Zinc dust (0.748 g, 11.4 mmol) was added followed by saturated aqueous NH₄Cl (23 mL). The mixture was stirred at 0° C. for 2 hours, then warmed to ambient temperature with stirring for an additional 3 hours. The mixture was diluted with MeOH and filtered. To the filtrate was added saturated aqueous NH₄OAc and the mixture was concentrated to remove bulk MeOH. The mixture was extracted with EtOAc and the combined organic extracts were washed with saturated aqueous NaHCO₃ followed by brine, dried over Na₂SO₄, filtered and concentrated. The product was purified by column chromatography (25 to 100% EtOAc/hexane) to afford 0.398 g (61%) of the title compound as a sticky orange foam.

Step C: Preparation of methyl 3-((4-(7-(2-(4-methylpiperazin-1-yl)ethoxy)imidazo[1,2-a]pyridine-3-carboxamido)-1H-indazol-1-yl)methyl)benzoate dihydrochloride A mixture of lithium 7-(2-(4-methylpiperazin-1-yl)ethoxy)imidazo[1,2-a]pyridine-3-carboxylate (0.09578 g, 0.2933 mmol) and NMP (1.5 mL) were warmed to provide a homogeneous solution and then cooled to ambient temperature. 2,4,6-Trichlorobenzoyl chloride (0.04277 mL, 0.2737 mmol) was added and the mixture stirred at ambient temperature for 0.5 hours. Methyl 3-((4-amino-1H-indazol-1-yl)methyl)benzoate (0.055 g, 0.1955 mmol) was added as a NMP solution (1.5 mL) and the mixture was heated to 80° C. and stirred for 4 hours. The mixture was dissolved in MeOH and concentrated. The residue was dissolved in saturated aqueous NaHCO₃ and EtOAc and the organic layer was washed with brine and dried over Na₂SO₄. The crude material was purified by column chromatography (15% MeOH/CH₂Cl₂ adding 1% 7N NH₃/MeOH) to provide methyl 3-((4-(7-(2-(4-methylpiperazin-1-yl)ethoxy)imidazo[1,2-a]pyridine-3-carboxamido)-1H-indazol-1-yl)methyl)benzoate as the free base. This material was dissolved in MeOH (3.0 mL) and CHCl₃ (1.0 mL), and HCl (1.955 mL, 3.910 mmol, 2.0M Et₂O) was added and the mixture was stirred for 2 hours and then concentrated. The resulting solid was washed with Et₂O and then with hexanes, and dried under vacuum to afford 0.085 g (64%) of the title compound. MS (ES+APCI) m/z=568 (M+H-2HCl).

Example 97

N-(1-(3-(dimethylcarbamoyl)benzyl)-1H-indazol-4-yl)-7-(2-(4-methylpiperazin-1-yl)ethoxy)imidazo[1,2-a]pyridine-3-carboxamide dihydrochloride

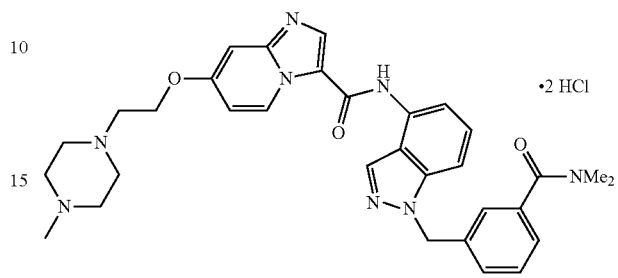

Step A: Preparation of 3-(chloromethyl)-N,N-dimethylbenzamide

A solution of dimethylamine (2.91 mL, 5.82 mmol, 2.0M THF), NEt₃ (0.885 mL, 6.35 mmol) and CH₂Cl₂ 30 mL was cooled to 0° C. 3-(Chloromethyl)benzoyl chloride (1.0 g, 5.29 mmol) was added as a CH₂Cl₂ solution (3 mL) and the solution was stirred at 0° C. for 2 hours and then at ambient temperature for 2 hours. The reaction was washed with 1N HCl followed by brine, and the organic layer was dried over Na₂SO₄, filtered and concentrated. The product was purified by column chromatography (EtOAc) to provide 0.745 g (71%) of the product as colorless oil.

Step B: Preparation of 3-((3-iodo-4-nitro-1H-indazol-1-yl)methyl)-N,N-dimethylbenzamide To a flask was added 3-iodo-4-nitro-1H-indazole (0.500 g, 1.73 mmol) and CH₃CN (6 mL) followed by 2-tert-butyl-1,1,3,3-tetramethylguanidine (0.523 ml, 2.59 mmol). The mixture was stirred for 5 minutes, and then 3-(chloromethyl)-N,N-dimethylbenzamide (0.479 g, 2.42 mmol) was added as a CH₃CN (4 mL) solution. The reaction was stirred at ambient temperature for 5 hours. The mixture was concentrated and diluted with saturated aqueous NH₄Cl (20 mL) and EtOAc (60 mL). The layers were mixed and separated and the organic phase was washed with brine, dried over Na₂SO₄, filtered and concentrated. The crude product was purified by column chromatography (EtOAc) to provide 0.567 g (72%) of the desired product as an orange foam.

Step C: Preparation of 3-((4-amino-1H-indazol-1-yl)methyl)-N,N-dimethylbenzamide A solution of 3-((3-iodo-4-nitro-1H-indazol-1-yl)methyl)-N,N-dimethylbenzamide (0.400 g, 0.888 mmol) and MeOH (8.8 mL) was cooled to 0° C. Zinc dust (0.290 g, 4.44 mmol) was added and the mixture was stirred vigorously for 15 minutes, followed by the dropwise addition of saturated aqueous NH₄Cl (9 mL). The mixture was stirred vigorously for 15 minutes at 0° C. and then warmed to ambient temperature and stirred for an additional 1 hour. The mixture was diluted with MeOH and filtered. To the filtrate was added saturated aqueous NH₄OAc and the mixture was concentrated to remove bulk MeOH. The mixture was extracted with EtOAc and the combined organic extracts were washed with saturated aqueous NaHCO$_3$ and brine, dried over Na$_2$SO$_4$, filtered and concentrated. The crude product was purified by column chromatography (2 to 20% IPA/CHCl$_3$) to afford 0.160 g (61%) of the title compound as a yellow/orange solid.

Step D: Preparation of N-(1-(3-(dimethylcarbamoyl)benzyl)-1H-indazol-4-yl)-7-(2-(4-methylpiperazin-1-yl)ethoxy)imidazo[1,2-a]pyridine-3-carboxamide dihydrochloride A solution of 3-((4-amino-1H-indazol-1-yl)methyl)-N,N-dimethylbenzamide (0.15 g, 0.51 mmol) and THF (1.0 mL) was cooled to −5° C. in an ice/brine bath, then LHMDS (0.48 ml, 0.48 mmol, 1.0M THF) was added drop-wise and the mixture was stirred for 10 minutes, during which a dark emulsion formed. Ethyl 7-(2-(4-methylpiperazin-1-yl)ethoxy)imidazo[1,2-a]pyridine-3-carboxylate (Preparation A; 0.080 g, 0.24 mmol) was added dropwise as a THF solution (1.0 mL). The reaction was stirred at −5 to 0° C. for 1 hour, then quenched with saturated aqueous NH$_4$Cl (10 mL). The mixture was extracted with CH$_2$Cl$_2$ and the combined organic layers were washed with brine, dried over Na$_2$SO$_4$, filtered and concentrated. The crude residue was slurried in Et$_2$O with vigorous stirring and then filtered through a nylon filter providing crude product with >90% purity (0.083 g). The crude product was purified by column chromatography (5 to 20% MeOH/CH$_2$Cl$_2$ using 5% NH$_4$OH/MeOH). The fractions were concentrated and the product dissolved in CH$_2$Cl$_2$ and then filtered. The filtrate was concentrated to provide N-(1-(3-(dimethylcarbamoyl)benzyl)-1H-indazol-4-yl)-7-(2-(4-methylpiperazin-1-yl)ethoxy)imidazo[1,2-a]pyridine-3-carboxamide as a pale orange solid (0.060 g). This product was dissolved in MeOH (2.4 mL) and then HCl (2.41 mL, 4.81 mmol, 2.0M Et$_2$O) was added. The mixture was stirred for 2 hours and then concentrated. The resulting solid was washed with Et$_2$O and hexanes and dried under vacuum to provide 0.050 g (31%) of the title product as a pale brown powder. MS (ES+APCI) m/z=581 (M+H-2HCl).

Example 98

7-(2-(4-methylpiperazin-1-yl)ethoxy)-N-(1-(3-(trifluoromethyl)benzyl)-1H-indazol-4-yl)imidazo[1,2-a]pyridine-3-carboxamide dihydrochloride

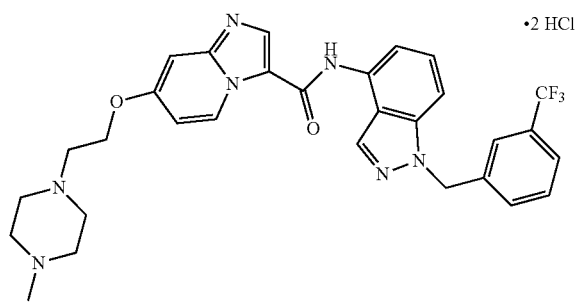 [SMILES: CN1CCN(CCOc2ccn3c(C(=O)Nc4cccc5c4cnn5Cc4cccc(C(F)(F)F)c4)cnc3c2)CC1]

Step A: Preparation of 3-iodo-4-nitro-1-(3-(trifluoromethyl)benzyl)-1H-indazole

To a slurry of 3-iodo-4-nitro-1H-indazole (0.410 g, 1.42 mmol) and CH$_3$CN (7.0 mL) was added 1-(bromomethyl)-3-(trifluoromethyl)benzene (0.261 mL, 1.70 mmol) and the solution was cooled to 0° C. 2-tert-Butyl-1,1,3,3-tetramethylguanidine (0.372 mL, 1.84 mmol) was added and the mixture was gradually warmed to ambient temperature where it stirred for 2 hours. The mixture was concentrated and diluted with saturated aqueous NH$_4$Cl (20 mL) and EtOAc (75 mL). The layers were mixed and separated and the organic phase was washed with brine, dried over Na$_2$SO$_4$, filtered and concentrated. The crude product was passed through a silica gel plug eluting with 20% EtOAc/hexane to provide 0.542 g (85%) of the product as dark yellow/orange oil.

Step B: Preparation of 1-(3-(trifluoromethyl)benzyl)-1H-indazol-4-amine

To a round bottom flask was added 3-iodo-4-nitro-1-(3-(trifluoromethyl)benzyl)-1H-indazole (0.540 g, 1.21 mmol) and MeOH (12 mL). Zinc dust (0.395 g, 6.04 mmol) was added followed by saturated aqueous NH$_4$Cl (12 mL). The mixture was stirred vigorously at ambient temperature for 2 hours. The reaction mixture was filtered and the solids were washed with EtOAc (30 mL). Saturated aqueous NH$_4$OAc (25 mL) was added to the filtrate and the mixture was concentrated to remove organic solvents. The aqueous phase was then extracted with EtOAc (3×20 mL). The combined organic extracts were washed with a saturated aqueous NaHCO$_3$ solution and brine, dried over Na$_2$SO$_4$, filtered and concentrated. The crude residue was purified by 1 mm preparative TLC using 5% MeOH/CH$_2$Cl$_2$ to afford 0.120 g (34%) of the product as a dark yellow/orange oil.

Step C: Preparation of 7-(2-(4-methylpiperazin-1-yl)ethoxy)-N-(1-(3-(trifluoromethyl)benzyl)-1H-indazol-4-yl)imidazo[1,2-a]pyridine-3-carboxamide dihydrochloride To a solution of 1-(3-(trifluoromethyl)benzyl)-1H-indazol-4-amine (0.053 g, 0.18 mmol) in THF (1.1 mL) was cooled to −10° C. in an ice/salt bath. LiHMDS (0.19 mL, 0.19 mmol, 1.0M THF) was added and the mixture was stirred for 15 minutes. To this dark solution was added a THF (1.1 mL) solution of ethyl 7-(2-(4-methylpiperazin-1-yl)ethoxy)imidazo[1,2-a]pyridine-3-carboxylate (Preparation A; 0.030 g, 0.090 mmol). The mixture was slowly warmed to 0° C. where it stirred for 3 hours. The reaction was quenched with saturated aqueous NaHCO$_3$ and extracted with CHCl$_3$. The combined organic layers were washed with brine, dried over Na$_2$SO$_4$, filtered and concentrated. The crude product was purified by preparative TLC (1 mm, 10% MeOH/CH$_2$Cl$_2$ adding 1% NH$_3$ (7N MeOH) to afford 0.026 g of the title compound as the freebase as a tan solid. The solid was slurried in Et$_2$O and filtered, and the solid was washed with Et$_2$O and hexanes. The material was dissolved in MeOH (2.0 mL), and HCl (0.90 mL, 1.8 mmol, 2.0M Et$_2$O) was added. The solution was stirred for 2 hours forming a white suspension. The mixture was filtered through a polypropylene filter to isolate the solids. The solids were washed with Et$_2$O followed by hexanes and dried under vacuum to afford 0.026 g (44%) of the title compound as an off-white solid. MS (ES+APCI) m/z=578 (M+H-2HCl).

Example 99

N-(1-(3-cyanobenzyl)-1H-indazol-4-yl)-7-(2-(4-methylpiperazin-1-yl)ethoxy)imidazo[1,2-a]pyridine-3-carboxamide

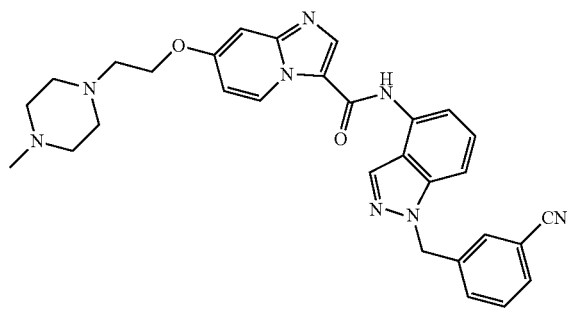 [SMILES: CN1CCN(CCOc2ccn3c(C(=O)Nc4cccc5c4cnn5Cc4cccc(C#N)c4)cnc3c2)CC1]

Step A: Preparation of 3-((3-iodo-4-nitro-1H-indazol-1-yl)methyl)benzonitrile Prepared according to the method of Example 104, replacing 3-(bromomethyl)-1-methylpyridin-2(1H)-one with 3-(bromomethyl)benzonitrile.

Step B: Preparation of 3-((4-amino-1H-indazol-1-yl)methyl)benzonitrile

A slurry of 3-((3-iodo-4-nitro-1H-indazol-1-yl)methyl)benzonitrile (0.200 g, 0.495 mmol) and MeOH (10.0 mL) was cooled to 0° C., then Zn dust (0.162 g, 2.47 mmol) was added followed by saturated aqueous NH₄Cl (10 mL). The mixture was stirred at 0° C. for 1 hour, then warmed to ambient temperature and stirred overnight. The mixture was diluted with MeOH and filtered. The solid was washed with CH$_2$Cl$_2$ and MeOH. To the filtrate was added saturated aqueous NH$_4$OAc and the mixture was concentrated to remove bulk MeOH. The mixture was then extracted with EtOAc, and the combined organic extracts were washed with saturated aqueous NaHCO$_3$ and brine, dried over Na$_2$SO$_4$, filtered and concentrated. The crude product was purified by column chromatography (25 to 100% EtOAc/hexane) to afford 0.090 g (73%) of the desired product as an orange oil.

Step C: Preparation of N-(1-(3-cyanobenzyl)-1H-indazol-4-yl)-7-(2-(4-methylpiperazin-1-yl)ethoxy)imidazo[1,2-a]pyridine-3-carboxamide To a vial was added lithium 7-(2-(4-methylpiperazin-1-yl)ethoxy)imidazo[1,2-a]pyridine-3-carboxylate (0.187 g, 0.544 mmol) and NMP (3.0 mL), and the mixture was warmed until homogeneous and then cooled to ambient temperature. 2,4,6-Trichlorobenzoyl chloride (0.0793 mL, 0.507 mmol) was added and the dark solution was stirred at ambient temperature for 0.5 hours. 3-((4-Amino-1H-indazol-1-yl)methyl)benzonitrile (0.090 g, 0.362 mmol) was added as a NMP solution (3.0 mL) and the mixture was heated to 75° C. with stirring for 3 hours. The reaction was equilibrated to ambient temperature and the mixture was diluted with EtOAc (30 mL) and saturated aqueous NaHCO$_3$ (10 mL). The organic layer was washed with brine, dried over Na$_2$SO$_4$, concentrated and purified by column chromatography (15% MeOH/CH$_2$Cl$_2$ adding 1% 7N NH$_3$/MeOH). The red/brown solid was slurried in Et$_2$O and then filtered, and the isolated solid was washed with Et$_2$O providing a pale red/brown solid that was dried under vacuum to provide 0.095 g (42%) of the desired product. MS (ES+APCI) m/z=535 (M+H).

Example 100

N-(5-chloro-1-(3-(trifluoromethyl)benzyl)-1H-indazol-4-yl)-7-(2-(4-methylpiperazin-1-yl)ethoxy)imidazo[1,2-a]pyridine-3-carboxamide

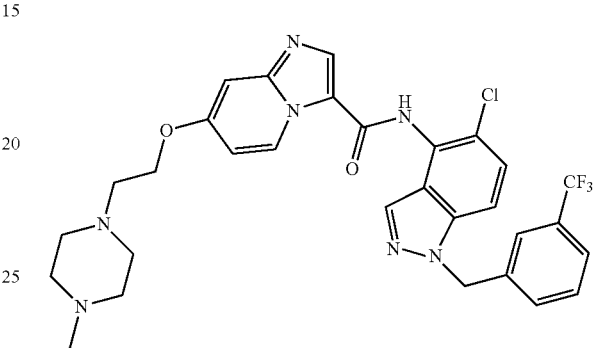

Step A

Preparation of 5-chloro-1-(3-(trifluoromethyl)benzyl)-1H-indazol-4-amine

A solution of 1-(3-(trifluoromethyl)benzyl)-1H-indazol-4-amine (0.056 g, 0.192 mmol) in THF (1.0 mL) was cooled to −78° C. under N$_2$. H$_2$SO$_4$ (0.00512 mL, 0.0961 mmol) was added and the mixture was stirred for 5 minutes. N-chlorosuccinimide (0.0257 g, 0.192 mmol) was added in one portion and the reaction was stirred at −78° C. for 1 hour. Sodium carbonate (0.0204 g, 0.192 mmol) was added and the mixture was warmed to ambient temperature. The mixture was diluted with water (5 mL) and extracted with EtOAc (3×10 mL). The combined organic layers were then washed with brine and dried over Na$_2$SO$_4$, filtered and concentrated. The crude product was purified by preparative TLC (40% EtOAc/hexane) in which two major bands were observed. The higher band was determined to be the title compound (0.028 g, 44%) and was isolated as a dark yellow/green solid.

Step B: Preparation of N-(5-chloro-1-(3-(trifluoromethyl)benzyl)-1H-indazol-4-yl)-7-(2-(4-methylpiperazin-1-yl)ethoxy)imidazo[1,2-a]pyridine-3-carboxamide A solution of 5-chloro-1-(3-(trifluoromethyl)benzyl)-1H-indazol-4-amine (0.024 g, 0.074 mmol) in THF (0.750 mL) was cooled to −10° C. and LHMDS (0.096 mL, 0.096 mmol) was added. The mixture was stirred for 15 minutes, and ethyl 7-(2-(4-methylpiperazin-1-yl)ethoxy)imidazo[1,2-a]pyridine-3-carboxylate (Preparation A; 0.049 g, 0.15 mmol) was added as a THF solution (0.750 mL). The mixture was slowly warmed to 0° C. where it stirred for 3 hours. The reaction was quenched with saturated aqueous NaHCO$_3$ and extracted with CH$_2$Cl$_2$. The combined organic extracts were washed with brine and dried over Na$_2$SO$_4$, filtered and concentrated. The crude product was purified by preparative TLC (1 mm, 10% MeOH/CH$_2$Cl$_2$ with 1% NH$_3$ (7N MeOH)). The resulting solid was slurried in Et$_2$O and filtered and the solid washed with Et$_2$O and then finally with hexanes to provide the title compound (0.002 g, 4%) as a tan powder. MS (ES+APCI) m/z=612 (M).

Example 101

N-(7-chloro-1-((6-methylpyridin-2-yl)methyl)-1H-indazol-4-yl)-7-(2-(4-methylpiperazin-1-yl)ethoxy)imidazo[1,2-a]pyridine-3-carboxamide trihydrochloride

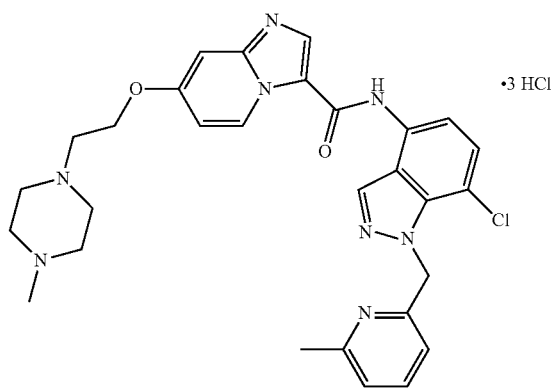 [SMILES: Cc1cccc(Cn2ncc3c(NC(=O)c4cnc5cc(OCCN6CCN(C)CC6)ccn45)ccc(Cl)c32)n1]

Step A: Preparation of 1-((6-methylpyridin-2-yl)methyl)-1H-indazol-4-amine

A solution of 3-iodo-1-((6-methylpyridin-2-yl)methyl)-4-nitro-1H-indazole (1.00 g, 2.54 mmol) in MeOH (25 mL) was cooled to 0° C. Zinc dust (0.829 g, 12.7 mmol) was added and the mixture was stirred for 10 minutes. Saturated aqueous NH$_4$Cl was added (25 mL) and the mixture was stirred vigorously for 2 hours at 0° C., then warmed to ambient temperature and stirred for an additional 2 hours. Additional saturated aqueous NH$_4$Cl was added (12.5 mL) and the mixture was stirred at ambient temperature for an additional 2 hours. The mixture was diluted with MeOH and filtered. To the filtrate was added saturated aqueous NH$_4$OAc and the mixture was concentrated to remove bulk MeOH. The mixture was extracted with EtOAc and the combined organic extracts were washed with saturated aqueous NaHCO$_3$ and brine, dried over Na$_2$SO$_4$, filtered and concentrated. The product was purified by column chromatography (2 to 20% IPA/CHCl$_3$) to afford 0.428 g (70%) of the product as an orange solid.

Step B: Preparation of 7-chloro-1-((6-methylpyridin-2-yl)methyl)-1H-indazol-4-amine A solution of 1-((6-methylpyridin-2-yl)methyl)-1H-indazol-4-amine (0.390 g, 1.64 mmol) and THF (8.0 mL) was cooled to −78° C. under N$_2$. H$_2$SO$_4$ (0.0436 mL, 0.818 mmol) was added and the resulting brown suspension was stirred for 5 minutes. N-chlorosuccinimide (0.219 g, 1.64 mmol) was added in one portion and the reaction was stirred at −78° C. for 1 hour. Sodium carbonate (0.173 g, 1.64 mmol) was added and the mixture was warmed to ambient temperature. The mixture was diluted with water (20 mL) and extracted with EtOAc. The combined organic layers were washed with brine and dried over Na$_2$SO$_4$, filtered and concentrated. The crude product was purified by column chromatography (5 to 30% EtOH/hexanes). The desired product was found in the lower band from the column but it was contaminated with succinimide, so the product was dissolved in 0.5N HCl and extracted with CHCl3. The aqueous phase was basified with NaHCO3 and extracted with EtOAc. The EtOAc was washed with brine, dried over Na$_2$SO$_4$, filtered and concentrated providing the title compound as a pale orange solid (0.150 g, 33%).

Step C: Preparation of N-(7-chloro-1-((6-methylpyridin-2-yl)methyl)-1H-indazol-4-yl)-7-(2-(4-methylpiperazin-1-yl)ethoxy)imidazo[1,2-a]pyridine-3-carboxamide trihydrochloride A vial containing lithium 7-(2-(4-methylpiperazin-1-yl)ethoxy)imidazo[1,2-a]pyridine-3-carboxylate (0.171 g, 0.550 mmol) and NMP (3.0 mL) was warmed to provide a homogeneous solution and then cooled to ambient temperature. 2,4,6-Trichlorobenzoyl chloride (0.0803 mL, 0.513 mmol) was added and the dark solution was stirred at ambient temperature for 0.5 hours. 7-Chloro-1-((6-methylpyridin-2-yl)methyl)-1H-indazol-4-amine (0.100 g, 0.367 mmol) was added as a NMP (3.0 mL) solution and the mixture was heated to 80° C. with stirring overnight. The reaction was equilibrated to ambient temperature and the mixture was diluted with EtOAc (30 mL) and saturated aqueous NaHCO$_3$ (10 mL). The organic layer was washed with brine, dried over Na$_2$SO$_4$, filtered and concentrated. The crude product was purified by column chromatography (15% IPA/CHCl$_3$ adding 1% 7N NH$_3$/MeOH) to provide N-(7-chloro-1-((6-methylpyridin-2-yl)methyl)-1H-indazol-4-yl)-7-(2-(4-methylpiperazin-1-yl)ethoxy)imidazo[1,2-a]pyridine-3-carboxamide. This product was dissolved in MeOH (4.0 mL) and CH$_2$Cl$_2$ (1.0 mL), and HCl (3.67 mL, 7.33 mmol, 2.0M Et$_2$O) was added. The mixture was stirred for 2 hours and then concentrated. The resulting solid was then washed with Et$_2$O and finally with hexanes and dried under vacuum overnight to provide 0.140 g (50%) of the title compound. MS (ES+APCI) m/z=559 (M+H-3HCl).

Example 102

7-(2-(4-methylpiperazin-1-yl)ethoxy)-N-(1-(pyridin-3-ylmethyl)-1H-indazol-4-yl)imidazo[1,2-a]pyridine-3-carboxamide trihydrochloride

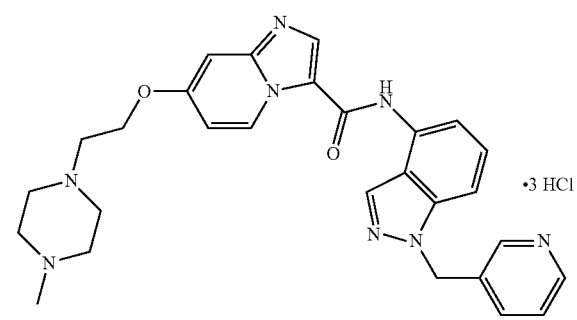 [SMILES: CN1CCN(CCOc2ccn3c(C(=O)Nc4cccc5c4cnn5Cc4cccnc4)cnc3c2)CC1]

Step A: Preparation of 3-iodo-4-nitro-1-(pyridin-3-ylmethyl)-1H-indazole

To a flask was added 3-iodo-4-nitro-1H-indazole (0.300 g, 1.04 mmol) and 4-(bromomethyl)pyridine hydrobromide (0.315 g, 1.25 mmol) which were slurried in $CH_3CN$ (5.0 mL). 2-tert-Butyl-1,1,3,3-tetramethylguanidine (0.460 mL, 2.28 mmol) was added and the mixture was stirred overnight. The mixture was diluted with water (20 mL) and stirred for 15 minutes and filtered. The collected solids were washed with water followed by $Et_2O$ and hexanes, and dried under vacuum to provide the title compound as a brown powder (0.304 g, 71%), which was used directly in the subsequent step.

Step B: Preparation of 1-(pyridin-3-ylmethyl)-1H-indazol-4-amine

To a vial containing 3-iodo-4-nitro-1-(pyridin-3-ylmethyl)-1H-indazole (0.145 g, 0.381 mmol) was added THF (2.4 mL) and MeOH (1.2 mL). To this solution was added Zn dust (0.249 g, 3.81 mmol) followed by HCl (2.54 mL, 7.63 mmol, 3.0 M aqueous). The mixture was stirred for 1.0 hours. The mixture was filtered through GF/F paper and the collected solids were washed with $CHCl_3$ (30 mL). A saturated aqueous KOAc solution was added to the filtrate until the pH was neutral and then a saturated aqueous Rochelle's Salt solution was added. The mixture was stirred vigorously, the layers were separated and the aqueous phase was extracted with $CHCl_3$. The combined organic extracts were washed with brine and dried over $Na_2SO_4$, filtered and concentrated. The product was purified by column chromatography (1 to 10% $MeOH/CH_2Cl_2$) to afford the product as a thick oil (0.041 g, 47%).

Step C: Preparation of 7-(2-(4-methylpiperazin-1-yl)ethoxy)-N-(1-(pyridin-3-ylmethyl)-1H-indazol-4-yl)imidazo[1,2-a]pyridine-3-carboxamide trihydrochloride A solution of 1-(pyridin-3-ylmethyl)-1H-indazol-4-amine (0.040 g, 0.18 mmol) in THF (1.1 mL) was cooled to −10° C. in an ice/salt bath. LHMDS (0.19 mL, 0.19 mmol, 1.0M THF) was added and the mixture was stirred for 15 minutes. To this dark solution was added a THF (1.1 mL) solution of ethyl 7-(2-(4-methylpiperazin-1-yl)ethoxy)imidazo[1,2-a]pyridine-3-carboxylate (Preparation A; 0.030 g, 0.090 mmol) at 0° C. The mixture was slowly warmed to 0° C. where it stirred for 3 hours. The reaction was quenched with a saturated aqueous $NaHCO_3$ solution and extracted with $CH_2Cl_2$. The combined organic extracts were washed with brine and dried over $Na_2SO_4$, filtered and concentrated. The crude product was purified by preparative TLC (1 mm, 15% $MeOH/CH_2Cl_2$ with $NH_3$) to afford 0.028 g of 7-(2-(4-methylpiperazin-1-yl)ethoxy)-N-(1-(pyridin-3-ylmethyl)-1H-indazol-4-yl)imidazo[1,2-a]pyridine-3-carboxamide as a tan powder. This material was suspended in MeOH (4.0 mL) and HCl (0.90 mL, 1.8 mmol, 2.0M $Et_2O$) was added. The resulting suspension was stirred for 3 hours and then concentrated. The solid was slurried in $Et_2O$ and isolated by vacuum filtration. The solid was dried under vacuum overnight to afford 0.035 g of the title compound (62%). MS (ES+APCI) m/z=511 (M+H-3HCl).

Example 103

7-(2-(4-Methylpiperazin-1-yl)ethoxy)-N-(1-((5-(trifluoromethyl)pyridin-2-yl)methyl)-1H-indazol-4-yl)imidazo[1,2-a]pyridine-3-carboxamide trihydrochloride

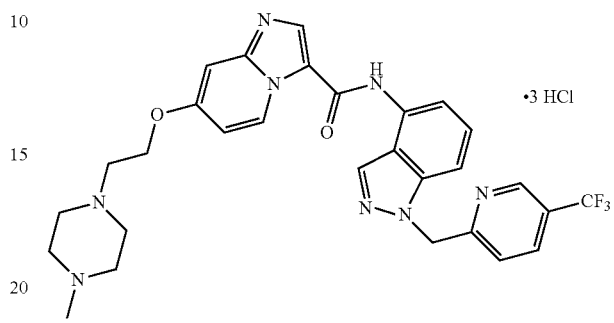

Step A: Preparation of 2-(chloromethyl)-5-(trifluoromethyl)pyridine hydrochloride A solution of (5-(trifluoromethyl)pyridin-2-yl)methanol (0.400 g, 2.26 mmol) in $CH_2Cl_2$ (4.4 mL) was cooled to 0° C. and $SOCl_2$ (0.494 mL, 6.77 mmol) was added as a $CH_2Cl_2$ solution (2.2 mL). The reaction was allowed to gradually warm to ambient temperature over 1 hour and then stirred for an additional 1 hour. The reaction was concentrated and dried under vacuum to provide the desired product (0.520 g, 99%) as dark oil that was used directly in the subsequent step.

Step B: Preparation of 3-iodo-4-nitro-1-((5-(trifluoromethyl)pyridin-2-yl)methyl)-1H-indazole To a round bottom flask was added 3-iodo-4-nitro-1H-indazole (0.580 g, 2.01 mmol) and $CH_3CN$ (10 mL). 2-tert-Butyl-1,1,3,3-tetramethylguanidine (0.890 mL, 4.41 mmol) was added and the mixture was stirred for 5 minutes. 2-(Chloromethyl)-5-(trifluoromethyl)pyridine hydrochloride (0.512 g, 2.21 mmol) was added as a $CH_3CN$ solution (4 mL) and the mixture was stirred at ambient temperature overnight. The mixture was concentrated and diluted with saturated aqueous $NH_4Cl$ (20 mL) and EtOAc (60 mL). The layers were mixed and separated and the organic phase was washed with brine, dried over $Na_2SO_4$, filtered and concentrated. The crude product was purified by column chromatography (50% EtOAc/hexane) to provide 0.490 g (54%) of the product as an orange solid.

Step C: Preparation of 1-((5-(trifluoromethyl)pyridin-2-yl)methyl)-1H-indazol-4-amine To a solution of 3-iodo-4-nitro-1-((5-(trifluoromethyl)pyridin-2-yl)methyl)-1H-indazole (0.464 g, 1.04 mmol) in MeOH (10 mL) at 0° C. was added Zn dust (0.339 g, 5.18 mmol) followed by saturated aqueous $NH_4Cl$ (10 mL). The mixture was stirred at 0° C. for 1 hour, then warmed to ambient temperature and stirred for an additional 1 hour. The mixture was diluted with MeOH and filtered. Saturated aqueous $NH_4OAc$ was added to the filtrate and the mixture was concentrated to remove bulk MeOH. The mixture was extracted with EtOAc, and the combined organic extracts were washed with saturated aqueous NaHCO₃ and brine, dried over Na₂SO₄, filtered and concentrated. The product was purified by column chromatography (25 to 100% EtOAc/hexane) to afford 0.230 g (76%) of the product as yellow/orange oil.

Step D: Preparation of 7-(2-(4-methylpiperazin-1-yl)ethoxy)-N-(1-((5-(trifluoromethyl)pyridin-2-yl)methyl)-1H-indazol-4-yl)imidazo[1,2-a]pyridine-3-carboxamide trihydrochloride To a solution of 7-(2-(4-methylpiperazin-1-yl)ethoxy)imidazo[1,2-a]pyridine-3-carboxylic acid lithium chloride (0.0653 g, 0.188 mmol) in dry DMA (2.0 mL) at 0° C. was added POCl3 (0.0345 mL, 0.376 mmol) and the mixture was stirred at 0° C. for 30 minutes. 1-((5-(Trifluoromethyl)pyridin-2-yl)methyl)-1H-indazol-4-amine (0.055 g, 0.188 mmol) was added as a DMA solution (1.0 mL) and the mixture was gradually warmed to ambient temperature and stirred overnight. The mixture was concentrated under vacuum and 2M LiOH (2.5 mL) was added. The mixture was stirred for 10 minutes. The mixture was diluted with CHCl₃ (20 mL) and with saturated aqueous NaHCO₃ and the layers were mixed and separated. The aqueous phase was further extracted with CHCl₃ and the combined organic layers were washed with brine and dried over Na₂SO₄, filtered and concentrated. The product was purified by preparative TLC (15% MeOH/CH2C₁₂ adding 1% 7N NH₃/MeOH) to provide 7-(2-(4-methylpiperazin-1-yl)ethoxy)-N-(1-((5-(trifluoromethyl)pyridin-2-yl)methyl)-1H-indazol-4-yl)imidazo[1,2-a]pyridine-3-carboxamide as a tan solid (0.028 g). The solid was dissolved in MeOH (2.0 mL) and HCl (1.88 mL, 3.76 mmol, 2.0M in Et₂O) was added. The mixture was stirred for 2 hours and then concentrated. The resulting solid was washed with Et₂O and finally with hexanes and dried under vacuum to provide the title compound (0.032 g, 24%). MS (ES+APCI) m/z=579 (M+H-3HCl).

Example 104

N-(1-((1-methyl-2-oxo-1,2-dihydropyridin-3-yl)methyl)-1H-indazol-4-yl)-7-(2-(4-methylpiperazin-1-yl)ethoxy)imidazo[1,2-a]pyridine-3-carboxamide dihydrochloride

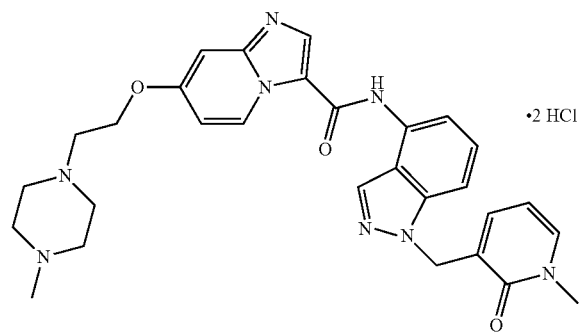 [SMILES: CN1CCN(CCOc2ccn3c(C(=O)Nc4cccc5c4cnn5Cc4cccn(C)c4=O)cnc3c2)CC1]

Step A: Preparation of 3-(bromomethyl)-1-methylpyridin-2(1H)-one 1,3-Dimethylpyridin-2(1H)-one (0.54 g, 4.4 mmol) was added to CCl₄ (100 mL). N-Bromosuccinimide (0.78 g, 4.4 mmol) and benzoyl peroxide (0.11 g, 0.44 mmol) were added and the reaction mixture was refluxed for 3 hours. The reaction was cooled, filtered and concentrated. The residue was suspended in Et₂O (10 mL) and filtered to provide 3-(bromomethyl)-1-methylpyridin-2(1H)-one (0.29 g, 32% yield) as a solid.

Step B: Preparation of 3-((3-iodo-4-nitro-1H-indazol-1-yl)methyl)-1-methylpyridin-2(1H)-one 3-Iodo-4-nitro-1H-indazole (0.38 g, 1.3 mmol) was reacted with K₂CO₃ (0.36 g, 2.6 mmol) in DMF (4 mL) for 15 minutes. 3-(Bromomethyl)-1-methylpyridin-2(1H)-one (0.28 g, 1.4 mmol) was added and the reaction mixture was stirred overnight. The reaction mixture was diluted with CH₂Cl₂ (30 mL), filtered and concentrated. The residue was partitioned between CHCl₃ and saturated aqueous NaHCO₃. The organic layer was dried over MgSO₄ and concentrated. The residue was suspended in EtOAc (8 mL), stirred for 20 minutes and then filtered to provide 3-((3-iodo-4-nitro-1H-indazol-1-yl)methyl)-1-methylpyridin-2(1H)-one (0.27 g, 50% yield) as a solid.

Step C: Preparation of 3-((4-amino-1H-indazol-1-yl)methyl)-1-methylpyridin-2(1H)-one 3-((3-Iodo-4-nitro-1H-indazol-1-yl)methyl)-1-methylpyridin-2(1H)-one (0.26 g, 0.63 mmol) was added to MeOH (6 mL) and cooled to 0° C. Zinc (0.21 g, 3.2 mmol) was added to the reaction mixture. Saturated aqueous NH₄Cl (6 mL) was added drop-wise and the reaction mixture was stirred for 90 minutes at ambient temperature. The reaction was diluted with MeOH (50 mL), stirred for 5 minutes and filtered. The filtrate was diluted with saturated NH₄OAc and the MeOH was removed under vacuum. The aqueous mixture was extracted with CHCl₃. The organic layer was washed with brine, dried over MgSO₄ and concentrated to provide 3-((4-amino-1H-indazol-1-yl)methyl)-1-methylpyridin-2(1H)-one (0.12 g, 71% yield) as a solid.

Step D: Preparation of N-(1-((1-methyl-2-oxo-1,2-dihydropyridin-3-yl)methyl)-1H-indazol-4-yl)-7-(2-(4-methylpiperazin-1-yl)ethoxy)imidazo[1,2-a]pyridine-3-carboxamide dihydrochloride 7-(2-(4-Methylpiperazin-1-yl)ethoxy)imidazo[1,2-a]pyridine-3-carboxylic acid (0.072 g, 0.21 mmol) was added to DMA (1 mL) and cooled to 0° C. Phosphorus oxychloride (0.038 mL, 0.41 mmol) was added and the reaction mixture was stirred for 30 minutes. 3-((4-Amino-1H-indazol-1-yl)methyl)-1-methylpyridin-2(1H)-one (0.035 g, 0.14 mmol) was added and the reaction mixture was stirred at ambient temperature overnight. The reaction was concentrated and then suspended in 2 M LiOH (2 mL). The resulting mixture was stirred for 30 minutes and then diluted with CHCl3 and saturated aqueous NaHCO₃. The layers were separated and the aqueous phase was extracted with CHCl₃. The combined organic layers were dried over MgSO₄ and concentrated. The residue was purified by preparative thin layer chromatography (1:6 2.3 M NH₃ in MeOH:CH₂Cl₂), added to MeOH (2 mL) and reacted with HCl (2 M in Et₂O, 2 mL). The mixture was stirred for 60 minutes and then concentrated. The resulting solids were suspended in Et₂O and filtered to provide N-(1-((1-methyl-2-oxo-1,2-dihydropyridin-3-yl)methyl)-1H-indazol-4-yl)-7-(2-(4-methylpiperazin-1-yl)ethoxy)imidazo[1,2- a]pyridine-3-carboxamide dihydrochloride (0.035 g, 41% yield) as a solid. MS (ES+ APCI) m/z=541 (M+H-2HCl).

Example 105

N-(1-((6-ethoxypyridin-2-yl)methyl)-1H-indazol-4-yl)-7-(2-(4-methylpiperazin-1-yl)ethoxy)imidazo[1,2-a]pyridine-3-carboxamide

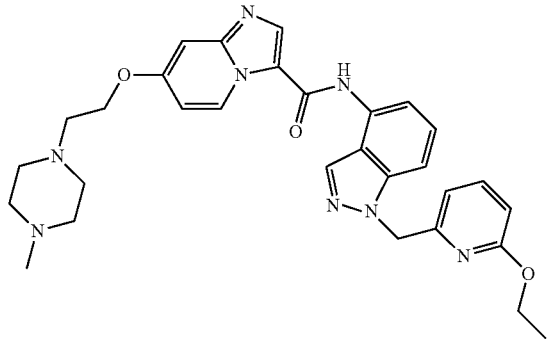 [SMILES: CCOc1cccc(Cn2ncc3c(NC(=O)c4cnc5cc(OCCN6CCN(C)CC6)ccn45)cccc32)n1]

Prepared according to the method of Example 104, replacing 3-(bromomethyl)-1-methylpyridin-2(1H)-one with 1-(bromomethyl)-3-methoxybenzene. MS (ES+APCI) m/z=555 (M+H).

Example 106

N-(1-((1-methyl-1H-imidazol-4-yl)methyl)-1H-indazol-4-yl)-7-(2-(4-methylpiperazin-1-yl)ethoxy)imidazo[1,2-a]pyridine-3-carboxamide dihydrochloride

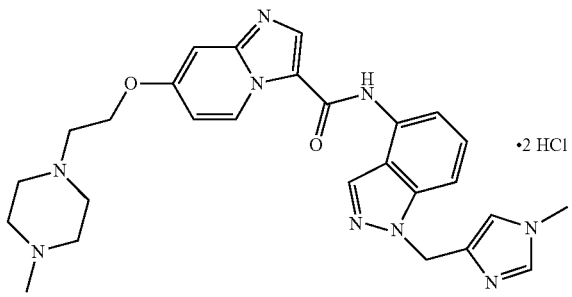 [SMILES: CN1CCN(CCOc2ccn3c(C(=O)Nc4cccc5c4cnn5Cc4cn(C)cn4)cnc3c2)CC1]

Prepared according to the method of Example 104, replacing 3-(bromomethyl)-1-methylpyridin-2(1H)-one with 4-(chloromethyl)-1-methyl-1H-imidazole hydrochloride. MS (ES+APCI) m/z=514 (M+H).

Example 107

7-(2-(4-methylpiperazin-1-yl)ethoxy)-N-(1-(2-(pyridin-2-yl)ethyl)-1H-indazol-4-yl)imidazo[1,2-a]pyridine-3-carboxamide

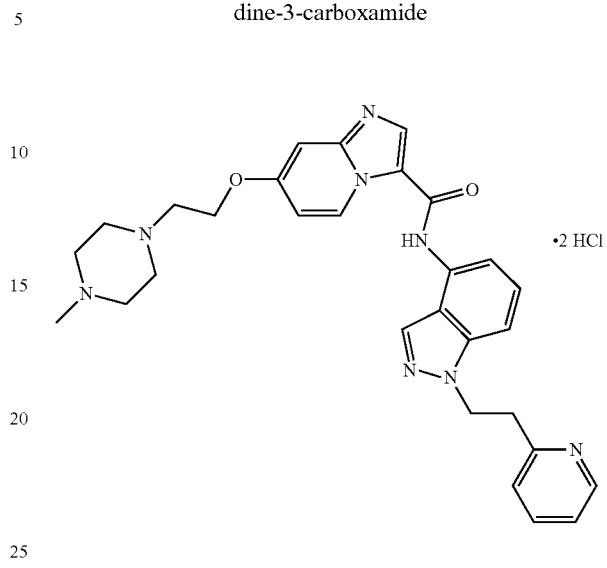

Step A: Preparation of 3-iodo-4-nitro-1-(2-(pyridin-2-yl)ethyl)-1H-indazole

2-Tert-butyl-1,1,3,3-tetramethyl-guanidine (0.48 mL, 2.4 mmol) was added to a mixture of 3-iodo-4-nitro-1H-indazole (0.30 g, 1.0 mmol) and 2-(2-bromoethyl)pyridine hydrobromide (0.30 g, 1.1 mmol) in CH₃CN (4 mL). The mixture was stirred at ambient temperature overnight, diluted with H₂O (35 mL), stirred for 30 minutes, and then extracted with CHCl₃. The combined organic extracts were dried over MgSO₄ and concentrated. The residue was purified by silica gel chromatography, eluting with EtOAc, to provide 3-iodo-4-nitro-1-(2-(pyridin-2-yl)ethyl)-1H-indazole (0.14 mg, 34%) as a solid.

Step B: 7-(2-(4-methylpiperazin-1-yl)ethoxy)-N-(1-(2-(pyridin-2-yl)ethyl)-1H-indazol-4-yl)imidazo[1,2-a]pyridine-3-carboxamide dihydrochloride Prepared according to Example 104, Steps C-E, replacing 3-((3-iodo-4-nitro-1H-indazol-1-yl)methyl)-1-methylpyridin-2(1H)-one with 3-iodo-4-nitro-1-(2-(pyridin-2-yl)ethyl)-1H-indazole. MS (ES+APCI) m/z=525 (M+H).

Example 108

N-(1-((1H-benzo[d]imidazol-5-yl)methyl)-1H-indazol-4-yl)-7-(2-(4-methylpiperazin-1-yl)ethoxy)imidazo[1,2-a]pyridine-3-carboxamide dihydrochloride

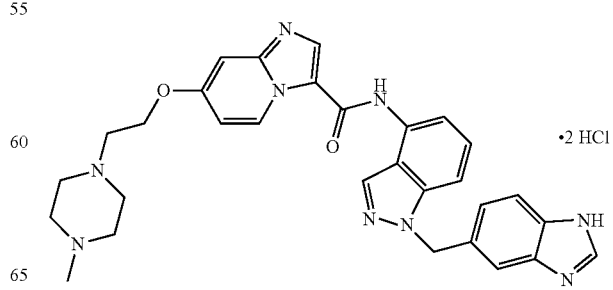

Prepared according to the method of Example 104, replacing 3-(bromomethyl)-1-methylpyridin-2(1H)-one with a mixture of tert-butyl 5-(bromomethyl)-1H-benzo[d]imidazole-1-carboxylate and tert-butyl 6-(bromomethyl)-1H-benzo[d]imidazole-1-carboxylate. MS (ES+APCI) m/z=550 (M+H).

Example 109

N-(1-(2,4-difluorobenzyl)-1H-indazol-4-yl)-7-(2-methoxyethoxyl)imidazo[1,2-a]pyridine-3-carboxamide

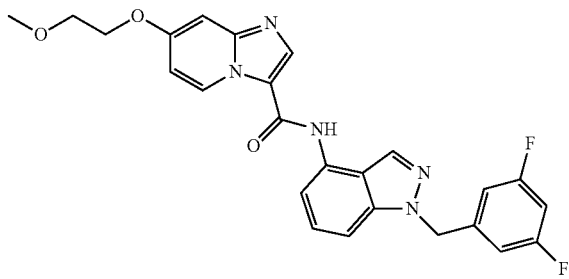 [SMILES: COCCOc1ccn2c(C(=O)Nc3cccc4c3cnn4Cc3cc(F)cc(F)c3)cnc2c1]

Step A: 1-(2,4-difluorobenzyl)-4-nitro-1H-indazole

To a solution of 4-nitro-1H-indazole (0.200 g, 1.226 mmol) in acetone (3 mL) cooled to 0° C., was added KOH (0.103 g, 1.839 mmol). After 15 minutes at 0° C., 1-(bromomethyl)-2,4-difluorobenzene (0.173 mL, 1.349 mmol) was added. The mixture was allowed to stir at ambient temperature overnight, concentrated and the residue purified on silica gel (5-25% EtOAc in hexanes) to provide 1-(2,4-difluorobenzyl)-4-nitro-1H-indazole (0.142 g, 40% yield) as a pale yellow solid.

Step B: 1-(2,4-difluorobenzyl)-1H-indazol-4-amine

A solution of 1-(2,4-difluorobenzyl)-4-nitro-1H-indazole (0.142 g, 0.491 mmol), ammonium chloride (0.013 g, 0.245 mmol) in 4:1 v/v EtOH/water (5 mL) was treated with iron (0.274 g, 4.91 mmol) and refluxed for 2 hours. The mixture was concentrated and the residue taken in EtOAc/water, filtered through glass fiber filter paper and concentrated again to provide 1-(2,4-difluorobenzyl)-1H-indazol-4-amine (0.096 mg, 75% yield) as an amber oil.

Step C: N-(1-(2,4-difluorobenzyl)-1H-indazol-4-yl)-7-(2-methoxyethoxyl)imidazo[1,2-a]pyridine-3-carboxamide 7-(2-Methoxyethoxyl)imidazo[1,2-a]pyridine-3-carboxylic acid (0.070 g, 0.296 mmol) and a 2M solution of oxalyl chloride in methylene chloride (0.163 mL, 0.326 mmol) were suspended in methylene chloride (2 mL) with a catalytic amount of DMF. The mixture was stirred for a few minutes and then treated with 1-(2,4-difluorobenzyl)-1H-indazol-4-amine (0.084 g, 0.326 mmol) as a solution in about 1 mL methylene chloride, followed by addition of diisopropylethylamine (0.062 mL, 0.356 mmol). After stirring the mixture overnight, the residue was shaken in water/methylene chloride and suspended solids collected by filtration to provide N-(1-(2,4-difluorobenzyl)-1H-indazol-4-yl)-7-(2-methoxyethoxyl)imidazo[1,2-a]pyridine-3-carboxamide (0.070 g, 50% yield). MS (APCI) m/z=478 (M+H).

Example 110

N-(1-(cyclopropylmethyl)-1H-indazol-4-yl)-7-(2-methoxyethoxyl)imidazo[1,2-a]pyridine-3-carboxamide

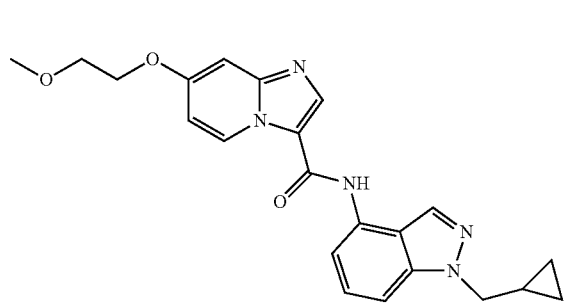 [SMILES: COCCOc1ccn2c(C(=O)Nc3cccc4c3cnn4CC3CC3)cnc2c1]

Prepared according to the method of Example 109, replacing 1-(2,4-difluorobenzyl)-1H-indazol-4-amine in Step C with 1-(cyclopropylmethyl)-1H-indazol-4-amine. MS (APCI) m/z=406 (M+H).

Example 111

7-(2-methoxyethoxy)-N-(1-(pyridin-4-ylmethyl)-1H-indazol-4-yl)imidazo[1,2-a]pyridine-3-carboxamide

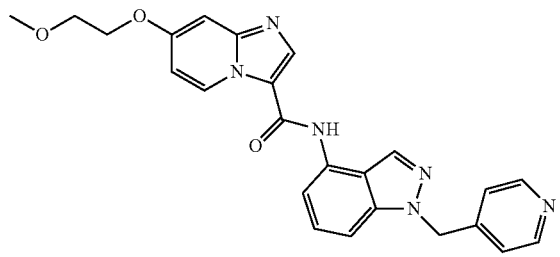 [SMILES: COCCOc1ccn2c(C(=O)Nc3cccc4c3cnn4Cc3ccncc3)cnc2c1]

Prepared according to the method of Example 109, replacing 1-(2,4-difluorobenzyl)-1H-indazol-4-amine in Step C with 1-(pyridin-4-ylmethyl)-1H-indazol-4-amine. MS (APCI) m/z=443 (M+H).

Example 112

7-(2-methoxyethoxy)-N-(1-(pyridin-2-ylmethyl)-1H-indazol-4-yl)imidazo[1,2-a]pyridine-3-carboxamide

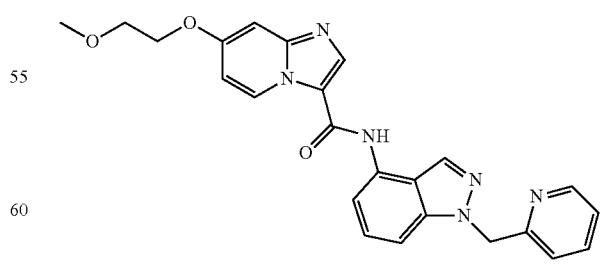

Prepared according to the method of Example 109, replacing 1-(2,4-difluorobenzyl)-1H-indazol-4-amine in Step C with 1-(pyridin-2-ylmethyl)-1H-indazol-4-amine. MS (APCI) m/z=443 (M+H).

Example 113

7-(2-methoxyethoxy)-N-(1-((tetrahydro-2H-pyran-4-yl)methyl)-1H-indazol-4-yl)imidazo[1,2-a]pyridine-3-carboxamide

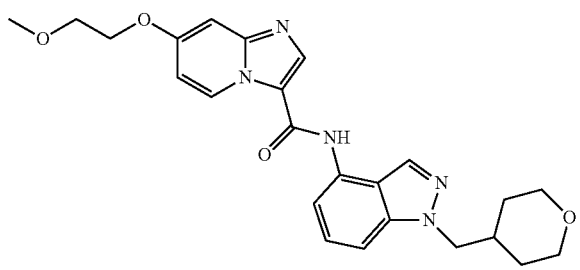 [SMILES: COCCOc1ccn2c(C(=O)Nc3cccc4c3cnn4CC3CCOCC3)cnc2c1]

Prepared according to the method of Example 109, replacing 1-(2,4-difluorobenzyl)-1H-indazol-4-amine in Step C with 1-((tetrahydro-2H-pyran-4-yl)methyl)-1H-indazol-4-amine. MS (APCI) m/z=450 (M+H).

Example 114

N-(1-(4-methoxybenzyl)-1H-indazol-4-yl)-7-(2-methoxyethoxy)imidazo[1,2-a]pyridine-3-carboxamide

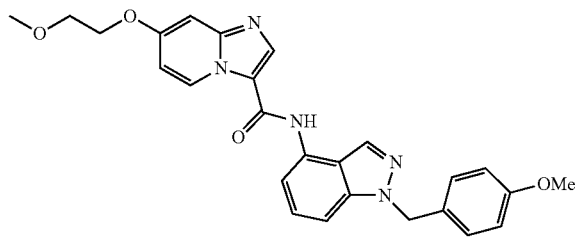 [SMILES: COCCOc1ccn2c(C(=O)Nc3cccc4c3cnn4Cc3ccc(OC)cc3)cnc2c1]

Prepared according to the method of Example 109, replacing 1-(2,4-difluorobenzyl)-1H-indazol-4-amine in Step C with 1-(4-methoxybenzyl)-1H-indazol-4-amine. MS (APCI) m/z=472 (M+H).

Example 115

N-(1-(cyclohexylmethyl)-1H-indazol-4-yl)-7-(2-methoxyethoxyl)imidazo[1,2-a]pyridine-3-carboxamide

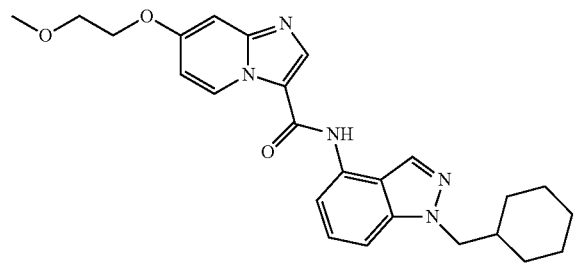 [SMILES: COCCOc1ccn2c(C(=O)Nc3cccc4c3cnn4CC3CCCCC3)cnc2c1]

Prepared according to the method of Example 109, replacing 1-(2,4-difluorobenzyl)-1H-indazol-4-amine in Step C with 1-(cyclohexylmethyl)-1H-indazol-4-amine. MS (APCI) m/z=448 (M+H).

Example 116 tert-butyl 3-((4-(7-(2-methoxyethoxyl)imidazo[1,2-a]pyridine-3-carboxamido)-1H-indazol-1-yl)methyl)piperidine-1-carboxylate

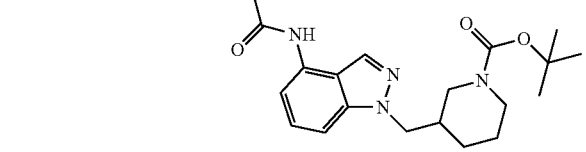

Prepared according to the method of Example 109, replacing 1-(2,4-difluorobenzyl)-1H-indazol-4-amine in Step C with tert-butyl 3-((4-amino-1H-indazol-1-yl)methyl)piperidine-1-carboxylate. MS (APCI) m/z=549 (M+H).

Example 117

(R)-tert-butyl 3-((4-(7-(2-methoxyethoxyl)imidazo[1,2-a]pyridine-3-carboxamido)-1H-indazol-1-yl)methyl)piperidine-1-carboxylate

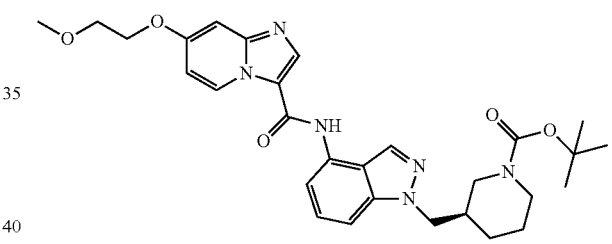

Prepared according to the method of Example 109, replacing 1-(2,4-difluorobenzyl)-1H-indazol-4-amine in Step C with (R)-tert-butyl 3-((4-amino-1H-indazol-1-yl)methyl)piperidine-1-carboxylate. MS (APCI) m/z=549 (M+H).

Example 118

7-(2-methoxyethoxy)-N-(1-((2-methylpyridin-3-yl)methyl)-1H-indazol-4-yl)imidazo[1,2-a]pyridine-3-carboxamide

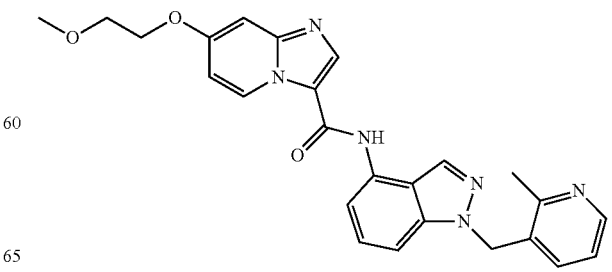

Prepared according to the method of Example 109, replacing 1-(2,4-difluorobenzyl)-1H-indazol-4-amine in Step C with 1-((2-methylpyridin-3-yl)methyl)-1H-indazol-4-amine. MS (APCI) m/z=457 (M+H).

Example 119

N-(1-(3-(benzyloxy)benzyl)-1H-indazol-4-yl)-7-(2-methoxyethoxy)imidazo[1,2-a]pyridine-3-carboxamide

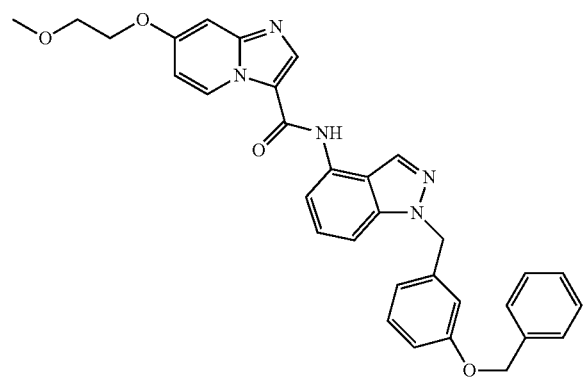 [SMILES: COCCOc1ccn2c(C(=O)Nc3cccc4c3cnn4Cc3cccc(OCc4ccccc4)c3)cnc2c1]

Prepared according to the method of Example 109, replacing 1-(2,4-difluorobenzyl)-1H-indazol-4-amine in Step C with 1-(3-(benzyloxy)benzyl)-1H-indazol-4-amine. MS (APCI) m/z=548 (M+H).

Example 120

7-(2-methoxyethoxy)-N-(1-(4-(trifluoromethyl)benzyl)-1H-indazol-4-yl)imidazo[1,2-a]pyridine-3-carboxamide

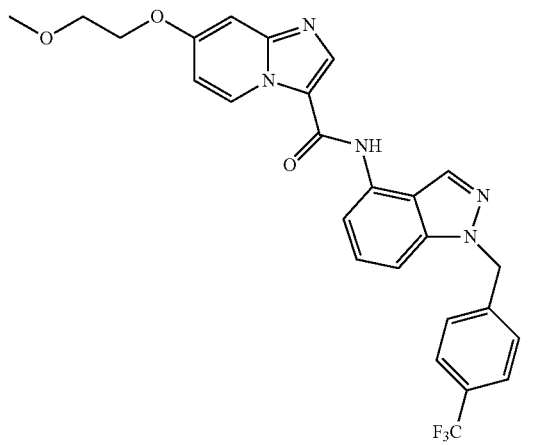 [SMILES: COCCOc1ccn2c(C(=O)Nc3cccc4c3cnn4Cc3ccc(C(F)(F)F)cc3)cnc2c1]

Prepared according to the method of Example 109, replacing 1-(2,4-difluorobenzyl)-1H-indazol-4-amine with 1-(4-(trifluoromethyl)benzyl)-1H-indazol-4-amine. MS (APCI) m/z=510 (M+H).

Example 121

7-(2-methoxyethoxy)-N-(1-(pyridin-3-ylmethyl)-1H-indazol-4-yl)imidazo[1,2-a]pyridine-3-carboxamide

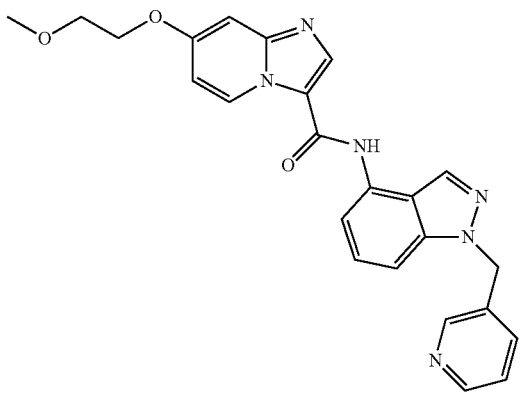 [SMILES: COCCOc1ccn2c(C(=O)Nc3cccc4c3cnn4Cc3cccnc3)cnc2c1]

Prepared according to the method of Example 109, replacing 1-(2,4-difluorobenzyl)-1H-indazol-4-amine in Step C with 1-(pyridin-3-ylmethyl)-1H-indazol-4-amine. MS (APCI) m/z=443 (M+H).

Example 122 tert-butyl 4-((4-(7-(2-methoxyethoxy)imidazo[1,2-a]pyridine-3-carboxamido)-1H-indazol-1-yl)methyl)piperidine-1-carboxylate

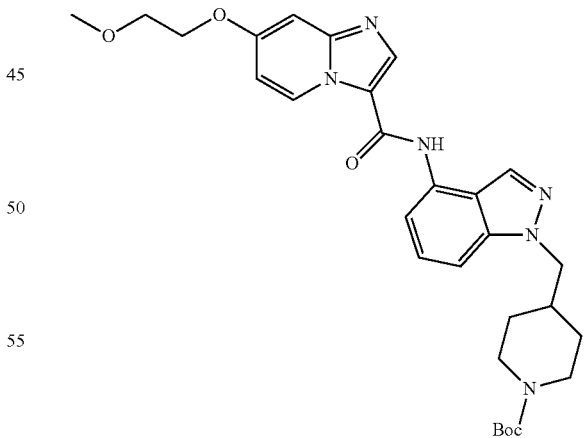

Prepared according to the method of Example 109, replacing 1-(2,4-difluorobenzyl)-1H-indazol-4-amine in Step C with tert-butyl 4-((4-amino-1H-indazol-1-yl)methyl)piperidine-1-carboxylate. MS (APCI) m/z=549 (M+H).

Example 123 tert-butyl 2-((4-(7-(2-methoxyethoxy)imidazo[1,2-a]pyridine-3-carboxamido)-1H-indazol-1-yl)methyl)morpholine-4-carboxylate

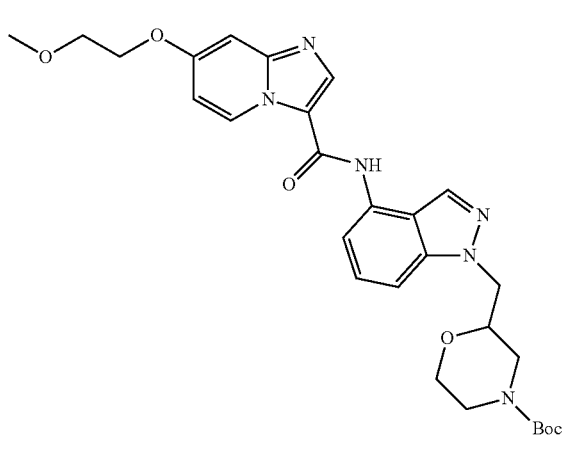 [SMILES: COCCOc1ccn2c(C(=O)Nc3cccc4c3cnn4CC3CN(C(=O)OC(C)(C)C)CCO3)cnc2c1]

Prepared according to the method of Example 109, replacing 1-(2,4-difluorobenzyl)-1H-indazol-4-amine in Step C with tert-butyl 2-((4-amino-1H-indazol-1-yl)methyl)morpholine-4-carboxylate. MS (APCI) m/z=551 (M+H).

Example 124

7-(2-methoxyethoxy)-N-(1-(((6-methylpyridin-3-yl)methyl)-1H-indazol-4-yl)imidazo[1,2-a]pyridine-3-carboxamide

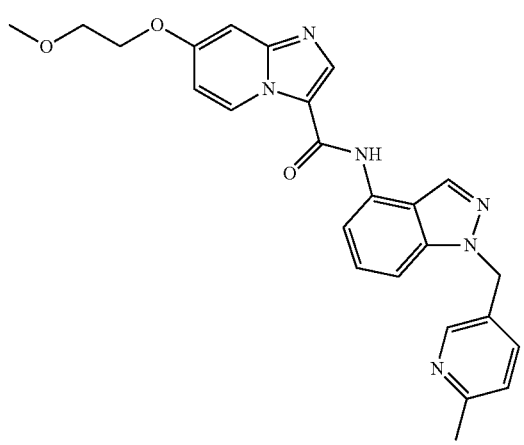 [SMILES: COCCOc1ccn2c(C(=O)Nc3cccc4c3cnn4Cc3ccc(C)nc3)cnc2c1]

Prepared according to the method of Example 109, replacing 1-(2,4-difluorobenzyl)-1H-indazol-4-amine in Step C with 1-((6-methylpyridin-3-yl)methyl)-1H-indazol-4-amine. MS (APCI) m/z=457 (M+H).

Example 125

N-(1-benzyl-1H-indazol-4-yl)-7-methoxyimidazo[1,2-a]pyridine-3-carboxamide

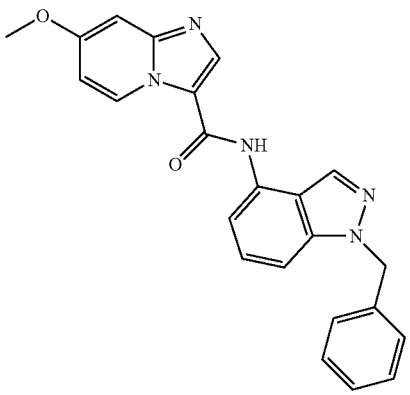 [SMILES: COc1ccn2c(C(=O)Nc3cccc4c3cnn4Cc3ccccc3)cnc2c1]

Prepared according to the method of Example 109, replacing 7-(2-methoxyethoxy)imidazo[1,2-a]pyridine-3-carboxylic acid and 1-(2,4-difluorobenzyl)-1H-indazol-4-amine with 7-methoxyimidazo[1,2-a]pyridine-3-carboxylic acid and 1-benzyl-1H-indazol-4-amine, respectively. MS (APCI) m/z=398 (M+H).

Example 126

N-(1-benzyl-1H-indazol-4-yl)imidazo[1,2-a]pyridine-3-carboxamide

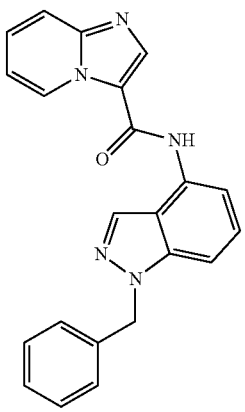 [SMILES: O=C(Nc1cccc2c1cnn2Cc1ccccc1)c1cnc2ccccn12]

Prepared according to the method of Example 109, replacing 7-(2-methoxyethoxy)imidazo[1,2-a]pyridine-3-carboxylic acid and 1-(2,4-difluorobenzyl)-1H-indazol-4-amine with imidazo[1,2-a]pyridine-3-carboxylic acid and 1-benzyl-1H-indazol-4-amine, respectively. MS (APCI) m/z=368 (M+H).

Example 127

N-(1-benzyl-1H-indazol-4-yl)-7-ethoxyimidazo[1,2-a]pyridine-3-carboxamide

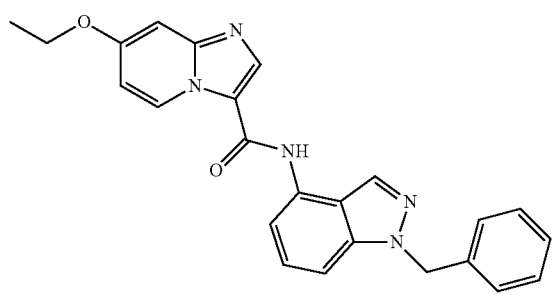 [SMILES: CCOc1ccn2c(C(=O)Nc3cccc4c3cnn4Cc3ccccc3)cnc2c1]

Prepared according to the method of Example 109, replacing 7-(2-methoxyethoxyl)imidazo[1,2-a]pyridine-3-carboxylic acid and 1-(2,4-difluorobenzyl)-1H-indazol-4-amine with 7-ethoxyimidazo[1,2-a]pyridine-3-carboxylic acid and 1-benzyl-1H-indazol-4-amine, respectively. MS (APCI) m/z=412 (M+H).

Example 128

N-(1-((tetrahydro-2H-pyran-2-yl)methyl)-1H-indazol-4-yl)imidazo[1,2-a]pyridine-3-carboxamide

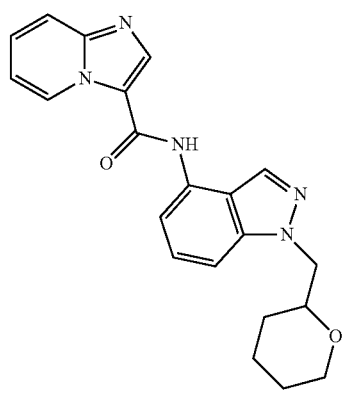 [SMILES: O=C(Nc1cccc2c1cnn2CC1CCCCO1)c1cnc2ccccn12]

Prepared according to the method of Example 109, replacing 7-(2-methoxyethoxyl)imidazo[1,2-a]pyridine-3-carboxylic acid and 1-(2,4-difluorobenzyl)-1H-indazol-4-amine with imidazo[1,2-a]pyridine-3-carboxylic acid and 1-((tetrahydro-2H-pyran-2-yl)methyl)-1H-indazol-4-amine, respectively. MS (APCI) m/z=376 (M+H).

Example 129

N-(1-(pyridin-2-ylmethyl)-1H-indazol-4-yl)imidazo[1,2-a]pyridine-3-carboxamide

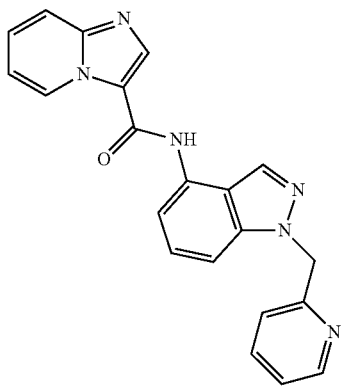 [SMILES: O=C(Nc1cccc2c1cnn2Cc1ccccn1)c1cnc2ccccn12]

Prepared according to the method of Example 109, replacing 7-(2-methoxyethoxyl)imidazo[1,2-a]pyridine-3-carboxylic acid and 1-(2,4-difluorobenzyl)-1H-indazol-4-amine with imidazo[1,2-a]pyridine-3-carboxylic acid and 1-(pyridin-2-ylmethyl)-1H-indazol-4-amine, respectively. MS (APCI) m/z=369 (M+H).

Example 130

N-(1-(3-hydroxybenzyl)-1H-indazol-4-yl)-7-(2-methoxyethoxyl)imidazo[1,2-a]pyridine-3-carboxamide

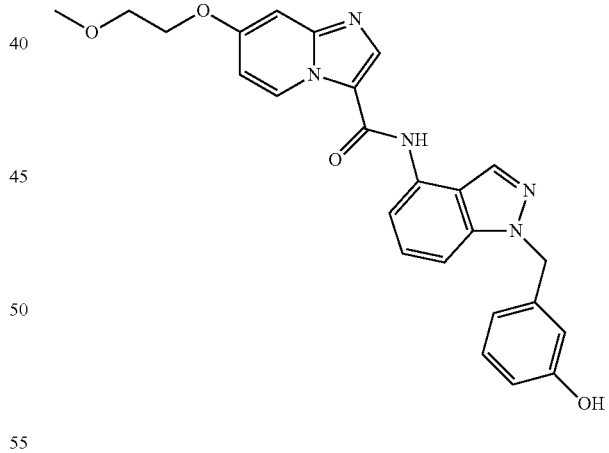

A solution of N-(1-(3-(benzyloxy)benzyl)-1H-indazol-4-yl)-7-(2-methoxyethoxyl)imidazo[1,2-a]pyridine-3-carboxamide (0.022 g, 0.040 mmol) in MeOH (2 mL) was purged with Argon, treated with 10% palladium on carbon (0.002 g), purged with more Argon, and then attached to a hydrogen balloon. The mixture was stirred at ambient temperature overnight, filtered through glass fiber filter paper, washed with MeOH, concentrated and the residue purified on silica gel (1-3% MeOH in DCM) to provide N-(1-(3-hydroxybenzyl)-1H-indazol-4-yl)-7-(2-methoxyethoxyl)imidazo[1,2-a]pyridine-3-carboxamide (0.003 g, 18% yield) as a beige oil. MS (APCI) m/z=458 (M+H).

Example 131

7-(2-methoxyethoxy)-N-(1-(piperidin-3-ylmethyl)-1H-indazol-4-yl)imidazo[1,2-a]pyridine-3-carboxamide hydrochloride

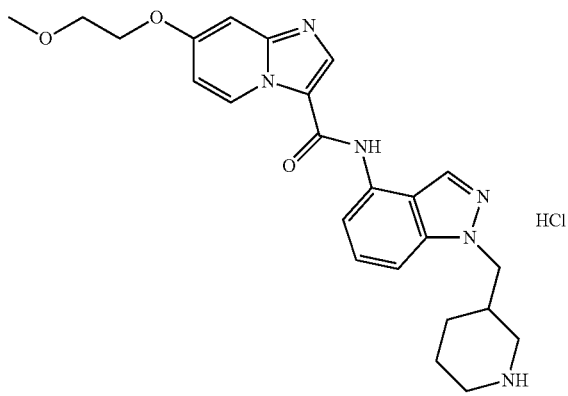 [SMILES: COCCOc1ccn2c(C(=O)Nc3cccc4c3cnn4CC3CCCNC3)cnc2c1 ; Cl]

A solution of tert-butyl 3-((4-(7-(2-methoxyethoxyl)imidazo[1,2-a]pyridine-3-carboxamido)-1H-indazol-1-yl)methyl)piperidine-1-carboxylate (0.056 g, 0.10 mmol) in DCM (1 mL) was treated with 4N hydrochloric acid in dioxane (1 mL) at ambient temperature. The mixture was stirred at ambient temperature overnight, concentrated to afford 7-(2-methoxyethoxy)-N-(1-(piperidin-3-ylmethyl)-1H-indazol-4-yl)imidazo[1,2-a]pyridine-3-carboxamide hydrochloride (0.0046 g, 93% yield) as a brown oil. MS (APCI) m/z=449 (M+H).

Example 132

N-(1-((1-acetylpiperidin-3-yl)methyl)-1H-indazol-4-yl)-7-(2-methoxyethoxy)imidazo[1,2-a]pyridine-3-carboxamide

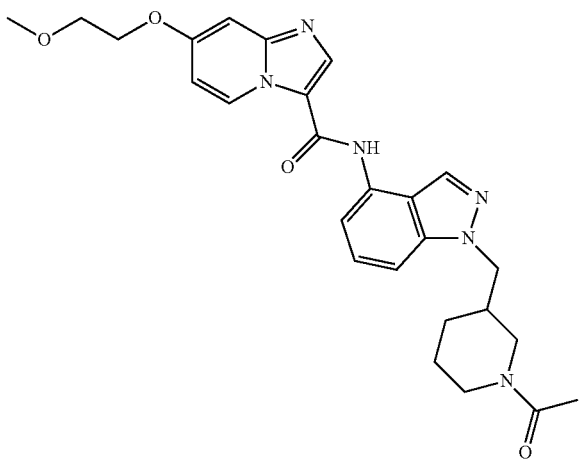 [SMILES: COCCOc1ccn2c(C(=O)Nc3cccc4c3cnn4CC3CCCN(C(C)=O)C3)cnc2c1]

Step A: tert-Butyl 3-((4-nitro-1H-indazol-1-yl)methyl)piperidine-1-carboxylate To a solution of 4-nitro-1H-indazole (0.200 g, 1.23 mmol) in DMA (3 mL) was added 60% sodium hydride (0.074 g, 1.84 mmol) at ambient temperature. After 30 minutes, tert-butyl 3-(tosyloxymethyl)piperidine-1-carboxylate (0.544 g, 1.47 mmol) was added. The mixture was heated at 100° C. overnight, diluted with water, extracted with DCM, dried (phase separator silicone treated filter paper), concentrated and the residue purified on silica gel (10-50% EtOAc in DCM) to provide tert-butyl 3-((4-nitro-1H-indazol-1-yl)methyl)piperidine-1-carboxylate (0.176 g, 40% yield) as a yellow gum.

Step B: 4-Nitro-1-(piperidin-3-ylmethyl)-1H-indazole

A solution of tert-butyl 3-((4-nitro-1H-indazol-1-yl)methyl)piperidine-1-carboxylate (0.118 g, 0.327 mmol) in DCM (1.6 mL) was treated with trifluoroacetic acid (0.4 mL) at ambient temperature and stirring continued for 2 hours. The solvent was concentrated and the resulting gum was dried under high vacuum to afford 4-nitro-1-(piperidin-3-ylmethyl)-1H-indazole (0.108 g, 92% yield) as a brown oil.

Step C: 1-(3-((4-Nitro-1H-indazol-1-yl)methyl)piperidin-1-yl)ethanone

A solution of 4-nitro-1-(piperidin-3-ylmethyl)-1H-indazole (0.050 g, 0.139 mmol), triethylamine (0.097 mL, 0.699 mmol) in DCM (1 mL) was treated with acetic anhydride (0.0158 mL, 0.168 mmol) at ambient temperature and stirring continued for 1 hour. The mixture was quenched with saturated aqueous sodium bicarbonate, extracted with DCM, dried (phase separator silicone treated filter paper) and concentrated to provide 1-(3-((4-nitro-1H-indazol-1-yl)methyl)piperidin-1-yl)ethanone (0.022 g, 52% yield) as a yellow oil.

Step D: 1-(3-((4-Amino-1H-indazol-1-yl)methyl)piperidin-1-yl)ethanone

A solution of 1-(3-((4-nitro-1H-indazol-1-yl)methyl)piperidin-1-yl)ethanone (0.022 g, 0.073 mmol) in MeOH (1 mL) was purged with Argon, treated with 10% palladium on carbon (0.002 g) purged with more Argon, and then attached to a hydrogen balloon. The mixture was stirred at ambient temperature overnight, filtered through glass fiber filter paper, washed with MeOH and concentrated to give 1-(3-((4-amino-1H-indazol-1-yl)methyl)piperidin-1-yl)ethanone (0.020 g, 100% yield) as an amber oil.

Step E: N-(1-((1-acetylpiperidin-3-yl)methyl)-1H-indazol-4-yl)-7-(2-methoxyethoxy)imidazo[1,2-a]pyridine-3-carboxamide Prepared according to the method of Example 109, replacing 1-(2,4-difluorobenzyl)-1H-indazol-4-amine with 1-(3-((4-amino-1H-indazol-1-yl)methyl)piperidin-1-yl)ethanone. MS (APCI) m/z=491 (M+H).

Example 133

7-(2-Methoxyethoxy)-N-(1-phenyl-1H-indazol-4-yl)imidazo[1,2-a]pyridine-3-carboxamide

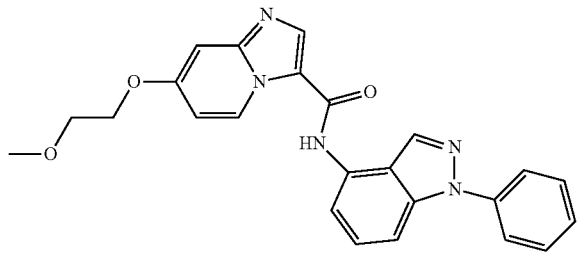 [SMILES: COCCOc1ccn2c(C(=O)Nc3cccc4c3cnn4-c3ccccc3)cnc2c1]

Step A: 4-Nitro-1-phenyl-1H-indazole

A mixture of 2,6-dinitrobenzaldehyde (0.200 g, 1.020 mmol) and phenyl hydrazine (0.120 mL, 1.224 mmol) in EtOH (1.5 mL) and acetic acid (0.15 mL) was stirred at ambient temperature for 2 hours. The resulting red solution was concentrated and the red residue was dissolved in EtOH (20 mL) and treated with a solution of potassium hydroxide (0.224 g, 4.0 mmol) in water (2 mL). Stirring was continued at ambient temperature for 2 hours. The solution was concentrated to a black solid, dissolved in EtOAc (100 mL), washed with 1N hydrochloric acid (50 mL×3), saturated aqueous sodium bicarbonate (25 mL), brine (25 mL), dried (phase separator silicone treated filter paper), concentrated to a brown solid and then purified on silica gel (10-50% EtOAc in hexanes) to provide 4-nitro-1-phenyl-1H-indazole (0.140 g, 57% yield) as a pale yellow solid.

Step B: 1-Phenyl-1H-indazol-4-amine

A solution of 4-nitro-1-phenyl-1H-indazole (0.140 g, 0.585 mmol), ammonium chloride (0.016 g, 0.293 mmol) in 4:1 v/v EtOH/water (5 mL) was treated with iron (0.327 g, 5.85 mmol) and refluxed for 2 hours. The mixture was concentrated and the residue taken in EtOAc/water, filtered through glass fiber filter paper and concentrated again to provide 1-phenyl-1H-indazol-4-amine (0.071 g, 58% yield) as a beige solid.

Step C: 7-(2-Methoxyethoxy)-N-(1-phenyl-1H-indazol-4-yl)imidazo[1,2-a]pyridine-3-carboxamide Prepared according to the method of Example 109, replacing 1-(2,4-difluorobenzyl)-1H-indazol-4-amine with 1-phenyl-1H-indazol-4-amine. MS (APCI) m/z=428 (M+H).

Example 134

N-(1-Benzyl-5-bromo-1H-indazol-4-yl)-7-(2-methoxyethoxyl)imidazo[1,2-a]pyridine-3-carboxamide

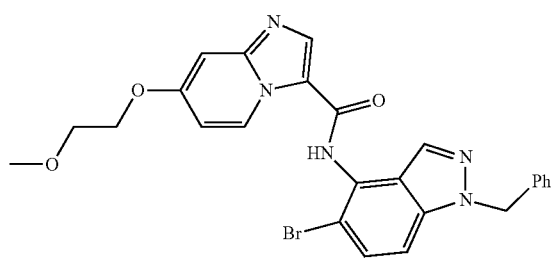 [SMILES: COCCOc1ccn2c(C(=O)Nc3c(Br)ccc4c3cnn4Cc3ccccc3)cnc2c1]

Step A: 1-Benzyl-1H-indazol-4-amine

A solution of 1-benzyl-4-nitro-1H-indazole (0.404 g, 1.595 mmol), ammonium chloride (0.043 g, 0.798 mmol) in 4:1 v/v EtOH/water (10 mL) was treated with iron (0.891 g, 15.95 mmol) and refluxed for 2 hours. The mixture was concentrated and the residue taken in EtOAc/water, filtered through glass fiber filter paper and concentrated again to provide 1-benzyl-1H-indazol-4-amine (0.353 mg, 99% yield).

Step B: 1-Benzyl-5-bromo-1H-indazol-4-amine

A solution of 1-benzyl-1H-indazol-4-amine (0.087 g, 0.39 mmol) in DMF (2 mL) was treated with N-bromosuccinimide (0.069 g, 0.39 mmol) at ambient temperature and stirred for 4 hours. The mixture was diluted with water, extracted with EtOAc, dried (phase separator silicone treated filter paper), concentrated and purified on silica gel (10-50% EtOAc in hexanes) to provide 1-benzyl-5-bromo-1H-indazol-4-amine (0.005 g, 4% yield).

Step C: N-(1-Benzyl-5-bromo-1H-indazol-4-yl)-7-(2-methoxyethoxyl)imidazo[1,2-a]pyridine-3-carboxamide Prepared according to the method of Example 109, replacing 1-(2,4-difluorobenzyl)-1H-indazol-4-amine with 1-benzyl-5-bromo-1H-indazol-4-amine. MS (APCI) m/z=522 (M+2H).

Example 135

N-(1-benzyl-7-chloro-1H-indazol-4-yl)-7-(2-methoxyethoxyl)imidazo[1,2-a]pyridine-3-carboxamide

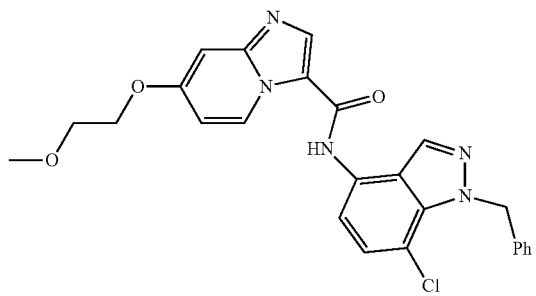 [SMILES: COCCOc1ccn2c(C(=O)Nc3ccc(Cl)c4c3cnn4Cc3ccccc3)cnc2c1]

Step A: 1-benzyl-5-chloro-1H-indazol-4-amine

A solution of 1-benzyl-1H-indazol-4-amine (0.080 g, 0.36 mmol) in DMF (2 mL) was treated with N-chlorosuccinimide (0.053 g, 0.39 mmol) at ambient temperature and stirred for 4 hours. The mixture was diluted with water, extracted with EtOAc, dried (phase separator silicone treated filter paper), concentrated and purified on silica gel (10-50% EtOAc in hexanes) to provide 1-benzyl-5-chloro-1H-indazol-4-amine (0.035 g, 38% yield).

Step B: N-(1-benzyl-7-chloro-1H-indazol-4-yl)-7-(2-methoxyethoxy)imidazo[1,2-a]pyridine-3-carboxamide Prepared according to the method of Example 109, replacing 1-(2,4-difluorobenzyl)-1H-indazol-4-amine with 1-benzyl-7-chloro-1H-indazol-4-amine. MS (APCI) m/z=476 (M+H).

Example 136

N-(1-benzyl-5,7-dichloro-1H-indazol-4-yl)-7-(2-methoxyethoxy)imidazo[1,2-a]pyridine-3-carboxamide

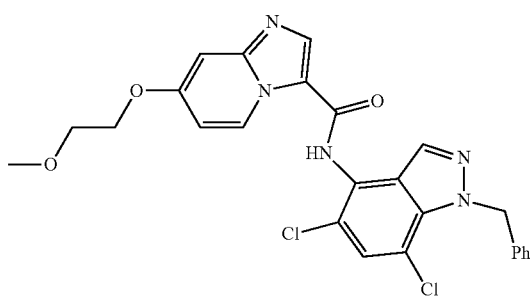 [SMILES: COCCOc1ccn2c(C(=O)Nc3c(Cl)cc(Cl)c4c3cnn4Cc3ccccc3)cnc2c1]

Step A: 1-benzyl-5,7-dichloro-1H-indazol-4-amine

A solution of 1-benzyl-1H-indazol-4-amine (0.080 g, 0.36 mmol) in DMF (2 mL) was treated with N-chlorosuccinimide (0.053 g, 0.39 mmol) at ambient temperature and stirred for 4 hours. The mixture was diluted with water, extracted with EtOAc, dried (phase separator silicone treated filter paper), concentrated and purified on silica gel (10-50% EtOAc in hexanes) to provide 1-benzyl-5,7-dichloro-1H-indazol-4-amine (0.008 g, 9% yield).

Step B: N-(1-benzyl-5,7-dichloro-1H-indazol-4-yl)-7-(2-methoxyethoxy)imidazo[1,2-a]pyridine-3-carboxamide Prepared according to the method of Example 109, replacing 1-(2,4-difluorobenzyl)-1H-indazol-4-amine with 1-benzyl-5,7-dichloro-1H-indazol-4-amine. MS (APCI) m/z=510 (M+).

Example 137

N-(1-benzyl-5-chloro-1H-indazol-4-yl)-7-(2-methoxyethoxy)imidazo[1,2-a]pyridine-3-carboxamide

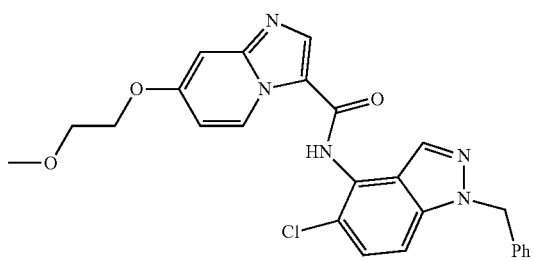 [SMILES: COCCOc1ccn2c(C(=O)Nc3c(Cl)ccc4c3cnn4Cc3ccccc3)cnc2c1]

Step A: 1-Benzyl-5-chloro-1H-indazol-4-amine

A solution of 1-benzyl-1H-indazol-4-amine (0.080 g, 0.36 mmol) in DMF (2 mL) was treated with N-chlorosuccinimide (0.053 g, 0.39 mmol) at ambient temperature and stirred for 4 hours. The mixture was diluted with water, extracted with EtOAc, dried (phase separator silicone treated filter paper), concentrated and purified on silica gel (10-50% EtOAc in hexanes) to provide 1-benzyl-5-chloro-1H-indazol-4-amine (0.035 g, 38% yield).

Step B: N-(1-benzyl-5-chloro-1H-indazol-4-yl)-7-(2-methoxyethoxy)imidazo[1,2-a]pyridine-3-carboxamide Prepared according to the method of Example 109, replacing 1-(2,4-difluorobenzyl)-1H-indazol-4-amine with 1-benzyl-5-chloro-1H-indazol-4-amine. MS (APCI) m/z=476 (M+).

Example 138

N-(1-((6-isopropylpyridin-2-yl)methyl)-1H-indazol-4-yl)-7-(2-(4-methylpiperazin-1-yl)ethoxy)imidazo[1,2-a]pyridine-3-carboxamide

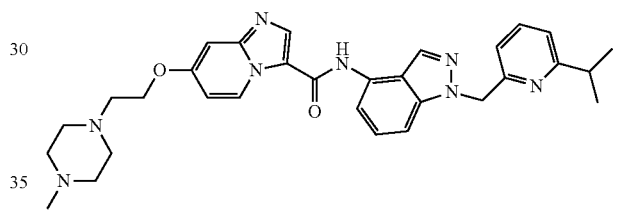

Step A: Preparation of ethyl 6-chloropicolinate

To 6-chloropicolinic acid (5.01 g, 31.8 mmol) in EtOH (100 mL) was added concentrated HCl (6 mL, 78 mmol). The reaction was heated to reflux for overnight, cooled to ambient temperature and concentrated under reduced pressure. The residue was dissolved in DCM (100 mL) and NaOH (2M) aqueous solution was added until pH=8. The aqueous layer was then extracted with DCM. The combined organic layer was combined, dried ($Na_2SO_4$) and concentrated under reduced pressure to give the desired product (85%).

Step B: Preparation of ethyl 6-(prop-1-en-2-yl)picolinate

A first flask was charged with 1,4-dioxane/$H_2O$ (50 mL/10 mL). The flask was cooled to 0° C. and vacuum was applied for 20 minutes. A second flask was charged with ethyl 6-chloropicolinate (4.200 g, 22.63 mmol), potassium isopropenyltrifluoroborate (4.353 g, 29.42 mmol), $K_2CO_3$ (4.378 g, 31.68 mmol), diacetoxypalladium (0.1524 g, 0.6789 mmol) and sodium 2'-(dicyclohexylphosphino)-2,6-dimethoxybiphenyl-3-sulfonate (0.6959 g, 1.358 mmol). The flask was also evacuated with vacuum and back filled with $N_2$ three times. The cold degassed dioxane/$H_2O$ solution was added to the second flask, which was evacuated with vacuum and back filled with argon five times. The reaction mixture was then heated to 80° C. for 3 hours. The reaction was cooled to ambient temperature, filtered and concentrated under reduced pressure. The residue was diluted with EtOAc (200 mL), washed with saturated NaHCO$_3$, dried (Na$_2$SO$_4$) and concentrated to give the desired product, which was used without further purification.

Step C: Preparation of ethyl 6-isopropylpicolinate

To ethyl 6-(prop-1-en-2-yl)picolinate (4.63 g, 24.2 mmol) in EtOH (50 mL) was added Pd/C (0.61 g, 0.573 mmol). The reaction mixture was purged with nitrogen and hydrogen three times each. A hydrogen balloon was applied to the reaction for three hours. The reaction was then purged with nitrogen, filtered through Celite® and washed with EtOH (100 mL). Solvent was removed under reduced pressure to give the desired product (93%).

Step D: Preparation of (6-isopropylpyridin-2-yl)methanol

To ethyl 6-isopropylpicolinate (4.63 g, 24.0 mmol) in THF (50 mL) at 0° C. was added LAH (0.909 g, 24.0 mmol). The cold bath was removed, and the reaction mixture was stirred for 2 hours and quenched carefully with sodium sulfate decahydrate. The reaction mixture was then filtered through Celite® and washed with Et$_2$O (200 mL). The filtrate was concentrated under reduced pressure to give the desired product (86%).

Step E: Preparation of 2-(chloromethyl)-6-isopropylpyridine hydrochloride

To (6-isopropylpyridin-2-yl)methanol (3.13 g, 20.7 mmol) in DCM (20 mL) at 0° C. was added sulfurous dichloride (12.3 g, 104 mmol). The cold bath was removed and the reaction mixture was stirred for one hour. Solvent was removed under reduced pressure to give the desired product (98%).

Step F: Preparation of 3-bromo-1-((6-isopropylpyridin-2-yl)methyl)-4-nitro-1H-indazole To 3-bromo-4-nitro-1H-indazole (4.91 g, 20.3 mmol) in DMF (50 mL) was added 2-(chloromethyl)-6-isopropylpyridine hydrochloride (4.18 g, 20.3 mmol) and K$_2$CO$_3$ (8.41 g, 60.8 mmol). The reaction mixture was stirred for 18 hours. Solvent was removed under reduced pressure. The residue was diluted with EtOAc (100 mL). The resulting suspension was washed with water and brine. The combined organic extracts were dried (Na$_2$SO$_4$), filtered and purified by silica gel flash chromatography (1:2 EtOAc/hexanes) to give the desired product (67%).

Step G: Preparation of 1-((6-isopropylpyridin-2-yl)methyl)-1H-indazol-4-amine

To 3-bromo-1-((6-isopropylpyridin-2-yl)methyl)-4-nitro-1H-indazole (2.10 g, 5.60 mmol) in EtOH (30 mL) was added Pd(OH)$_2$/C (1.21 g, 1.72 mmol). The reaction mixture purged with N$_2$ and H$_2$ three times each. The reaction was then charged with H$_2$ to 45 psi. The reaction mixture was stirred for 4 hours and filtered through Celite®. The Celite® was washed with EtOH (200 mL) and the filtrate was concentrated under reduced pressure. The residue was purified by silica gel flash chromatography (EtOAc/hexane, 2:1) to give the desired product (68%).

Step H: Preparation of 1 N-(1-((6-isopropylpyridin-2-yl)methyl)-1H-indazol-4-yl)-7-(2-(4-methylpiperazin-1-yl)ethoxy)imidazo[1,2-a]pyridine-3-carboxamide To lithium 7-(2-(4-methylpiperazin-1-yl)ethoxy)imidazo[1,2-a]pyridine-3-carboxylate (188 mg, 0.595 mmol) was added NMP (5 mL, distilled over oven dried MgSO$_4$ directly into the 25 mL flask charged with the lithium salt). A heat gun was used to dissolve the starting material. The flask was cooled to 0° C. and 2,4,6-trichlorobenzoyl chloride (94.2 µL, 0.590 mmol) was added drop-wise. The cold bath was removed after addition was complete, and the reaction mixture was stirred for another hour. The reaction mixture turned from a clear solution to slightly cloudy. 1-((6-Isopropylpyridin-2-yl)methyl)-1H-indazol-4-amine (120 mg, 0.451 mmol) was added in one portion to the reaction mixture and the reaction was heated to 88° C. for 5 hours. NMP was removed by a vacuum distillation (at the same bath temperature) until the reaction mixture became a thick oil. NaOH (1.8 mmol) in H$_2$O (10 mL) was added to the thick oil and the solution was stirred at 80° C. for 30 minutes. The solution was cooled to ambient temperature and the pH of the dark solution was adjusted to pH 12 to 13 with saturated NH$_4$Cl. The solution was cooled to 0° C. and H$_2$O (20 mL) was added. Stirring was continued for 30 minutes, during which time solids precipitated out of solution. The mixture was filtered and the filtrate was washed with saturated NaHCO$_3$ and H$_2$O. The resulting solid was dissolved in DCM, dried (Na$_2$SO$_4$), filtered and concentrated. The residue was triturated with MTBE give final product (15%). MS (ES+APCI) m/z=553.1 (M+H).

Example 139

N-(1-((1-isopropyl-5-methyl-1H-pyrazol-3-yl)methyl)-1H-indazol-4-yl)-7-(2-(4-methylpiperazin-1-yl)ethoxy)imidazo[1,2-a]pyridine-3-carboxamide

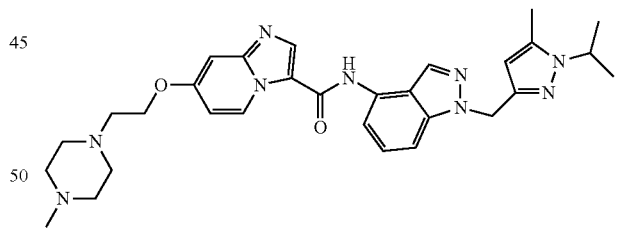

Step A: Preparation of ethyl 1-isopropyl-5-methyl-1H-pyrazole-3-carboxylate

To ethyl 2,4-dioxopentanoate (20.1 g, 127 mmol) in acetic acid (100 mL) at 0° C. was added drop-wise isopropylhydrazine (9.42 g, 127 mmol). The cold bath was removed and the reaction mixture was stirred for 2 hours. The reaction mixture was then diluted with EtOAc/H$_2$O (300 mL/100 mL). The organic layer was washed with saturated NaHCO$_3$ aqueous solution (100 mL), H$_2$O (50 mL) and brine (50 mL). The organic layer was dried (Na$_2$SO$_4$) and concentrated. The residue was purified by silica gel flash chromatography (1:2 EtOAc/hexane) to give the desired product (31%).

Step B: Preparation of (1-isopropyl-5-methyl-1H-pyrazol-3-yl)methanol

To ethyl 1-isopropyl-5-methyl-1H-pyrazole-3-carboxylate (7.68 g, 39.1 mmol) in THF (50 mL) at 0° C. was added LAH (1.49 g, 39.1 mmol). The cold bath was removed, and the reaction mixture was stirred for 2 hours and quenched carefully with sodium sulfate decahydrate. The reaction mixture was filtered through Celite® and washed with Et₂O (200 mL). The filtrate was concentrated under reduced pressure to give the desired product (88%).

Step C: Preparation of 3-(chloromethyl)-1-isopropyl-5-methyl-1H-pyrazole hydrochloride To (1-isopropyl-5-methyl-1H-pyrazol-3-yl)methanol (5.3 g, 34 mmol) in DCM (20 mL) at 0° C. was added sulfurous dichloride (20 g, 172 mmol). The cold bath was removed and the reaction mixture was stirred for one hour. Solvent was removed under reduced pressure to give the desired product (99%).

Step D: Preparation of N-(1-((1-isopropyl-5-methyl-1H-pyrazol-3-yl)methyl)-1H-indazol-4-yl)-7-(2-(4-methylpiperazin-1-yl)ethoxy)imidazo[1,2-a]pyridine-3-carboxamide Prepared from 3-(chloromethyl)-1-isopropyl-5-methyl-1H-pyrazole hydrochloride according to the method of Example 66 (Steps F to H), replacing 2-(chloromethyl)-6-isopropylpyridine hydrochloride in Step F with 3-(chloromethyl)-1-isopropyl-5-methyl-1H-pyrazole hydrochloride. MS (ES+APCI) m/z=556.1 (M+H).

Example 140

N-(1-(3-methoxybenzyl)-1H-indazol-4-yl)-7-(2-methoxyethoxyl)imidazo[1,2-a]pyridine-3-carboxamide

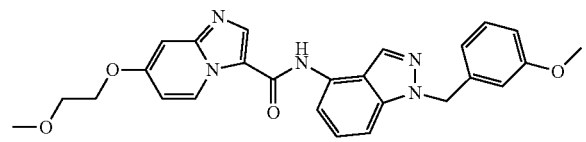

Prepared according to the method of Example 139 from 7-(methoxymethoxy)imidazo[1,2-a]pyridine-3-carboxylic acid, 3-iodo-4-nitro-1H-indazole and 1-(bromomethyl)-3-methoxybenzene. MS (ES+APCI) m/z=472.3 (M+H).

Example 141

N-(1-(3-chlorobenzyl)-1H-indazol-4-yl)-7-(2-methoxyethoxyl)imidazo[1,2-a]pyridine-3-carboxamide

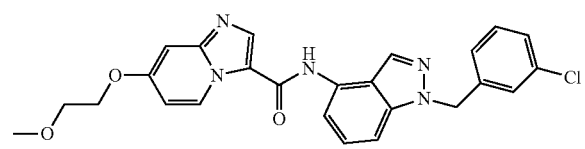 [SMILES: COCCOc1ccn2c(C(=O)Nc3cccc4c3cnn4Cc3cccc(Cl)c3)cnc2c1]

Prepared according to the method of Example 139 from 7-(methoxymethoxy)imidazo[1,2-a]pyridine-3-carboxylic acid, 3-iodo-4-nitro-1H-indazole and 1-(bromomethyl)-3-chlorobenzene. MS (ES+APCI) m/z=476.2 (M+H).

Example 142

7-(2-methoxyethoxy)-N-(1-((6-methylpyridin-2-yl)methyl)-1H-indazol-4-yl)imidazo[1,2-a]pyridine-3-carboxamide

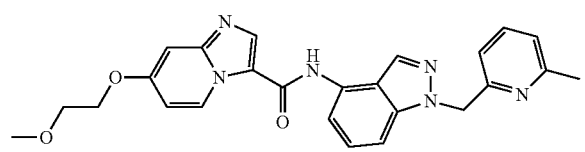

Prepared according to the method of Example 139 from 7-(methoxymethoxy)imidazo[1,2-a]pyridine-3-carboxylic acid, 3-iodo-4-nitro-1H-indazole and 2-(bromomethyl)-6-methylpyridine. MS (ES+APCI) m/z=457.2 (M+H).

Example 143

7-(2-methoxyethoxy)-N-(1-(3-methylbenzyl)-1H-indazol-4-yl)imidazo[1,2-a]pyridine-3-carboxamide

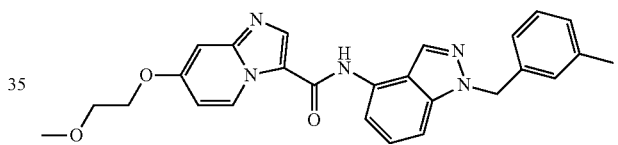

Prepared according to the method of Example 139 from 7-(methoxymethoxy)imidazo[1,2-a]pyridine-3-carboxylic acid, 3-iodo-4-nitro-1H-indazole and 1-(bromomethyl)-3-methylbenzene. MS (ES+APCI) m/z=456.3 (M+H).

Example 144

N-(1-benzyl-1H-indazol-4-yl)-6-fluoroimidazo[1,2-a]pyridine-3-carboxamide

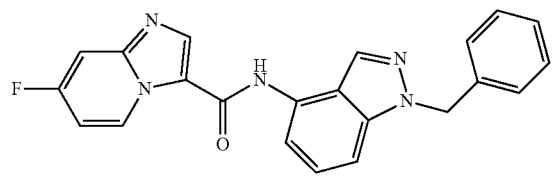 [SMILES: O=C(Nc1cccc2c1cnn2Cc1ccccc1)c1cnc2cc(F)ccn12]

Step A: Preparation of ethyl 6-fluoroimidazo[1,2-a]pyridine-3-carboxylate

5-Fluoropyridine-2-amine (1 g, 8.92 mmol) and ethyl 2,3-dichloro-3-oxopropanoate (39.6 g, 10.7 mmol, 5% in benzene) were added to a flask along with 75 mL of ethanol and stirred overnight at ambient temperature. The material was purified on Silica gel using methanol and ethyl acetate (Rf=0.4 in 5% MeOH/ethyl acetate) to provide 110 mg of the desired compound as a waxy solid, 95% pure by LC. MS (ES+APCI) m/z=209.2 (M+H).

Step B: Preparation of 6-fluoroimidazo[1,2-a]pyridine-3-carboxylic acid

Ethyl 6-fluoroimidazo[1,2-a]pyridine-3-carboxylate (0.10 g, 0.48 mmol) and lithium hydroxide monohydrate (0.020 g, 0.48 mmol) were added to a mixture of water, THF and ethanol (1:2:1) and heated in a sealed vial at 65° C. for 6 hours. The solvent was removed by rotary evaporation to yield 87 mg of the desired product. MS (ES+APCI) m/z=181.1 (M+H).

Step C: Preparation of 1-benzyl-4-nitro-1H-indazole

4-Nitro-1H-indazole (1.0 g, 6.13 mmol) and potassium carbonate (1.69 g, 12.3 mmol) were added to DMF and stirred at room temperature overnight. Water (50 mL) was added and the product was extracted with ethyl acetate and dried over magnesium sulfate. Crude, brown solid was purified on silica gel using hexanes/ethyl acetate. First isolated peak (730 mg) was the desired 1-benzyl regioisomer, as confirmed by NMR.

Step D: Preparation of 1-benzyl-1H-indazol-4-amine 1-benzyl-4-nitro-1H-indazole (0.40 g, 1.59 mmol) in 4:1 ethanol/water (10 mL) was treated with ammonium chloride (0.043 g, 0.79 mmol), followed by Fe (0) (0.89 g, 15.95 mmol) and heated for 1 hr. A single product was observed on HPLC. The solvent was removed and residue shaken in ethyl acetate and filtered through GF/F paper, and concentrated to yield 353 of orange, crude gum. MS (ES+APCI) m/z=224.3 (M+H).

Step E: Preparation of N-(1-benzyl-1H-indazol-4-yl)-6-fluoroimidazo[1,2-a]pyridine-3-carboxamide 6-Fluoroimidazo[1,2-a]pyridine-3-carboxylic acid (0.083 g, 0.46 mmol) was added as a suspension to dichloromethane, and then oxalyl dichloride (0.28 mL, 0.55 mmol) was added slowly. The mixture was allowed to stir for 10 minutes, then a solution of 1-benzyl-1H-indazole-4-amine (0.10 g, 0.46 mmol, above, step D) and N-ethyl-isopropyl-propan-2-amine (0.11 mL, 0.60 mmol) were added and the reaction stirred for 2 hours. The solvent was concentrated and the resulting crude material was purified on silica gel using ethyl acetate and methanol (Rf=0.18 in 5% MeOH in ethyl acetate) to provide 20 mg of the desired product. MS (ES+APCI) m/z=386.4 (M+H).

Example 145

N-(1-benzyl-1H-indazol-4-yl)-7-(1H-pyrazol-4-yl)imidazo[1,2-a]pyridine-3-carboxamide

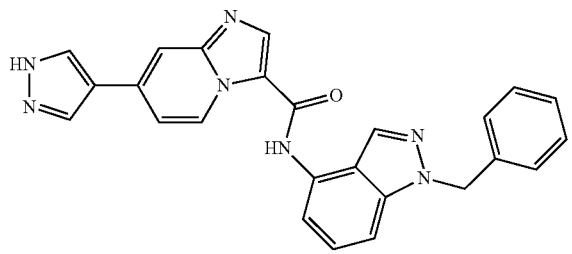 [SMILES: O=C(Nc1cccc2c1cnn2Cc1ccccc1)c1cnc2cc(-c3cn[nH]c3)ccn12]

A dried round bottom flask equipped with a reflux condenser and a nitrogen line was charged with tert-butyl 4-(4,4,5,5-tetramethyl-1,3,2-dioxaborolan-2-yl)-1H-pyrazole-1-carboxylate (16.7 mg, 0.057 mmol), N-(1-benzyl-1H-indazol-4-yl)-7-bromoimidazo[1,2-a]pyridine-3-carboxamide (23 mg, 0.052 mmol), Pd(PPh$_3$)$_4$ (3.0 mg, 0.003 mmol), and potassium carbonate (36 mg, 0.26 mmol). To the flask was added a water/DMF/CH$_3$CN mixture (1:1:4.5; 0.1:0.1:0.6 mL), and the reaction mixture was degassed under nitrogen and heated at 80° C. for 6 hours. The cooled reaction mixture was diluted with water and the resulting suspension was extracted with EtOAc and DCM. The combined organic extracts were dried over anhydrous sodium sulfate and concentrated to afford the crude product. The crude product was subjected to preparative thin-layer chromatography on silica with 8% MeOH/DCM as eluent to afford 13.9 mg of the desired product as a yellow solid. MS (ES+APCI) m/z=534 (M+H) detected.

Example 146

7-acetyl-N-(1-benzyl-1H-indazol-4-yl)imidazo[1,2-a]pyridine-3-carboxamide

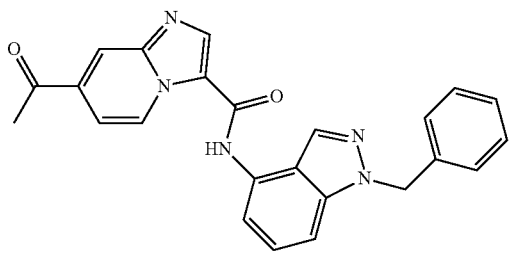 [SMILES: CC(=O)c1ccn2c(C(=O)Nc3cccc4c3cnn4Cc3ccccc3)cnc2c1]

A dried flask flushed with nitrogen was charged with N-(1-benzyl-1H-indazol-4-yl)-7-bromoimidazo[1,2-a]pyridine-3-carboxamide (150 mg, 0.34 mmol), tri-o-tolylphosphine (20 mg, 0.067 mmol), tris-dibenzylideneacetone dipalladium (0) (31 mg, 0.033 mmol), anhydrous DMF (4.5 mL) and tributyl(1-ethoxyvinyl)stannane (0.13 mL, 0.39 mmol). The resulting mixture was immediately degassed under a nitrogen atmosphere, triethylamine (0.056 mL, 0.40 mmol) was added, and the flask was heated at 100° C. for 6 hours. To the cooled reaction was added concentrated aqueous hydrochloric acid (0.5 mL) and stirring was continued at ambient temperature for two hours. The reaction was quenched with excess saturated aqueous sodium bicarbonate, and the resulting suspension was extracted with EtOAc and DCM. The combined organic extracts were dried over anhydrous sodium sulfate and concentrated to afford the crude product. The crude product was subjected to preparative thin-layer chromatography on silica with 4% MeOH/DCM as eluent to afford 55 mg of desired product as an off-white solid. MS (ES+APCI) m/z=410 (M+H) detected.

Example 147

N-(1-benzyl-1H-indazol-4-yl)-7-(1-hydroxyethyl)imidazo[1,2-a]pyridine-3-carboxamide

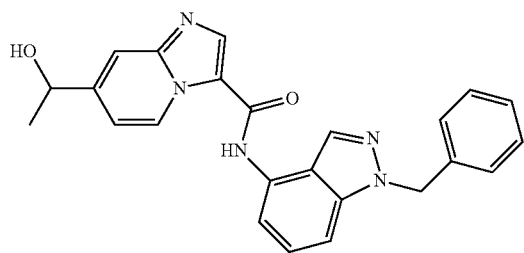 [SMILES: CC(O)c1ccn2c(C(=O)Nc3cccc4c3cnn4Cc3ccccc3)cnc2c1]

A solution of 7-acetyl-N-(1-benzyl-1H-indazol-4-yl)imidazo[1,2-a]pyridine-3-carboxamide (Example 146; 10 mg, 0.024 mmol) in a 1:1 THF/MeOH mixture (0.2 mL) was treated at ambient temperature with excess sodium borohydride (3.7 mL, 0.10 mmol), and stirring continued overnight. The reaction was quenched with excess saturated aqueous sodium bicarbonate and the resulting suspension was extracted with EtOAc and DCM. The combined organic extracts were dried over anhydrous sodium sulfate, and concentrated to afford the crude product. The crude product was subjected to preparative thin-layer chromatography on silica with MeOH/DCM as eluent to afford 8.8 mg of the desired product as a white solid. MS (ES+APCI) m/z=412 (M+H) detected.

Example 148

N-(1-benzyl-1H-indazol-4-yl)-7-(1-morpholinoethyl)imidazo[1,2-a]pyridine-3-carboxamide

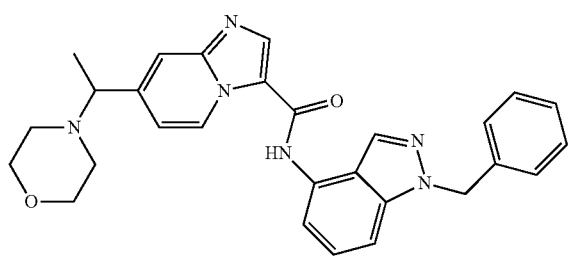 [SMILES: CC(c1ccn2c(C(=O)Nc3cccc4c3cnn4Cc3ccccc3)cnc2c1)N1CCOCC1]

To a solution of 7-acetyl-N-(1-benzyl-1H-indazol-4-yl)imidazo[1,2-a]pyridine-3-carboxamide (Example 146; 10.8 mg, 0.026 mmol) in DCM (0.6 mL) was added morpholine (3 equivalents). The resulting solution was stirred at ambient temperature for two hours, after which sodium triacetoxyborohydride (28 mg, 0.13 mmol, 5 equivalents) was added. The resulting suspension was stirred at ambient temperature for 100 hours. The reaction was quenched with excess saturated aqueous sodium bicarbonate, and the resulting suspension was extracted with EtOAc and DCM. The combined organic extracts were dried over anhydrous sodium sulfate, and concentrated to afford the crude product. The crude product was subjected to preparative thin-layer chromatography on silica with MeOH/DCM as eluent to afford 0.3 mg of the desired product as a white solid. MS (ES+APCI) m/z=481 (M+H) detected.

Example 149

7-(2-(4-methylpiperazin-1-yl)ethoxy)-N-(1-((2-methylthiazol-5-yl)methyl)-1H-indazol-4-yl)imidazo[1,2-a]pyridine-3-carboxamide

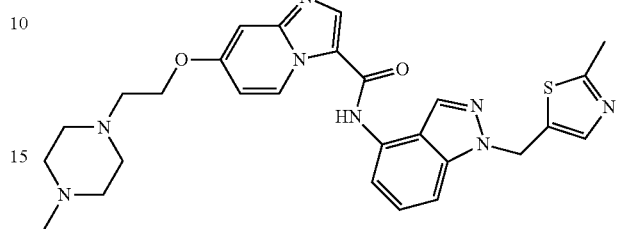

Step A: Preparation of 5-(bromomethyl)-2-methylthiazole

To a solution of (2-methylthiazol-5-yl)methanol (335 mg, 2.59 mmol) in anhydrous DMF (3 mL) were added triphenylphosphine (1.02 g, 3.89 mmol) and carbon tetrabromide (1.29 g, 3.89 mmol). The resulting mixture was stirred at ambient temperature overnight (about 18 hours), then diluted with water (10 mL), and EtOAc (20 mL), and the phases separated. The aqueous phase was extracted with EtOAc (2×25 mL), and the organic extracts were combined, dried over sodium sulfate, filtered and concentrated. The crude product was purified by flash liquid chromatography on silica with Hexanes:EtOAc (10:1) as the eluent to provide the desired product (0.498 mg).

Step B: Preparation of 5-((3-iodo-4-nitro-1H-indazol-1-yl)methyl)-2-methylthiazole To a solution of 3-iodo-4-nitro-1H-indazole (441 mg, 1.53 mmol) in anhydrous DMF (3 mL) were added potassium carbonate (422 mg, 3.05 mmol), and 5-(bromomethyl)-2-methylthiazole (440 mg, 2.30 mmol) at ambient temperature and under a nitrogen atmosphere. The resulting mixture was stirred at ambient temperature overnight (about 18 hours). The reaction mixture was diluted with water (10 mL) and EtOAc (20 mL). The phases were separated and the aqueous phase was extracted with EtOAc (2×25 mL). The combined organic extracts were concentrated, and the residue subjected to flash liquid chromatography on silica with Hexanes:EtOAc (10:1) as the eluent to afford the desired product (611 mg).

Step C: Preparation of 3-iodo-1-((2-methylthiazol-5-yl)methyl)-1H-indazol-4-amine To a solution of 5-((3-iodo-4-nitro-1H-indazol-1-yl)methyl)-2-methylthiazole (332 mg, 0.830 mmol) in EtOH/water (4:1, 10 mL) was added iron powder (463 mg, 8.30 mmol) and ammonium chloride (44.4 mg, 0.83 mmol). The resulting mixture was heated at 85° C. with vigorous magnetic stirring for three hours. The mixture was cooled to ambient temperature, concentrated, and EtOAc (40 mL) and triethylamine (10 mL) were added. The resulting mixture was heated at 85° C. for 20 minutes, then cooled to 45° C., filtered through a Celite plug, and the plug was rinsed with MeOH (30 mL). The combined organic filtrates were concentrated, the residue was extracted with DCM (3×30 mL), the combined organic extracts dried over sodium sulfate, filtered and concentrated to afford the desired product (307 mg).

Step D: Preparation of N-(3-iodo-1-((2-methylthiazol-5-yl)methyl)-1H-indazol-4-yl)-7-(2-(4-methylpiperazin-1-yl)ethoxy)imidazo[1,2-a]pyridine-3-carboxamide A solution of 3-iodo-1-((2-methylthiazol-5-yl)methyl)-1H-indazol-4-amine (40 mg, 0.11 mmol) in anhydrous THF (3 mL) was treated at ambient temperature under a nitrogen atmosphere with lithium bis(trimethylsilyl)amide (1.0 M in THF, 0.24 mL). The resulting brown solution was added dropwise to a cooled (ice-water) solution of ethyl 7-(2-(4-methylpiperazin-1-yl)ethoxy)imidazo[1,2-a]pyridine-3-carboxylate (35.9 mg, 0.11 mmol) in anhydrous THF (3 mL). The reaction mixture was allowed to warm to ambient temperature, and was diluted with water (10 ml). The resulting mixture was extracted thoroughly with ethyl acetate and dichloromethane. The combined organic extracts were dried over sodium sulfate, the solids removed by filtration, and the filtrate was concentrated to afford an oil. The crude oil was subjected to preparative thin-layer chromatography on silica with MeOH/DCM as the eluent to afford 11.6 mg of the desired product.

Step E: Preparation of 7-(2-(4-methylpiperazin-1-yl)ethoxy)-N-(1-((2-methylthiazol-5-yl)methyl)-1H-indazol-4-yl)imidazo[1,2-a]pyridine-3-carboxamide A solution of N-(3-iodo-1-((2-methylthiazol-5-yl)methyl)-1H-indazol-4-yl)-7-(2-(4-methylpiperazin-1-yl)ethoxy)imidazo[1,2-a]pyridine-3-carboxamide (11.5 mg, 0.018 mmol) in absolute EtOH (1 mL) was treated with Pd/C (Degussa, wet, 10% wt, 2 mg), the reaction flask was flushed with hydrogen, and stirring at ambient temperature was continued for seven hours. The reaction was diluted with DCM, the catalyst was removed by filtration, and the filtrate concentrated to afford the crude product. The crude product was subjected to preparative thin-layer chromatography on silica with ammonia/MeOH/DCM as eluent to afford 1.9 mg of the desired product. MS (ES+APCI) m/z=531 (M+H) detected.

Example 150

7-(2-(4-methylpiperazin-1-yl)ethoxy)-N-(1-((6-methylpyridin-2-yl)methyl)-1H-indazol-4-yl)imidazo[1,2-a]pyridine-3-carboxamide Step A: Preparation of 1-((6-methylpyridin-2-yl)methyl)-1H-indazol-4-amine A solution of 3-iodo-1-((6-methylpyridin-2-yl)methyl)-4-nitro-1H-indazole (Example 89, Steps A-B; 1.00 g, 2.54 mmol) in MeOH (25 mL) was cooled to 0° C. Zinc dust (0.829 g, 12.7 mmol) was added and the mixture was stirred for 10 minutes. Saturated aqueous NH$_4$Cl was added (25 mL) and the mixture was stirred vigorously for 2 hours at 0° C. and then warmed to ambient temperature and stirred for an additional 2 hours. Additional saturated aqueous NH$_4$Cl was added (12.5 mL) and the mixture was stirred at ambient temperature for an additional 2 hours. The mixture was diluted with MeOH and filtered. To the filtrate was added saturated aqueous NH$_4$OAc and the mixture was concentrated to remove bulk MeOH. The mixture was then extracted with EtOAc and the combined organic extracts were washed with saturated aqueous NaHCO$_3$ and brine, dried over Na$_2$SO$_4$, filtered and concentrated. The crude material was purified by column chromatography (2 to 20% IPA/CHCl$_3$) to afford 0.428 g (70%) of the desired product as an orange solid.

Step B: Preparation of 7-(2-(4-methylpiperazin-1-yl)ethoxy)-N-(1-((6-methylpyridin-2-yl)methyl)-1H-indazol-4-yl)imidazo[1,2-a]pyridine-3-carboxamide LHMDS (1.595 mL, 1.595 mmol, 1.0M THF) was added drop-wise to a solution of 1-((6-methylpyridin-2-yl)methyl)-1H-indazol-4-amine (0.190 g, 0.7974 mmol) in THF (4 mL) at 0° C., resulting in a dark solution. The mixture was stirred at 0° C. for 10 minutes, then ethyl 7-(2-(4-methylpiperazin-1-yl)ethoxy)imidazo[1,2-a]pyridine-3-carboxylate (Preparation A; 0.5566 g, 1.674 mmol) was added in one portion and the mixture was stirred overnight. The reaction mixture was diluted with saturated aqueous NaHCO$_3$ and extracted with CH$_2$Cl$_2$. The combined organic layers were dried over Na$_2$SO$_4$, filtered and concentrated. The crude product was purified by column chromatography (5 to 20% MeOH/CH$_2$Cl$_2$ using 5% NH$_4$OH/MeOH) to provide 0.254 g (61%) of the desired product as a pale brown powder. MS (ES+APCI) m/z=525 (M+H).

Example 151

7-(2-methoxyethoxy)-N-(1-phenethyl-1H-indazol-4-yl)imidazo[1,2-a]pyridine-3-carboxamide

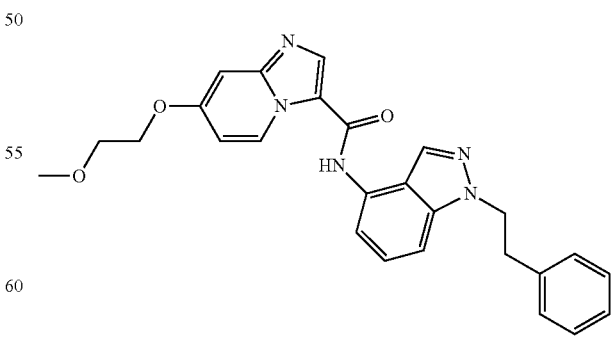

Prepared according to the method of Example 109, replacing 1-(2,4-difluorobenzyl)-1H-indazol-4-amine with 1-phenethyl-1H-indazol-4-amine. MS (APCI) m/z=456 (M+H).

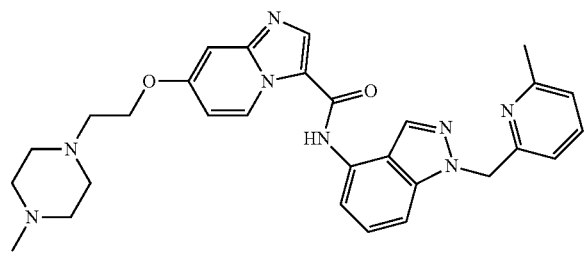 [SMILES: Cc1cccc(Cn2ncc3c(NC(=O)c4cnc5cc(OCCN6CCN(C)CC6)ccn45)cccc32)n1]

Example 152

N-(1-benzyl-1H-indazol-4-yl)-7-cyanoimidazo[1,2-a]pyridine-3-carboxamide

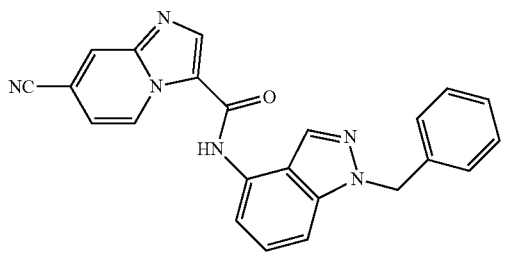 [SMILES: N#Cc1ccn2c(C(=O)Nc3cccc4c3cnn4Cc3ccccc3)cnc2c1]

Step A: Preparation of ethyl 7-cyanoimidazo[1,2-a]pyridine-3-carboxylate

To 2-aminoisonicotinonitrile (4.6 g, 38.6 mmol) was added ethyl 2-chloro-3-oxopropanoate (184 mL, 57.9 mmol) and EtOH (10 mL) and the reaction was heated to 75° C. for 6 hours. A precipitated solid was removed by vacuum filtration and was partitioned between saturated aqueous $NaHCO_3$ and EtOAc. The aqueous layer was extracted with EtOAc and the combined organic extracts were dried over $Na_2SO_4$ and concentrated to give 1.4 g of unreacted amino-isonicotinonitrile (30%). The filtrate was concentrated to give a beige solid which was also partitioned between EtOAc and saturated aqueous $NaHCO_3$. The aqueous layer was extracted with EtOAc and the combined organic extracts were dried over $Na_2SO_4$ and concentrated to give 6.4 g of a beige solid. This crude material was purified by column chromatography (30 to 50% EtOAc/hexanes) providing 2.23 g (26%) of the title compound.

Step B: Preparation of 7-cyanoimidazo[1,2-a]pyridine-3-carboxylic acid

To a mixture of ethyl 7-cyanoimidazo[1,2-a]pyridine-3-carboxylate (2.23 g, 10.4 mmol) in 100 mL of THF:EtOH:water (1:2:1) was added LiOH (0.248 g, 10.4 mmol). The reaction mixture was stirred at ambient temperature overnight. The reaction was concentrated and diluted with water, cooled in an ice bath and acidified to pH=3 with 1 M HCl producing a white precipitate. The precipitate was removed by vacuum filtration and dried under vacuum with a methanol azeotrope providing 1.62 g of the title compound as a white solid.

Step C: Preparation of N-(1-benzyl-1H-indazol-4-yl)-7-cyanoimidazo[1,2-a]pyridine-3-carboxamide To a solution of 7-cyanoimidazo[1,2-a]pyridine-3-carboxylic acid (0.0527 g, 0.282 mmol) in 0.200 mL of $CH_2Cl_2$ was added a drop of DMF followed by oxalyl chloride (1.1 equivalents, 2M $CH_2Cl_2$). The reaction was stirred for 5 minutes until bubbling ceased. 1-Benzyl-1H-indazol-4-amine (0.0629 g, 0.282 mmol) was added as a solution in 0.600 mL of $CH_2Cl_2$ followed by DIEA (1.2 equivalents). The reaction was stirred at ambient temperature overnight. The reaction was concentrated and the solids were washed with $Et_2O$, water, 2M $Na_2CO_3$, water, and finally with $Et_2O$ again to provided the desired product as a beige solid 0.072 g (65%). MS (ES+APCI) m/z=393 (M+H).

Example 153

N-(1-benzyl-1H-indazol-4-yl)-7-(2-(4-methylpiperazin-1-yl)ethoxy)imidazo[1,2-a]pyridine-3-carboxamide

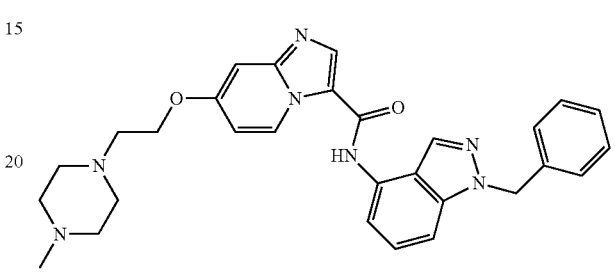

Step A: Preparation of lithium 7-(2-(4-methylpiperazin-1-yl)ethoxy)imidazo[1,2-a]pyridine-3-carboxylate To a mixture of ethyl 7-(2-(4-methylpiperazin-1-yl)ethoxy)imidazo[1,2-a]pyridine-3-carboxylate (Preparation A; 0.239 g, 0.719 mmol) in THF (3 mL) was added $H_2O$ followed by LiOH (0.0344 g, 1.44 mmol) and the reaction was stirred at ambient temperature overnight. The reaction was transferred to a sealed tube and heated to 100° C. for 8 hours. The reaction mixture was concentrated providing 0.230 g of the crude desired product as a pale yellow foam, which was used directly in the subsequent step.

Step B: Preparation of N-(1-benzyl-1H-indazol-4-yl)-7-(2-(4-methylpiperazin-1-yl)ethoxy)imidazo[1,2-a]pyridine-3-carboxamide To a solution of lithium 7-(2-(4-methylpiperazin-1-yl)ethoxy)imidazo[1,2-a]pyridine-3-carboxylate (0.0585 g, 0.189 mmol) in $CH_2Cl_2$ was added a drop of DMF. Oxalyl chloride (1.1 equivalents, 2M $CH_2Cl_2$) was added and the reaction stirred at ambient temperature until bubbling ceased (about 5 minutes). 1-Benzyl-1H-indazol-4-amine (0.042 g, 0.189 mmol) was added followed by DIEA (1.2 equivalents). The reaction was stirred at ambient temperature for 4 hours. The reaction was concentrated and washed with $Et_2O$, water, and finally with $Et_2O$ again. The pale yellow solid was dried, providing 0.027 g of crude product. The crude material was purified using reverse phase chromatography eluting with a gradient of 0 to 90% ACN/water to give 0.007 g (7%) of the desired product. MS (ES+APCI) m/z=510 (M+H).

Example 154

N-(1-benzyl-1H-indazol-4-yl)-6-cyanoimidazo[1,2-a]pyridine-3-carboxamide

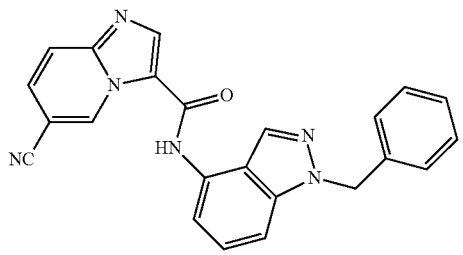 [SMILES: N#Cc1ccc2ncc(C(=O)Nc3cccc4c3cnn4Cc3ccccc3)n2c1]

Prepared according to the method of Example 152, replacing 7-cyanoimidazo[1,2-a]pyridine-3-carboxylic acid with 6-cyanoimidazo[1,2-a]pyridine-3-carboxylic acid. MS (ES+APCI) m/z=393 (M+H).

Example 155

N-(1-benzyl-1H-indazol-4-yl)-6-bromoimidazo[1,2-a]pyridine-3-carboxamide

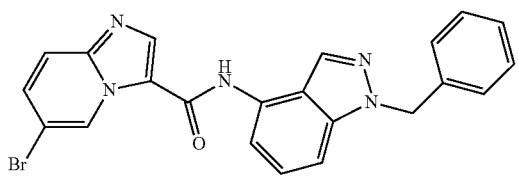 [SMILES: O=C(Nc1cccc2c1cnn2Cc1ccccc1)c1cnc2ccc(Br)cn12]

Step A: Preparation of 1-benzyl-4-nitro-1H-indazole

4-Nitro-1H-indazole (1.00 g; 6.13 mmol), benzyl bromide (1.15 g; 6.74 mmol) and potassium carbonate (1.69 g; 12.3 mmol) were mixed with DMF (15 mL) and stirred at ambient temperature under nitrogen for 16 hours. The reaction mixture was added to water (50 mL) and extracted into ethyl acetate. The combined extracted were dried (sodium sulfate), filtered and evaporated under reduced pressure to give a brown solid. The material was purified by silica gel chromatography eluting with hexane/ethyl acetate (20:1 to 10:1 to 5:1). The first component to elute was the desired regioisomer, which was obtained as a yellow solid (730 mg). The other regioisomer was the second component to elute (650 mg).

Step B: Preparation of 1-benzyl-1H-indazol-4-amine

A mixture of 1-benzyl-4-nitro-1H-indazole (150 mg; 0.592 mmol), iron powder (331 mg; 5.92 mmol) and ammonium chloride (16 mg; 0.296 mmol) in ethanol/water (4:1; 5 mL) was heated at reflux for 5 hours. The solvent was removed under vacuum and the residue was mixed with ethyl acetate/triethylamine (4:1; 5 mL) and heated at reflux for 1 hour. The mixture was allowed to cool and then filtered through a pad of silica, washing with ethyl acetate. The solvent was removed under vacuum to give the desired product that was used directly in the next step.

Step C: Preparation of ethyl 6-bromoimidazo[1,2-a]pyridine-3-carboxylate

A mixture of 5-bromopyridin-2-amine (5.22 g, 30.2 mmol) and ethyl 2-chloro-3-oxopropanoate (5.00 g, 33.2 mmol) (Toronto Research Chemicals; 5% solution on benzene) was stirred in ethanol (151 mL, 30.2 mmol) under nitrogen. The mixture was heated to 75° C. for 4 hours and then at ambient temperature for 2 days. The solvent was removed under vacuum to give a solid residue which was purified by silica gel chromatography, eluting with hexane/ethyl acetate (6:4 to 4:6) to give the desired product as a solid (2.40 g; 30%).

Step D: Preparation of 6-bromoimidazo[1,2-a]pyridine-3-carboxylic acid

Lithium hydroxide (0.427 g, 17.8 mmol) was added to a stirred suspension of ethyl 6-bromoimidazo[1,2-a]pyridine-3-carboxylate (2.40 g, 8.92 mmol) in 20 mL of a 4:1 mixture of THF/ethanol. The mixture was stirred under nitrogen for 3 days at ambient temperature. The pH of the mixture was adjusted to neutral (by the addition of aqueous mineral acid) inducing a heavy precipitation of off-white colored solids. The solids were isolated by filtration and dried under reduced pressure to give the desired product (2.0 g; 93%).

Step E: Preparation of N-(1-benzyl-1H-indazol-4-yl)-6-bromoimidazo[1,2-a]pyridine-3-carboxamide 6-Bromoimidazo[1,2-a]pyridine-3-carboxylic acid (200 mg; 0.83 mmol) was suspended in methylene chloride (2 mL) with a catalytic (0.005 mL) amount of DMF. A solution of oxalyl chloride (0.913 mmol; 2M solution on dichloromethane) was added. The mixture was stirred in a sealed vial (with occasional venting to release gas) until effervescence ceased (about 30 minutes). A white suspension resulted. Diisopropylethylamine (188 µL; 1.08 mmol) was added. A clear solution resulted. 1-Benzyl-1H-indazol-4-amine (185 mg; 0.83 mmol) was added as a solution in methylene chloride followed by addition of further diisopropylethylamine (188 µL). The mixture was stirred at ambient temperature for 24 hours. A suspension resulted. The mixture was diluted with ether (10 mL) and the solids were collected by filtration. The filter pad was washed with ether and water and the solids were dried under vacuum to provide the desired product as a white solid (175 mg). MS (APCI) positive scan, m/z=446, 449 (M+H).

Example 156

N-(1-benzyl-1H-indazol-4-yl)-7-(2-methoxyethoxyl)imidazo[1,2-a]pyridine-3-carboxamide

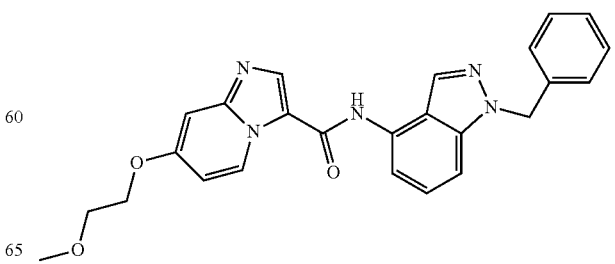

Step A: Preparation of 2-chloro-4-(2-methoxyethoxyl)pyridine

A flask was charged with 2-chloro-4-nitropyridine (100 g, 630.7 mmol) and 2-methoxyethanol (746.8 mL, 9461 mmol) under an atmosphere of dry nitrogen. The mixture was cooled with stirring to 0° C. utilizing an ice/water bath. Potassium 2-methylpropan-2-olate (81.95 g, 693.8 mmol) was added and the mixture was stirred for 30 minutes. The ice/water bath was removed and the mixture was stirred for an additional 2 hours at ambient temperature. The mixture was concentrated under vacuum. Water (500 mL) was added and the mixture was extracted with dichloromethane. The combined extracts were dried over sodium sulfate, filtered and concentrated under vacuum to give 2-chloro-4-(2-methoxyethoxyl)pyridine as a gold colored oil (115 g).

Step B: Preparation of 4-(2-methoxyethoxyl)pyridin-2-amine

2-Chloro-4-(2-methoxyethoxyl)pyridine (30.0 g; 159.9 mmol), X-PHOS (3.03 g, 6.356 mmol), and tris(dibenzylideneacetone)dipalladium (2.26 g; 2.468 mmol) were combined in a reaction flask under an atmosphere of dry nitrogen. Anhydrous tetrahydrofuran (150 mL) was added. The mixture was degassed by alternately evacuating the flask followed by filling with dry nitrogen (three times). The mixture was cooled to 0-5° C. using an ice/water bath. LHMDS (325 mL, 325.0 mmol) was added by addition funnel while maintaining the temperature below 5° C. The ice/water bath was removed and the mixture was heated to reflux (60-65° C.) for 1.5 hours. After allowing the mixture to cool an ice/water bath was put in place. Hydrochloric acid (2N; 300 mL) was added with stirring, maintaining the temperature below 30° C. After stirring for 15 minutes the mixture was transferred to a reparatory funnel with the addition of methyl t-butyl ether (300 mL) and water (20 mL). The phases were separated. The aqueous phase was basified by the addition of sodium hydroxide (50%; 10 mL) and then extracted with dichloromethane. The combined dichloromethane extracts were dried over sodium sulfate and filtered. Heptane (300 mL) was added. The solution was concentrated under vacuum to about one third the initial volume. Heptane (200 mL) was added. Further concentration resulted in solids precipitating. The solids were collected by filtration and washed with heptane (100 mL). The solids were dried under vacuum at 55° C. to give 4-(2-methoxyethoxyl)pyridin-2-amine as an off white solid (23.62 g).

Step C: Preparation of ethyl 7-(2-methoxyethoxyl)imidazo[1,2-a]pyridine-3-carboxylic acid 4-(2-Methoxyethoxyl)pyridin-2-amine (5.00 g; 29.7 mmol) was mixed with ethanol (20 mL) in a reaction flask, under an atmosphere of dry nitrogen. A solution of ethyl 2-chloro-3-oxopropanoate (5% in benzene; 110 mL; Commercial solution from Toronto Research Chemicals Inc.) was added. The mixture was heated to 60° C. under nitrogen for 4 hours. After allowing the mixture to cool the solvent was removed under vacuum to give a give a brown solid (9 g). The solid was mixed with ethyl acetate (200 mL) and sodium bicarbonate solution (50 mL) and stirred to dissolve. The phases were separated and the bicarbonate solution was extracted with further ethyl acetate (50 mL). The combined ethyl acetate extracts were dried over sodium sulfate, filtered and concentrated under vacuum to give a brown solid (7.0 g). The material was dissolved in ethyl acetate and passed through a short column of silica, eluting with ethyl acetate. Factions containing product were concentrated to give ethyl 7-(2-methoxyethoxyl)imidazo[1,2-a]pyridine-3-carboxylate as a cream colored solid (3.77 g).

Step D: Preparation of 7-(2-methoxyethoxyl)imidazo[1,2-a]pyridine-3-carboxylic acid Ethyl 7-(2-methoxyethoxyl)imidazo[1,2-a]pyridine-3-carboxylate (6.06 g; 22.9 mmol) was mixed with tetrahydrofuran (225 mL), ethanol (110 mL) and water (55 mL). Lithium hydroxide monohydrate (0.962 g; 22.9 mmol) was added. The mixture was stirred under an atmosphere of nitrogen and heated at 40° C. for 22 hours. The mixture was allowed to cool and then concentrated under reduced pressure to give a yellow gum. Water (50 mL) was added and the mixture stirred to until homogeneous. Hydrochloric acid (2N) was added with stirring to adjust to pH 3. The mixture was cooled with an ice/water bath. The resulting precipitate was collected by filtration and washed with a small amount of water (10 mL). The material was dried under vacuum to give 7-(2-methoxyethoxyl)imidazo[1,2-a]pyridine-3-carboxylic acid as a white solid (4.90 g).

Step E: Preparation of N-(1-benzyl-1H-indazol-4-yl)-7-(2-methoxyethoxyl)imidazo[1,2-a]pyridine-3-carboxamide To a suspension of 7-(2-methoxyethoxyl)imidazo[1,2-a]pyridine-3-carboxylic acid (50 mg; 0.21 mmol) in methylene chloride (2 mL) was added a catalytic (0.005 mL) amount of DMF followed by oxalyl chloride (0.23 mmol; 2M solution in methylene chloride). The mixture was stirred in a sealed vial until effervescence ceased (approximately 30 minutes), with occasional venting to release gas. 1-Benzyl-1H-indazol-4-amine (Example 155, Steps A-B; 47 mg; 0.21 mmol) was added as a solution in methylene chloride (1 mL) followed by diisopropylethylamine (33 mg; 0.25 mmol). The mixture was stirred for 16 hours at ambient temperature, during which time a suspension formed. The mixture was partitioned between water and methylene chloride and the suspension was extracted multiple times with methylene chloride. The combined organic phases (which contained suspended solids) were concentrated under reduced pressure. The resulting solid material was triturated with ether and collected by filtration. The solids were washed with ether, water and then ether again. The material was dried under vacuum to give an off white solid (67 mg). MS (APCI), m/z=442.2 (M+H).

Example 157

N-(1-benzyl-1H-indazol-4-yl)-7-(1,2-dihydroxyethyl)imidazo[1,2-a]pyridine-3-carboxamide

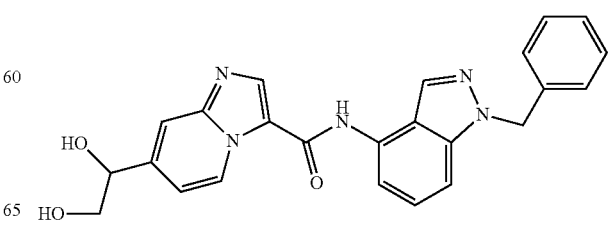

Step A: Preparation of ethyl 7-bromoimidazo[1,2-a]pyridine-3-carboxylate 4-bromopyridin-2-amine (10.0 g, 0.06 mol) was mixed with ethanol (50 mL) in a reaction flask, under an atmosphere of dry nitrogen. A solution of ethyl 2-chloro-3-oxopropanoate (5% in benzene; 222 mL; Commercial solution from Toronto Research Chemicals Inc.) was added. The mixture was heated to 60° C. under nitrogen for 5 hours. After allowing the mixture to cool the solvent was removed under vacuum to give a brown solid. The solid was mixed with ethyl acetate (500 mL) and sodium bicarbonate solution (200 mL) and stirred to dissolve. The phases were separated and the bicarbonate solution was extracted further with ethyl acetate (100 mL). The combined ethyl acetate extracts were dried over sodium sulfate, filtered and concentrated under vacuum to give a solid. The crude material was dissolved in ethyl acetate and passed through a short column of silica, eluting with ethyl acetate to give ethyl 7-bromoimidazo[1,2-a]pyridine-3-carboxylate as a pale yellow solid (15 g).

Step B: Preparation of 7-bromoimidazo[1,2-a]pyridine-3-carboxylic acid

Added ethyl 7-bromoimidazo[1,2-a]pyridine-3-carboxylate (15 g, 56 mmol) and lithium hydroxide monohydrate (3 g, 71.4 mmol) into tetrahydrofuran/ethanol/water (1:2:1, 560 mL total) solution. After stirring at ambient temperature overnight, the solvent was removed under vacuum to give a yellow gum. Water (300 mL) and dichloromethane was added, and the phases were separated. The aqueous layer was cooled in an ice-water bath before adjusting the pH to 3 using 2N sulfuric acid. The product precipitated out and was collected by filtration and washed with a small amount of water (50 mL) before drying under vacuum to give 7-bromoimidazo[1,2-a]pyridine-3-carboxylic acid as an off-white solid (8.3 g).

Step C: Preparation of N-(1-benzyl-1H-indazol-4-yl)-7-bromoimidazo[1,2-a]pyridine-3-carboxamide To a solution of 7-bromoimidazo[1,2-a]pyridine-3-carboxylic acid (42 mg; 0.17 mmol) in dichloromethane (1 mL) was added oxalyl chloride (1.1 equivalents; 2M solution in dichloromethane) followed by a catalytic amount of DMF. The mixture was stirred in a sealed container stirred until effervescence stopped, venting occasionally to release gas. 1-Benzyl-1H-indazol-4-amine (Example 155, Steps A-B; 39 mg; 0.17 mmol) was added followed by diisopropylethylamine (2 equivalents). The mixture was stirred at ambient temperature for 2 days. The mixture was diluted with methanol and the solids were collected by filtration and washed twice with 2M aqueous sodium carbonate solution, water and ether. The solids were then dried to give the desired product as an off-white solid (53 mg).

Step D: Preparation of N-(1-benzyl-1H-indazol-4-yl)-7-vinylimidazo[1,2-a]pyridine-3-carboxamide A mixture of N-(1-benzyl-1H-indazol-4-yl)-7-bromoimidazo[1,2-a]pyridine-3-carboxamide (50 mg; 0.112 mmol), tributylvinyltin (43 mg; 0.13 mmol) and cesium fluoride (34 mg; 0.22 mmol) were mixed with DMF (1 mL) under nitrogen. Palladium (II) chloride (0.8 mg; 0.005 mmol), tri-tert-butylphosphine (18 mg; 0.009 mmol) and copper (I) iodide (1.7 mg; 0.009 mmol) were added and the mixture was purged with nitrogen and then heated in a sealed vessel at 45° C. for 16 hours. The mixture was added to water (30 mL) and extracted into ethyl acetate. The combined extracts were washed with water, dried (sodium sulfate) and filtered through a pad of silica. The solvent was removed under vacuum to provide a white solid which was triturated with ether to provide the desired product (27 mg) of sufficient purity to take to the next step.

Step E: Preparation of N-(1-benzyl-1H-indazol-4-yl)-7-(1,2-dihydroxyethyl)imidazo[1,2-a]pyridine-3-carboxamide To a solution of N-(1-benzyl-1H-indazol-4-yl)-7-vinylimidazo[1,2-a]pyridine-3-carboxamide (27 mg; 0.069 mmol) in acetone/water (3:2; 1 mL) were added osmium tetroxide (0.1 equivalents as a 2% solution in t-butanol) and N-methylmorpholine N-oxide (1.2 equivalents as a 50% solution on water). The mixture was stirred at ambient temperature for several days. Further aliquots of osmium tetroxide and N-methyl morpholine N-oxide were added at intervals until the reaction was complete by LC. The mixture added to water and extracted into ethyl acetate. Some insoluble material was isolated by filtration. The extracts were combined, concentrated under vacuum and combined with the solids isolated by filtration. The combined material was purified by preparative thin layer chromatography on silica, eluting with dichloromethane/ethanol/ammonium hydroxide (100:20:0.5) to give the desired product (2.6 mg). MS (APCI), m/z=428.2 (M+H).

Example 158

N-(1-benzyl-1H-indazol-4-yl)-6-(1,2-dihydroxyethyl)imidazo[1,2-a]pyridine-3-carboxamide

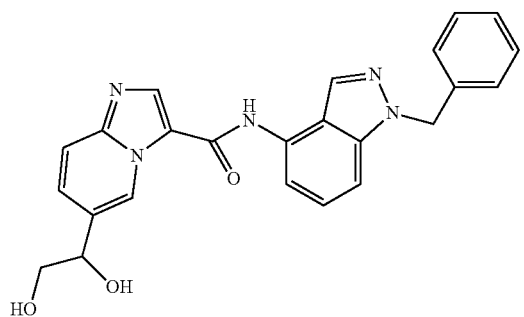 [SMILES: O=C(Nc1cccc2c1cnn2Cc1ccccc1)c1cnc2ccc(C(O)CO)cn12]

Step A: Preparation of N-(1-benzyl-1H-indazol-4-yl)-6-vinylimidazo[1,2-a]pyridine-3-carboxamide A mixture of N-(1-benzyl-1H-indazol-4-yl)-6-bromoimidazo[1,2-a]pyridine-3-carboxamide (Example 155; 75 mg; 0.168 mmol), tributyl(vinyl)stannane (59 mg; 0.185 mmol), tris(dibenzylideneacetone)dipalladium(0) (2.3 mg; 0.0025 mmol), bis(tri-tert-butylphosphine)palladium(0) (2.6 mg; 0.0050 mmol) and cesium fluoride (56 mg; 0.37 mmol) in NMP was stirred under nitrogen at 60° C. for 5 hours. Additional amounts of the palladium catalysts and the tributyl(vinyl)tin (similar quantities to those added initially) were added and the mixture was heated for an additional 12 hours. The mixture was added to water (20 mL) and extracted into ethyl acetate. The combined extracts were washed with water and brine and dried (sodium sulfate). The filtered solution was concentrated under reduced pressure. The material was purified by silica gel chromatography, eluting with ethyl acetate, to provide the desired product as an oil (66 mg) which solidified on standing.

Step B: Preparation of N-(1-benzyl-1H-indazol-4-yl)-6-(1,2-dihydroxyethyl)imidazo[1,2-a]pyridine-3-carboxamide A mixture of N-(1-benzyl-1H-indazol-4-yl)-6-vinylimidazo[1,2-a]pyridine-3-carboxamide (63 mg; 0.16 mmol), osmium tetroxide (0.008 mmol; 2.5% solution in t-butanol) and N-methylmorpholine N-oxide (21 mg; 0.18 mmol) in acetone/water (3:2; 1 mL) was stirred at ambient temperature for 24 hours. Additional osmium tetroxide was added (250 µL of a 2.5% solution in t-butanol) and the mixture was stirred for an additional 24 hours. The mixture was diluted with ethyl acetate and solids were isolated by filtration. The material was purified by reverse phase chromatography (acetonitrile/water) to give the desired product as a solid (3.6 mg). MS (APCI), m/z=428.2 (M+H).

Example 159

N-(1-benzyl-1H-indazol-4-yl)-6-methoxyimidazo[1,2-a]pyridine-3-carboxamide

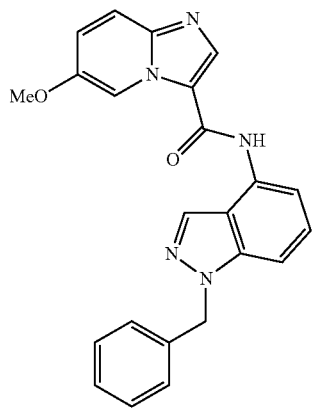 [SMILES: COc1ccc2ncc(C(=O)Nc3cccc4c3cnn4Cc3ccccc3)n2c1]

Step A: Preparation of 6-methoxyimidazo[1,2-a]pyridine-3-carboxylic acid

Prepared according to the method of Example 152, Steps A-B replacing 2-aminoisonicotinonitrile with 5-methoxypyridin-2-amine.

Step B: Preparation of 1-benzyl-4-nitro-1H-indazole

To a solution of 4-nitro-1H-indazole (0.500 g, 3.06 mmol) in acetone (0.4M, 7.5 mL) cooled to 0° C. was added KOH (0.258 g, 4.60 mmol). After 15 minutes at 0° C., (bromomethyl)benzene (0.400 mL, 3.37 mmol) was added. The reaction mixture was allowed to stir at ambient temperature overnight. The reaction mixture was concentrated under reduced pressure and the residue was purified by column chromatography (50% EtOAc/hexanes) providing 256 mg (33%) of the title compound.

Step C: Preparation of 1-benzyl-1H-indazol-4-amine

1-Benzyl-4-nitro-1H-indazole (672 mg, 2.65 mmol) was taken up in 26 mL of EtOH/water (4:1) and treated with NH4Cl (0.5 equivalents) and Fe powder (10 equivalents). The reaction was heated to reflux for 2 hours. The reaction was concentrated under reduced pressure, diluted with EtOAc:Et₃N (4:1) and stirred for two hours. The reaction mixture was filtered over GF/F paper and concentrated to give a brown, viscous oil. This crude material was purified by column chromatography (30% EtOAc/hexanes) providing 363 mg (61%) of the title compound.

Step D: Preparation of N-(1-benzyl-1H-indazol-4-yl)-6-methoxyimidazo[1,2-a]pyridine-3-carboxamide 6-Methoxyimidazo[1,2-a]pyridine-3-carboxylic acid (29.5 mg, 0.154 mmol) was taken up in DCM. Oxalyl chloride (1.1 equivalents) was added followed by a drop of DMF. The reaction was stirred at ambient temperature until bubbling ceased, and then 1-benzyl-1H-indazol-4-amine (34.3 mg, 0.154 mmol) was added followed by DIEA (1.2 equivalents). The reaction was stirred at ambient temperature overnight. The reaction was concentrated, triturated with ether and purified by Preparative TLC (1 mm) eluting with 10% MeOH/DCM to give 15 mg (25%) of the desired product. MS (ES+APCI) m/z=398.3 (M+H).

Example 160

Preparation of N3-(1-benzyl-1H-indazol-4-yl)imidazo[1,2-a]pyridine-3,6-dicarboxamide

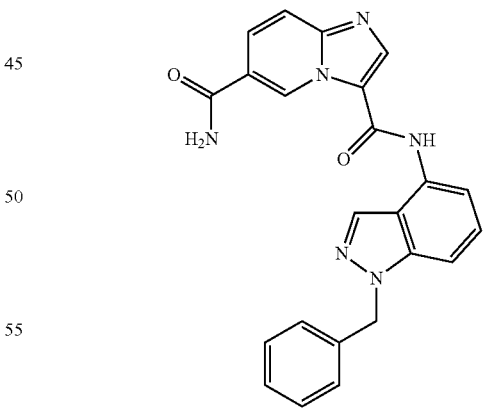

Prepared according to the method of Example 159, replacing 6-methoxyimidazo[1,2-a]pyridine-3-carboxylic acid with 6-carbamoylimidazo[1,2-a]pyridine-3-carboxylic acid. MS (ES+APCI) m/z=411.3 (M+H).

Example 161

N-(1-benzyl-1H-indazol-4-yl)-7-bromoimidazo[1,2-a]pyridine-3-carboxamide

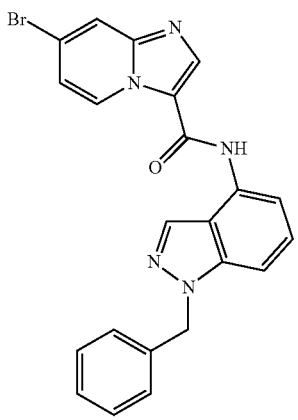 [SMILES: O=C(Nc1cccc2c1cnn2Cc1ccccc1)c1cnc2cc(Br)ccn12]

Prepared according to the method of Example 159, replacing 6-methoxyimidazo[1,2-a]pyridine-3-carboxylic acid with 7-bromoimidazo[1,2-a]pyridine-3-carboxylic acid.

What is claimed is:
1. A compound having the general formula I

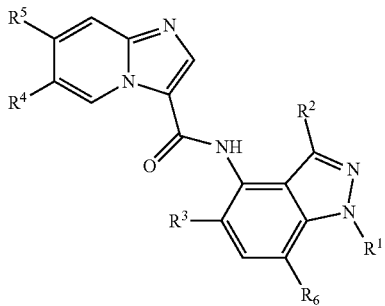

or a pharmaceutically acceptable salt thereof, wherein:

$R^1$ is hetAr$^1$(CH$_2$)$_m$—, hetAr$^2$CH$_2$— or hetAr$^3$CH$_2$;

hetAr$^1$ is a 6-membered heteroaryl having 1-2 ring N atoms and optionally substituted with one or more substituents independently selected from (1-6C)alkyl, (1-4C)alkoxy, halogen, CF$_3$, or (3-6C)cycloalkyl;

m is 0, 1 or 2;

hetAr$^2$ is a 5-membered heteroaryl ring having 2-3 ring heteroatoms independently selected from N and S where at least one of said heteroatoms is N, wherein said ring is optionally substituted with one or more substituents independently selected from (1-6C)alkyl;

hetAr$^3$ is a bicyclic 5,6-fused heteroaryl ring having two ring nitrogen atoms;

$R^2$ is CH$_3$;

$R^3$ is H;

$R^4$ is H;

$R^5$ is hetCyc$^4$(1-4C)alkoxy or hetCyc$^5$(1-4C)alkoxy;

hetCyc$^4$ is a 4-7 membered heterocycle having 1-2 ring heteroatoms independently selected from N, O and S, wherein one of said ring nitrogen atoms is optionally oxidized to N(O) and wherein said S ring atom is optionally oxidized to SO or SO$_2$, wherein hetCyc$^4$ is optionally substituted with one or more substituents independently selected from halogen, OH, (1-6C)alkyl, (1-4C alkoxy)(1-6C)alkyl, (1-4C)alkyl-OC(=O)— and (1-6C)alkoxy;

hetCyc$^5$ is a spiro heterocycle having 2 ring heteroatoms independently selected from N and O, wherein hetCyc$^5$ is optionally substituted with a group selected from (1-6C)alkyl; and $R^6$ is H.

2. The compound of claim 1, or a pharmaceutically acceptable salt thereof, wherein:

$R^1$ is hetAr$^1$(CH$_2$)$_m$—;

m is 1; and $R^5$ is hetCyc$^4$(1-4C)alkoxy.

3. A compound of claim 2, selected from:

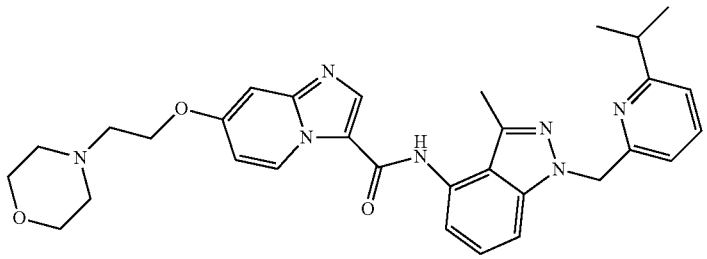

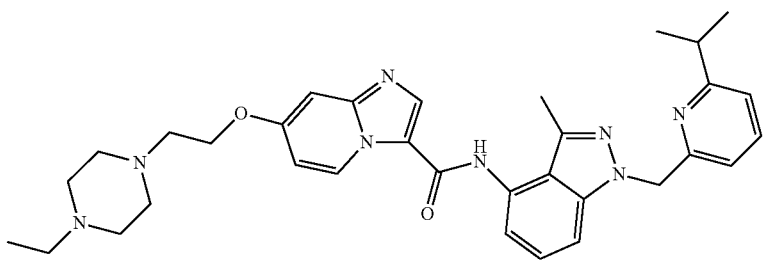

-continued
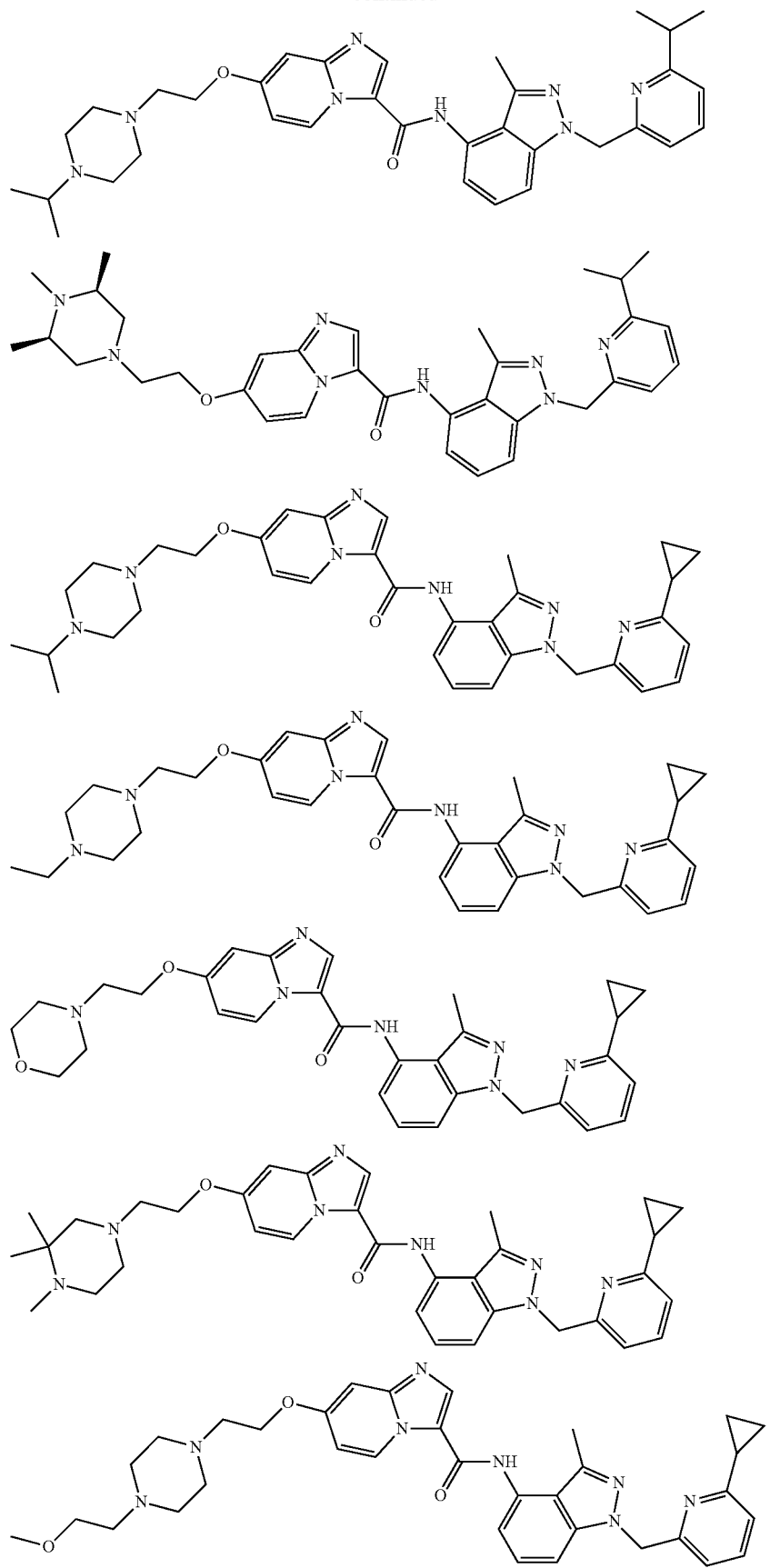

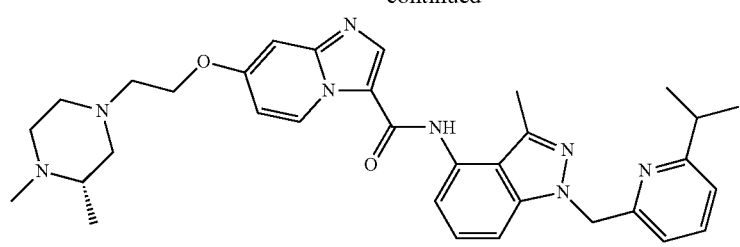
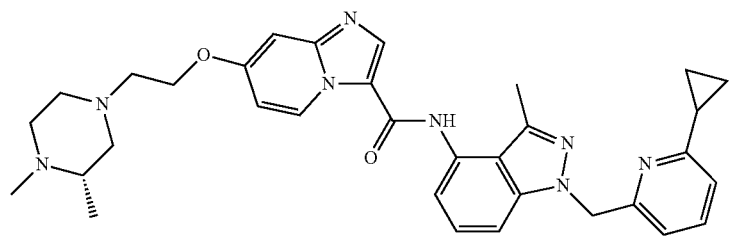
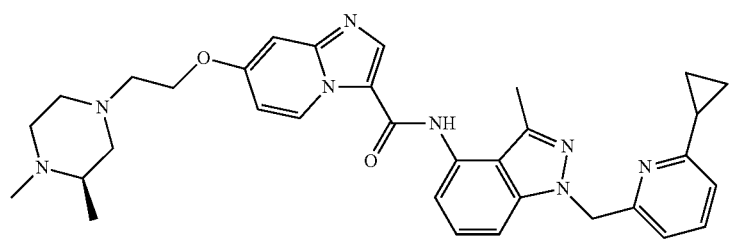
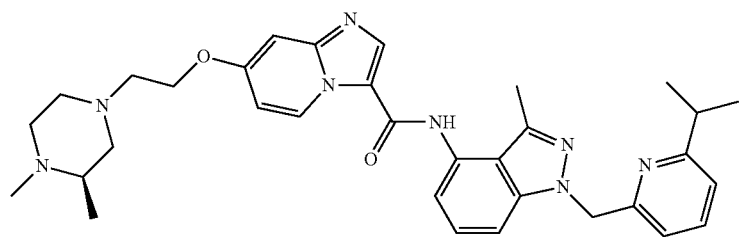
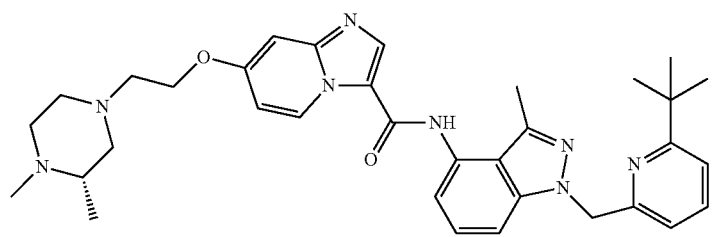 [SMILES: Cc1nn(Cc2cccc(C(C)(C)C)n2)c2cccc(NC(=O)c3cnc4cc(OCCN5CCN(C)[C@@H](C)C5)ccn34)c12]
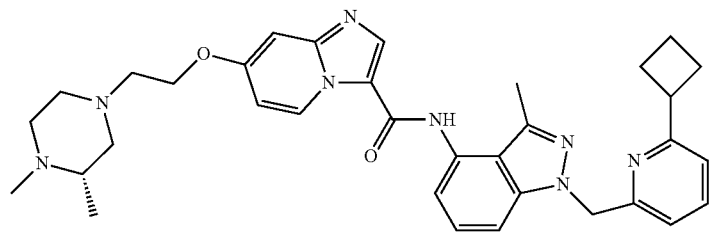 [SMILES: Cc1nn(Cc2cccc(C3CCC3)n2)c2cccc(NC(=O)c3cnc4cc(OCCN5CCN(C)[C@@H](C)C5)ccn34)c12]
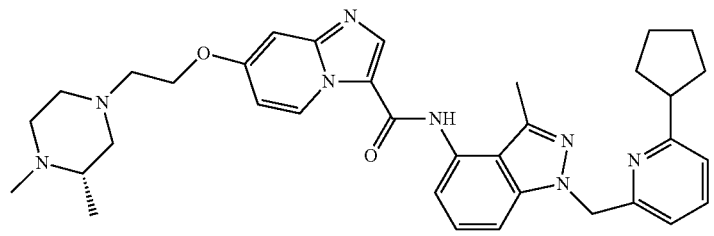

-continued
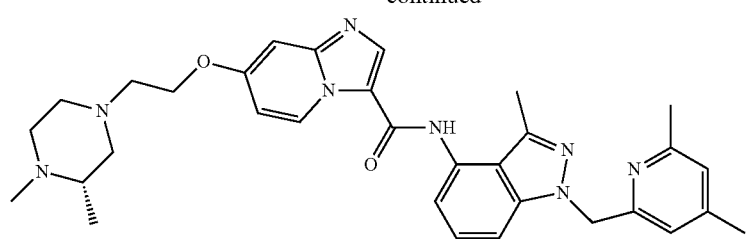
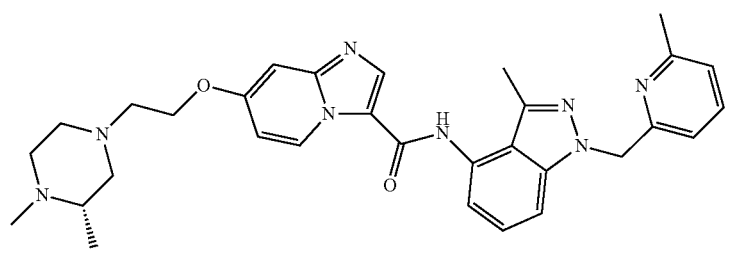
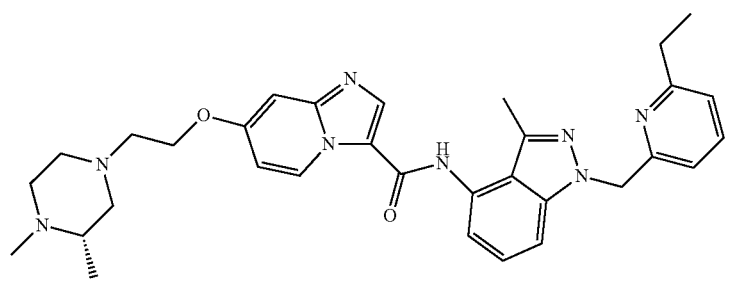 [SMILES: CCc1cccc(Cn2nc(C)c3c(NC(=O)c4cnc5cc(OCCN6CCN(C)[C@@H](C)C6)ccn45)cccc32)n1]
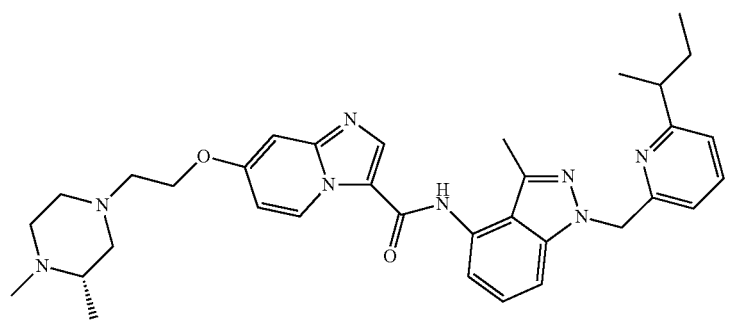
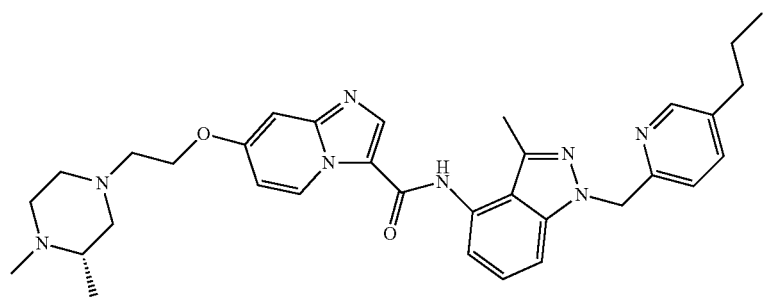
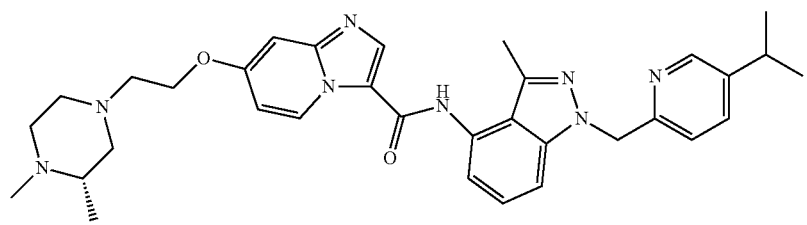

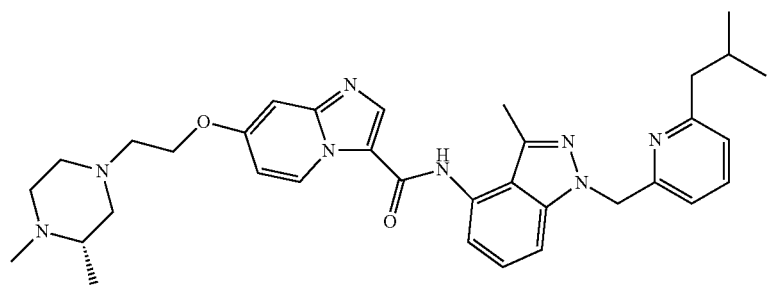 [SMILES: Cc1nn(Cc2cccc(CC(C)C)n2)c2cccc(NC(=O)c3cnc4cc(OCCN5CCN(C)[C@@H](C)C5)ccn34)c12]
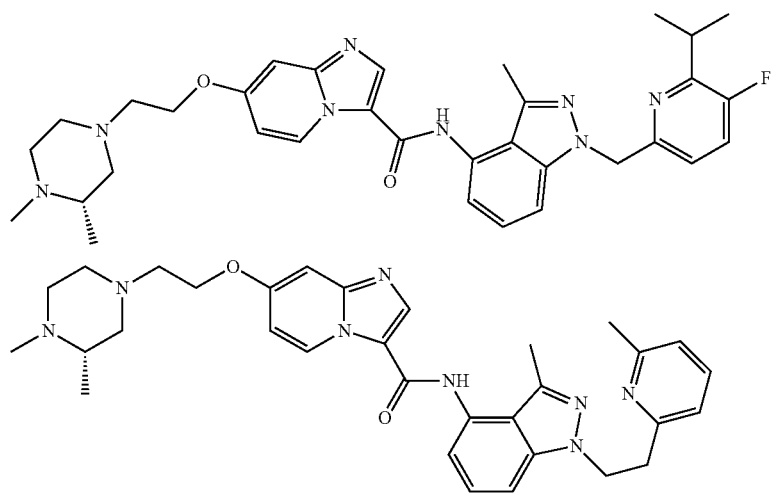
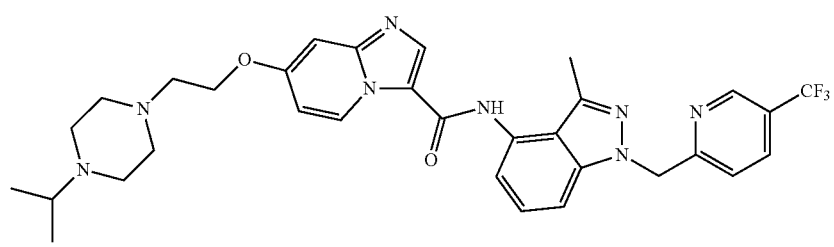
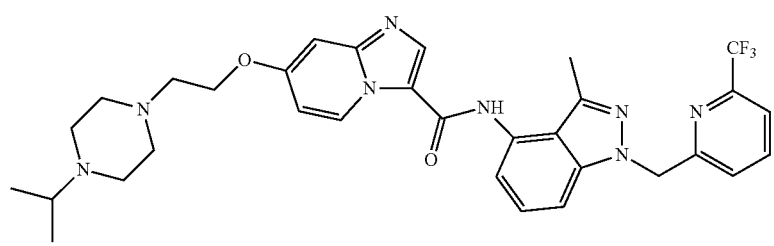
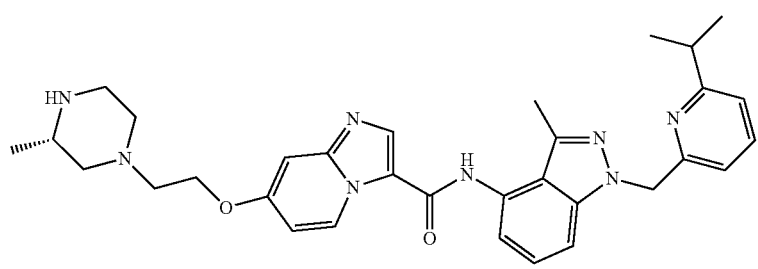

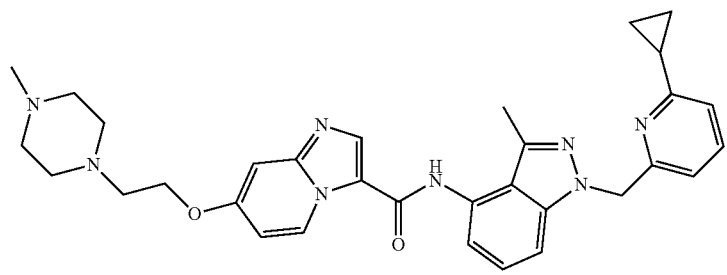
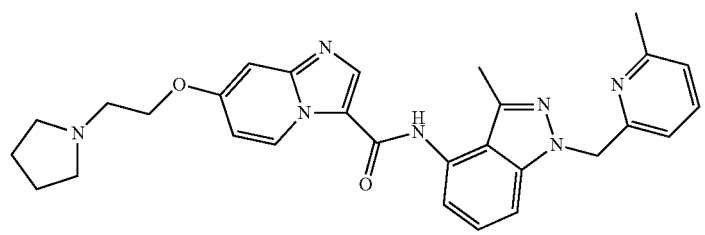
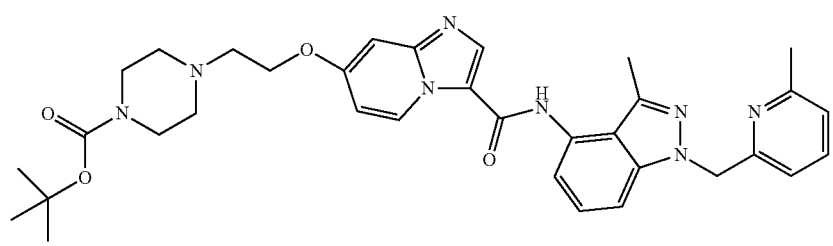
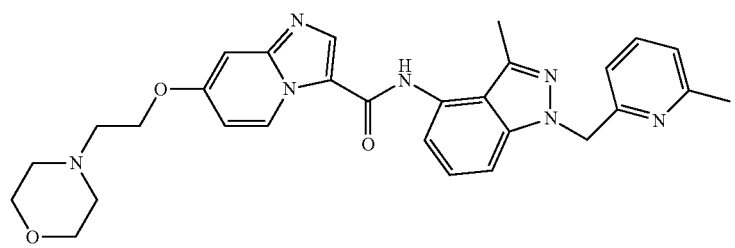
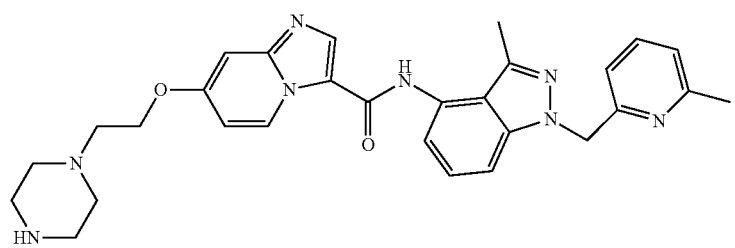
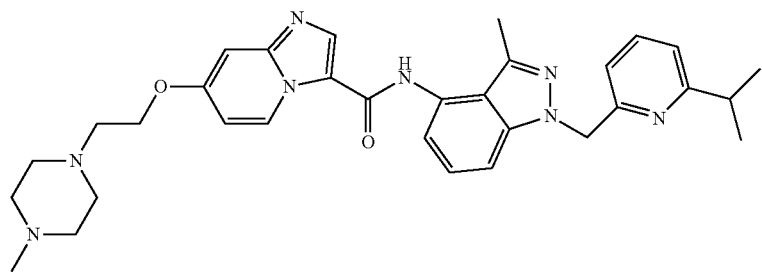 [SMILES: Cc1nn(Cc2cccc(C(C)C)n2)c2cccc(NC(=O)c3cnc4cc(OCCN5CCN(C)CC5)ccn34)c12]

-continued
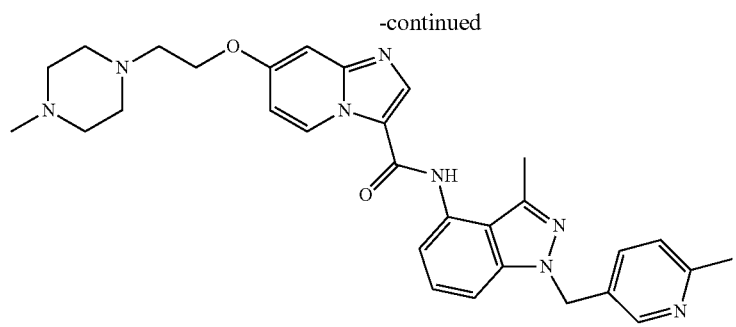
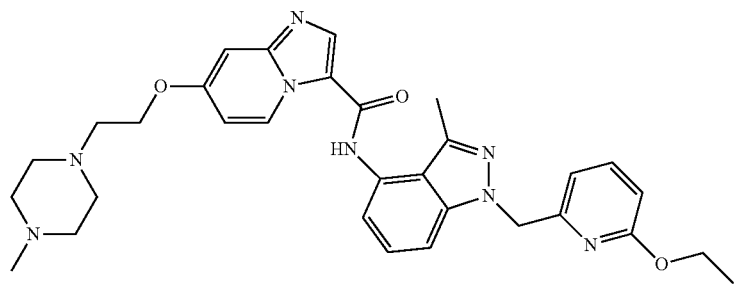
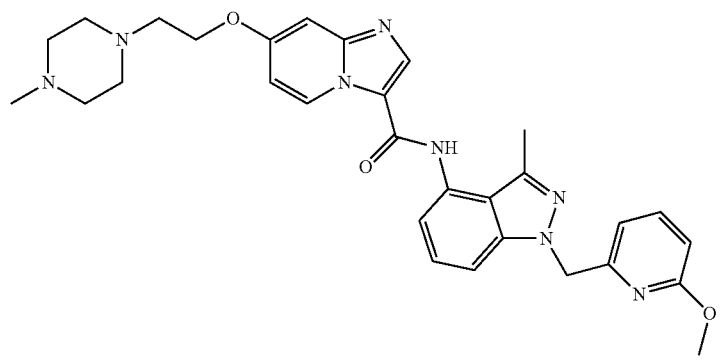
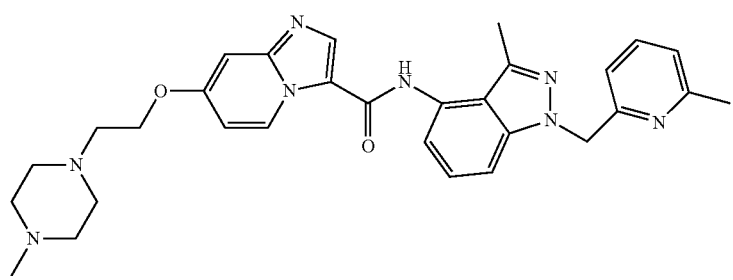
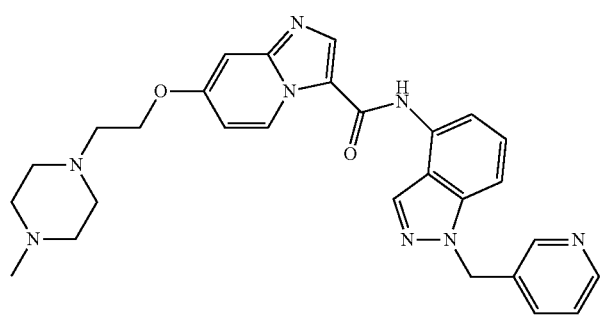

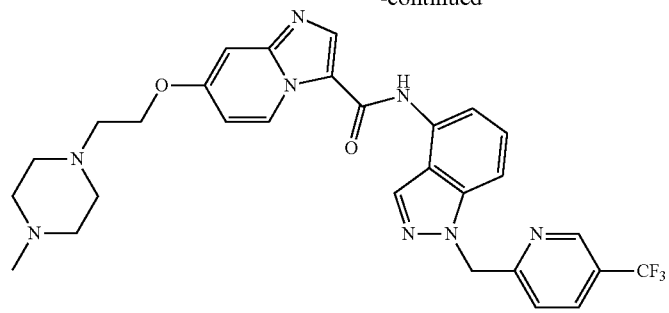
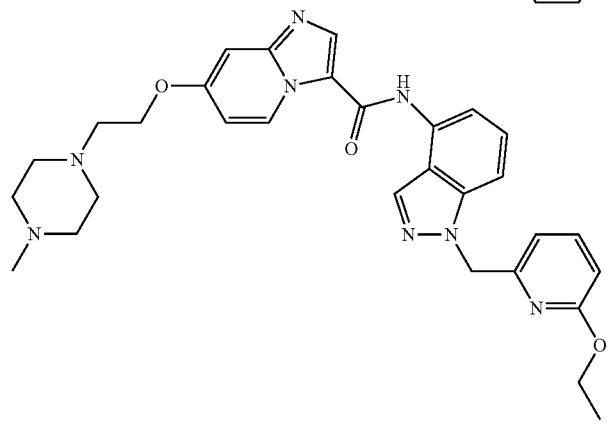
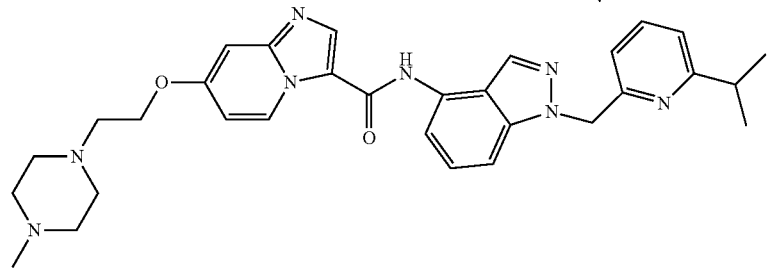
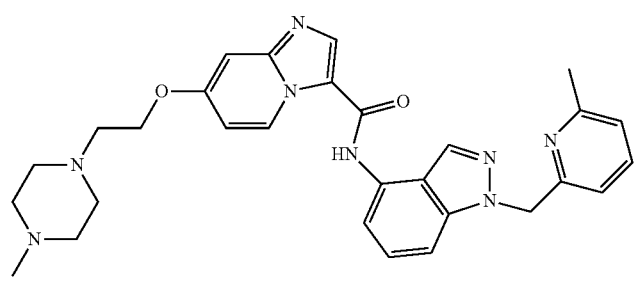
and pharmaceutically acceptable salts thereof.
4. A compound according to claim 3, which is:
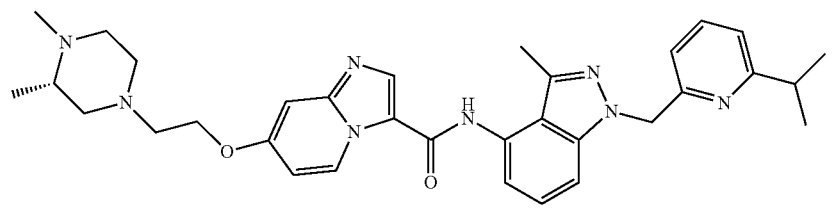
or a pharmaceutically acceptable salt thereof.

5. A compound according to claim 3, which is:

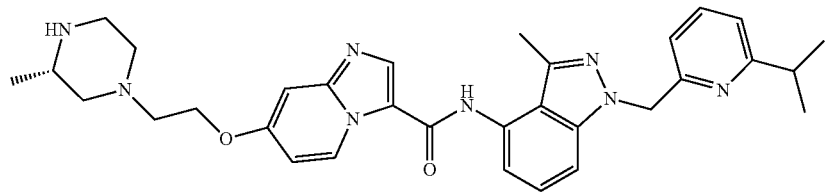

or a pharmaceutically acceptable salt thereof.

6. A compound according to claim 3, which is:

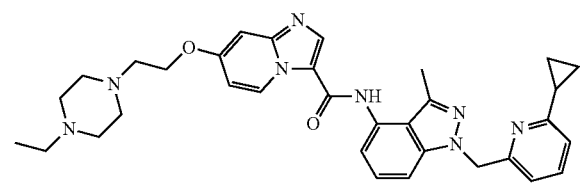

or a pharmaceutically acceptable salt thereof.

7. A compound according to claim 3, which is:

or a pharmaceutically acceptable salt thereof.

8. A compound according to claim 3, which is:

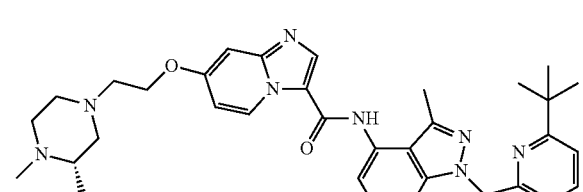

or a pharmaceutically acceptable salt thereof.

9. A compound according to claim 3, which is:

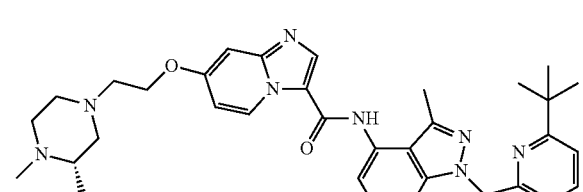

or a pharmaceutically acceptable salt thereof.

10. A compound according to claim 3, which is:

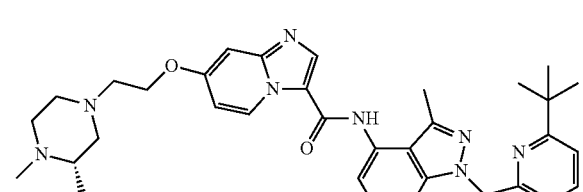

or a pharmaceutically acceptable salt thereof.

11. A compound according to claim 3, which is:

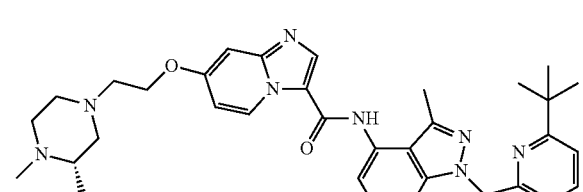

or a pharmaceutically acceptable salt thereof.

12. A compound according to claim 3, which is:

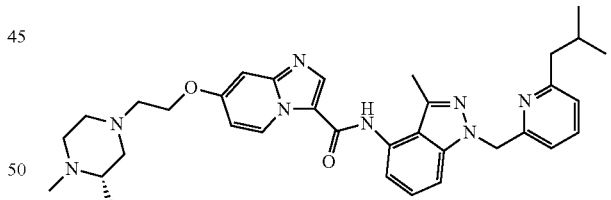

or a pharmaceutically acceptable salt thereof.

13. A compound according to claim 3, which is:

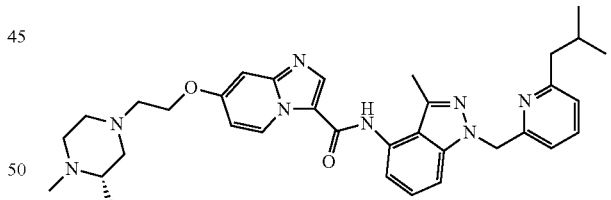

or a pharmaceutically acceptable salt thereof.

14. A pharmaceutical composition comprising a compound of Formula I according to claim 1, or a pharmaceutically acceptable salt thereof, and a pharmaceutically acceptable diluent or carrier.

15. The pharmaceutical composition according to claim 14, wherein said composition is formulated for oral administration.

16. A pharmaceutical composition comprising a compound of Formula I according to claim 2, or a pharmaceutically acceptable salt thereof, and a pharmaceutically acceptable diluent or carrier.

17. The pharmaceutical composition according to claim 16, wherein said composition is formulated for oral administration.

18. A pharmaceutical composition comprising a compound of Formula I according to claim 3, or a pharmaceutically acceptable salt thereof, and a pharmaceutically acceptable diluent or carrier.

19. The pharmaceutical composition according to claim 18, wherein said composition is formulated for oral administration.

20. A method for treating cancer in a mammal, wherein said cancer is acute myeloid leukemia or gastrointestinal stromal tumor, which comprises administering to a mammal in need thereof a therapeutically effective amount of a compound of Formula I according to claim 2, or a pharmaceutically acceptable salt thereof.

21. The method according to claim 20, wherein said cancer is acute myeloid leukemia.

22. The method according to claim 20, wherein said cancer is gastrointestinal stromal tumor.

23. A method for treating cancer in a mammal, wherein said cancer is acute myeloid leukemia or gastrointestinal stromal tumor, which comprises administering to a mammal in need thereof a therapeutically effective amount of a compound of Formula I according to claim 3, or a pharmaceutically acceptable salt thereof.

24. The method according to claim 23, wherein said cancer is acute myeloid leukemia.

25. The method according to claim 23, wherein said cancer is gastrointestinal stromal tumor.

26. The method according to claim 20, wherein the compound of Formula I according to claim 2 or a pharmaceutically acceptable salt thereof is orally administered.

27. The method according to claim 23, wherein the compound of Formula I according to claim 3 or a pharmaceutically acceptable salt thereof is orally administered.

28. The method according to claim 20, further comprising administering one or more agents selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors.

29. The method according to claim 23, further comprising administering one or more agents selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors.

* * * * *

UNITED STATES PATENT AND TRADEMARK OFFICE
CERTIFICATE OF CORRECTION

PATENT NO. : 9,809,590 B2
APPLICATION NO. : 14/858029
DATED : November 7, 2017
INVENTOR(S) : Boys et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 24 days.

Signed and Sealed this
Twenty-fifth Day of September, 2018

Andrei Iancu
*Director of the United States Patent and Trademark Office*